(12) United States Patent
Hansen et al.

(10) Patent No.: US 9,757,368 B2
(45) Date of Patent: Sep. 12, 2017

(54) ANTI-INFLAMMATORY AGENTS

(75) Inventors: Henrik C. Hansen, Calgary (CA); Gregory S. Wagner, Foster City, CA (US); Sarah C. Attwell, Calgary (CA); Kevin G. McLure, Calgary (CA); Ewelina B. Kulikowski, Calgary (CA)

(73) Assignee: Resverlogix Corp., Calgary, Alberta (CA)

(*) Notice: Subject to any disclaimer, the term of this patent is extended or adjusted under 35 U.S.C. 154(b) by 0 days.

(21) Appl. No.: 13/265,060

(22) PCT Filed: Apr. 21, 2010

(86) PCT No.: PCT/US2010/031870
§ 371 (c)(1),
(2), (4) Date: Nov. 22, 2011

(87) PCT Pub. No.: WO2010/123975
PCT Pub. Date: Oct. 28, 2010

(65) Prior Publication Data
US 2012/0059002 A1 Mar. 8, 2012

Related U.S. Application Data

(60) Provisional application No. 61/171,620, filed on Apr. 22, 2009.

(51) Int. Cl.
| A61K 31/5377 | (2006.01) |
| A61K 31/517 | (2006.01) |
| C07D 401/12 | (2006.01) |
| C07D 403/10 | (2006.01) |
| C07D 413/10 | (2006.01) |
| C07D 471/04 | (2006.01) |
| A61K 31/519 | (2006.01) |
| C07D 405/10 | (2006.01) |
| C07D 403/12 | (2006.01) |
| C07D 413/12 | (2006.01) |
| C07D 217/24 | (2006.01) |
| A61K 31/472 | (2006.01) |
| A61P 9/00 | (2006.01) |
| A61P 29/00 | (2006.01) |
| C07D 239/91 | (2006.01) |
| A61K 31/47 | (2006.01) |
| C07D 403/04 | (2006.01) |
| C07D 405/04 | (2006.01) |

(52) U.S. Cl.
CPC ............ *A61K 31/47* (2013.01); *C07D 239/91* (2013.01); *C07D 401/12* (2013.01); *C07D 403/04* (2013.01); *C07D 403/12* (2013.01); *C07D 405/04* (2013.01); *C07D 413/12* (2013.01)

(58) Field of Classification Search
CPC ............ A61K 31/5377; A61K 31/517; A61K 31/519; A61K 31/472; C07D 401/12; C07D 403/10; C07D 413/10; C07D 471/04; C07D 405/10; C07D 403/12; C07D 413/12; C07D 217/24; A61P 9/00; A61P 29/00

USPC ..................................................... 514/234.5
See application file for complete search history.

(56) References Cited

U.S. PATENT DOCUMENTS

| 2,065,593 A | 12/1936 | Lubs |
| 2,065,900 A | 12/1936 | Laska et al. |
| 2,071,329 A | 2/1937 | Brown |
| 3,251,837 A | 5/1966 | Holland |
| 3,600,394 A | 8/1971 | Coyne et al. |
| 3,773,946 A | 11/1973 | Creger |
| 3,930,024 A | 12/1975 | Creger |
| 3,965,128 A | 6/1976 | Fürst et al. |
| 4,159,330 A | 6/1979 | Doria et al. |
| 4,251,531 A | 2/1981 | Doria et al. |
| 4,613,593 A | 9/1986 | Yamatsu et al. |
| 4,689,344 A | 8/1987 | Bar-Tana |
| 4,711,896 A | 12/1987 | Bar-Tana et al. |
| 4,825,005 A | 4/1989 | Frey et al. |
| 5,098,903 A | 3/1992 | Magarian et al. |
| 5,124,337 A | 6/1992 | Dugar et al. |

(Continued)

FOREIGN PATENT DOCUMENTS

| AU | 719140 B2 | 7/1998 |
| CA | 2104981 A1 | 3/1994 |

(Continued)

OTHER PUBLICATIONS

Brian J. Van Lenten, Mohamad Navab, G.M. Anantharamaiah, Georgette M. Buga, Srinivasa T. Reddy, and Alan M. Fogelman, Multiple indications for anti-inflammatory peptides, Curr Opin Investig Drugs. Nov. 2008 ; 9(11): 1157-1162.*
Zbigniew Stelmasiak, Maria Koziol-Montewka, Beata Dobosz, Konrad Rejdak, Halina Bartosik-Psujek, Krystyna Mitosek-Szewczyk, Ewa Belniak-Legie, Interleukin-6 concentration in serum and cerebrospinal fluid in multiple sclerosis patients, Med Sci Monit, 2000; 6(6): 1104-1108.*
F. Perez-Villa, B. Benito, M. Llancaqueo, A. Cuppoletti, and E. Roig, Elevated Levels of Serum Interleukin-6 are Associated With Low Grade Cellular Rejection in Patients With Heart Transplantation, Transplantation Proceedings, 38, 3012-3015 (2006).*
Abdel-Jalil et al., "Synthesis and Antitumor Activity of 2-Aryl-7-fluoro-6-(4-methyl-1-piperazinyl)-4(3H)-quinazolinones" *Heterocycles* 65(9):2061-2070 (2005).

(Continued)

*Primary Examiner* — Sarah Pihonak
*Assistant Examiner* — Jason A Deck
(74) *Attorney, Agent, or Firm* — Finnegan, Henderson, Farabow, Garrett & Dunner, LLP

(57) ABSTRACT

Disclosed are methods of regulating interleukin-6 (IL-6) and/or vascular cell adhesion molecule-1 (VCAM-1) and methods of treating and/or preventing cardiovascular and inflammatory diseases and related disease states, such as, for example, atherosclerosis, asthma, arthritis, cancer, multiple sclerosis, psoriasis, and inflammatory bowel diseases, and autoimmune disease(s) by administering a naturally occurring or synthetic quinazolone derivative. The invention provides novel synthetic quinazolone compounds, as well as pharmaceutical compositions comprising those compounds.

36 Claims, No Drawings

(56) References Cited

U.S. PATENT DOCUMENTS

| | | |
|---|---|---|
| 5,126,351 A | 6/1992 | Luzzio et al. |
| 5,244,904 A | 9/1993 | Nagase et al. |
| 5,280,024 A | 1/1994 | Bolland et al. |
| 5,354,749 A | 10/1994 | Dressel et al. |
| 5,407,942 A | 4/1995 | Dressel et al. |
| 5,409,930 A | 4/1995 | Spada et al. |
| 5,446,071 A | 8/1995 | Grese |
| 5,474,994 A | 12/1995 | Leonardi et al. |
| 5,480,883 A | 1/1996 | Spada et al. |
| 5,539,119 A | 7/1996 | Nagase et al. |
| 5,576,322 A | 11/1996 | Takase et al. |
| 5,595,974 A | 1/1997 | Tomaru |
| 5,693,652 A | 12/1997 | Takase et al. |
| 5,707,987 A | 1/1998 | Nakagawa et al. |
| 5,733,913 A | 3/1998 | Blankley et al. |
| 5,756,344 A | 5/1998 | Onda et al. |
| 5,756,544 A | 5/1998 | Bisgaier et al. |
| 5,756,736 A | 5/1998 | Arzeno et al. |
| 5,756,763 A | 5/1998 | Takeuchi et al. |
| 5,763,414 A | 6/1998 | Bok et al. |
| 5,783,577 A | 7/1998 | Houghten et al. |
| 5,792,461 A | 8/1998 | Bok et al. |
| 5,792,902 A | 8/1998 | Benoit et al. |
| 5,798,344 A | 8/1998 | Kuroki et al. |
| 5,801,180 A | 9/1998 | Takase et al. |
| 5,817,674 A | 10/1998 | Clemence et al. |
| 5,854,264 A | 12/1998 | Anthony et al. |
| 5,877,208 A | 3/1999 | Bok et al. |
| 5,922,866 A | 7/1999 | Miyata et al. |
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |
| 6,168,776 B1 | 1/2001 | Klunk et al. |
| 6,239,114 B1 | 5/2001 | Guthrie et al. |
| 6,291,456 B1 | 9/2001 | Stein et al. |
| 6,303,629 B1 | 10/2001 | Kun |
| 6,340,759 B1 | 1/2002 | Ueno et al. |
| 6,414,037 B1 | 7/2002 | Pezzuto et al. |
| 6,455,577 B2 | 9/2002 | Bok et al. |
| 6,479,499 B1 | 11/2002 | Kuo et al. |
| 6,482,479 B1 | 11/2002 | Dübal et al. |
| 6,512,161 B1 | 1/2003 | Rouy et al. |
| 6,521,253 B1 | 2/2003 | Forsman et al. |
| 6,541,045 B1 | 4/2003 | Charters et al. |
| 6,541,522 B2 | 4/2003 | Inman et al. |
| 6,548,548 B2 | 4/2003 | Campbell et al. |
| 6,613,772 B2 | 9/2003 | Schindler et al. |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 6,723,319 B1 | 4/2004 | Ito et al. |
| 7,087,612 B2 | 8/2006 | Rodriguez Sarmiento et al. |
| 7,173,128 B2 | 2/2007 | Ravichandran et al. |
| 7,244,776 B2 | 7/2007 | Ravichandran et al. |
| 7,655,699 B1* | 2/2010 | Boehm et al. ............... 514/569 |
| 7,846,915 B2 | 12/2010 | Wong et al. |
| 8,053,440 B2 | 11/2011 | Hansen |
| 8,093,273 B2 | 1/2012 | Wong et al. |
| 8,114,995 B2 | 2/2012 | Hansen et al. |
| 8,242,130 B2 | 8/2012 | Wong et al. |
| 8,242,144 B2 | 8/2012 | Wong et al. |
| 8,410,109 B2 | 4/2013 | Wong et al. |
| 8,440,196 B1 | 5/2013 | Funakoshi et al. |
| 8,569,288 B2 | 10/2013 | Kempen et al. |
| 8,884,046 B2 | 11/2014 | Lozanov et al. |
| 8,889,698 B2 | 11/2014 | Hansen |
| 8,952,021 B2 | 2/2015 | Hansen |
| 9,199,990 B2 | 12/2015 | Hansen |
| 9,238,640 B2 | 1/2016 | Hansen |
| 2002/0004608 A1 | 1/2002 | Alig et al. |
| 2002/0025301 A1 | 2/2002 | Haremza et al. |
| 2002/0091263 A1 | 7/2002 | Trova |
| 2003/0064967 A1 | 4/2003 | Luchoomun et al. |
| 2003/0068526 A1 | 4/2003 | Kamatani et al. |
| 2003/0072964 A1 | 4/2003 | Kwong et al. |
| 2003/0171429 A1 | 9/2003 | Chen et al. |
| 2004/0001834 A1 | 1/2004 | Kim et al. |
| 2004/0033480 A1 | 2/2004 | Wong |
| 2004/0058903 A1 | 3/2004 | Takasugi et al. |
| 2004/0097493 A1 | 5/2004 | Chen et al. |
| 2004/0198750 A1 | 10/2004 | Green et al. |
| 2004/0235888 A1 | 11/2004 | Yamamori et al. |
| 2004/0242615 A1 | 12/2004 | Yamamori et al. |
| 2004/0248950 A1 | 12/2004 | Ishizuka et al. |
| 2005/0043300 A1 | 2/2005 | Middleton et al. |
| 2005/0080021 A1 | 4/2005 | Tucker et al. |
| 2005/0080024 A1 | 4/2005 | Tucker et al. |
| 2005/0261319 A1 | 11/2005 | Deuschle et al. |
| 2006/0116364 A1 | 6/2006 | Hamaoka et al. |
| 2007/0099826 A1 | 5/2007 | Wong et al. |
| 2007/0185160 A1 | 8/2007 | Hattori et al. |
| 2007/0218155 A1 | 9/2007 | Kuhrts |
| 2008/0152595 A1 | 6/2008 | Emigh et al. |
| 2008/0275069 A1 | 11/2008 | Mizutani et al. |
| 2009/0029987 A1 | 1/2009 | Wong et al. |
| 2010/0093636 A1* | 4/2010 | Schultz et al. ............... 514/13 |
| 2010/0137400 A1 | 6/2010 | Karavas et al. |
| 2011/0201608 A1 | 8/2011 | Hoffmann et al. |
| 2011/0294807 A1 | 12/2011 | Hansen |
| 2012/0015905 A1 | 1/2012 | Hansen |
| 2012/0040954 A1 | 2/2012 | Hansen |
| 2014/0107369 A1 | 4/2014 | Lozanov et al. |
| 2015/0072955 A1 | 3/2015 | Hansen |
| 2016/0106750 A1 | 4/2016 | Hansen |
| 2016/0137613 A1 | 5/2016 | Hansen |
| 2016/0206617 A1 | 7/2016 | Lebioda et al. |
| 2016/0263126 A1 | 9/2016 | Kulikowski et al. |

FOREIGN PATENT DOCUMENTS

| | | |
|---|---|---|
| CA | 2345406 A1 | 4/2000 |
| CA | 2676984 A1 | 8/2008 |
| CA | 2815127 A1 | 4/2012 |
| CA | 2851996 A1 | 5/2013 |
| CN | 1067070 C | 6/2001 |
| CN | 1430599 A | 7/2003 |
| DE | 637259 | 10/1936 |
| DE | 652772 | 11/1937 |
| DE | 35 32 279 A1 | 3/1987 |
| DE | 36 01 417 A1 | 7/1987 |
| DE | 42 15 588 A1 | 11/1993 |
| DE | 196 51 099 A1 | 6/1998 |
| DE | 197 56 388 A1 | 6/1999 |
| DE | 199 34 799 A1 | 2/2001 |
| EP | 0 210 342 A2 | 2/1987 |
| EP | 0 182 213 B1 | 9/1990 |
| EP | 0 407 217 A1 | 1/1991 |
| EP | 0 410 834 A1 | 1/1991 |
| EP | 0 258 190 B1 | 11/1991 |
| EP | 0 488 602 A1 | 6/1992 |
| EP | 0 272 455 B1 | 2/1993 |
| EP | 0 375 404 B1 | 2/1994 |
| EP | 0 333 175 B1 | 6/1994 |
| EP | 0 343 499 B1 | 7/1994 |
| EP | 0 409 413 B1 | 8/1994 |
| EP | 0 420 511 B1 | 8/1994 |
| EP | 0 633 022 A2 | 1/1995 |
| EP | 0 569 795 B1 | 4/1995 |
| EP | 0 330 108 B1 | 12/1995 |
| EP | 0 747 051 A2 | 12/1996 |
| EP | 0 564 350 B1 | 5/1997 |
| EP | 0 643 119 B1 | 4/2000 |
| EP | 1 125 908 A1 | 8/2001 |
| EP | 0 498 723 B1 | 9/2001 |
| EP | 0 607 439 B1 | 1/2002 |
| EP | 0 776 893 B1 | 2/2002 |
| EP | 1 195 378 A1 | 4/2002 |
| EP | 1 277 738 A1 | 1/2003 |
| EP | 1 398 032 A1 | 3/2004 |
| EP | 1 418 164 A1 | 5/2004 |
| EP | 1 426 046 A1 | 6/2004 |

(56) References Cited

FOREIGN PATENT DOCUMENTS

| | | |
|---|---|---|
| EP | 1 477 481 A1 | 11/2004 |
| EP | 1 637 523 A1 | 3/2006 |
| EP | 1 757 594 A1 | 2/2007 |
| EP | 1 944 301 A1 | 7/2008 |
| EP | 2 005 941 A2 | 12/2008 |
| FR | 803201 | 9/1936 |
| FR | 803619 | 10/1936 |
| FR | 2 244 492 | 4/1975 |
| FR | 2 244 493 | 4/1975 |
| GB | 472489 | 9/1937 |
| GB | 728767 | 4/1955 |
| GB | 1175808 | 12/1969 |
| GB | 1179019 | 1/1970 |
| GB | 2 292 149 A | 2/1996 |
| IE | 902587 A1 | 7/1990 |
| JP | 6-80656 A | 3/1994 |
| JP | 7-41442 A | 2/1995 |
| JP | 7- 61942 A | 3/1995 |
| JP | 7-118241 A | 5/1995 |
| JP | 7-179380 A | 7/1995 |
| JP | 7-233109 A | 9/1995 |
| JP | 7-247289 A | 9/1995 |
| JP | 8-104679 A | 4/1996 |
| JP | 10-287678 A | 10/1998 |
| JP | 2004-511502 A | 4/2001 |
| JP | 2001-131151 A | 5/2001 |
| JP | 2001-139550 A | 5/2001 |
| JP | 2001-335476 A | 12/2001 |
| JP | 2002-249483 A | 9/2002 |
| JP | 2004-203751 A | 7/2004 |
| JP | 2004-307440 A | 11/2004 |
| JP | 2005-532275 A | 10/2005 |
| JP | 2008-503537 A | 2/2008 |
| JP | 2010-530438 A | 9/2010 |
| KR | 10-0707532 B1 | 8/2005 |
| NZ | 556545 A | 3/2009 |
| WO | WO 91/18901 A1 | 12/1991 |
| WO | WO 92/09374 A1 | 6/1992 |
| WO | WO 92/18123 A2 | 10/1992 |
| WO | WO 92/20642 A1 | 11/1992 |
| WO | WO 9220642 A1 * | 11/1992 |
| WO | WO 92/21661 A1 | 12/1992 |
| WO | WO 93/07124 A1 | 4/1993 |
| WO | WO 93/08174 A1 | 4/1993 |
| WO | WO 93/12095 A1 | 6/1993 |
| WO | WO 94/14763 A1 | 7/1994 |
| WO | WO 95/03277 A1 | 2/1995 |
| WO | WO 95/23150 A1 | 8/1995 |
| WO | WO 96/15128 A2 | 5/1996 |
| WO | WO 96/31206 A2 | 10/1996 |
| WO | WO 97/10221 A1 | 3/1997 |
| WO | WO 97/15308 A1 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 A1 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 A1 | 11/1998 |
| WO | WO 98/51308 A1 | 11/1998 |
| WO | WO 98/55124 A1 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 99/47170 A1 | 9/1999 |
| WO | WO 00/10607 A1 | 3/2000 |
| WO | WO 00/13671 A1 | 3/2000 |
| WO | WO 00/17184 A1 | 3/2000 |
| WO | WO 00/23075 A1 | 4/2000 |
| WO | WO 00/35865 A2 | 6/2000 |
| WO | WO 00/44362 A2 | 8/2000 |
| WO | WO 00/55168 A1 | 9/2000 |
| WO | WO 00/64888 A1 | 11/2000 |
| WO | WO 01/00554 A2 | 1/2001 |
| WO | WO 01/60775 A1 | 8/2001 |
| WO | WO 01/82916 A2 | 11/2001 |
| WO | WO 01/83456 A1 | 11/2001 |
| WO | WO 01/90051 A1 | 11/2001 |
| WO | WO 02/32377 A2 | 4/2002 |
| WO | WO 02/44189 A1 | 6/2002 |
| WO | WO 02/074307 A1 | 9/2002 |
| WO | WO 02/087556 A2 | 11/2002 |
| WO | WO 02/096426 A1 | 12/2002 |
| WO | WO 03/007959 A1 | 1/2003 |
| WO | WO 03/016292 A1 | 2/2003 |
| WO | WO 03/018008 A1 | 3/2003 |
| WO | WO 03/040256 A1 | 5/2003 |
| WO | WO 03/040257 A1 | 5/2003 |
| WO | WO 03/070236 A2 | 8/2003 |
| WO | WO 03/076427 A1 | 9/2003 |
| WO | WO 03/099274 A1 | 12/2003 |
| WO | WO 03/106435 A1 | 12/2003 |
| WO | WO 2004/017920 A2 | 3/2004 |
| WO | WO 2004/019933 A1 | 3/2004 |
| WO | WO 2004/032846 A2 | 4/2004 |
| WO | WO 2004/037176 A2 | 5/2004 |
| WO | WO 2004/039795 A2 | 5/2004 |
| WO | WO 2004/047755 A2 | 6/2004 |
| WO | WO 2004/054985 A1 | 7/2004 |
| WO | WO 2004/056355 A1 | 7/2004 |
| WO | WO 2004/058717 A1 | 7/2004 |
| WO | WO 2004/065392 A1 | 8/2004 |
| WO | WO 2004/072042 A2 | 8/2004 |
| WO | WO 2004/092196 A2 | 10/2004 |
| WO | WO 2004/094452 A2 | 11/2004 |
| WO | WO 2004/108139 A2 | 12/2004 |
| WO | WO 2004/112710 A2 | 12/2004 |
| WO | WO 2005/042712 A2 | 5/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005/115993 A1 | 12/2005 |
| WO | WO 2006/000420 A1 | 1/2006 |
| WO | WO 2006/012577 A2 | 2/2006 |
| WO | WO 2006/071095 A1 | 7/2006 |
| WO | WO 2006/105081 A2 | 10/2006 |
| WO | WO 2007016525 A2 * | 2/2007 |
| WO | WO 2007/071055 A1 | 6/2007 |
| WO | WO 2008/092231 A1 | 8/2008 |
| WO | WO 2008/152471 A1 | 12/2008 |
| WO | WO 2008/157575 A1 | 12/2008 |
| WO | WO 2010/015520 A1 | 2/2010 |
| WO | WO 2010/049466 A1 | 5/2010 |
| WO | WO 2010/100178 A1 | 9/2010 |
| WO | WO 2010/127099 A2 | 11/2010 |
| WO | WO 2011/135376 A1 | 11/2011 |
| WO | WO 2012/112531 A1 | 8/2012 |
| WO | WO 2014/062428 A1 | 4/2014 |
| WO | WO 2015/025226 A2 | 2/2015 |
| WO | WO 2015/025228 A2 | 2/2015 |

OTHER PUBLICATIONS

Abdul-Rahman et al., "Dinuclear molybdenum complexes derived from diphenols: electrochemical interactions and reduced species" *Polyhedron* 16(24):4353-4362 (1997).

Acton, S. et al., "Identification of Scavenger Receptor SR-BI as a High Density Lipoprotein Receptor" *Science* 271:518-520 (1996).

Asztalos, "High-Density Lipoprotein Metabolism and Progression of Atherosclerosis: New Insights from the Hdl Atherosclerosis Treatment Study" *Curr. Opin. Cardiol.* 19:385-391 (2004).

Baba et al., "Continuous intake of polyphenolic compounds containing cocoa powder reduces LDL oxidative susceptibility and has beneficial effects on plasma HDL-cholesterol concentrations in humans" *Am. J. Clin. Nutr.* 85:709-717 (2007).

Badimon et al., "Role of High Density Lipoproteins in the Regression of Atherosclerosis" *Circulation* 86(Suppl. III):86-94 (1992).

Barrans et al., "Pre-β HDL: Structure and Metabolism" *Biochim. Biophys. Acta* 1300:73-85 (1996).

(56) References Cited

OTHER PUBLICATIONS

Barter et al., "Antiinflammatory Properties of HDL" *Circ. Res.* 95:764-772 (2004).
Barter et al., "High Density Lipoproteins and Coronary Heart Disease" *Atherosclerosis* 121:1-12 (1996).
Bayly et al., "Electronic and magnetic metal-metal interactions in dinuclear oxomolybdenum(V) complexes across bis-phenolate bridging ligands with different spacers between the phenolate termini: ligand-centered vs. metal-centered redox activity" *J. Chem. Soc., Dalton Transactions* 9:1401-1414 (2001).
Bertele et al., "Platelet Thromboxane Synthetase Inhibitors with Low Doses of Aspirin: Possible Resolution of the 'Aspirin Dilemma'" *Science* 220:517-519 (1983).
Beugelmans et al., "One-pot Synthesis of 1-Oxo-1,2-Dihydroisoquinolines (Isocarbostyrils) via $S_{RN}1$ (Ar) Reactions" *Synthesis* 9:729-731 (1981).
Bhilare et al., "Ionic-Liquid-Influenced Expeditious and Stereoselective Synthesis of Olefins" *Synthetic Communications* 37(18):3111-3117 (2007).
Bisagni et al., "A Convenient Way to Dibenzo[c,h]-1,5-Naphthyridines (11-Aza-Benzo[c]phenanthridines)" *Tetrahedron* 52:10427-10440 (1996).
Bisgaier et al., "A Novel Compound that Elevates High Density Lipoprotein and Activates the Peroxisome Proliferator Activated Receptor" *J. Lipid Res.* 39:17-30 (1998).
Boyce et al., "The Acylation and Alkylation of o-Tolunitrile. A New Route to 3-Substituted Isocarbostyrils" *J. Org. Chem.* 31:3807-3809 (1966).
Bradsher et al., "A New Isoquinoline Synthesis Via ORTHO-Substituted Benzylamines" *Tetrahedron Lett.* 31:3149-3150 (1972).
Bradsher et al., "α-Acyl-o-Tolunitriles as Intermediates in the Preparation of 3-Substituted Isoquinolines and 1-Amino-2-benzopyrylium Derivatives" *J. Org. Chem.* 43:3817-3820 (1978).
Buhle et al., "Trivalent Carbon. II. Unsymmetrical Hexaaryldimethylperoxides" *J. Am. Chem. Soc.* 65:584-586 (1943).
CAPLUS Accession No. 1991:449453, Liu et al. "Synthesis of 2-aryl-9-bromo-4-oxo-4H-pyrano[3,2-c] quinolines" [online]. Retrieved from STN on Jan. 31, 2011. Also published in: *Youji Huaxue* 11(2):191-195.
CAPLUS Accession No. 2003:554477, Qin et al., "Synthesis and fungicidal activity of novel diazaflavanones" [online]. Retrieved from STN on Jan. 31, 2011. Also published in. *Nongyaoxue Xuebao* 4(4):28-32 (2002).
CAPLUS Accession No. 2004:11346, Hu et al., "Synthesis and fungicidal activity of flavanone derivatives containing isopentenyl group" [online]. Retrieved from STN on Jan. 31, 2011. Also published in: *Yingyong Huaxue* 20(12):1161-1165 (2003).
CAPLUS Accession No. 2005:46491, Qin et al., "Synthesis and fungicidal activity of 5,7-dihydroxyldiazinflavanones" [online]. Retrieved from STN on Jan. 31, 2011. Also published in: *Huazhong Shifan Daxue Xuebao Zirankexueban* 38(3):323-325 (2004).
Chakrabarty et al., "Induction of apoptosis in human cancer cell lines by diospyrin, a plant-derived bisnaphthoquinonoid, and its synthetic derivatives" *Cancer Letters* 188(1-2):85-93 (2002).
Chartier et al., "Synthese de diazaflavones" *Bull. Soc. Chim. Fr.* 11-12(Pt. 2):1916-1918 (1976).
Cherubini et al., "Role of Antioxidants in Atherosclerosis: Epidemiological and Clinical Update" *Curr. Pharm. Des.* 11:2017-2032 (2005).
Cho et al., "Molecular Modeling of 3-Arylisoquinoline Antitumor Agents Active Against A-549. A Comparative Molecular Field Analysis Study" *Bioorg. Med. Chem.* 10:2953-2961 (2002).
Cho et al., "Synthesis and Antitumor Activity of 3-Arylisoquinoline Derivatives" *Arch. Pharm. Res.* 20:264-268 (1997).
Cho et al., "Synthesis and Biological Evaluation of 3-Arylisoquinolines As Antitumor Agents" *Bioorg. Med. Chem. Lett.* 8:41-46 (1998).
Cho et al., "Synthesis and Comparative Molecular Field Analysis (CoMFA) of Antitumor 3-Arylisoquinoline Derivatives" *Bioorg. Med. Chem.* 6(12):2449-2458 (1998).
Chyu et al., "Differential Effects of Green Tea-Derived Catechin on Developing Versus Established Atherosclerosis in Apolipoprotein E-Null Mice" *Circulation* 109:2448-2453 (2004).
Clarkson et al., "Inhibition of Postmenopausal Atherosclerosis Progression: A Comparison of the Effects of Conjugated Equine Estrogens and Soy Phytoestrogens" *J. Clin. Endocrinol. Metab.* 86(1):41-47 (2001).
Clauson-Kaas et al., "Reactions of 3,4-dihydor-2H-pyrrido[3,2-b]-1,4-oxazines" *Acta Chemica Scandinavica* 25(8):3135-3143 (1971). Retrieved from STN, file HCAPLUS, Accession No. 1972:34186 (Abstract).
Connolly et al., "Synthesis of quinazolinones and quinazolines" *Tetrahedron* 61(43):10153-10202 (2005).
Cooper et al., "Wine polyphenols and promotion of cardiac health" *Nutr. Res. Rev.* 17:111-129 (2004).
Cramer et al., "New Syntheses of Aryl Fluorides and Aryl Fluorosulfonates from Oxyflourides of Sulfur" *J. Org. Chem.* 26:4164-4165 (1961).
Dai et al., "Synthesis of 3,4-Disubstituted Isoquinolines via Palladium-Catalyzed Cross-Coupling of 2-(1-alkynyl)benzaldimines and Organic Halides" *J. Org. Chem.* 68:920-928 (2003).
Dai et al., "Synthesis of 3-Substituted 4-Aroylisoquinolines via Pd-Catalyzed Carbonylative Cyclization of 2-(1-Alkynyl)benzaldimines" *J. Org. Chem.* 67:7042-7047 (2002).
Dansky et al., "High-Density Lipoprotein and Plaque Regression. The Good Cholesterol Gets Even Better" *Circulation* 100:1762-1763 (1999).
Decossin et al., "Subclasses of LpA-I in Coronary Artery Disease: Distribution and Cholesterol Efflux Ability" *Eur. J. Clin. Invest.* 27:299-307 (1997).
Devitt et al., "Synthesis of Heterocyclic-Substituted Chromones and Chalcones" *J. Org. Chem.* 26:4941-4944 (1961).
Edwards et al., "Inhibition of myeloperoxidase release from rat polymorphonuclear leukocytes by a series of azachalcone derivatives" *J. Med. Chem.* 37(25):4357-4362 (1994).
Eiden et al., "1,2-Bisbenzopyranyl-ethene" *Archiv. der Pharmazie* 313(2):120-128 (1980) (German).
Esterbauer et al., "Continuous Monitoring of In Vitro Oxidation of Human Low Density Lipoprotein" *Free Rad. Res. Comms.* 6:67-75 (1989).
Ferreira et al., "Diversity of Structure and Function in Oligomeric Flavanoids" *Tetrahedron* 48:1743-1803 (1992).
Fielding et al., "Molecular Physiology of Reverse Cholesterol Transport" *J. Lipid Res.* 36:211-228 (1995).
Fieser, L.F., "The potentials of some unstable oxidation-reduction systems" *J. Am. Chem. Soc.* 52:4915-4940 (1930).
Fisher Center for Alzheimer's Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from the Internet: http://www.alzinfo.org/newsarticle/templates/archivenewstemplate.asp?articleid=156&zoneid=7 on Jul. 28, 2010.
Flammang et al., "2,3-Benzodiazepines: 2-Aminoisoquinolinones From Ring Contraction of 1-oxo-2,3-Benzodiazepines" *C R Acad. Sci. Paris, Series C* 290:361-363 (1980) (French).
Fokialakis et al., "A New Class of Phytoestrogens: Evaluation of the Estrogenic Activity of Deoxybenzoins" *Chem. Biol.* 11:397-406 (2004).
Gaziano et al., "Relation Between Systemic Hypertension and Blood Lipids on the Risk of Myocardial Infarction" *Am. J. Cardiol.* 84(7):768-773 (1999).
Gerritsen et al., "Flavenoids inhibit cytokine-induced endothelial cell adhesion protein gene expression" *Am. J. Pathol.* 147(2):278-292 (1995).
Gidez et al., "Separation and Quantitation of Subclasses of Human Plasma High Density Lipoproteins by a Simple Precipitation Procedure" *J. Lipid Res.* 23:1206-1223 (1982).
Gordon et al., "High Density Lipoprotein As a Protective Factor Against Coronary Heart Disease" *Am. J. Med.* 62(5):707-714 (1977).

(56) References Cited

OTHER PUBLICATIONS

Grundy et al., "Definition of Metabolic Syndrome. Report of the National Heart, Lung and Blood Institute/American Heart Association Conference on Scientific Issues Related to Definition" *Circulation* 109:433-438 (2004).

Gugler et al., "Disposition of Quercetin in Man after Single Oral and Intravenous Doses" *Eur. J. Clin. Pharmacol.* 9:229-234 (1975).

Guillory, J.K., "Generation of Polymorphs, Hydrates, Solvates, and Amorphous Solids" Brittain, Harry G. (ed.) *Polymorphism in Pharmaceutical Solids*. vol. 95. Marcel Dekker, Inc., New York; pp. 202-208 (1999).

Hakamata et al., "Differential effects of an acyl-coenzyme A: cholesterol acyltransferase inhibitor on HDL-induced cholesterol efflux from rat macrophage foam cells" *FEBS Letters* 363:29-32 (1995).

Haneke, "trans-Resveratrol, [501-36-0], Review of Toxicological Literature" Nat. Inst. Environ. Health Sciences Contract No. N01-ES-65402 (Mar. 2002).

Hazra et al., "New diospyrin derivatives with improved tumour inhibitory activity towards Ehrlich ascites carcinoma" *Medical Science Research* 22(5).351-353 (1994).

Hazra et al., "Synthesis of an antitumor derivative of diospyrin" *IRCS Medical Science* 14(1):35-36 (1986).

Heeg et al., "Plasma Levels of Probucol in Man after Single and Repeated Oral Doses" *La Nouvelle Presse Medicale* 9:2990-2994 (1980).

Hemingway et al., "A gas-liquid chromatographic examination of stilbene derivatives" *J. Chromatog.* 50(3):391-399 (1970).

Hertog et al., "Dietary Antioxidant Flavonoids and Risk of Coronary Heart Disease: the Zutphen Elderly Study" *Lancet* 342:1007-1011 (1993).

Hidaka et al., "Affinity Purification of the Hepatic High-Density Lipoprotein Receptor Identifies Two Acidic Glycoproteins and Enables Further Characterization of Their Binding Properties" *Biochem. J.* 284:161-167 (1992).

Hirano et al., "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity" *Arterioscler. Thromb. Vasc. Biol.* 17:1053-1059 (1997).

Hisano et al., "Studies on Organosulfur Compounds. XII. Syntheses and Pharmacological Activities of 2-Heterocyclic Substituted 4(3H)-Quinazolinones" *Chem. Pharm. Bull.* 23(9):1910-1916 (1975).

Huang et al., "Synthesis of Isoquinolines by Palladium-Catalyzed Cyclization, Followed by a Heck Reaction" *Tetrahedron Lett.* 43:3557-3560 (2002).

Hwang et al., "Syntergistic inhibition of LDL oxidation by phytoestrogens and ascorbic acid" *Free Radical Biology and Medicine* 29(1).79-89 (Jul. 1, 2000).

International Search Report and Written Opinion issued in International Application No. PCT/CA2004/001818; Date of Mailing: Feb. 28, 2005.

International Search Report and Written Opinion issued in International Application No. PCT/CA2007/000146; Date of Mailing: Oct. 29, 2007.

International Search Report and Written Opinion issued in International Application No. PCT/IB2010/000159; Date of Mailing: Aug. 5, 2010.

International Search Report and Written Opinion issued in International Application No. PCT/IB2010/000826; Date of Mailing: Oct. 12, 2010.

International Search Report and Written Opinion issued in International Application No. PCT/US2005/037719; Date of Mailing: Mar. 9, 2007.

International Search Report and Written Opinion issued in International Application No. PCT/US2005/038048; Date of Mailing: Mar. 7, 2007.

International Search Report and Written Opinion issued in International Application No. PCT/US2006/029827; Date of Mailing: Apr. 16, 2007.

International Search Report and Written Opinion issued in International Application No. PCT/US2009/048457; Date of Mailing: Oct. 16, 2009.

International Search Report and Written Opinion issued in International Application No. PCT/US2010/031870; Date of Mailing: Jul. 1, 2010.

Ishibashi et al., "Hypercholesterolemia in Low Density Lipoprotein Receptor Knockout Mice and its Reversal by Adenovirus-Mediated Gene Delivery" *J. Clin. Invest.* 92:883-893 (1993).

Ishibashi et al., "Massive Xanthomatosis and Atherosclerosis in Cholesterol-Fed Low Density Lipoprotein Receptor-Negative Mice" *J. Clin. Invest.* 93:1885-1893 (1994).

Japanese Office Action issued in Japanese Patent Application No. 2008-524272, mailed Jul. 24, 2012, with English translation.

Jayatilake et al., "Kinase Inhibitors From *Polygonum cuspidatum*" *J. Nat. Prod.* 56:1805-1810 (1993).

Jensen et al., "Serum Lipids and Anthropometric Factors Related to the Prevalence of Intermittent Claudication" *Eur. J. Vasc. Endovasc. Surg.* 30:582-587 (2005).

Jeong et al., "Hypocholesterolemic activity of hesperetin derivatives" *Bioorg. Med. Chem. Lett.* 13:2663-2665 (2003).

Jin et al., "Antiplatelet and antithrombotic activities of CP201, a newly synthesized 1,4-naphthoquinone derivative" *Vasc. Pharmacol.* 41(1):35-41 (2004).

Kalusa et al., "An efficient synthesis of 2,3-diaryl (3H)-quinazolin-4-ones via imidoyl chlorides" *Tetrahedron Letters* 49(41):5840-5842 (2008).

Kawamatsu et al., "2-Amino-4-Phenylthiazole Derivatives As Anti-Atherogenic Agents" *Eur. J. Med. Chem.—Chimica Therapeutica* 16(4):355-362 (1981).

Kilbourne et al., "Involvement of Early Growth Response Factor Egr-1 in Apolipoprotein Al Gene Transcription" *J. Biol. Chem.* 270:7004-7010 (1995).

Kim et al., "Hypothetical Drug Binding Receptor Site Analysis Using CoMFA Method for 3-Arylisoquinolines Active Against SK-OV-3 Tumor Cell Line" *Yakhak Hoechi* 46(4):219-225 (2002).

Koudinov et al., "Alzheimer's amyloid beta and lipid metabolism: a missing link?" *FASEB J.* 12:1097-1099 (1998).

Kublak et al., "The preparation of the aza-spirobicyclic system of discorhabdin C via an intramolecular phenolate alkylation" *Tetrahedron Lett.* 31(27):3845-3848 (1990).

Kulkarni, K.R. et al.,"Quantification of $HDL_2$ and $HDL_3$ Cholesterol by the Vertical Auto Profile-II (VAP-II) Methodology" *J. Lipid Res.* 38:2353-2364 (1997).

Kurata et al., "A Candidate High Density Lipoprotein (HDL) Receptor, $HB_2$, with Possible Multiple Functions Shows Sequence Homology with Adhesion Molecules" *J. Atheroscler. Thromb.* 4:112-117 (1998).

Kurowska et al., "Essential Amino Acids in Relation to Hypercholesterolemia Induced in Rabbits by Dietary Casein" *J. Nutr.* 120:831-836 (1990).

Kuzuya et al., "Probucol Prevents Oxidative Injury to Endothelial Cells" *J. Lipid Res.* 32:197-204 (1991).

Laarhoven et al., "Syntheses, infrared spectra and molecular refractions of some sterically hindered p,p'- dimethoxystilbenes. Influence of non-planarity in styrene and stilbene derivatives IV" *Recueil des Travaux Chimiques des Pays-Bas* 80:775-791 (1961).

Lagrost et al., "Opposite Effects of Cholesteryl Ester Transfer Protein and Phospholipid Transfer Protein on the Size Distribution of Plasma High Density Lipoproteins" *J. Biol. Chem.* 271:19058-19065 (1996).

Lamon-Fava, "Genistein activates apolipoprotein A-I gene expression in the human hepatoma cell line Hep G2" *J. Nutrition* 130:2489-2492 (2000).

Landshulz et al., "Regulation of Scavenger Receptor, Class B, Type I, a High Density Lipoprotein Receptor, in Liver and Steroidogenic Tissues of the Rat" *J. Clin. Invest.* 98:984-995 (1996).

Letan, "The Relation of Structure to Antioxidant Activity of Quercetin and some of Its Derivatives. I. Primary Activity" *J. Food Sci.* 13(4):518-523 (1966).

(56) References Cited

OTHER PUBLICATIONS

Lin et al., "Chemoprevention of Cancer and Cardiovascular Disease by Resveratrol" *Proc. Natl. Sci. Counc. ROC* (B) 23:99-106 (1999).
Lin et al., "Potential bioreductive alkylating agents. 7. Antitumor effects of phenyl-substituted 2-chloromethyl-3-phenyl-1,4-naphthoquinones" *J. Med. Chem.* 19(11):1336-1338 (1976).
Lin et al., "Solvent Effects on Aza-Anionic Cycloaromatization of 2-(2-Substituted-Ethynyl)Benzonitriles" *J. Chinese Chem. Soc.* 48:211-214 (2001).
Lin et al., "The Role of Absorption, Distribution, Metabolism, Excretion and Toxicity in Drug Recovery" *Curr. Top. Med. Chem.* 3:1125-1154 (2003).
Linnell et al. "Isomers of stilbestrol. II." *Q. J. Pharm. Pharmacol.* 15:384-388 (1942).
Lopez et al., "The Synthesis of Substituted 2-Aryl-4(3H)-quinazolinones using NaHSO$_3$/DMA. Steric Effect Upon the Cyclisation-Dehydrogenation Step" *J. Chem. Research (S)*, pp. 258-259 (2000).
Maher et al.,"Lipoprotein (a) and coronary heart disease" *Curr. Opin. Lipidol.* 6:229-235 (1995).
Mahto et al., "Synthesis of 3-Aryl-7-Hydroxy Isochromenes" *Asian J. Chem.* 11(2):431-435 (1999).
Manach et al., "Polyphenols and prevention of cardiovascular diseases" *Curr. Opin. Lipidol.* 16:77-84 (2005).
Marks, F., "Epidermal Growth Control Mechanisms, Hyperplasia, and Tumor Promotion in the Skin" *Cancer Res.* 36:2636-2343 (1976).
Martin et al., "Modified Flavinoids As Strong Photoprotecting UV-Absorbers and Antioxidants" in *Strategies for Safe Food*. Eklund, T. et al.(Eds.), vol. 1, pp. 288-291 (2003).
McKee et al., "Some Basically Substituted Quinazolines" *J. Am. Client. Soc.* 68(10):1902-1903 (1946).
Meckes et al., "The effects of chrysin and pinostrobin, 2 flavonoids isolated from *Teloxys graveolens* leaves, on isolated guinea-pig ileum" *Phytomedicine* 5(6):459-463 (1998).
Melani et al., "Tricyclic heterocyclic systems: pyrazolo[5',4':4,5]- and pyrazolo-[3',4':4,5]pyrano[2,3-B]pyridine derivatives" *J. Heterocyclic Chem.* 25:1367-1371 (1988).
Middleton et al., "Quercetin inhibits lipopolysaccharide-induced expression of endothelial cell intracellular adhesion molecule-1" *Int. Arch. Allergy Immunol.* 107:435-436 (1995).
Moffett, "Azacoumarins" *J. Org. Chem.* 35(11):3596-3600 (1970).
Mondal et al "Two-Stage Chemical Oncogenesis in Cultures of C3H/10T1/2 Cells" *Cancer Res.* 36:2254-2260 (1976).
Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990).
Nissen et al., "Effect of Recombinant ApoA-I Milano on Coronary Atherosclerosis in Patients with Acute Coronary Syndroms: A Randomized Controlled Trial" *JAMA* 290(17):2292-2300 (2003).
Nourooz-Zadeh, "Ferrous Ion Oxidation in Presence of Xylenol Orange for Detection of Lipid Hydroperoxides in Plasma" *Methods Enzymol.* 300:58-62 (1999).
Ohtomo et al., "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).
Ordovas, J.M., "Gene-diet interaction and plasma lipid responses to dietary intervention" *Biochem. Soc. Trans.* 30(2):68-73 (2002).
Parra et al., "A Case-Control Study of Lipoprotein Particles in Two Populations at Contrasting Risk for Coronary Heart Disease" *Arterioscler. Thromb.* 12:701-707 (1992).
Patani et al., "Bioisosterism: A Rational Approach in Drug Design" *Chem. Rev.* 96(8):3147-3176 (1996).
Pearson et al., "The ortho Bromination of Phenols" *J. Org. Chem.* 32:2358-2360 (1967).

Pettit et al., "Antineoplastic Agents. 465. Structural Modification of Resveratrol: Sodium Resverastatin Phosphate" *J. Med. Chem.* 45:2534-2542 (2002).
Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).
Quinones et al., "The egr-1 gene is induced by DNA-damaging agents and non-genotoxic drugs in both normal and neoplastic human cells" *Life Sciences* 72(26):2975-2992 (2003).
Ragione et al., "Antioxidants induce different phenotypes by a distinct modulation of signal transduction" *FEBS Letters* 523:289-294 (2002).
Ragione et al., "p21$^{CIP}$1 Gene Expression Is Modulated by Egr1: A Novel Regulatory Mechanism Involved in the Resveratrol Antiproliferative Effect" *J. Biol. Chem.* 278:23360-23368 (2003).
Rajakumar et al., "TiCl$_4$, Dioxane—A facile and efficient system for de-O-benzylation, de-O-allylation, and de-O-xylylation of phenolic ethers" *Synthetic Communications* 33(22):3891-3896 (2003).
Raun et al., "Apolipoprotein A-I possesses an anti-obesity effect associated with increase of energy expenditure and upregulation of UCP1 in brown fat" *J. Cell. Mol. Med.* (2010). "Postprint"; 10.1111/j.1582.4934.2010.01045.x.
Rice-Evans, "Flavonoids and Isoflavones: Absorption, Metabolism, and Bioactivity" *Free Radical Biol. Med.* 36:827-828 (2004).
Richtzenhain, H. "Estrogenic stilbene and diphenylethane derivatives. II." *Chemische Berichte* 82:405-407 (1949) (German).
Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland" *J. Biol. Chem.* 271:33545-33549 (1996).
Rimando et al., "Pterostilbene, a New Agonist for the Peroxisome Proliferator-Activated Receptor α-Isoform, Lowers Plasma Lipoproteins and Cholesterol in Hypocholesterolemic Hamsters" *Journal of Agricultural and Food Chemistry* 53(9):3403-3407 (2005).
Rodriguez et al., "Novel Effects of the Acyl-Coenzyme A: Cholesterol Acyltransferase Inhibitor 58-035 on Foam Cell Development in Primary Human Monocyte-Derived Macrophages" *Arterioscler. Thromb. Vasc. Biol.* 19:2199-2206 (1999).
Rose et al., "Oxygen Heterocycles. XIII. From 3-Arylisocoumarins to 3-Arylisoquinolines and 4-Aryl-5H-2,3- Benzodiazepines" *J. Chem. Soc. [Section] C: Organic* 17:2205-2208 (1968).
Rubin et al., "Expression of Human Apolipoprotein A-I in Transgenic Mice Results in Reduced Plasma Levels of Murine Apolipoprotein A-I and the Appearance of Two New High Density Lipoprotein Size Subclasses" *Proc. Natl. Acad. Sci. USA* 88:434-438 (1991).
Rubin et al., "Inhibition of Early Atherogenesis in Transgenic Mice by Human Apolipoprotein AI" *Nature* 353:265-267 (1991).
Rubins et al., "Reduction in Stroke with Gemfibrozil in Men with Coronary Heart Disease and Low HDL Cholesterol" *Circulation* 103:2828-2833 (2001).
Sarkhel et al., "3-Arylisocoumarin: Synthesis of 3-(4-Methoxyphenyl)Isocoumarin" *J. Indian Chem. Soc.* 53:915-916 (1976).
Schiess et al., "Thermolytic Ring Opening of Acyloxybenzocyclobutenes: An Efficient Route to 3-Substituted Isoquinolines" *Tetrahedron Lett.* 26:3959-3962 (1985).
Schmutz et al., "Synthese von basisch substituierten Chromonen" *Helv. Chim. Acta* 36:620-626 (1953) (German).
Schork, N.J., "Genetics of Complex Disease. Approaches, Problems, and Solutions" *Am. J. Respir. Crit. Care Med.* 156(4):S103-109 (Oct. 1997).
Schultz et al., "Role of stilbenes in the natural durability of wood: fungicidal structure-activity relationships" *Phytochemistry* 29(5):1501-1507 (1990).
Shah et al., "Effects of Recombinant Apolipoprotein A-I$_{Milano}$ on Aortic Atherosclerosis in Apolipoprotein E-Deficient Mice" *Circulation* 97(8):780-785 (1998).
Shapiro et al., "Micro Assay for 3-Hydroxy-3-Methylglutaryl-CoA Reductase in Rat Liver and L-Cell Fibroblasts" *Biochim. Biophys. Acta* 370:369-377 (1974).

(56) References Cited

OTHER PUBLICATIONS

Sharrett et al., "Associations of Lipoprotein Cholesterols, Apolipoproteins A-I and B, and Triglycerides with Carotid Atherosclerosis and Coronary Heart Disease. The Atherosclerosis Risk in Communities (ARIC) Study" *Arterioscler. Thromb.* 14:1098-1104 (1994).
Sieber, R.H., "Reactions of chloroacetaldehyde with aromatic hydrocarbons, phenols, and phenol ethers" *Justus Liebigs Annalen der Chemie* 730:31-46 (1969) (German).
Sliwa et al., "Tautomerie entre structures α-aleoxy-enaminocetone et β-ceto iminoether presentee par les piperidines resultant de la semihydrogenation d'alcoxy-2-acyl-3 pyridines" *J. Heterocyclic Chem.* 16:939-944 (1979) (French).
Slowing et al. "Anti-Inflammatory Activity of Leaf Extracts of *Eugenia jambos* in Rats" *J. Ethnopharmacol.* 43:9-11 (1994).
Smyth et al.,"Non-amine based analogues of lavendustin A as protein-tyrosine kinase inhibitors" *J. Med. Chem.* 36(20):3010-3014 (1993).
Sun et al., "In Vitro Testing of Drug Absorption for Drug 'Developability' Assessment: Forming an Interface Between in Vitro Preclinical Data and Clinical Outcome" *Curr. Opin. Drug Discov. Devel.* 7:75-85 (2004).
Suryadevara et al., "Association of Abnormal Serum Lipids in Elderly Persons with Artherosclerotic Vascular Disease and Demetia, Artheroslerotic Vascular Disease Without Demetia, Demetia Without Artherosclerotic Vascular Disease, and No Dementia or Artherosclerotic Vascular Disease" *J. Gerontol. Med. Sci.* 58A(9):859-861 (2003).
Tait et al., "Synthesis and Free Radical Scavenging Activity of 4-(2H-1,2,4-Benzothiadiazine-1,1-dioxide-3-yl)-2,6-bis(1,1-dimethylethyl)phenols" *Tetrahedron* 52(38):12587-12596 (1996).
Talbert, "Current Recommendations for the Treatment of Dyslipidemia" *Pharm. Ther.* 29:104-112 (2004).
Tanne et al., "High-Density Lipoprotein Cholesterol and Risk of Ischemic Stroke Mortaility" *Stroke* 28:83-87 (1997).
Tardif et al., "Probucol and Multivitamins in the Prevention of Restenosis After Coronary Angioplasty" *N. Engl. J. Med.* 337:365-367 (1997).
Theriault et al., "Modulation of hepatic lipoprotein synthesis and secretion by taxifolin, a plant flavonoid," *J. Lipid Res.* 41:1969-1979 (2000).
Toth et al., "Therapeutic Interventions Targeted at the Augmentation of Reserve Cholesterol Transport" *Curr. Opin. Cardiol.* 19:374-379 (2004).
Tovar et al., "Pyrylium Salts via Electrophilic Cyclization: Applications for Novel 3-Arylisoquinoline Syntheses" *J. Org. Chem.* 64:6499-6504 (1999).
Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)" *Biochem. Pharmacol.* 58:1869-1880 (1999).
Utermann, "The Mysteries of Lipoprotein(a)" *Science* 246:904-910 (1989).
Van Der Goot et al., "The Growth-Inhibitory Action of Some 1-Aminoisoquinolines and Related Compounds on Mycoplasma Gallisepticum" *Eur. J. Med. Chem.* 10:603-606 (1975).
Varin et al., "Enzymatic Assay for Flavonoid Sulfotransferase" *Anal. Biochem.* 161:176-180 (1987).
Vippagunta et al., "Crystalline solids" *Adv. Drug Delivery Rev.* 48:3-26 (2001).
Walle, "Absorption and Metabolism of Flavonoids" *Free Radical Biol. Med.* 36(7):829-837 (2004).
Webster Ninth New Collegiate Dictionary, Definition of 'Prevent', 1 page (2000).
Wei et al., "Total Cholesterol and High Density Lipoprotein Cholesterol as Important Predictors of Erectile Dysfunction" *Am. J. Epidemiol.* 140(10):930-937 (1994).
Welsh et al., "Dyslipidemia in Diabetic Patients" *Prospectives in Cardiology*, Aug. 2002, pp. 40-48.
Wölle et al., "Selective inhibition of tumor necrosis factor-induced vascular cell adhesion molecule-1 gene expression by a novel flavonoid: lack of effect on transcription factor NF-kappa-B" *Arterioscler. Thromb. Vasc. Biol.* 16(12):1501-1508 (1996).
Wurm, "1,4-Naphthoquinones, XXI: 2-(3,5 Di-tert-butyl-4-hydroxyphenyl)-1,4-naphtoqu nones as 5- lipozxygenase inhibitors" *Archie. der Pharmazie* 324(8):491-495 (1991).
Wurm et al., "1,4-Naphthoquinones, XXVI: Phenyl-1,4-naphthoquinone derivatives with the hydroxylation patterns of bioflavonoids" *Pharmazie* 52(10):739-743 (1997) (German).
Yamakoshi et al., "Isoflavone aglycone-rich extract without soy protein attenuates atherosclerosis development in cholesterol-fed rabbits" *Journal of Nutrition* 130(8):1887-1893 (2000).
Yardley et al., "In vitro activity of diospyrin and derivatives against *Leishmania donovani*, *Trypanosoma cruzi* and *Trypanosoma brucei brucer*" *Phytotherapy Research* 10(7):559-562 (1996).
Yoshioka et al., "Semiempirical Investigation of Stilbene-Linked Diradicals and Magnetic Study of Their Bis(N-tert-butylnitroxide) Variants" *J. Org. Chem.* 59(15):4272-4280 (1994).
Office Action in U.S. Appl. No. 11/255,103: Restriction Requirement, mailed Mar. 26, 2008.
Office Action in U.S. Appl. No. 11/255,103, mailed Sep. 24, 2008.
Office Action in U.S. Appl. No. 11/255,103 mailed Aug. 31, 2009.
Office Action in U.S. Appl. No. 11/255,103, mailed Mar. 31, 2010.
Office Action in U.S. Appl. No. 11/255,103, mailed Nov. 10, 2010.
Office Action in U.S. Appl. No. 11/255,103: Notice of Allowance, mailed Jun. 7, 2011.
Office Action in U.S. Appl. No. 11/255,103: Notice of Allowance, mailed Sep. 15, 2011.
Office Action in U.S. Appl. No. 11/670,238: Restriction Requirement, mailed Mar. 31, 2010.
Office Action in U.S. Appl. No. 11/670,238: Restriction Requirement, mailed Jul. 20, 2010.
Office Action in U.S. Appl. No. 11/670,238, mailed Oct. 7, 2010.
Office Action in U.S. Appl. No. 11/670,238, mailed Apr. 19, 2011.
Office Action in U.S. Appl. No. 11/670,238, mailed Jun. 22, 2011.
Office Action in U.S. Appl. No. 11/670,238: Notice of Allowance, mailed Aug. 3, 2011.
Office Action in U.S. Appl. No. 11/670,238: Notice of Allowance, mailed Sep. 16, 2011.
Office Action in U.S. Appl. No. 11/990,162: Restriction Requirement, mailed Jul. 10, 2009.
Office Action in U.S. Appl. No. 11/990,162, mailed Oct. 14, 2009.
Office Action in U.S. Appl. No. 11/990,162, mailed Apr. 1, 2010.
Office Action in U.S. Appl. No. 11/990,162, mailed Dec. 28, 2010.
Office Action in U.S. Appl. No. 11/990,162, mailed Sep. 26, 2011.
Office Action in U.S. Appl. No. 11/990,162, mailed Mar. 19, 2012.
Office Action in U.S. Appl. No. 12/369,296, mailed Nov. 10, 2011.
Office Action in U.S. Appl. No. 12/369,296, mailed Mar. 13, 2012.
Office Action in U.S. Appl. No. 12/369,296: Notice of Allowance, mailed Apr. 12, 2012.
Office Action in U.S. Appl. No. 12/490,877, mailed Sep. 15, 2011.
Office Action in U.S. Appl. No. 12/490,877: Notice of Allowance, mailed Nov. 25, 2011.
Andersson, "Pharmacology of apolipoprotein A-I" *Curr. Opin. Lipidol.*8:225-228 (1997).
Badimon et al. "Regression of Atherosclerotic Lesions by High Density Lipoprotein Plasma Fraction in the Cholesterol-fed Rabbit" *J. Clin. invest* 85: 1234-1241 (1990).
International Search Report and Written Opinion issued in International Application No. PCT/IB2012/002721; Date of Mailing: Mar. 14, 2013.
Miyazaki, et al. "Intravenous Injection of Rabbit Apolipoprotein A-I Inhibits the Progression of Atherosclerosis in Cholesterol-Fed Rabbits" *Arterioscler, Thromb, Vasc Biol.* 15: 1882-1888 (1995).
Nicholls et al., "Efficacy and Safety of a Novel Oral Inducer of Apolipoprotein A-I Synthesis in Statin-Treated Patients with Stable Coronary Artery Disease" *J. Am. Coll. Cardiol.* 57(9):1111-1119 (2011).
Tall "Plasma High Density Lipoproteins" *J. Clin. Invest.* 86: 379-384 (1990)

(56) References Cited

OTHER PUBLICATIONS

Adamis, "Is diadetic retinopathy an inflammatory disease?" *Br. J. Ophthamol.*, 86:363-365 (2002).
Atreya and Neurath, "Involvement of IL-6 in the Pathogenesis of Inflammatory Bowel Disease and Colon Cander" *Clin. Rev. Allergy Immunol.*, 28:187-195 (2005).
Avicel PH, product information from FMC, downloaded from http://www.fmcbiopolymer.com/Portals/Pharm/Content/Docs.pdf on Aug. 15, 2013 (2 pages).
Baron et al., "The pathogenesis of adoptive murine autoimmure diabetes requires an interaction between α4-integrins and vascular cell adhesion molecule-1" *J. Clin. Invest.*, 93:1700-1708 (1994).
Bauer and Hermann, "Interleukin-6 in clincal medicine" *Ann. Hematol.*, 62:203-210 (1991).
Benson et al., "Topical steroid treatment of allergic thinitis decreases nasal fluid $T_H2$ cytokines, eosinophils, eosinophil cationic protein, and IgE but has no significant effect on IFN-γ, ILβ, TNF-α, or neutrophils" *J. Allergy Clin. Immunol.*, 106:307-312 (2000).
Berliner et al., "Atherosclerosis: Basic Mechanisms. Oxidation, Inflammation and Genetics" *Circulation*, 91:2488-2496 (1995).
Bindu et al., "Friend Turns Foe: Transformation of Anti-Inflammatory HDL to Proinflammatory HDL during Acute-Phase Response" *Cholesterol*, 2011: Article ID 274629 [online] doi:10.1155/2011/274629, 7 pages (2011).
Booth and Bishop, "TGF-β, IL-6, IL-17 and CTGF direct multiple pathologies of chronic cardiac allograft rejection" *Immunotherapy*, 2(4):511-520 (2010). Author manuscript, NIH Public Access, May 1, 2011.
Borgatti et al., "Induction by TNF-α of IL-6 and IL-8 in Cystic Fibrosis Bronchial IB3-1 Epithelial Cells Encapsulated in Alginate Microbeads" *J. Biomed. Biotechnol.*, 2010: Article ID 907964, doi: 10.1155/2010/907964, 11 pages (2010).
Burkly et al., "Protection against adoptive transfer of autoimmune diabetes mediated through very late antigen-4 integrin" *Diabetes*, 43:529-534 (1994).
Cahlin et al., "Experimental Cancer Cachexia: The Role of Host-derived Cytokines Interieukin (IL)-6, IL-12, Interferon-γ, and Tumor Necrosis Factor α Evaluated in Gene Knockout, Tumor-bearing Mice on C57 BI Background and Eicosanoid-dependent Cachexia" *Cancer Res.*, 60:5488-5493 (2000).
Campbell et al, "Essential role for interferon-γ and interleukin-6 in autoimmune insulin-dependent diabetes in NOD/Wehi mice" *J. Clin. Invest.*, 87(2):739-742 (1991).
Campbell et al., "Neurologic disease induced in transgenic mice by cerebral overexpression of interleukin 6" *Proc. Natl. Acad. Sci. USA*; 90(21):10061-10065 (1993).
Choudhary and Ahlawat, "Interleukin-6 and C-Reactive Protein in Pathogenesis of Diabetic Nephropathy" *Iran J. Kidney Dis.*, 2:72-79 (2008).
Chung et al., "Characterization of the Role of IL-6 in the Progression of Prostate Cancer" *The Prostate*, 38(3):199-207 (1999).
Colotta et al., "Cancer-related inflammation, the seventh hallmark of cancer: links to genetic instability" *Carcinogenesis*, 30(7):1073-1081 (2009).
Cordoba-Lanùs et al., "Association of IL-6 Gene Polymorphisms and COPD in a Spanish Population" *Respiratory Medicine*, 102:1805-1811 (2008).
Emilie et al., "Administration of an anti-interleukin-6 monoclonal antibody to patients with acquired immunodeficiency syndrome and lymphoma: effect on lymphoma growth and on B clinical symptoms" *Blood*, 84:2472-2479 (1994).
Exner et al., "Interleukin-6 Promoter Genotype and Restenosis after Femoropopliteal Balloon Angioplasty: Initial Observations" *Radiology* 231:839-844 (2004).
Fattori et al., "Development of Progressive Kidney Damage and Myeloma Kidney in Interleukin-6 Transgenic Mice" *Blood*, 83(9):2570-2579 (1994).
Fisher et al., "Increased post-traumatic survival of neurons in IL-6-knockout mice on a background of EAE susceptibility" *J. Neuroimrnunol.*, 119:1-9 (2001).

Folkman and Shing, "Angiogenesis" *J. Biol. Chem.*, 267(16):10931-10934 (1992).
Frei et al., "Interleukin-6 is elevated in plasma in multiple sclerosis" *J. Neuroimmunol.*, 31:147-153 (1991).
Gabay, "Interleukin-6 and chronic inflammation" *Arthritis Research & Therapy*. 8(Suppl 2):S3 (2006).
Grau, "Implications of cytokines in immunopathology: experimental and clinical data" *Eur Cytokine Netw.*, 1(4):203-210 (1990).
Grossman et al, "Interleukin 6 is expressed in high levels in psoriatic skin and stimulates proliferation of cultured human keratinocytes" *Proc. Natl. Acad. Sci. USA*, 86:6367-6371 (1989).
Hirano et al., "Biological and clinical aspects of interleukin 6" *Immunol. Today*, 11:443-449 (1990).
Hirano et al., "Excessive production of interleukin 6/B cell stimulatory factor-2 in rheumatoid arthritis" *Eur J. Immunol.*, 18(11)1797-1801 (1988).
Hoekzema et al., "Analysis of Interleukin-6 in Endotoxin-Induced Uveitis" *Invest. Ophthalmol. Vis. Sci.*, 32(1):88-95 (1991).
International Search Report and Written Opinion issued in International Application No. PCT/IB2013/003031; Date of Mailing: May 28, 2014.
Ishihara and Hirano, "IL-6 in autoimmune disease and chronic inflammatory proliferative disease" *Cytokine Growth Factor Rev.*, 13(4-5):357-368 (2002).
Jafri et al., "Baseline and on-treatment high-density lipoprotein cholesteroi and the risk of cancer in randomized controlled trials of lipid-altering therapy" *J. Am Coll. Cardiol,*, 55:2846-2854 (2010).
Jilka et al., "Increased osteoclast development after estrogen loss: mediation by interleukin-6" *Science*, 257(5066):88-91 (1992).
Kishimoto and Hirano., "Molecular regulation of B lymphocyte response" *Ann. Rev. Immunol.*, 6:485-512 (1988).
Kishimoto, "The biology of interleukin-6" *Blood*, 74:1-10 (1989).
Klein et al., "Murine anti-interleukin-6 monoclonal antibody therapy for a patient with plasma cell leukemia" *Blood*, 78:1198-1204 (1991).
Koch et al, "Angiogenesis mediated by soluble forms of E-selectin and vascular cell adhesion molecule-1" *Nature*, 376:517-519 (1995).
Koch et al., "Immunolocalization of endothelial and leukocyte adhesion molecules in human rheumatoid and osteoarthritic synovial tissues" *Lab. Invest.*, 64:313-322 (1991).
Landi et al., "HDL-cholesterol and physical performance: results from the ageing and longevity study in the sirente geographic area (ilSirente Study)" *Age and Ageing*, 36(5):514-520 (2007).
Leszczynska and Mesquida, "IL-6 Receptor Antagonist: Tocilizumab" in *Advances in the Treatment of Noninfectious Uveitis with Biologics: Anti-TNF and Beyond*. Marina Mesquida (Ed.), OMICS Group eBooks, Foster City, CA, 2014; 9 pages [online]. www. esciencecentral.org/ebooks.
McGrowder et al., "The role of high density lipoproteins in reducing the risk of vascular diseases, neurogenerative disorders, and cancer" *Cholesterol*, 2011, Article 496925, 9 pages.
Mitchell et al., "Bromination of 4,6-dimethoxyindoles" *Tetrahedron* 68(39):8163-8171 (2012).
Molnàr and Balàzs, "High Circulating IL-6 Level in Graves' Ophthalmopathy" *Autoimmunity*, 25:91-96 (1997).
Morales-Ducret et al.; "α4/β1 integrins (VLA-4) ligands in arthritis. Vascular cell adhesion molecule-1 expression in synovium and on fibroblast like synoviocytes" *J. Immunol.*, 149:1424-1431 (1992).
Musselman et al. "Higher than normal plasma interleukin-6 concentrations in cancer patients with depression: preliminary findings" *Am. J. Psychiatry*, 158:1252-1257 (2001).
Nakagiri et al., "Immunology Mini-review: The Basics of $T_h17$ and Interleukin-6 in Transplantation" *Transplantation Proceedings*, 44:1035-1040 (2012).
Neurath and Finotto, "IL-6 signaling in autoimmunity, chronic inflammation and inflammation associated cancer" *Cytokine & Growth Factor Reviews*, 22:83-89 (2011).
Ohkawara et al., "In situ expression of the cell adhesion molecules in bronchial tissues from asthmatics with air flow limitation; in vivo evidence of VCAM-1/VLA-4 interaction in selective eosinophil infiltration" *Am. J. Respir. Cell Mol. Biol.*, 12:4-12 (1995).

(56) References Cited

OTHER PUBLICATIONS

Orosz et al., "Role of the endothelial adhesion molecule VCAM in murine cardiac ailograft rejection" *Immunol Lett.*, 32(1):7-12 (1992).
Pilewski et al., "Cell adhesion molecules in asthma; homing, activation, and airway remodeling" *Am. J. Respir. Cell Mol. Biol.*, 12:1-3 (1995).
Quintanilla et al, "Interleukin-6 induces Alzheimer-type phosphorylation of tau protein by deregulating the cdk5/p35 pathway" *Exp. Cell Res.*, 295:245-257 (2004).
Rabb et al., "The role of the leukocyte adhesion molecules VLA-4, LFA-1 and Mac-1 in allergic airway responses in the rat" *Am. J. Respir. Care Med.*, 149:1186-1191 (1994).
Reitz et al., "Association of higher levels of high-density lipoprotein cholesterol in elderly individuals and lower risk of late-onset Alzheimer Disease" *Arch Neurol*, 67(12):1491-1497 (2010).
Roodman et al, "Interleukin 6. A potential autocrine/paracrine factor in Paget's disease of bone" *J. Clin. Invest.*, 89:46-52 (1992).
Rose-John et al., "The IL-6/sIL-6R complex as a novel target for therapeutic approaches" *Expert Opin. Ther. Targets*, 11(5):613-624 (2007).
Rose-John and Schooltink, "Cytokines Are a Therapeutic Target for the Prevention of Inflammation-Induced Cancers" *Recent Results in Cancer Research*, 174:57-66 (2007).
Rossi et al., "Optimizing the use of anti-interleukin-6 monoclonal antibody with dexamethasone and 140 mg/m2 of melphalan in multiple myeloma: results of a pilot study including biological aspects" *Bone Marrow Transplantation*, 36:771-779 (2005).
Rubins et al., for the Veterans Affairs High-Density Lipoprotein Cholesterol Intervention Trial Study Group, "Gemfibrozil for the secondary prevention of coronary heart disease in men with low levels of high-density lipoprotein cholesterol" *N. Engl. J. Med.*, 341:410-418 (1999).
Saito et al., "Topical Antigen Provocation Increases the No. Of Immunoreactive IL-4-, IL-5 and IL-6-Posittive Cells in the Nasal Mucosa of Patients with Perennial Allergic Rhinitis" *Int. Arch. Allergy Immunol.*, 114:81-85 (1997).
Scheller et al., "The pro- and anti-inflammatory properties of the cytokine interleukin-6" *Biochim. Biophys. Acta*, 1813:878-888 (2011).
Scheller et al., "Interleukin-6 Trans-Signalling in Chronic Inflammation and Cancer" *Scand. J. Immunol.*, 63:321-329 (2006).
Schultz et al., "Protein composition determines the anti-atherogenic properties of HDL in transgenic mice" *Nature*, 365:762-764 (1993).
Sehgal, "Interleukin 6 in infection and cancer" *Exp. Biol. Med.*, 195:183-191 (1990).
Shoji et al., "Concentration of Soluble Interleukin-6 Receptors in Tears of Allergic Conjunctival Disease in Patients" *Jpn. J. Ophthalmol.*, 51:332-337 (2007).
Singh-Manoux et al., "Low HDL cholesterol is a risk factor for deficit and decline in memory in midlife: the Whitehall II Study" *Atherosclerosis, Thrombosis and Vascular Biology*, 28(8):1556-1562 (2008).
Stampfer, "Cardiovascular disease and Alzheimer's disease: common links" *J Intern Med*, 260(3):211-223 (2006).
Tackey et al., "Rationale for interleukin-6 blockade in systemic lupus" *Lupus*, 13(5):339-343 (2004). Author manuscript, NIH Public Access, Oct. 11, 2007.
Taga et al, "Receptors for B cell stimulatory factor 2. Quantitation, specificity, distribution, and regulation of their expression" *J. Exp. Med.*, 166:967-981 (1987).
Toshitani et al., "Increased Interleukin 6 Production by T Cells Derived from Patients with Atopic Dermatitis" *J. Invest. Dermatol.*, 100:299-304 (1993).
Trikha et al., "Targeted anti-interleukin-6 monoclonal antibody therapy for cancer: a review of the rationale and clinical evidence" *Clin. Cancer Res.*, 9:4653-4665 (2003).
Turner et al., "Interleukin-6 Levels in the Conjuctival Epithelium of Patients with Dry Eye Disease Treated with Cyclosporine Ophthalmic Emulsion" *Cornea*, 19(4):492-496 (2000).

Tuttle, "Linking Metabolism and Immunology: Diabetic Nepnropathy Is an inflammatory Disease" *J. Am, Soc. Nephrol.*, 16:1537-1538 (2005).
Wijdenes et al., "Human recombinant dimeric IL-6 binds to its receptor as detected by anti-IL-6 monoclonal antibodies" *Mol. Immunol.*, 28:1183-1192 (1991).
Yang at al., "Inhibition of insulitis and prevention of diabetes in nonobese diabetic mice by blocking L-selectin and very late antigen 4 adhesion receptors" *Proc. Natl. Acad. Sci. USA*, 90:10494-10498 (1993).
"Gildants", in *Remington. The Science and Practice of Pharmacy*. 21st Edition. David B. Troy (Ed.). Philadelphia, PA: Lippincott Williams & Wilkins, 2006; p. 893.
"RVX 208" R&D Insight Profile in *Drugs* 11(2):207-213 (2011).
Abbott et al., "High density lipoprotein cholesterol, total cholesterol screening, and myocardial infarction" *Arteriosclerosis* 8:207-211 (1988).
Aiello et al. "ABCA1-Deficient Mice. Insights Into the Role of Monocyte Lipid Efflux in HDL Formation and Inflammation" *Arterioscler. Thromb. Vasc. Biol.* 23:972-980 (2003).
Alla et al., "A Reappraisal of the Risks and Benefits of Treating to Target with Cholesterol Lowering Drugs" *Drugs* 73(10):1025-1054 (2013).
Anderson et al. (2010) "The pivotal role of the complement system in aging and age-related macular degeneration: Hypothesis revisited" *Prog. Retin. Eye Res.* 29(2):95-112. NIH Author Manuscript; available in PMC May 2, 2013 (40 pages).
Ansell et al., "The paradox of dysfunctional high-density lipoprotein" *Curr. Opin. Lipidol.* 18:427-434 (2007).
Assmann et al., "The Münster Heart Study (PROCAM). Results of Follow-up at 8 Years" *Eur. Heart J.* 19(A):A2-A11 (1998).
ATBC Cancer Prevention Study Group, "The Alpha-Tocopherol, Beta-Carotene Lung Cancer Prevention Study: Design, Methods, Participant Characteristics, and Compliance," *Elsevier Science Inc.*, AEP 4(1):1-10 (1994).
Avicel® PH-301, Product Specification Bulletin, FMC Corporation [online]; downloaded from http://www.signetchem.com/downloads/datasheets/Fmc-biopolymer/Avicel-Ph-301-Specifications.pdf, on May 13, 2015.
Bailey et al., "RVX-208: A small molecule that increases apolipoprotein A-I and high-density lipoprotein cholesterol in vitro and in vivo" *J. Am. Coll. Cardiol.* 55:2580-2589 (2010).
Bayraktar et al., "The clinical spectrum of catastrophic antiphospholipid syndrome in the absence and presence of lupus" *J. Rhematol.*, 34(2):346-352 (2007).
Beckers et al, "Single nucleotide polymorphisms in inflammation-related genes are associated with venous thromboembolism" *Eur. J. Int. Med.*, 21:289-292 (2010).
Belalcazar et al., "Long-Term Stable Expression of Human Apolipoprotein A-I Mediated by Helper-Dependent Adenovirus Gene Transfer Inhibits Atherosclerosis Progression and Remodels Atherosclerotic Plaques in a Mouse Model of Familial Hypercholesterolemia" *Circulation* 107:2726-2732 (2003).
Berman et al., "Emerging anti-inflammatory drugs for atherosclerosis" *Expert Opin. Emerg. Drugs*, 18:193-205 (2013).
Bjerre et al., "High osteopontin levels predict long-term outcome after STEMI and primary percutaneous coronary intervention" *Eur. J. Prev. Cardiol.* 20:922-929 (2013).
Brewer, Jr. et al., "Human plasma proapoA-I: Isolation and amino-terminal sequence" *Biochem. Biophys. Res. Commun.* 113:626-632 (1983).
Brown et al., "NF-kappaB Directs Dynamic Super Enhancer Formation in Inflammation and Atherogenesis" *Mol. Cell* 56:219-231 (2014). NIH Public Access Author Manuscript, available in PMC Oct. 23, 2015 (24 pages).
Brugaletta et al., "NIRS and IVUS for Characterization of Atherosclerosis in Patients Undergoing Coronary Angiography" *JACC: Cardiovasc Imaging* 4(6):647-655 (2011).
Cabot Corporation, "Untreated Fumed Silica: CAB-O-SIL® M-5" Product Information, PDS-147 (2004) (2 pages).
Castelli, "The triglyceride issue: A view from Framingham" *Am. Heart J.* 112:432-437 (1986).

(56) References Cited

OTHER PUBLICATIONS

Castillo et al., "Associations of four circulating chemokines with multiple atherosclerosis phenotypes in a large population-based sample: results from the Dallas Heart Study" *J Interferon Cytokine Res*, 30:339-347 (2010).
Chambon, "A decade of molecular biology of retinoic acid receptors" *FASEB Journal*, 10:940-954 (1996).
Chang et al, "Biomarkers for neuromyelitis optica" *Clin. Chim. Acta*, 440:64-71 (2015).
Cheng et al., "Lipoprotein (a) and its relationship to risk factors and severity of atherosclerotic peripheral vascular disease" *Eur. J. Vasc. Endovasc. Surg.* 14:17-23 (1997).
Clinical trials.gov, U.S. National Institutes of Health, "ApoA-I Synthesis Stimulation and Intravascular Ultrasound for Coronary Atheroma Regression Evaluation (ASSURE I)" Study Identifier NCT01067820; first received Feb. 10, 2010. [online] Retrieved from: www.clinicaltrials.gov (4 pages).
Clinical trials.gov, U.S. National Institutes of Health, "Investigate the Efficacy and Safety of GSK1070806 in Obese Subjects With T2DM" Study Identifier NCT01648153; first received Jul. 12, 2012. [online] Retrieved from: www.clinicaltrials.gov (4 pages).
Clinical trials.gov, U.S. National Institutes of Health, "The Study of Quantitative Serial Trends in Lipids With Apolipoprotein A-I Stimulation (SUSTAIN)" Study Identifier NCT01423188; first received Aug. 22, 2011. [online] Retrieved from: www.clinicaltrials.gov (4 pages).
Cui et al., "Interleukin-6 receptor blockade suppresses subretinal fibrosis in a mouse model" *Int. J. Ophthalmol.*, 7(2):194-197 (2014).
Dashti et al., "Leptin and Interleukin-6 in End-Stage Renal Disease" *Pak. J. Med. Sci.*, 24(5):694-697 (2008).
Dave, Rutesh H., "Overview of pharmaceutical excipients used in tablets and capsules" *Drug topics*, published Oct. 24, 2008 [online]. Retrieved from the Internet: http://drugtonics.modernmedicine.com/drug-topics/news/modernmedicine/modern-medicine-news/overview-pharmaceutical-excipients-used-tablets, Mar. 11, 2015 (11 pages).
De Jager et al., "Chemokines CCL3/MIP1alpha, CCL5/RANTES and CCL18/PARC are independent risk predictors of short-term mortality in patients with acute coronary syndromes" *PloS one* 7:e45804 (2012).
Depta et al., "New approaches to inhibiting platelets and coagulation" *Annu. Rev. Pharmacol. Toxicol.* 55:373-397 (2015).
Diaz et al., "Critical Role for IL-6 in Hypertrophy and Fibrosis in Chronic Cardiac Allograft Rejection" *Am. J. Transplant.*, 9(8):1773-1783 (2009). NIH Public Access Author Manuscript; available in PMC Aug. 1, 2010 (20 pages).
Diepenhorst et al. (2009) "Complement-mediated ischemia-reperfusion injury: lessons learned from animal and clinical studies" *Ann. Surg.* 249(6):889-899.
Discipio (1982) "The activation of the alternative pathway C3 convertase by human plasma kallikrein" *Immunology* 45(3):587-595.
Dunkelberger and Song (2010) "Complement and its role in innate and adaptive immune responses" *Cell Res.* 20(1):34-50.
Duong et al., "The molecular physiology of nuclear retinoic acid receptors. From health to disease," *Biochimica et Biophysica Acta* 1812:1023-1031 (2011).
ESMON (2004) "The impact of the inflammatory response on coagulation" *Thromb Res.* 114(5-6):321-327.
Extended European Search Report, including Supplementary Search Report and Opinion, issued Jun. 1, 2015, in European Patent Application 12844794.3, filed May 12, 2014, by Resverlogix Corp.
Extended European Search Report, including Supplementary Search Report and Opinion, issued Apr. 29, 2015, in European Patent Application 13846466, by Resverlogix Corp. (8 pp.).
Feng et al., "Human ApoA-I Transfer Attenuates Transplant Arteriosclerosis via Enhanced Incorporation of Bone marrow-derived Endothelial Progenitor Cells" *Arterioscler. Thromb. Vasc. Biol.*, 28:278-283 (2008).

Fiane et al. (1999) "Compstatin, a peptide inhibitor of C3, prolongs survival of ex vivo perfused pig xenografts" *Xenotransplantation* 6(1):52-65.
Filippakopoulos et al., "Histone recognition and large-scale structural analysis of the human bromodomain family" *Cell* 149:214-231 (2012).
Filippakopoulos et al., "Selective inhibition of BET bromodomains" *Nature*, 468:1067-1073 (2010).
Finkel et al, "Interleukin-6 (IL-6) as a Mediator of Stunned Myocardium" *Am. J. Cardiol.*, 71:1231-1232 (1993).
Fisher et al., "High-Density Lipoprotein Function, Dysfunction, and Reverse Cholesterol Transport" *Arterioscler Thromb. Vasc. Biol.* 32:2813-2820 (2012).
Fonseca et al. (2009) "Treatment with a C5aR antagonist decreases pathology and enhances behavioral performance in murine models of Alzheimer's disease" *J. Immunol.* 183(2):1375-1383.
Forastiero et al. "Circulating levels of tissue factor and proinflammatory cytokines in patients with primary antiphospholipid syndrome or leprosy related antiphospholipid antibodies" *Lupus*, 129-136 (2005).
Francone et al., "Disruption of the murine procollagen C-proteinase enhancer 2 gene causes accumulation of pro-apoA-I and increased HDL levels" *J. Lipid Res.*, 52:1974-1983 (2011).
Freireich et al., "Quantitative Comparison of Toxicity of Anticancer Agents in Mouse, Rat, Hamster, Dog, Monkey, and Man" *Cancer Chemother. Reports*, 50(4):219-244 (1966).
Fukuyo et al., "IL-6-accelerated calcification by induction of ROR2 in human adipose tissue-derived mesenchymal stem cells is STAT3 dependent" *Rheumatology*, 53:1282-1290 (2014).
Furuya et al., "Interleukin-6 as a Potential Therapeutic Target for Pulmonary Arterial Hypertension" *Int. J. Rheumatol.*, 2010:Article ID 720305, doi:10.1155/2010/720305, 8 pages. (2010).
Gaziano et al., "Multivitamins in the Prevention of Cancer in Men—The Physicians' Health Study II Randomized Controlled Trial" *JAMA*, 308(18):1871-1880 (2012) (Corrected 2014).
Gehrs et al. (2010) "Complement, age-related macular degeneration and a vision of the future" *Arch. Ophthalmol.* 128(3):349-358. HHS Public Access Author Manuscript; available in PMC Apr. 21, 2015 (21 pages).
Gilham et al., "RVX-208, a BET-inhibitor for treating atherosclerotic cardiovascular disease, raises ApoA-I/HDL and represses pathways that contribute to cardiovascular disease" *Atherosclerosis* 247:48-57 (2016).
Gordin et al., "Osteopontin is a strong predictor of incipient diabetic nephropathy, cardiovascular disease, and all-cause mortality in patients with type 1 diabetes" *Diabetes Care* 37:2593-2600 (2014).
Gordon et al., "High-density lipoprotein cholesterol and cardiovascular disease. Four prospective American studies" *Circulation* 79:8-15 (1989).
Gosmini et al., "The discovery of I-BET726 (GSK1324726A), a potent tetrahydroquinoline ApoA1 up-regulator and selective BET bromodomain inhibitor" *J. Med. Chem.* 57:8111-8131 (2014).
Greene, T.W. and P.G.M. Wuts (Eds.), *Protective Groups in Organic Synthesis*. 3rd ed. John Wiley & Sons., Inc., 1999; pp. 552-559.
Grundy et al., "Assessment of cardiovascular risk by use of multiple-risk-factor assessment equations. A statement for healthcare professionals from the American Heart Association and the American College of Cardiology" *J. Am. Coll. Cardiol.* 34:1348-1359 (1999).
Hafiane et al., "HDL, Atherosclerosis, and Emerging Therapies" *Cholesterol* 2013:891403 (2013) (18 pages).
He et al., "Local inflammation occurs before systemic inflammation in patients with COPD" *Respirology*, 15:478-484 (2010).
Heeringa and Cohen (2012) "Kidney diseases caused by complement dysregulation: Acquired, inherited, and still more to come" *Clin. Dev. Immunol.* 2012:Article ID 695131, 6 pages.
Hertle et al., "The complement system in human cardiometabolic disease" *Mol. Immunol.* 61:135-148 (2014).
Hietala et al. (2002) "Complement deficiency ameliorates collagen-induced arthritis in mice" *J. Immunol.* 169(1):454-459.
Hill et al., "Thrombosis in paroxysmal nocturnal hemoglobinuria" *Blood*, 121(25):4986-4996 (2013).

(56) References Cited

OTHER PUBLICATIONS

Holland et al. (2004) "Synthetic small-molecule complement inhibitors" *Curr. Opin. Investig. Drugs* 5(11):1164-1173.
Hopkins, "Molecular biology of atherosclerosis" *Physiol. Rev.* 93:1317-1542 (2013).
Hoppensteadt et al., "Dystregulation of Inflammatory and Hemostatic Markers in Sepsis and Suspected Disseminated Intravascular Coagulation" *Clin. Appl. Thromb. Hemost.*, 21(2):120-127 (2015).
Hughes et al., "Shiga toxin-1 regulation of cytokine production by human proximal tubule cells" *Kidney Intl.*, 54:1093-1106 (1998).
Humbert et al., "Increased Interleukin-I and Interleukin-6 Serum Concentrations in Severe Primary Pulmonary Hypertension" *Am. J. Respir. Crit. Care Med.*, 151:1628-1631 (1995).
Husten, "Global epidemic of cardiovascular disease predicted" *Lancet* 352:1530 (1998).
Husten, "More data reported for HDL's role in heart disease" *Lancet* 352:1603 (1998).
Ifergan et al., "Statins Reduce Human Blood-Brain Barrier Permeability and Restrict Leukocyte Migration: Relevance to Multiple Sclerosis" *Ann. Neurol.*, 60:45-55 (2006).
International Search Report and Written Opinion issued in International Application No. PCT/IB2014/002546; Date of Mailing: Mar. 13, 2015.
International Search Report and Written Opinion issued in International Application No. PCT/IB2015/002560; Date of Mailing: Mar. 19, 2015.
Itzen et al., "Brd4 activates P-TEFb for RNA polymerase II CTD phosphorylation" *Nucl. Acids Res.* 42:7577-7590 (2014).
Iwata et al., "The Role of Cytokine in the Lupus Nehpritis" *J. Biomed. Biotechnol.*, 2011:Article IDS 594809, doi:10.1155/2011/5948009, 7 pages (2011).
Jahagirdar et al., "A novel BET bromodomain inhibitor, RVX-208, shows reduction of atherosclerosis in hyperlipidemic ApoE deficient mice" *Atherosclerosis* 236:91-100 (2014).
Kamel et al. "Pharmaceutical significance of cellulose: A review" *eXPRESS Polymer Letters* 2(11):758-778 (2008).
Kannel et al., "Fibrinogen and risk of cardiovascular disease. The Framingham Study" *JAMA* 258:1183-1186 (1987).
Kayikcioglu et al., "Benefits of statin treatment in cardiac syndrome-$X^1$" *Eur. Heart. J.*, 24:1999-2005 (2003).
Keel and Trentz (2005) "Pathophysiology of polytrauma" *Injury* 36(6): 691-709.
Kempen et al., "Stimulation of Hepatic Apolipoprotein A-I Production by Novel Thieno-Triazolodiazepines: Roles of the Classical Benzodiazepine Receptor, PAF Receptor, and Bromodomain Binding" *Lipid Insights* 6:4754 (2013).
Kerr et al., "Review. Interleukin 6 and Haemostasis" *Br. J. Haematol.*, 115:3-12 (2001).
Khera et al., "Cholesterol efflux capacity, high-density lipoprotein function, and atherosclerosis" *N. Engl. J. Med.*, 364:127-135 (2011).
Khetani et al, "Microscale culture of human liver cells for drug development" *Nat Biotechnol* 26:120-126 (2008).
Kita et al., "Daily Serum Interleukin-6 Monitoring in Multiple Organ Transplantation With or Without Liver Allografts" *Transplant. Proc.*, 28(3):1229-1234 (1996).
Klein et al. (2005) "Complement factor H polymorphism in age-related macular degeneration" *Science* 308(5720):385-389. NIH Public Access Author Manuscript; available in PMC Jul. 18, 2006 (12 pages).
Kobayashi et al., "Regulation mechanism of ABCA1 expression by statins in hepatocytes" *Eur. J. Pharmacol.* 662:9-14 (2011).
Kostis and Dobrzynski, "The Effect of Statins on Erectile Dysfunction: A Meta-Analysis of Randomized Trials" *J. Sex Med.*, 11:1626-1635 (2014).
Kukielka et al., "Interleukin-8 Gene Induction in the Myocardium after Ischemia and Reperfusion in Vivo" *J. Clin. Invest.*, 95:89-103 (1995).
Kuwahata et al., "High expression level of Toll-like receptor 2 on monocytes is an important risk factor for arteriosclerotic disease" *Atherosclerosis* 209:248-254 (2010).
Lambertsen et al., "Inflammatory cytokines in experimental and human stroke" *J. Cerebral Blood Flow & Metabol.*, 32:1677-1698 (2012).
Larach et al., "Targeting high density lipoproteins in the prevention of cardiovascular disease?" *Curr. Cardiol. Rep.* 14:684-691 (2012). NIH Public Access Author Manuscript, available in PMC Dec. 1, 2013 (12 pages).
Lee and Parks, "ATP-binding cassette transporter Al and its role in HDL formation" *Curr. Opin. Lipidol.* 16:19-25 (2005).
Lefer et al., "Vascular effects of HMG CoA-reductase inhibitors (statins) unrelated to cholesterol lowering: new concepts for cardiovascular disease" *Cardiovasc. Res.*, 49:281-287 (2001).
Libby et al., "Inflammation and Atherosclerosis" *Circulation* 105:1135-1143 (2002).
Libby, "The Forgotten Majority: Unfinished Business in Cardiovascular Risk Reduction" *J. Am. Coll. Cardiol.* 46(7):1225-1228 (2005).
Liebman and Feinstein (2003) "Thrombosis in patients with paroxysmal noctural hemoglobinuria is associated with markedly elevated plasma levels of leukocyte-derived tissue factor" *Thromb. Res.* 111(4-5):235-238.
Litalien et al., "Circulating inflammatory cytokine levels in hemolytic uremic syndrome" *Pediatr. Nephrol.*, 13:840-845 (1999).
Lowenstein and Matsushita, "The acute phase response and atherosclerosis" *Drug Discovery Today: Disease Mechanisms* 1:17-22 (2004).
Malik et al. (2012) "A hybrid CFHR3-1 gene causes familial C3 glomerulopathy" *J. Am. Soc. Nephrol.* 23(7):1155-1160.
Markiewski et al. (2007) "Complement and coagulation: strangers or partners in crime?" *Trends Immunol.* 28(4):184-192.
Mazzone et al., "Cardiovascular disease risk in type 2 diabetes mellitus: insights from mechanistic studies" *Lancet* 371(9626): 1800-1809 (2008).
McFarlane et al., "Pleiotropic Effects of Statins: Lipid Reduction and Beyond" *J. Clin. Endocrinol. Metab.*, 87:1451-1458 (2002).
McLure et al., "RVX-208, an Inducer of ApoA-I in Humans, Is a BET Bromodomain Antagonist" *PLOS One*, 8(12):e83190 (2013) (12 pages).
Milláan et al., "Lipoprotein ratios: Physiological significance and clinical usefulness in cardiovascular prevention" *Vascular Health and Risk Management*, 5:757-765 (2009).
Minoretti et al., "Prognostic significance of plasma osteopontin levels in patients with chronic stable angina" *Eur. Heart J.* 27:802-807 (2006).
Mirguet et al., "From ApoA1 upregulation to BET family bromodomain inhibition: Discovery of I-BET151" Article in Press, *Bioorg. Med. Chem. Lett.*, doi:10.1016/j.bmcl.2012.01.125 (Feb. 8, 2012) (5 pages) Final publication in 22:2963-2967 (Apr. 15, 2012).
Moreau et al., "Elevated IL-6 and TNF-α levels in patients with ALS: Inflammation or hypoxia?" *Neurology*, 65:1958-1960 (2005).
Mozaffarian et al., "Heart disease and stroke statistics—2015 update. A report from the American Heart Association" *Circulation* 131:e29-e322 (2015).
Muller et al. "Bromodomains as therapeutic targets" *Expert Rev. Mol. Med.* 13:e29 (2011).
Murray and Lopez, "Mortality by cause for eight regions of the world: Global Burden of Disease Study" *Lancet* 349:1269-1276 (1997).
Muscari et al. (1995) "Association of serum C3 levels with the risk of myocardial infarction" *Am. J. Med.* 98(4):357-364.
Muscari et al. (1988) "Association of serum IgA and C4 with severe atherosclerosis" *Atherosclerosis* 74(12):179-186.
Naden, C., "Methaqualone" in *The Facts About the A-Z of Drugs*. Tarrytown, NY: Marshall Cavendish Benchmark, 2008; pp. 92-94.
Naughton et al. "A stereotypic, transplantable liver tissue-culture system" *Appl. Biochem. Biotechnol.* 54:65-91 (1995).
Naughton et al., "Stereotypic culture systems for liver and bone marrow: Evidence for the development of functional tissue in vitro and following implantation in vivo" *Biotechnol. Bioeng*, 43:810-825 (1994).

(56) References Cited

OTHER PUBLICATIONS

Navab et al., "Apolipoprotein A-I Mimetic Peptides" *Arteriosder Thromb Vasc Biol*, 25:1325-1331 (2005).
Navab et al., "HDL and cardiovascular disease: atherogenic and atheroprotective mechanisms" *Nat. Rev. Cardiol* 8:222-232 (2011).
Neves et al., "Anemia and Interleukin-6 Are Associated with Faster Progression to End-Stage Renal Disease" *Dialysis & Transplantation* 36(8):445-456 (2007).
New et al., "Calcific Uremic Arteriolopathy in Peritoneal Dialysis Populations" *Int. J. Nephrol.*, 2011:Article ID 982854, doi:10.4061/2011/982854, 9 pages (2011).
Nicholls et al., "Relationship Between Cardiovascular Risk Factors and Atherosclerotic Disease Burden Measured by Intravascular Ultrasound" *J. Am. Coll. Cardiol.* 47(10):1967-1975 (2006).
Nicholls et al., "Statins, High-Density Lipoprotein Cholesterol, and Regression of Coronary Atherosclerosis" *JAMA* 297(5):499-508 (2007).
Nicholls et al., "ApoA-I induction as a potential cardioprotective strategy: Rationale for the SUSTAIN and ASSURE studies" *Cardiovasc. Drugs Ther.* 26:181-187 (2012).
Nicholls et al., "Effect of Two Intensive Statin Regimens on Progression of Coronary Disease" *N. Engl. J. Med.* 365:2078-2087 (2011).
Nicodeme et al., "Suppression of inflammation by a synthetic histone mimic" *Nature* 468:1119-1123 (2010).
Nissen et al., "Effect of Intensive Compared with Moderate Lipid-Lowering Therapy on Progression of Coronary Atherosclerosis: A Randomized Controlled Trial" *JAMA* 291(9):1071-1080 (2004).
Nissen et al., "Effect of Very High-Intensity Statin Therapy on Regression of Coronary Atherosclerosis: The Asteroid Trial" *JAMA* 295(13):1556-1565 (2006).
Noris and Remuzzi (2009) "Atypical hemolytic-uremic syndrome" *N. Engl. J. Med.* 361(17):1676-1687.
O'Brien et al., "Interleukin-18 as a therapeutic target in acute myocardial infarction and heart failure" *Mol. Med.* 20:221-229 (2014).
Ogata et al. (1989) "Sequence of the gene for murine complement component C4" *J. Biol. Chem.* 264(28):16565-16572.
Ohta et al., "Detection and clinical usefulness of urinary interleukin-6 in the diseases of the kidney and the urinary tract" *Clin. Nephrol.*, 38(4):185-189 (1992).
Okroj et al. (2007) "Rheumatoid arthritis and the complement system" *Ann. Med.* 39(7):517-530.
Ono et al., "Increased interleukin-6 of skin and serum in amyotrophic lateral sclerosis" *J. Neurol. Sci.*, 187:27-34 (2001).
Park et al., "Serum biomarkers for neurofibromatosis type 1 and early detection of malignant peripheral nerve-sheath tumors" *BMC Med.*, 11:109, 9 pages (2013).
Pecoits-Filho et al., "Interleukin-6 is an independent predictor of mortality in patients starting dialysis treatment" *Nephrol. Dial. Transplant.*, 17:1684-1688 (2002).
Pecoits-Filho et al., "Updated on interleukin-6 and its role in chronic renal failure" *Nephrol. Dial. Transplant.*, 18:1042-1045 (2003).
Peng et al. (2005) "Role of C5 in the development of airway inflammation, airway hyperresponsiveness, and ongoing airway response" *J. Clin. Invest.* 115(6):1590-1600.
Picaud et al., "RVX-208, an inhibitor of BET transcriptional regulators with selectivity for the second bromodomain" *Proc Natl Acad Sci USA* 110:19754-19759 (2013).
Puri et al., "Effects of an apolipoprotein A-1 inducer on progression of coronary atherosclerosis and cardiovascular events in patients with elevated inflammatory markers" *J. Am. Coll. Cardiol.* 63:S0735-1097 (2014).
Qiu and Hill, "Atorvastatin Inhibits ABCA1 Expression and Cholesterol Efflux in THP-1 Macrophages by an LXR-dependent Pathway" *Cardiovasc. Pharmacol.* 51: 388-395 (2008).
Reuter et al., "Oxidative stress, inflammation, and cancer: How are they linked?" *Free Radic Biol Med.*, 49(11):1603-1616 (2010).
Ricklin and Lambris (2007) "Complement-targeted therapeutics" *Nat. Biotechnol.* 25(11):1265-1275.

Ricklin and Lambris (2013) "Progress and Trends in Complement Therapeutics" *Adv. Exp. Med. Biol.* 735:1-22. NIH Public Access Author Manuscript; available in PMC Jul. 1, 2013 (28 pages).
Ricklin et al. (2010) "Complement—a key system for immune surveillance and homeostasis" *Nat. Immunol.* 11(9):785-797. NIH Public Access Author Manuscript; available in PMC Sep. 1, 2011 (30 pages).
Rincon and Irvin, "Role of IL-6 in Asthma and Other Inflammatory Pulmonary Diseases" *Int. J. Biol.*, 8:1281-1290 (2012).
Rohatgi et al., "HDL Cholesterol Efflux Capacity and Incident Cardiovascular Events" *N. Engl. J. Med.* 371:2383-2393 (2014).
Röth et al. (2009) "Long-term efficacy of the complement inhibitor eculizumab in cold agglutinin disease" *Blood* 113(16):3885-3886.
Sarma and Ward (2011) "The complement system" *Cell Tissue Res.* 343(1):227-235. NIH Public Access Author Manuscript; available in PMC Jan. 1, 2012 (13 pages).
Sassano et al., "Interleukine-6 (IL-6) may be a link between myasthenia gravis and myoepithelioma of the parotid gland," Med. Hypoth., 68:314-317 (2007).
Scandinavian Simvastatin Survival Group, "Randomised Trial of Cholesterol Lowering in 4444 Patients with Coronary Heart Disease: The Scandinavian Simvastatin Survival Study (4S)" *Lancet* 344:1383-1389 (1994).
Scoble et al., "Lipid Profiles in Patients with Atherosclerotic Renal Artery Stenosis" *Nephron*, 83:117-121 (1999).
Seddon et al., "Progression of Age-Related Macular Degeneration. Prospective Assessment of C-Reactive Protein, Interleukin 6, and Other Cardiovascular Biomarkers" *Arch Ophthalmol.*, 123:774-782 (2005).
Seifert et al., "The complement system in atherosclerosis" *Atherosclerosis*, 73:91-104 (1988).
Sharma and Das "Role of Cytokines in myocardial ischemia and reperfusion" *Mediators of Inflammation*, 6:175-183 (1997).
Shimizu et al. "Effects of Rosuvastatin and Atorvastatin on Macrophage Reverse Cholesterol Transport in Vivo" AHA Scientific Sessions, 2011. Core 2. Epidemiology and Prevention of CV Disease: Physiology, Pharmacology and Lifestyle; Session Title: Lipids, Lipid Mediators and Lipoprotein Metabolism: Cellular and Animal I. *Circulation* 124(21 Suppl.):A11181 (2011).
Shichishima et al. (1999) "Complement sensitivity of erythrocytes in a patient with inherited complete deficiency of CD59 or with the Inab phenotype" *Brit. J. Haematol.* 104:303-306.
Skerka et al. (2013) "Complement factor H related proteins (CFHRs)" *Mol. Immunol.* 56:170-180.
Sowers et al., "Calcific uremic arteriolopathy. Pathophysiology, reactive oxygen species and therapeutic approaches" *Oxid. Med. Cell. Long.*, 3(2):109-121 (2010).
Steiner et al., "Interleukin-6 Overexpression Induces Pulmonary Hyertension" *Circ. Res.*, 104:236-244, with Supplemental Material, 28 pages (2009).
Suzuki et al. (2014) "Development of animal models of human IgA nephropathy" *Drug Discov. Today Dis. Models* 11:5-11. NIH Public Access Author Manuscript; available in PMC Aug. 15, 2015 (12 pages).
Tacke et al., "Inflammatory Pathways in Liver Homeostasis and Liver Injury" *Clinic. Rev. Allerg. Immunol.*, 36:4-12 (2009).
Tardif et al. "Effects of reconstituted high-density lipoprotein infusions on coronary atherosclerosis: A randomized controlled trial" *JAMA* 297:1675-1682 (2007).
Tasaki et al., "Comparison of serum lipid values in variant angina pectoris and fixed coronary artery disease with normal subjects" *Am. J. Cardiol.* 63(20):1441-1445 (1989).
Tataru et al. "D-dimers in relation to the severity of arteriosclerosis in patients with stable angina pectoris after myocardial infarction" *Eur. Heart J.* 20:1493-1502 (1999).
Terinte et al., "Overview on native cellulose and microcrystalline cellulose I structure studied by x-ray diffraction (WAXD): Comparison between measurement techniques" *Lenzinger Berichte* 89:118-131 (2011).
Thoorens et al., "Microcrystalline cellulose, a direct compression binder in a quality by design environment—A review" *Intl. J. Pharmaceut.* 473:64-72 (2014).

(56) References Cited

OTHER PUBLICATIONS

Uzawa et al., "Cytokine and chemokine profiles in neuromyelitis optica: significance of interleukin-6" *Multiple Sclerosis*, 16(12):1443-1452 (2010).
Van Lenten et al., "Anti-inflammatory apoA-I-mimetic peptides bind oxidized lipids with much higher affinity than human apoA-I" *Journal of Lipid Research*, 49:2302-2311 (2008).
Van Lenten et al., "Apolipoprotein A-I Mimetic Peptides" *Curr Atheroscler Rep.*, 11(1):52-57 (2009).
Vega-Ostertag et al., "Involvement of p38 MAPK in the Up-Regulation of Tissue Factor on Endothelial Cells by Antiphospholipid Antibodies" *Arthritis & Rheumatism*, 52(5):1545-1554 (2005).
Vlaicu et al., "The role of complement activation in atherogenesis: the first 40 years" *Immunol. Res.* 64:1-13 (2016).
Vuilleumier et al., "Pro- or anti-inflammatory role of apolipoprotein A-1 in high-density lipoproteins?" *Swiss Medical Weekly, The European Journal of Medical Sciences*, 143:w13781 1-12 (2013).
Wada et al., "Increased plasma level of interleukin-6 in disseminated intravascular coagulation" *Blood Coagulation and Fibrinolysis*, 4:583-590 (1993).
Waiser et al., "Interleukin-6 expression after renal transplantation" *Nephrol. Dial. Transplant.*, 12:753-759 (1997).
Walldius et al., "The apoB/apoA-I ratio: a strong, new risk factor for cardiovascular disease and a target for lipid-lowering therapy—a review of the evidence" *J. Internal Med.* 259:493-519 (2006).
Walport (2001) "Complement First of two parts" *N. Engl. J. Med.* 344(14):1058-1066.
Walsh et al., High Levels of Human Apolipoprotein A-I in Transgenic Mice Result in Increased Plasma Levels of Small High Density Lipoprotein (HDL) Particles Comparable to Human $HDL_3$ *The Journal of Biological Chemistry*, 264(11):6488-6494 (1989).
Walters et al. (2002) "Complement factor 3 mediates particulate matter-induced airway hyperresponsiveness" *Am. J. Respir. Cell Mol. Biol.* 27(4):413-418.
Wang et al. (2000) "A role for complement in antibody-mediated inflammation: C5-deficient DbBA/1 mice are resistant to collagen-induced arthritis" *J. Immunol.* 164(8):4340-4347.
Wang et al. (2011) "Statins: Multiple neuroprotective mechanisms in neurodegenerative diseases" *Exp. Neurol.*, 230(1):27-34.
Wang et al. (2012) "Association analysis of cytokine polymorphisms and plasma level in Northern Chinese Han patients with paroxysmal nocturnal hemoglobinuria" *Chin. Med. J.*, 125(9):1576-1580.
Wannamethee et al., "Circulating inflammatory and hemostatic biomarkers are associated with risk of myocardial infarction and coronary death, but not angina pectoris, in older men" *J. Thromb. Haemost.* 7:1605-1611 (2009).
Warden et al., "Atherosclerosis in Transgenic Mice Overexpressing Apolipoprotein A-II" *Science*, 261:469-472 (1993).
Weitz et al., "Eculizumab therapy results in rapid and sustained decreases in markers of thrombin generation and inflammation in patients with PNH independent of its effects on hemolysis and microparticle formation" *Thromb. Res.*, 130:361-368 (2012).
Wellington et al. "Alterations of plasma lipids in mice via adenoviral-mediated hepatic overexpression of human ABCA1" *Lipid Res.* 44:1470-1480 (2003).
Westwood et al., "Complement and cytokine response in acute Thrombotic Thrombocytopenic Purpura" *Br. J. Haematol.*, 164:858-866 (2014).
Wolfrum et al., "Endothelium-Dependent Effects of Statins" *Arteriosder. Thromb. Vasc. Biol.*, 23:729-736 (2003).
Wright et al., "Statin Lipid-Lowering Therapy for Acute Myocardial Infarction and Unstable Angina: Efficacy and Mechanism of Benefit" *Mayo Clin. Proc.*, 77:1085-1092 (2002).
Yellon and Hausenloy (2007) "Myocardial reperfusion injury" *N. Engl. J. Med.* 357(11):1121-1135.
Yoshikawa et al., "Cytokine secretion by peripheral blood mononuclear cells in myasthenia gravis" *J. Clin. Neurosci.*, 9(2):133-136 (2002).
Zacharowski et al., "Fibrin(ogen) and its fragments in the pathophysiology and treatment of myocardial infarction" *J. Mol. Med.* 84:469-477 (2006).
Zamani et al., "Inflammatory Biomarkers, Death, and Recurrent Nonfatal Coronary Events After an Acute Coronary Syndrome in the MIRACL Study" *J. Am. Heart Assoc.*, 1:e003103, doi:10.1161/JAHA.112.003103 (2012).
Zannis et al., "Intracellular and extracellular processing of human apolipoprotein A-I: Secreted apolipoprotein A-1 isoprotein 2 is a propeptide" *Proc. Natl. Acad. Sci. USA* 80:2574-2578 (1983).
Zhang and Köhl (2010) "A complex role for complement in allergic asthma" *Expert Rev. Clin. Immunol.* 6(2):269-277. NIH Public Access Author Manuscript; available in PMC Jan. 1, 2011 (17 pages).
Zhang et al., "Inhibition of the Interleukin-6 Signaling Pathway: A Strategy to Induce Immune Tolerance" *Clinic. Rev. Allerg. Immunol.*, 47:163-173 (2014).
Zhu et al., "Regulation of apoAI processing by procollagen C-proteinase enhancer-2 and bone morphogenetic protein-1" *J. Lipid Res.* 50:1330-1339 (2009).
Angelucci, F. and L. Colantoni (2010) "Facioscapulohumeral muscular dystrophy: Do neurotrophins play a role?" *Muscle Nerve*, 41:120-127.
Blackburn Jr., W.D. et al., "Apolipoprotein A-I decreases neutrophil degranulation and superoxide production" *J. Lipid Res.* 32:1911-1918 (1991).
De Paepe, B. And De Bleecker, J.L. (2013) "Cytokines and Chemokines as Regulators of Skeletal Muscle Inflammation: Presenting the Case of Duchenne Muscular Dystrophy" *Mediators of Inflammation*, vol. 2013, Article 540370 (10 pages).
Ehrlich, M. and M. Lacey (Aug. 2012) "Deciphering transcription dysregulation in FSH muscular dystrophy" *J Hum Genet*, 57(8):477-484. NIH Public Access Author Manuscript; available in PMC Feb. 1, 2013 (17 pages).
Farini, a. et al. (May 19, 2014) "Influence of Immune Responses in Gene/Stem Cell Therapies for Muscular Dystrophies" *BioMed Res International*, vol. 2014, Article 818107 (16 pages).
Frisullo, G. et al. (2011) "$CD8^+T$ Cells in Facioscapulohumeral Muscular Dystrophy Patients with Inflammatory Features at Muscle MRI" *J Clin Immunol*, 31:155-166.
Genetics Home Reference (Nov. 1, 2016) "C3 glomerulopathy" [online]. U.S. National Institutes of Health. Retrieved from: https://ghr.nlm.nih.gov/condition/c3-glomerulopathy.
Hour, M-J. et al., "6-Alkylamino- and 2,3-Dihydro-3'-methoxy-2-phenyl-4-quinazolinones and Related Compounds: Their Synthesis, Cytotoxicity, and Inhibition of Tubulin Polymerization" *J. Med. Chem.* 43(23):4479-4487 (2000).
International Search Report and Written Opinion issued in International Application No. PCT/1B2016/000443; Date of Mailing: Jun. 22, 2016.
Lefkowitz, D.L. and S.S. Lefkowitz (2005) "Facioscapulohumeral muscular dystrophy: A progressive degenerative disease that responds to diltiazem" *Medical Hypotheses*, 65:716-721.
Mammen, A.L. and V. Sartorelli (2015) "IL-6 Blockade as a Therapeutic Approach for Duchenne Muscular Dystrophy" *EBioMedicine*, 2:274-275.
Merriam-Webster Dictionary, "Prevention" Definition [online]. Retrieved from: http://www.merriam-webster.com/dictionary/prevention, on Oct. 19, 2016 (1 page).
Messina, S. et al. (2011) "Activation of NF-kB pathway in Duchenne muscular dystrophy: relation to age" *Acta Myol*, 30(1):16-23.
Morgan and Harris, "Complement, a target for therapy in inflammatory and degenerative diseases" *Nat. Rev. Drug Disc.* 14:857-877 (2015).
Pelosi, L. et al. (2015) "Functional and Morphological Improvement of Dystrophic Muscle by IL6 Receptor Blockade" *EBioMedicine*, 2:285-293.
Rowe, R.C. et al. (Eds.) *Handbook of Pharmaceutical Excipients*. 5th ed. Great Britain: Pharmaceuticals Press and the American Pharmacists Association, 2006; 940 pages.
Rufo, A. et al. (2011) "Mechanisms Inducing Low Bone Density in Duchenne Muscular Dystrophy in Mice and Humans" *J Bone Miner Res*, 26(8):1891-1903.
Tsujinaka, T. et al. (1998) "Muscle Wasting and IL-6" *Basic Appl Myol*, 8(5):361-370.

(56) References Cited

OTHER PUBLICATIONS

Turki, A. et al. (2012) "Functional muscle impairment in facioscapulohumeral muscular dystrophy is correlated with oxidative stress and mitochondrial dysfunction" *Free Radical Biology and Medicine*, 53:1068-1079.

Wikipedia, "Complement system" [online] Retrieved from: https://en.wikipedia.org/wiki/Complement_system, on Nov. 4, 2016 (9 pages).

World Health Organization (WHO), "Cardiovascular Disease and Heredity: Possibilities for Prevention and Management with Genetics" [online]. Retrieved from: http://www.who.int/genomics/about/CVD.pdf?ua=1, on Oct. 19, 2016 (12 pages).

Xia, Y. et al., "Antitumor Agents. Part 204: Synthesis and Biological Evaluation of Substituted 2-Aryl Quinazolinones" *Bioorg. Med. Chem. Lett.*, 11(9):1193-1196 (2001).

Zhang et al. (2012) "Down-regulation of NF-↓B Transcriptional Activity in HIV-associated Kidney Disease by BRD4 Inhibition" *J Biol Chem*, 287(34):28840-28851.

\* cited by examiner

ANTI-INFLAMMATORY AGENTS

This application is a national stage entry under 35 U.S.C. §371 of PCT/US2010/031870, filed Apr. 21, 2010, which claims the benefit of U.S. Provisional Application No. 61/171,620, filed Apr. 22, 2009, the disclosure of which is incorporated herein by reference in its entirety.

The present invention relates to methods of regulating interleukin-6 (IL-6) and/or vascular cell adhesion molecule-1 (VCAM-1) and to methods of treating and/or preventing cardiovascular and inflammatory diseases and related disease states, such as, for example, atherosclerosis, asthma, arthritis, cancer, multiple sclerosis, psoriasis, and inflammatory bowel diseases, and autoimmune disease(s) by administering a naturally occurring or synthetic quinazolone derivative. The invention provides novel synthetic quinazolone compounds, as well as pharmaceutical compositions comprising those compounds.

Coronary heart disease (CHD) remains a leading cause of death in industrialized nations. A primary cause of CHD is atherosclerosis, a disease characterized by the deposition of lipids in the arterial vessel wall, resulting in a narrowing of the vessel passages and, ultimately, hardening of the vascular system.

It is generally accepted that atherosclerosis can begin with local injury to the arterial endothelium, followed by monocyte recruitment and maturation, and smooth muscle cell proliferation in the intimal arterial layer, along with the deposition of lipids and the accumulation of foam cells in the lesion. As the atherosclerotic plaque develops, it progressively occludes more of the affected blood vessel and can eventually lead to ischemia or infarction. Thus, it continues to be desirable to develop treatments to inhibit or prevent the progression of atherosclerosis in patients in need thereof.

Cardiovascular disease has been linked to several causative factors, including hypercholesterolemia, hyperlipidemia, and vascular cell adhesion molecule-1 (VCAM-1) in vascular endothelial cells. VCAM-1 promotes the adhesion of lymphocytes, monocytes, eosinophils, and basophils. Certain melanoma cells can use VCAM-1 to adhere to the endothelium, and VCAM-1 may participate in monocyte recruitment to atherosclerotic sites. As a result, VCAM-1 is of interest as a drug target.

The VCAM-1 gene is a member of the immunoglobulin (Ig) superfamily and encodes a cell-surface sialoglycoprotein expressed by cytokine-activated endothelial cells. This type-1 membrane protein mediates leukocyte-endothelial cell adhesion and signal transduction, and may play a role in the development of artherosclerosis and rheumatoid arthritis. VCAM-1, also known as CD106, has several roles in the immune system. The VCAM-1 protein contains six or seven immunoglobulin domains, and is expressed in both large and small vessels only after endothelial cells are stimulated by cytokines.

Adhesion of leukocytes to the endothelium represents a fundamental, early event in many inflammatory conditions, including atherosclerosis, autoimmune disorders, and bacterial and viral infections. Leukocyte recruitment to the endothelium begins when inducible adhesion molecule receptors on the surface of endothelial cells interact with their counter-receptors on immune cells. Vascular endothelial cells determine which type(s) of leukocyte(s) (e.g., monocytes, lymphocytes, neutrophils) are recruited, by selectively expressing specific adhesion molecules, such as VCAM-1, intracellular adhesion molecule-1 (ICAM-1), and E-selectin.

In the early stage of the atherosclerotic lesion, there is localized endothelial expression of VCAM-1 and selective recruitment of mononuclear leukocytes that express the integrin counter-receptor VLA-4. Because of the selective expression of VLA-4 on monocytes and lymphocytes, but not neutrophils, VCAM-1 is important in mediating the selective adhesion of mononuclear leukocytes. Subsequent conversion of leucocytes to foamy macrophages results in the synthesis of a wide variety of inflammatory cytokines, growth factors, and chemoattractants that help expand leukocyte and platelet recruitment, smooth muscle cell proliferation, endothelial cell activation, and the extracellular matrix synthesis characteristic of maturing atherosclerotic plaques.

VCAM-1 is a mediator in chronic inflammatory disorders, such as asthma, rheumatoid arthritis, and diabetes. For example, it is known that VCAM-1 and ICAM-1 is increased in asthmatics (Pilewski et al. (1995) *Am. J. Respir. Cell Mol. Biol.* 12, 1-3; Ohkawara et al. (1995) *Am. J. Respir. Cell Mol. Biol.* 12, 4-12). Further examples of non-cardiovascular inflammatory diseases mediated by VCAM-1 include rheumatoid and osteoarthritis, asthma, dermatitis, and multiple sclerosis. Blocking the integrin receptors for VCAM-1 and ICAM-1 (VLA-4 and LFA-1, respectively) suppresses both early- and late-phase responses in an ovalbumin-sensitized rat model of allergic airway responses (Rabb et al. (1994) *Am. J. Respir. Care Med.* 149, 1186-1191). There is also increased expression of endothelial adhesion molecules, including VCAM-1, in the microvasculature of rheumatoid synovium (Koch et al. (1991) *Lab. Invest.* 64, 313-322; Morales-Ducret et al. (1992) *Immunol.* 149, 1421-31).

Neutralizing antibodies directed against VCAM-1 or its counter receptor, VLA-4, can delay the onset of diabetes in a mouse model (NOD mice) which spontaneously develop the disease (Yang et al. (1993) *Proc. Natl. Acad. Sci. USA* 90, 10494-10498; Burkly et al. (1994) *Diabetes* 43, 523-534; Baron et al. (1994) *J. Clin. Invest.* 93, 1700-1708). Monoclonal antibodies to VCAM-1 can also have beneficial effects in animal models of allograft rejection, suggesting that inhibitors of VCAM-1 expression may also have utility in preventing transplant rejection (Oroez et al. (1992) *Immunol. Lett.* 32, 7-12).

VCAM-1 is expressed by cells both in a membrane-bound form and a soluble form. The soluble form has been shown to induce chemotaxis of vascular endothelial cells in vitro and to stimulate an angiogenic response in rat cornea (Koch et al. (1995) *Nature* 376, 517-519). Inhibitors of VCAM-1 have potential therapeutic value in treating diseases with an angiogenic component, including tumor growth and metastasis (Folkman & Shing (1992) *Biol. Chem.* 10931-10934).

Because cardiovascular disease is currently a leading cause of death and disability in the developed world, there is a strong need to identify new methods and pharmaceutical agents for its treatment. Thus, there is a need to identify and manipulate synthetic compounds that can affect mediators of the inflammatory process, such as, for example, VCAM-1.

Interleukin-6 (IL-6) is a 22-27-kDa secreted glycoprotein that exhibits growth stimulatory and pro-inflammatory activities. IL-6 has also been called interferon-β2 (IFN-β2), IL-1-inducible 26-kDa protein, hepatocyte-stimulating factor, cytotoxic T-cell differentiation factor, and B-cell stimulatory factor (Trikha et al. (2003) *Clin. Cancer Res.* 9, 4653-4665). IL-6 was originally identified in monocytes/macrophages, fibroblasts, and endothelial cells.

IL-6 is secreted by various cell types and exerts its activities by binding to a high-affinity receptor complex, consisting of two membrane glycoproteins, an 80-kDa component receptor that binds IL-6 with low affinity (IL-6R) and a signal-transducing component of 130 kDa (also known as gp130) that does not bind IL-6 itself, but is required for high-affinity binding of IL-6 by the complex. The IL-6R can be cleaved by a transmembrane metalloproteinase to yield a soluble IL-6R.

IL-6 levels are rapidly elevated in the circulation in numerous infectious, inflammatory, and autoimmune diseases, and in some cancers, in association with increased synthesis of other cytokines, stimulated by infection, trauma, and immunological challenge. (Trikha et al. (2003) *Clin. Cancer Res.* 9, 4653-4665). IL-6 has been implicated in various diseases and disorders, including multiple myeloma (Rossi et al. (2005) *Bone Marrow Transplantation* 36, 771-779), lymphomas (Emilie et al. (1994) *Blood* 84, 2472-2479), neurological disorders, such as neurodegeneration, astrocytosis, and cerebral angiogenesis (Campbell et al. (1993) *Proc. Natl. Acad. Sci. USA* 90, 10061-10065), autoimmune disorders (such as, e.g., rheumatoid arthritis), inflammatory diseases, Alzheimer's disease, myocardial infarction, Paget's disease, osteoporosis, solid tumors, prostate and bladder cancers (Trikha et al. (2003) *Clin. Cancer Res.* 9, 4653-4665), septic shock, transplants, acute infections of the central nervous system, cardiac myxoma (Wijdenes et al. (1991) *Mol. Immunol.* 28, 1183-1192), tumor-induced cachexia (Cahlin et al. (2000) *Cancer Res.* 60, 5488-5489), cancer-associated depression, and cerebral edema secondary to brain tumors (Musselman et al. (2001) *Am. J. Psychiatry* 158, 1252-1257). Inflammation and IL-6 are now specifically thought to be linked to heart attacks (Taubes (2002) *Science* 296, 242).

Generally, it is known that IL-6 is abnormally produced in some inflammatory, autoimmune, and neoplastic diseases; further, it has been proposed that abnormal production of IL-6 is an aspect of the mechanisms of these diseases (Hirano et al. (1990) *Immunol. Today*, 11, 443-449; Sehgal (1990) *Proc. Soc. Exp. Biol. Med.* 195, 183-191; Grau (1990) *Eur. Cytokine Net* 1, 203-210; Bauer et al. (1991) *Ann. Hematol.* 62, 203-210; Campbell et al. (1991) *J. Clin. Invest.* 7, 739-742; Roodman et al. (1992) *J. Clin. Invest.* 89, 46-52). In particular, it is known that IL-6 is associated with neuropathological processes, and its level in blood is increased in diseases invading the central nervous system. It has been found that IL-6 increases the level of tau epitope, by stimulating the dementia-associated phosphorylation of the tau protein in neuronal cells (Quintanilla et al. (2004) *Exp. Cell Res.* 295, 245-257), and mice lacking IL-6 have enhanced resistance to glutamate toxicity and increased viability of neuronal cells (Fisher et al. (2001) *J. Neuroimmunol.* 119, 1-9). It has also been found that IL-6 amplifies a calcium influx signal for the neurotransmitter N-methyl-D-aspartate (NMDA), through voltage-sensitive calcium channels, which provides a clue that the increased IL-6 level may have a role in inducing pathological changes in central nervous system diseases (Qiu et al. (1998) 18, 10445-10456). It has also been reported that the abnormal levels of IL-6 is a pathogenic mechanism in other diseases, including cardiac myxoma, uterine cancer (Kishimoto et al. (1988) *Ann. Rev. Immunol.* 6, 485; multiple myeloma; histiocytomas (Taga et al. (1987) *J. Exp. Med.* 166, 967), plasmacytoma, hematological diseases, including plasma cell dyscrasias, leukemia, and lymphoma (Kishimoto (1989) *Blood* 74, 1; Taga et al. (1987) *J. Exp. Med.* 166, 967; Klein et al. (1991) *Blood* 78, 1198-1204); proliferative glomerulonephritis; activated multiclonal B-cell (types I-IV) allergic diseases, rheumatoid arthritis (Hirano et al. (1988) *Eur. J. Immunol.* 18, 1797), diabetes (Campbell et al. (1991) *J. Clin. Invest.* 87, 739-742), multiple sclerosis, SLE, septic shock, bacterial infections, viral infections, osteoporosis (Roodman et al. (1992) *J. Clin. Invest.* 89, 46-52; Jilka et al. (1992) *Science* 257, 88-91); chronic immunodeficiency syndrome and autoimmune immunodeficiency syndromes, including AIDS (*Med. Immunol.* 15, 195-201 (1988)), and inflammatory diseases, including inflammatory bowel diseases (such as Crohn's disease and ulcerative colitis) (WO99/47170). It is known that IL-6 is associated with some central nervous system diseases (Frei et al. (1991) *J. Neuroimmunol.* 31, 147).

Interleukin-6 is secreted by many advanced cancers, such as hormone-independent prostate cancer, and is believed to be a growth factor for such cancers. Additionally, the secretion of IL-6 by cancer cells is believed to cause cachexia, the wasting syndrome characteristic of advanced cancers. Thus, reducing the level of IL-6 would be useful in treating such cancers. IL-6 also plays a key role in B cell development. Autoimmune diseases with a significant antibody component, such as rheumatoid arthritis, could be treated by decreasing IL-6 levels. Disorders involving B cell proliferation, such as multiple myeloma and B cell lymphoma, could also be treated by reducing IL-6 activity. Additionally, IL-6 plays an important role in bone remodeling by promoting bone resorption. Reducing IL-6 activity would have the effect of reducing bone resorption and could be used to treat osteoporosis.

Accordingly, there have been various attempts to reduce the levels of IL-6, which are believed to be associated with the pathogenic mechanisms of these various diseases and conditions. A steroid formulation has been used for suppressing the cytokines in the art, but such medicines may causes severe side-effects, such as peptic ulcers, if administered for an extended period.

Anti-IL-6 antibodies have been shown to be effective in treating several diseases and disorders. For example, anti-IL-6 monoclonal antibodies have been shown to block the proliferation of myeloma cells both in vivo and in vitro (Rossi et al. (2005) *Bone Marrow Transplantation* 36, 771-779). Administration of anti-IL-6 antibodies to chronic rheumatoid arthritis patients was found to alleviate the symptoms of the disease (Wendling et al. (1993) *J. Rheumatol.* 20, 259-262). Anti-IL-6 antibodies have also been shown to be effective in treating AIDS-associated lymphoma (Emilie et al. (1994) *Blood* 84, 2472-2479), and metastatic renal cell carcinoma (Blay et al. (1997) *Int. J. Cancer* 72, 424-430). Clinical results involving the administration of anti-IL-6 antibodies to treat various other diseases and disorders are summarized in Trikha et al. (2003) *Clin. Cancer Res.* 9, 4653-4665.

Thus, the present invention provides methods of regulating interleukin-6 (IL-6) and vascular cell adhesion molecule-1 (VCAM-1) in a mammal by administering one or more compounds of Formula I or Formula II to the mammal. The invention also provides methods of treating and/or preventing cardiovascular and inflammatory diseases, such as, for example, atherosclerosis, asthma, arthritis, cancer, multiple sclerosis, psoriasis, and inflammatory bowel diseases, and autoimmune disease(s) in a mammal by administering one or more compounds of Formula I or Formula II to the mammal. The invention further provides novel compounds, pharmaceutical compositions comprising those compounds, and methods of preparing those compounds.

Without wishing to be bound by theory, it is believed that the compounds of Formula I and II act by inhibiting expression of IL-6 and/or VCAM-1 in the subject receiving the compound. However, regardless of the mechanism of action, administration of one or more compounds of Formula I and/or Formula II will reduce the levels of IL-6 and/or VCAM-1 in the subject and as a result treat or reduce the incidence of cardiovascular and/or inflammatory diseases.

One aspect of the invention provides a method for reducing IL-6 and/or VCAM-1 in a subject comprising administering to the subject in need thereof, a therapeutically effective amount of at least one compound of Formula I:

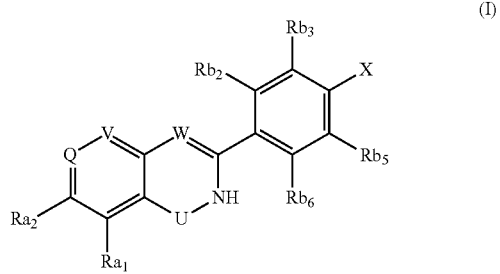

(I)

or a stereoisomer, tautomer, pharmaceutically acceptable salt, or hydrate thereof, wherein:

Q is selected from N and $CRa_3$;
V is selected from N and $CRa_4$;
W is selected from N and CH;
U is selected from C=O, C=S, $SO_2$, S=O, and $SR_1$;
X is selected from OH, SH, $NH_2$, S(O)H, $S(O)_2H$, $S(O)_2NH_2$, $S(O)NH_2$, NHAc, and $NHSO_2Me$;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, $C_3$-$C_6$ cycloalkyl, amino, amide, and halogen;
$Rb_2$ and $Rb_6$ are independently selected from hydrogen, methyl and fluorine;
$Rb_3$ and $Rb_5$ are independently selected from hydrogen, halogen, $C_1$-$C_6$ alkyl, $C_3$-$C_6$ cycloalkyl, and $C_1$-$C_6$ alkoxy; and
$Rb_2$ and $Rb_3$ and/or $Rb_5$ and $Rb_6$ may be connected to form a cycloalkyl or a heterocycle,
provided that at least one of $Ra_1$, $Ra_2$, $Ra_3$, and $Ra_4$ is not hydrogen.

In certain embodiments, the method for reducing IL-6 and/or VCAM-1 in a subject, comprises administering a therapeutically effective amount of at least one compound of Formula II:

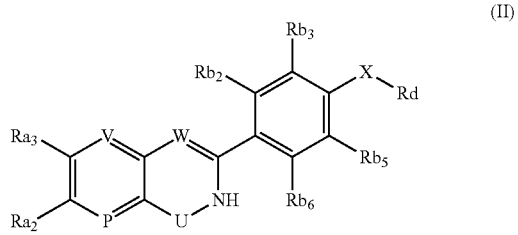

(II)

or a stereoisomer, tautomer, pharmaceutically acceptable salt, or hydrate thereof, wherein:

P is selected from N and $CRa_1$;
V is selected from N and $CRa_4$;
W is selected from N and CH;
U is selected from C=O, C=S, $SO_2$, S=O, and $SR_1$;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, amino, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_1$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$-morpholino.

DEFINITIONS

As used in the present specification, the following words, phrases and symbols are generally intended to have the meanings as set forth below, except to the extent that the context in which they are used indicates otherwise. The following abbreviations and terms have the indicated meanings throughout:

The terms "compound of Formula I" and "compound of Formula II" are intended to include any stereoisomer, tautomer, and/or pharmaceutically acceptable salt as defined herein. Compounds of Formula I and Formula II also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to. Compounds of Formula I and compounds of Formula II also include pharmaceutically acceptable forms of the recited compounds, including chelates, non-covalent complexes, prodrugs, and mixtures thereof.

As noted above, prodrugs also fall within the scope of compounds of Formula I and compounds of Formula II. In some embodiments, the "prodrugs" described herein include any compound that becomes a compound of Formula I and/or Formula II when administered to a patient, e.g., upon metabolic processing of the prodrug. Examples of prodrugs include derivatives of functional groups, such as a carboxylic acid group, in the compounds of Formula I and/or Formula II. Exemplary prodrugs of a carboxylic acid group include, but are not limited to, carboxylic acid esters such as alkyl esters, hydroxyalkyl esters, arylalkyl esters, and aryloxyalkyl esters.

A "solvate" is formed by the interaction of a solvent and a compound. The terms "compound of Formula I" and "compounds of Formula II" are intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'.

As used herein, "cardiovascular disease" refers to diseases, disorders and conditions of the heart and circulatory system that are mediated by VCAM-1 and/or IL-6. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's diseases and an inflammatory diseases.

As used herein, "inflammatory diseases" includes refers to diseases, disorders and conditions, that are mediated by VCAM-1 and/or IL-6. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "aldehyde" or "formyl" as used herein refers to —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as ($C_2$-$C_{22}$)alkenyl, ($C_2$-$C_8$)alkenyl, and ($C_2$-$C_6$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, and ($C_1$-$C_8$)alkoxy, respectively. Exemplary alkoxy groups include, but are not limited to methoxy and ethoxy.

The term "alkyl" as used herein refers to a saturated straight or branched hydrocarbon, such as a straight or branched group of 1-22, 1-8, or 1-6 carbon atoms, referred to herein as ($C_1$-$C_{22}$)alkyl, ($C_1$-$C_8$)alkyl, and ($C_1$-$C_6$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as ($C_2$-$C_{22}$)alkynyl, ($C_2$-$C_8$)alkynyl, and ($C_2$-$C_6$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —$NR_aC(O)(R_b)$— or —$C(O)NR_bR_c$, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example $R_b$ and $R_c$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —$NR_dR_e$ or —$N(R_d)R_e$—, where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example any two of $R_d$ and $R_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of $R_d$ or $R_e$ is an alkyl group.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "$(C_6)$aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "$(C_6)$arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "$(C_6)$arylsulfonyl."

The term "benzyl" as used herein refers to the group —$CH_2$-phenyl.

The term "bicyclic aryl" as used herein refers to an aryl group fused to another aromatic or non-aromatic carbocyclic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocyclic or heterocyclic ring. Exemplary bicyclic heteroaryls include, but are not limited to 5,6- or 6,6-fused systems, wherein one or both rings contain heteroatoms. The term "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur. The bicyclic system may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary bicyclic heteroaryl's include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to the form —$R_gOC(O)N(R_h)$—, —$R_gOC(O)N(R_h)R_i$—, or —$OC(O)NR_hR_i$, wherein $R_g$, $R_h$ and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl or heteroaryl, such as pyridine, pyridazine, pyrimidine, and pyrazine).

The term "carbonyl" as used herein refers to —$C(O)$—.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —$C(O)$—COOH or salts, such as —$C(O)$—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "$(C_3-C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —$R_l$O—$R_m$—, where $R_l$ and $R_m$ can independently be alkyl, alkenyl, alkynyl, aryl, cycloalkyl, heterocyclyl, and ether. The ether can be attached to the parent molecular group through $R_l$ or $R_m$. Exemplary ethers include, but are not limited to, alkoxyalkyl and alkoxyaryl groups. Ethers also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH$_3$ or —$R_n$—C(O)—$R_o$—. The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

The term "phosphate" as used herein refers to the structure $-OP(O)O_2-$, $-R_xOP(O)O_2-$, $-OP(O)O_2R_y-$, or $-R_xOP(O)O_2R_y-$, wherein $R_x$ and $R_y$ can be alkyl, alkenyl, alkynyl, aryl, cycloalkyl, heterocyclyl, hydrogen.

The term "sulfide" as used herein refers to the structure $-R_zS-$, where $R_z$ can be alkyl, alkenyl, alkynyl, aryl, arylalkyl, cycloalkyl, haloalkyl, heteroaryl, heterocyclyl. The sulfide may be cyclic, forming a 3 to 12-membered ring. The term "alkylsulfide" as used herein refers to an alkyl group attached to a sulfur atom.

The term "sulfinyl" as used herein refers to the structure $-S(O)O-$, $-R_pS(O)O-$, $-R_pS(O)OR_q-$, or $-S(O)OR_q-$, wherein $R_p$ and $R_q$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_p$ or $R_q$ is alkyl, alkenyl, or alkynyl.

The term "sulfonamide" as used herein refers to the structure $-(R_r)-N-S(O)_2-R_s-$ or $-R_t(R_r)-N-S(O)_2-R_s$, where $R_t$, $R_r$, and $R_s$ can be, for example, hydrogen, alkyl, alkenyl, alkynyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl).

The term "sulfonate" as used herein refers to $-OSO_3-$. Sulfonate includes salts such as $-OSO_3Na$, $-OSO_3K$ and the acid $-OSO_3H$.

The term "sulfonic acid" refers to $-SO_3H-$ and its corresponding salts (e.g., $-SO_3K-$ and $-SO_3Na-$).

The term "sulfonyl" as used herein refers to the structure $R_uSO_2-$, where $R_u$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "thioketone" refers to the structure $-R_v-C(S)-R_w-$. The ketone can be attached to another group through $R_v$ or $R_w$. $R_v$ or $R_w$ can be alkyl, alkenyl, alkynyl, cycloalkyl, heterocyclyl or aryl, or $R_v$ or $R_w$ can be joined to form a 3- to 12-membered ring.

"Alkyl" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, ketone, heteroaryl, heterocyclyl, hydroxyl, nitro, phosphate, sulfide, sulfinyl, sulfonyl, sulfonic acid, sulfonamide, thioketone, ureido and N. The substituents may be branched to form a substituted or unsubstituted heterocycle or cycloalkyl.

"Alkenyl," "alkynyl", "alkoxy", "amino" and "amide" groups can be substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a "suitable substituent" refers to a group that does not nullify the synthetic or pharmaceutical utility of the compounds of the invention or the intermediates useful for preparing them. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; $-CN$; $-OH$; oxo; halo, carboxy; amino, such as $-NH(C_{1-22}, C_{1-8},$ or $C_{1-6}$ alkyl), $-N(C_{1-22}, C_{1-8},$ and $C_{1-6}$ alkyl)$_2$, $-NH((C_6)aryl)$, or $-N((C_6)aryl)_2$; formyl; ketones, such as $-CO(C_{1-22}, C_{1-8},$ and $C_{1-6}$ alkyl), $-CO((C_6$ aryl) esters, such as $-CO_2(C_{1-22}, C_{1-8},$ and $C_{1-6}$ alkyl) and $-CO_2$ ($C_6$ aryl). One of skill in art can readily choose a suitable substituent based on the stability and pharmacological and synthetic activity of the compound of the invention.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, malate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

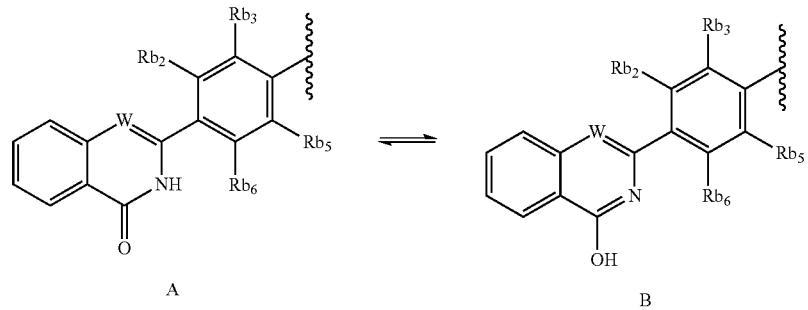

A                                              B

EXEMPLARY EMBODIMENTS

Formula I Methods and Compounds

In certain embodiments, the method for reducing IL-6 and/or VCAM-1 in a subject and the method for treating an inflammatory or cardiovascular disease comprise administering a therapeutically effective amount of at least one compound of Formula I or a stereoisomer, tautomer, pharmaceutically acceptable salt, or hydrate thereof, wherein:

Q is selected from $CRa_3$;
V is selected from N and $CRa_4$;
W is selected from N and CH;
U is C=O;
X is selected from OH, $NH_2$, $S(O)_2NH_2$, NHAc, and $NHSO_2Me$;
$Ra_1$ is selected from hydrogen and $C_1$-$C_6$ alkoxy;
$Ra_2$ is selected from hydrogen, $C_1$-$C_6$ alkoxy, amino, amide, and $C_1$-$C_6$ alkyl;
$Ra_3$ and $Ra_4$ are independently selected from hydrogen and $C_1$-$C_6$ alkoxy;
$Rb_2$ and $Rb_6$ are both hydrogen; and
$Rb_3$ and $Rb_5$ are independently selected from $C_1$-$C_6$ alkyl and halogen.

In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
Q is selected from CRa$_3$;
Ra$_3$ is selected from hydrogen, methoxy,

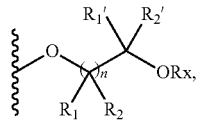

and

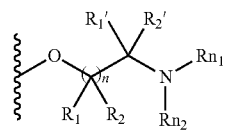

wherein
n is 0, 1, or 3;
R$_1$, R$_1$', R$_2$, and R$_2$' are independently selected from hydrogen, C$_1$-C$_3$ alkyl, cyclopropyl, and halogen wherein if n is 1, then R$_2$ and R$_2$', R$_1$ and R$_1$', R$_1$ and R$_2$', or R$_2$ and R$_1$' may form a double bond, wherein said double bond can be cis, trans, or a mixture thereof;
Rx is selected from C$_1$-C$_6$ alkyl, C$_3$-C$_6$ cycloalkyl, and aryl;
Rn$_1$ and Rn$_2$ are independently selected from C$_1$-C$_6$ alkyl, C$_3$-C$_6$ cycloalkyl, and aryl;
V is selected from N and CRa$_4$;
W is selected from N and CH;
X is selected from OH, SH, NH$_2$, S(O)H, S(O)$_2$H, S(O)$_2$NH$_2$, S(O)NH$_2$, NHAc, and NHSO$_2$Me;
Ra$_1$ and Ra$_4$ are independently selected from hydrogen, C$_1$-C$_6$ alkyl, C$_1$-C$_6$ alkoxy, C$_3$-C$_6$ cycloalkyl, and halogen;
Ra$_2$ is selected from hydrogen, C$_1$-C$_6$ alkyl, C$_1$-C$_6$ alkoxy, C$_3$-C$_6$ cycloalkyl, amino, amide, and halogen;
Rb$_2$ and Rb$_6$ are independently selected from hydrogen, methyl and fluorine;
Rb$_3$ and Rb$_5$ are independently selected from hydrogen, halogen, C$_1$-C$_6$ alkyl, C$_3$-C$_6$ cycloalkyl, and C$_1$-C$_6$ alkoxy; and
Rb$_2$ and Rb$_3$ and/or Rb$_5$ and Rb$_6$ may be connected to form a cycloalkyl or a heterocycle,
provided that at least one of Ra$_1$, R$_2$, Ra$_3$, and Ra$_4$ is not hydrogen.
In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
Ra$_3$ is selected from hydrogen, methoxy,

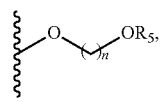

and

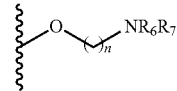

wherein
n is 1, 2, or 3;
R$_5$ is selected from C$_1$-C$_6$ alkyl substituted with one or more groups selected from methyl, phenyl, and pyridinyl;
R$_6$ and R$_7$ are independently selected from unsubstituted C$_1$-C$_6$ alkyl;
Q is selected from N and CRa$_3$;
V is selected from N and CRa$_4$;
W is selected from N and CH;
X is selected from OH, SH, NH$_2$, S(O)H, S(O)$_2$H, S(O)$_2$NH$_2$, S(O)NH$_2$, NHAc, and NHSO$_2$Me;
Ra$_1$ and Ra$_4$ are independently selected from hydrogen, C$_1$-C$_6$ alkyl, C$_1$-C$_6$ alkoxy, C$_3$-C$_6$ cycloalkyl, and halogen;
Ra$_2$ is selected from hydrogen, C$_1$-C$_6$ alkyl, C$_1$-C$_6$ alkoxy, C$_3$-C$_6$ cycloalkyl, amino, amide, and halogen;
Rb$_2$ and Rb$_6$ are independently selected from hydrogen, methyl and fluorine;
Rb$_3$ and Rb$_5$ are independently selected from hydrogen, halogen, C$_1$-C$_6$ alkyl, C$_3$-C$_6$ cycloalkyl, and C$_1$-C$_6$ alkoxy; and
Rb$_2$ and Rb$_3$ and/or Rb$_5$ and Rb$_6$ may be connected to form a cycloalkyl or a heterocycle,
provided that at least one of Ra$_1$, R$_2$, Ra$_3$, and Ra$_4$ is not hydrogen.
In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
Ra$_3$ is selected from hydrogen, methoxy, 2-methoxyethoxy, 2-dimethylamino-ethoxy, 2-benzyloxy-ethoxy, and 2-(pyridin-3-ylmethoxy)ethoxy;
Q is selected from N and CRa$_3$;
V is selected from N and CRa$_4$;
W is selected from N and CH;
X is selected from OH, SH, NH$_2$, S(O)H, S(O)$_2$H, S(O)$_2$NH$_2$, S(O)NH$_2$, NHAc, and NHSO$_2$Me;
Ra$_1$ and Ra$_4$ are independently selected from hydrogen, C$_1$-C$_6$ alkyl, C$_1$-C$_6$ alkoxy, C$_3$-C$_6$ cycloalkyl, and halogen;
Ra$_2$ is selected from hydrogen, C$_1$-C$_6$ alkyl, C$_1$-C$_6$ alkoxy, C$_3$-C$_6$ cycloalkyl, amino, amide, and halogen;
Rb$_2$ and Rb$_6$ are independently selected from hydrogen, methyl and fluorine;
Rb$_3$ and Rb$_5$ are independently selected from hydrogen, halogen, C$_1$-C$_6$ alkyl, C$_3$-C$_6$ cycloalkyl, and C$_1$-C$_6$ alkoxy; and
Rb$_2$ and Rb$_3$ and/or Rb$_5$ and Rb$_6$ may be connected to form a cycloalkyl or a heterocycle,
provided that at least one of Ra$_1$, R$_2$, Ra$_3$, and Ra$_4$ is not hydrogen.
In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
V is selected from N and CRa$_4$;

Ra$_4$ is selected from hydrogen and unsubstituted C$_1$-C$_6$ alkoxy;

Q is selected from N and CRa$_3$;

W is selected from N and CH;

X is selected from OH, SH, NH$_2$, S(O)H, S(O)$_2$H, S(O)$_2$NH$_2$, S(O)NH$_2$, NHAc, and NHSO$_2$Me;

Ra$_1$ and Ra$_3$ are independently selected from hydrogen, C$_1$-C$_6$ alkyl, C$_1$-C$_6$ alkoxy, C$_3$-C$_6$ cycloalkyl, and halogen;

Ra$_2$ is selected from hydrogen, C$_1$-C$_6$ alkyl, C$_1$-C$_6$ alkoxy, C$_3$-C$_6$ cycloalkyl, amino, amide, and halogen;

Rb$_2$ and Rb$_6$ are independently selected from hydrogen, methyl and fluorine;

Rb$_3$ and Rb$_5$ are independently selected from hydrogen, halogen, C$_1$-C$_6$ alkyl, C$_3$-C$_6$ cycloalkyl, and C$_1$-C$_6$ alkoxy; and Rb$_2$ and Rb$_3$ and/or Rb$_5$ and Rb$_6$ may be connected to form a cycloalkyl or a heterocycle, provided that at least one of Ra$_1$, R$_2$, Ra$_3$, and Ra$_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:

U is C=O;

Ra$_4$ is selected from hydrogen and methoxy;

Q is selected from N and CRa$_3$;

V is selected from N and CRa$_4$;

W is selected from N and CH;

X is selected from OH, SH, NH$_2$, S(O)H, S(O)$_2$H, S(O)$_2$NH$_2$, S(O)NH$_2$, NHAc, and NHSO$_2$Me;

Ra$_1$ and Ra$_3$ are independently selected from hydrogen, C$_1$-C$_6$ alkyl, C$_1$-C$_6$ alkoxy, C$_3$-C$_6$ cycloalkyl, and halogen;

Ra$_2$ is selected from hydrogen, C$_1$-C$_6$ alkyl, C$_1$-C$_6$ alkoxy, C$_3$-C$_6$ cycloalkyl, amino, amide, and halogen;

Rb$_2$ and Rb$_6$ are independently selected from hydrogen, methyl and fluorine;

Rb$_3$ and Rb$_5$ are independently selected from hydrogen, halogen, C$_1$-C$_6$ alkyl, C$_3$-C$_6$ cycloalkyl, and C$_1$-C$_6$ alkoxy; and Rb$_2$ and Rb$_3$ and/or Rb$_5$ and Rb$_6$ may be connected to form a cycloalkyl or a heterocycle, provided that at least one of Ra$_1$, R$_2$, Ra$_3$, and Ra$_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:

U is C=O;

X is OH;

Q is selected from N and CRa$_3$;

V is selected from N and CRa$_4$;

W is selected from N and CH;

Ra$_1$, Ra$_3$, and Ra$_4$ are independently selected from hydrogen, C$_1$-C$_6$ alkyl, C$_1$-C$_6$ alkoxy, C$_3$-C$_6$ cycloalkyl, and halogen;

Ra$_2$ is selected from hydrogen, C$_1$-C$_6$ alkyl, C$_1$-C$_6$ alkoxy, C$_3$-C$_6$ cycloalkyl, amino, amide, and halogen;

Rb$_2$ and Rb$_6$ are independently selected from hydrogen, methyl and fluorine;

Rb$_3$ and Rb$_5$ are independently selected from hydrogen, halogen, C$_1$-C$_6$ alkyl, C$_3$-C$_6$ cycloalkyl, and C$_1$-C$_6$ alkoxy; and Rb$_2$ and Rb$_3$ and/or Rb$_5$ and Rb$_6$ may be connected to form a cycloalkyl or a heterocycle, provided that at least one of Ra$_1$, R$_2$, Ra$_3$, and Ra$_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:

U is C=O;

Ra$_1$ is selected from hydrogen, methoxy,

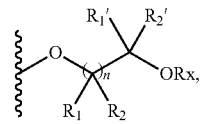

and

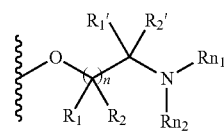

wherein n is 0, 1, or 3;

R$_1$, R$_1$', R$_2$, and R$_2$' are independently selected from hydrogen, C$_1$-C$_3$ alkyl, cyclopropyl, and halogen wherein if n is 1, then R$_2$ and R$_2$', R$_1$ and R$_1$', R$_1$ and R$_2$', or R$_2$ and R$_1$' may form a double bond, wherein said double bond can be cis, trans, or a mixture thereof;

Rx is selected from C$_1$-C$_6$ alkyl, C$_3$-C$_6$ cycloalkyl, and aryl;

Rn$_1$ and Rn$_2$ are independently selected from C$_1$-C$_6$ alkyl, C$_3$-C$_6$ cycloalkyl, and aryl;

Q is selected from N and CRa$_3$;

V is selected from N and CRa$_4$;

W is selected from N and CH;

X is selected from OH, SH, NH$_2$, S(O)H, S(O)$_2$H, S(O)$_2$NH$_2$, S(O)NH$_2$, NHAc, and NHSO$_2$Me;

Ra$_3$ and Ra$_4$ are independently selected from hydrogen, C$_1$-C$_6$ alkyl, C$_1$-C$_6$ alkoxy, C$_3$-C$_6$ cycloalkyl, and halogen;

Ra$_2$ is selected from hydrogen, C$_1$-C$_6$ alkyl, C$_1$-C$_6$ alkoxy, C$_3$-C$_6$ cycloalkyl, amino, amide, and halogen;

Rb$_2$ and Rb$_6$ are independently selected from hydrogen, methyl and fluorine;

Rb$_3$ and Rb$_5$ are independently selected from hydrogen, halogen, C$_1$-C$_6$ alkyl, C$_3$-C$_6$ cycloalkyl, and C$_1$-C$_6$ alkoxy; and Rb$_2$ and Rb$_3$ and/or Rb$_5$ and Rb$_6$ may be connected to form a cycloalkyl or a heterocycle, provided that at least one of Ra$_1$, R$_2$, Ra$_3$, and Ra$_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:

U is C=O;

Ra$_1$ is selected from hydrogen, methoxy,

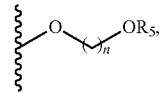

and

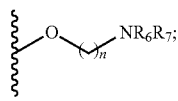

n is 1, 2, or 3;
$R_5$, $R_6$, and $R_7$ are independently selected from unsubstituted $C_1$-$C_6$ alkyl;
Q is selected from N and $CRa_3$;
V is selected from N and $CRa_4$;
W is selected from N and CH;
X is selected from OH, SH, $NH_2$, S(O)H, $S(O)_2H$, $S(O)_2NH_2$, $S(O)NH_2$, NHAc, and $NHSO_2Me$;
$Ra_3$ and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, $C_3$-$C_6$ cycloalkyl, amino, amide, and halogen;
$Rb_2$ and $Rb_6$ are independently selected from hydrogen, methyl and fluorine;
$Rb_3$ and $Rb_5$ are independently selected from hydrogen, halogen, $C_1$-$C_6$ alkyl, $C_3$-$C_6$ cycloalkyl, and $C_1$-$C_6$ alkoxy; and
$Rb_2$ and $Rb_3$ and/or $Rb_5$ and $Rb_6$ may be connected to form a cycloalkyl or a heterocycle,
provided that at least one of $Ra_1$, $R_2$, $Ra_3$, and $Ra_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
$Ra_1$ is selected from hydrogen, methoxy, 2-methoxyethoxy, and 2-dimethylamino-ethoxy;
Q is selected from N and $CRa_3$;
V is selected from N and $CRa_4$;
W is selected from N and CH;
X is selected from OH, SH, $NH_2$, S(O)H, $S(O)_2H$, $S(O)_2NH_2$, $S(O)NH_2$, NHAc, and $NHSO_2Me$;
$Ra_3$ and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, $C_3$-$C_6$ cycloalkyl, amino, amide, and halogen;
$Rb_2$ and $Rb_6$ are independently selected from hydrogen, methyl and fluorine;
$Rb_3$ and $Rb_5$ are independently selected from hydrogen, halogen, $C_1$-$C_6$ alkyl, $C_3$-$C_6$ cycloalkyl, and $C_1$-$C_6$ alkoxy; and
$Rb_2$ and $Rb_3$ and/or $Rb_5$ and $Rb_6$ may be connected to form a cycloalkyl or a heterocycle,
provided that at least one of $Ra_1$, $R_2$, $Ra_3$, and $Ra_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
$Ra_2$ is selected from hydrogen, unsubstituted $C_1$-$C_6$ alkoxy, $NHR_9$, and $C_1$-$C_6$ alkyl substituted with heterocycle or amino;
$R_9$ is selected from acyl, and heteroaryl;
Q is selected from N and $CRa_3$;
V is selected from N and $CRa_4$;
W is selected from N and CH;
X is selected from OH, SH, $NH_2$, S(O)H, $S(O)_2H$, $S(O)_2NH_2$, $S(O)NH_2$, NHAc, and $NHSO_2Me$;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, $C_3$-$C_6$ cycloalkyl, amino, amide, and halogen;
$Rb_2$ and $Rb_6$ are independently selected from hydrogen, methyl and fluorine;
$Rb_3$ and $Rb_5$ are independently selected from hydrogen, halogen, $C_1$-$C_6$ alkyl, $C_3$-$C_6$ cycloalkyl, and $C_1$-$C_6$ alkoxy; and
$Rb_2$ and $Rb_3$ and/or $Rb_5$ and $Rb_6$ may be connected to form a cycloalkyl or a heterocycle,
provided that at least one of $Ra_1$, $R_2$, $Ra_3$, and $Ra_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
$Ra_2$ is selected from hydrogen, methoxy, acetamido, morpholin-4-ylmethyl, pyridin-2-ylamino, (4-methylpiperazin-1-yl)methyl, and methanesulfonamido;
Q is selected from N and $CRa_3$;
V is selected from N and $CRa_4$;
W is selected from N and CH;
X is selected from OH, SH, $NH_2$, S(O)H, $S(O)_2H$, $S(O)_2NH_2$, $S(O)NH_2$, NHAc, and $NHSO_2Me$;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, $C_3$-$C_6$ cycloalkyl, amino, amide, and halogen;
$Rb_2$ and $Rb_6$ are independently selected from hydrogen, methyl and fluorine;
$Rb_3$ and $Rb_5$ are independently selected from hydrogen, halogen, $C_1$-$C_6$ alkyl, $C_3$-$C_6$ cycloalkyl, and $C_1$-$C_6$ alkoxy; and
$Rb_2$ and $Rb_3$ and/or $Rb_5$ and $Rb_6$ may be connected to form a cycloalkyl or a heterocycle,
provided that at least one of $Ra_1$, $R_2$, $Ra_3$, and $Ra_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:
U is C=O;
$Rb_3$ and $Rb_5$ are independently selected from unsubstituted $C_1$-$C_6$ alkyl and halogen;
Q is selected from N and $CRa_3$;
V is selected from N and $CRa_4$;
W is selected from N and CH;
X is selected from OH, SH, $NH_2$, S(O)H, $S(O)_2H$, $S(O)_2NH_2$, $S(O)NH_2$, NHAc, and $NHSO_2Me$;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, $C_3$-$C_6$ cycloalkyl, amino, amide, and halogen; and
$Rb_2$ and $Rb_6$ are independently selected from hydrogen, methyl and fluorine;

$Rb_3$ and $Rb_5$ are independently selected from hydrogen, halogen, $C_1$-$C_6$ alkyl, $C_3$-$C_6$ cycloalkyl, and $C_1$-$C_6$ alkoxy; and $Rb_2$ and $Rb_3$ and/or $Rb_5$ and $Rb_6$ may be connected to form a cycloalkyl or a heterocycle, provided that at least one of $Ra_1$, $R_2$, $Ra_3$, and $Ra_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula I, wherein:

U is C=O;

$Rb_3$ and $Rb_5$ are independently selected from methyl, tert-butyl, fluorine, and chlorine;

Q is selected from N and $CRa_3$;

V is selected from N and $CRa_4$;

W is selected from N and CH;

X is selected from OH, SH, $NH_2$, S(O)H, $S(O)_2H$, $S(O)_2NH_2$, $S(O)NH_2$, NHAc, and $NHSO_2Me$;

$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;

$Ra_2$ is selected from hydrogen, $C_1$-$C_6$ alkyl, $C_1$-$C_6$ alkoxy, $C_3$-$C_6$ cycloalkyl, amino, amide, and halogen; and $Rb_2$ and $Rb_6$ are independently selected from hydrogen, methyl and fluorine;

provided that at least one of $Ra_1$, $Ra_2$, $Ra_3$, and $Ra_4$ is not hydrogen.

In certain embodiments, the method for reducing IL-6 and/or VCAM-1 and the method for treating an inflammatory or cardiovascular disease in a subject, comprises administering a therapeutically effective amount of at least one compound selected from:

3-(3-fluoro-4-hydroxyphenyl)-5-methoxyisoquinolin-1 (2H)-one;

3-(4-hydroxy-3,5-dimethylphenyl)-6,8-dimethoxyisoquinolin-1(2H)-one;

2-(4-hydroxy-3,5-dimethylphenyl)-5,7-dimethoxyquinazolin-4(3H)-one;

7-(4-hydroxy-3,5-dimethylphenyl)-2,4-dimethoxy-1,6-naphthyridin-5(6H)-one;

2-(3,5-di-tert-butyl-4-hydroxyphenyl)-5,7-dimethoxyquinazolin-4(3H)-one;

2-(3-chloro-4-hydroxyphenyl)-5,7-dimethoxyquinazolin-4 (3H)-one;

2-(4-hydroxy-3,5-dimethylphenyl)-6,7-dimethoxyquinazolin-4(3H)-one;

N-(2-(4-hydroxy-3,5-dimethylphenyl)-4-oxo-3,4-dihydroquinazolin-6-yl)acetamide;

2-(4-hydroxy-3,5-dimethylphenyl)-6-(morpholinomethyl) quinazolin-4(3H)-one;

2-(4-hydroxy-3,5-dimethylphenyl)-5,7-dimethoxypyrido[2,3-d]pyrimidin-4(3H)-one;

2-(4-hydroxy-3,5-dimethylphenyl)-5,7-dimethoxy-6-(morpholinomethyl)quinazolin-4(3H)-one;

5-(2-dimethylamino-ethoxy)-2(4-hydroxy-3,5-dimethylphenyl)-7-methoxy-3H-quinazolin-4-one;

2-(4-hydroxy-3,5-dimethyl-phenyl)-7-methoxy-5-(2-methoxy-ethoxy)-3H-quinazolin-4-one;

7-(2-amino-ethoxy)-2-(4-hydroxy-3,5-dimethyl-phenyl)-5-methoxy-3H-quinazolin-4-one;

2-(4-hydroxy-3,5-dimethyl-phenyl)-5-methoxy-7-(2-methoxy-ethoxy)-3H-quinazolin-4-one;

7-(2-benzyloxy-ethoxy)-2-(4-hydroxy-3,5-dimethyl-phenyl)-5-methoxy-3H-quinazolin-4-one;

2-(4-hydroxy-3,5-dimethylphenyl)-5-methoxy-7-[2-(pyridin-3-ylmethoxy)ethoxy]-3H-quinazolin-4-one;

7-(2-dimethylamino-ethoxy)-2-(4-hydroxy-3,5-dimethyl-phenyl)-3H-quinazolin-4-one;

2-(4-hydroxy-3,5-dimethyl-phenyl)-6-(pyridin-4-ylamino)-3H-quinazolin-4-one;

2-(4-hydroxy-3,5-dimethyl-phenyl)-6-(pyridin-2-ylamino)-3H-quinazolin-4-one;

2-(4-hydroxy-3,5-dimethylphenyl)-6-((4-methylpiperazin-1-yl)methyl)quinazolin-4(3H)-one; and N-((2-(4-hydroxy-3,5-dimethylphenyl)-4-oxo-3,4-dihydroquinazolin-6-yl)methyl)methanesulfonamide, or a tautomer, stereoisomer, pharmaceutically acceptable salt, or hydrate thereof.

Another aspect of the invention provides compounds of Formula I selected from:

5-(2-dimethylamino-ethoxy)-2(4-hydroxy-3,5-dimethylphenyl)-7-methoxy-3H-quinazolin-4-one;

2-(4-hydroxy-3,5-dimethyl-phenyl)-7-methoxy-5-(2-methoxy-ethoxy)-3H-quinazolin-4-one;

7-(2-amino-ethoxy)-2-(4-hydroxy-3,5-dimethyl-phenyl)-5-methoxy-3H-quinazolin-4-one;

2-(4-hydroxy-3,5-dimethyl-phenyl)-5-methoxy-7-(2-methoxy-ethoxy)-3H-quinazolin-4-one;

7-(2-benzyloxy-ethoxy)-2-(4-hydroxy-3,5-dimethyl-phenyl)-5-methoxy-3H-quinazolin-4-one;

2-(4-hydroxy-3,5-dimethylphenyl)-5-methoxy-7-[2-(pyridin-3-ylmethoxy)ethoxy]-3H-quinazolin-4-one;

7-(2-dimethylamino-ethoxy)-2-(4-hydroxy-3,5-dimethyl-phenyl)-3H-quinazolin-4-one;

2-(4-hydroxy-3,5-dimethyl-phenyl)-6-(pyridin-4-ylamino)-3H-quinazolin-4-one;

2-(4-hydroxy-3,5-dimethyl-phenyl)-6-(pyridin-2-ylamino)-3H-quinazolin-4-one;

2-(4-hydroxy-3,5-dimethylphenyl)-6-((4-methylpiperazin-1-yl)methyl)quinazolin-4(3H)-one; and N-((2-(4-hydroxy-3,5-dimethylphenyl)-4-oxo-3,4-dihydroquinazolin-6-yl)methyl)methanesulfonamide, and tautomers, stereoisomers, pharmaceutically acceptable salts, and hydrates thereof.

Formula II Methods and Compounds

In certain embodiments, the method for reducing IL-6 and/or VCAM-1 and the method for treating an inflammatory or cardiovascular disease in a subject, comprises administering a therapeutically effective amount of at least one compound of Formula II or a stereoisomer, tautomer, pharmaceutically acceptable salt, or hydrate thereof, wherein:

P is $CRa_1$;

V is selected from N and $CRa_4$;

W is selected from N and CH;

U is C=O;

X is selected from O, S, $CH_2$, and NH;

$Ra_1$ is selected from hydrogen, $C_1$-$C_6$ alkyl, $C_1$-$C_6$ alkoxy, and halogen;

$Ra_2$ is selected from hydrogen, $C_1$-$C_6$ alkyl, $C_1$-$C_6$ alkoxy, heterocycle, amide, and amino;

$Ra_3$ and $Ra_4$ are independently selected from hydrogen, $C_1$-$C_6$ alkoxy, $C_1$-$C_6$ alkyl, and halogen;

$Rb_2$ and $Rb_6$ are independently selected from hydrogen, methyl, and fluoride;

$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino, wherein $Rb_2$ and $Rb_3$ and/or $Rb_5$ and $Rb_6$ may be connected to form a phenyl ring; and Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;
$Ra_1$ is selected from hydrogen, unsubstituted $C_1$-$C_6$ alkyl, unsubstituted $C_1$-$C_6$ alkoxy, and halogen;
P is selected from N and $CRa_1$;
V is selected from N and $CRa_4$;
W is selected from N and CH;
X is selected from O, S, $CH_2$, and NH;
$Ra_3$, $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O; and
$Ra_1$ is selected from hydrogen, methyl, methoxy, chlorine, and fluorine;
P is selected from N and $CRa_1$;
V is selected from N and $CRa_4$;
W is selected from N and CH;
X is selected from O, S, $CH_2$, and NH;
$Ra_3$, $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;
$Ra_2$ is selected from hydrogen, $C_1$-$C_6$ alkyl substituted with heterocyclyl, unsubstituted $C_1$-$C_6$ alkoxy, amino, and heterocycle;
P is selected from N and $CRa_1$;
V is selected from N and $CRa_4$;
W is selected from N and CH;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O; and
$Ra_2$ is selected from hydrogen, methoxy, acetamido, morpholino, morpholin-4-ylmethyl, and (4-methylpiperazin-1-yl)methyl;
P is selected from N and $CRa_1$;
V is selected from N and $CRa_4$;
W is selected from N and CH;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:
U is C=O;
$Ra_3$ is selected from selected from hydrogen, methoxy, unsubstituted $C_1$-$C_6$ alkyl, halogen, and

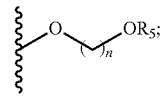

n is 1, 2, or 3;
$R_5$ is $C_1$-$C_6$ alkyl substituted with phenyl or heteroaryl;
P is selected from N and $CRa_1$;
V is selected from N and $CRa_4$;
W is selected from N and CH;
X is selected from O, S, $CH_2$, and NH;
$Ra_1$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:
U is C=O;
$Ra_3$ is selected from selected from hydrogen, methoxy, chlorine, fluorine, isopropoxy, methyl, 2-benzyloxy-ethoxy, and 2-(pyridin-3-ylmethoxy)ethoxy;
P is selected from N and $CRa_1$;
V is selected from N and $CRa_4$;
W is selected from N and CH;
X is selected from O, S, $CH_2$, and NH;
$Ra_1$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:
U is C=O;
$Ra_4$ is selected from hydrogen, unsubstituted $C_1$-$C_6$ alkoxy, and halogen;
P is selected from N and $CRa_1$;
V is selected from N and $CRa_4$;
W is selected from N and CH;
X is selected from O, S, $CH_2$, and NH;
$Ra_1$, and $Ra_3$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:
U is C=O;
$Ra_4$ is hydrogen, methoxy, and chlorine;
P is selected from N and $CRa_1$;
V is selected from N and $CRa_4$;
W is selected from N and CH;
X is selected from O, S, $CH_2$, and NH;
$Ra_1$, and $Ra_3$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;

$Rb_3$ and $Rb_5$ are independently selected from hydrogen, methyl, $C_1$-$C_6$ alkyl substituted with heterocyclyl, and unsubstituted $C_1$-$C_6$ alkoxy wherein $Rb_2$ and $Rb_3$ and/or $Rb_5$ and $Rb_6$ may be connected to form a phenyl ring;

P is selected from N and $CRa_1$;
V is selected from N and $CRa_4$;
W is selected from N and CH;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;

$Rb_3$ and $Rb_5$ are independently selected from hydrogen, methyl, methoxy, and morpholinomethyl, and wherein $Rb_2$ and $Rb_3$ and/or $Rb_5$ and $Rb_6$ may be connected to form a phenyl ring;

P is selected from N and $CRa_1$;
V is selected from N and $CRa_4$;
W is selected from N and CH;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride; and
Rd is selected from $C_1$-$C_6$ alkyl, $C_1$-$C_6$ alkoxy, and $C_3$-$C_6$ cycloalkyl, wherein Rd may be connected to $Rb_3$ or $Rb_5$ to form a heterocycle,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;

Rd is selected from $C_1$-$C_6$ alkoxy, $C_3$-$C_6$ cycloalkyl,

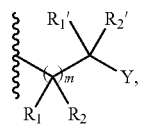

and

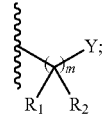

m is selected from 1, 2, or 3;
$R_1$, $R_1'$, $R_2$, and $R_2'$ are independently selected from hydrogen, fluorine, $C_1$-$C_6$ alkyl, hydroxyl, —$NH_2$, and $C_1$-$C_6$ alkoxy wherein $R_2$ and $R_2'$ may be eliminated to form a double bond;
Y is selected from OH, SH, $NH_2$, -Oalkyl, -Oaryl, —$CH_2$aryl, —C(O)NHalkyl, —C(O)N(alkyl)$_2$, —C(O)NHaryl, —NHacyl, —NHalkyl, —NHS(O)$_2$alkyl, —N(alkyl)$_2$, —NHS(O)$_2$N(alkyl)$_2$, —NHCN, and —NHC(O)N(alkyl)$_2$, —NHheterocyclyl, and heterocyclyl;
P is selected from N and $CRa_1$;
V is selected from N and $CRa_4$;
W is selected from N and CH;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
Rd may be connected to $Rb_3$ or $Rb_5$ to form a heterocycle, provided that for —N(alkyl)$_2$ the alkyl chains cannot be joined to form an aryl or heterocyclic ring.
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;

Rd is connected to $Rb_3$ or $Rb_5$ to form a heterocycle selected from substituted furanyl or substituted pyrrolyl;
P is selected from N and $CRa_1$;
V is selected from N and $CRa_4$;
W is selected from N and CH;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle;
provided that
at least one of $Ra_1$, $Ra_2$, $Ra_3$, and $Ra_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;
Rd is connected to $Rb_3$ or $Rb_5$ to form a heterocycle selected from 2-hydroxymethyl-furan-5-yl or 2-(4,5-dihydro-1H-pyrrol-2-yl)ethanol;
P is selected from N and $CRa_1$;
V is selected from N and $CRa_4$;
W is selected from N and CH;
X is selected from O, S, $CH_2$, and NH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino; and
$Rb_2$ and $Rb_3$ and/or $Rb_5$ and $Rb_6$ may be connected to form a cycloalkyl, phenyl, or heterocycle;
provided that
at least one of $Ra_1$, $Ra_2$, $Ra_3$, and $Ra_4$ is not hydrogen.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;
X—Rd is selected from 2-hydroxy-2-methylpropoxy, 2-hydroxyethoxy, methoxy, benzyloxyethoxy, 2,3-dihydroxypropoxy, aminocarbonylethoxy, methylaminocarbonylethoxy, (4-methoxyphenyl)aminocarbonylethoxy, benzylaminocarbonylethoxy, 4-hydroxybutoxy, (5-phenyl-4H-[1,2,4]triazol-3-ylamino)ethoxy, (3-methyl-[1,2,4]oxadiazol-5-ylamino)ethoxy, methylcarbonylaminoethoxy, methylcarbonylaminomethyl, (2,2,2-trifluoroethylamino)ethoxy, methanesulfonylaminoethoxy, isobutyrylaminoethoxy, methylaminoethoxy, isopropylsulfonylaminoethoxy, methylcarbonylaminoethoxy, dimethylaminoethoxy, N-(2-hydroxyethyl)-N-methylacetamide, formamide-N-2-ethoxy, methylformamide-N-2-ethoxy, dimethylsulfonylaminoethoxy, cyanoaminoethoxy, (5-methylisoxazol-3-ylamino)ethoxy, (pyrimidin-2-ylamino)ethoxy, (isoxazol-3-ylamino)ethoxy, (4,6-dimethoxypyrimidin-2-ylamino)ethoxy, 3-hydroxypropyl, and 2-hydroxyethyl;
P is selected from N and $CRa_1$;
V is selected from N and $CRa_4$;
W is selected from N and CH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine; and
if —XRd is —OMe, then $Ra_2$ is not —$CH_2$morpholino.

In some embodiments, the method for reducing IL-6 and/or VCAM-1 and the method for treating an inflammatory or cardiovascular disease in a subject, comprises administering a therapeutically effective amount of at least one compound of Formula II, wherein:

U is C=O;
X—Rd is selected from hydroxyethoxy, methylcarbonylaminoethoxy, (4-methoxyphenyl)aminocarbonylethoxy, and isobutyrylaminoethoxy; and
P is selected from N and $CRa_1$;
V is selected from N and $CRa_4$;
W is selected from N and CH;
$Ra_1$, $Ra_3$, and $Ra_4$ are independently selected from hydrogen, $C_1$-$C_6$ alkyl, $C_1$-$C_6$ alkoxy, $C_3$-$C_6$ cycloalkyl, and halogen;
$Ra_2$ is selected from hydrogen, $C_1$-$C_6$ alkyl, $C_1$-$C_6$ alkoxy, heterocycle, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl, or heterocycle; and
provided that
at least one of $Ra_1$, $Ra_2$, $Ra_3$, and $Ra_4$ is not hydrogen; and
if —XRd is —$OCH_2CH_2OH$, then $Rb_3$ is not pyrrolidine.

In certain embodiments, the method for reducing IL-6 and/or VCAM-1 and the method for treating an inflammatory or cardiovascular disease in a subject, comprises administering a therapeutically effective amount of at least one compound of Formula II, selected from:
3-(4-(2-hydroxy-2-methylpropoxy)-3,5-dimethylphenyl)-6,8-dimethoxyisoquinolin-1(2H)-one;
2-(4-(2-hydroxyethoxy)-3,5-dimethylphenyl)-5,7-dimethoxyquinazolin-4(3H)-one;
5,7-dimethoxy-2-(4-methoxyphenyl)quinazolin-4(3H)-one;
2-(4-(2-hydroxyethoxy)-3,5-dimethylphenyl)-6,7-dimethoxyquinazolin-4(3H)-one;
5,7-dimethoxy-2-(4-methoxy-3-(morpholinomethyl)phenyl)quinazolin-4(3H)-one;
2-(4-(2-hydroxyethoxy)-3,5-dimethylphenyl)-5,7-dimethoxypyrido[2,3-d]pyrimidin-4(3H)-one,
N-(2-(4-(2-hydroxyethoxy)-3,5-dimethylphenyl)-4-oxo-3,4-dihydroquinazolin-6-yl)acetamide;
2-(4-(2-hydroxyethoxy)-3,5-dimethylphenyl)-6-morpholinoquinazolin-4(3H)-one;
2-(4-(2-(benzyloxy)ethoxy)-3,5-dimethylphenyl)-5,7-dimethoxypyrido[2,3-d]pyrimidin-4(3H)-one;
2-(4-(2-hydroxyethoxy)-3,5-dimethylphenyl)-5,7-dimethylpyrido[2,3-d]pyrimidin-4(3H)-one;
5,7-difluoro-2-(4-(2-hydroxyethoxy)-3,5-dimethylphenyl)quinazolin-4(3H)-one;
5,7-dichloro-2-(4-(2-hydroxyethoxy)-3,5-dimethylphenyl)quinazolin-4(3H)-one;
2-[4-(2-hydroxy-ethoxy)-3,5-dimethyl-phenyl]-5,7-diisopropoxy-3H-quinazolin-4-one;
2-[4-(2-hydroxyethoxy)-3,5-dimethyl-phenyl]-6-morpholin-4-ylmethyl-3H-quinazolin-4-one;
2-[4-(2,3-Dihydroxy-propoxy)-3,5-dimethyl-phenyl]-5,7-dimethoxy-3H-quinazolin-4-one;
2-[4-(2-hydroxy-ethoxy)-3,5-dimethylphenyl]-5,7-dimethoxy-6-morpholin-4-ylmethyl-3H-quinazolin-4-one;

2-[4-(2-hydroxy-ethoxy)-phenyl]-5,7-dimethoxy-3H-quinazolin-4-one;
2-[4-(2-hydroxy-ethoxy)-naphthalen-1-yl]-5,7-dimethoxy-3H-quinazolin-4-one;
2-(2-hydroxymethyl-benzofuran-5-yl)-5,7-dimethoxy-3H-quinazolin-4-one;
7-(2-benzyloxy-ethoxy)-2-[4-(2-hydroxy-ethoxy)-3,5-dimethyl-phenyl]-5-methoxy-3H-quinazolin-4-one;
7-(2-benzyloxy-ethoxy)-2-(2-hydroxymethyl-benzofuran-5-yl)-5-methoxy-3H-quinazolin-4-one;
2-[4-(5,7-dimethoxy-4-oxo-3,4-dihydro-quinazolin-2-yl)-2,6-dimethyl-phenoxy]-acetamide;
2-[4-(5,7-dimethoxy-4-oxo-3,4-dihydro-quinazolin-2-yl)-2,6-dimethyl-phenoxy]-N-methyl-acetamide;
2-[4-(5,7-Dimethoxy-4-oxo-3,4-dihydro-quinazolin-2-yl)-2,6-dimethyl-phenoxy]-N-(4-methoxy-phenyl)-acetamide;
N-benzyl-2-[4-(5,7-dimethoxy-4-oxo-3,4-dihydroquinazolin-2-yl)-2,6-dimethylphenoxy]acetamide;
2-[4-(4-hydroxy-butoxy)-3,5-dimethyl-phenyl]-5,7-dimethoxy-3H-quinazolin-4-one;
2-(4-(2-hydroxyethoxy)-3,5-dimethylphenyl)-6-methoxyquinazolin-4(3H)-one;
2-(4-(2-hydroxyethoxy)-3,5-dimethylphenyl)-5-methoxyquinazolin-4(3H)-one;
7-chloro-2-(4-(2-hydroxyethoxy)-3,5-dimethylphenyl)quinazolin-4(3H)-one;
8-chloro-2-(4-(2-hydroxyethoxy)-3,5-dimethylphenyl)quinazolin-4(3H)-one;
2-(4-(2-hydroxyethoxy)-3,5-dimethylphenyl)-8-methoxyquinazolin-4(3H)-one;
5-chloro-2-(4-(2-hydroxyethoxy)-3,5-dimethylphenyl)quinazolin-4(3H)-one;
2-(4-(2-hydroxyethoxy)-3,5-dimethylphenyl)-7-methoxyquinazolin-4(3H)-one;
5,7-dimethoxy-2-(4-methoxy-3,5-dimethylphenyl)quinazolin-4(3H)-one;
2-(4-(2-hydroxyethoxy)-3-methylphenyl)-5,7-dimethoxyquinazolin-4(3H)-one;
2-(4-(2-hydroxyethoxy)-3,5-dimethylphenyl)-6-((4-methylpiperazin-1-yl)methyl)quinazolin-4(3H)-one;
5,7-Dimethoxy-2-{3-methyl-4-[2-(5-phenyl-4H-[1,2,4]triazol-3-ylamino)-ethoxy]-phenyl}-3H-quinazolin-4-one;
2-{3,5-Dimethyl-4-[2-(3-methyl-[1,2,4]oxadiazol-5-ylamino)-ethoxy]phenyl}-5,7-dimethoxy-3H-quinazolin-4-one;
N-{2-[4-(5,7-dimethoxy-4-oxo-3,4-dihydro-pyrido[2,3-d]pyrimidin-2-yl)-2,6-dimethyl-phenoxy]-ethyl}-acetamide;
N-(4-(5,7-dimethoxy-4-oxo-3,4-dihydroquinazolin-2-yl)-2,6-dimethylbenzyl)acetamide;
N-[4-(5,7-dimethoxy-4-oxo-3,4-dihydro-pyrido[2,3-d]pyrimidin-2-yl)-2,6-dimethyl-benzyl]-acetamide;
2-{3,5-Dimethyl-4-[2-(2,2,2-trifluoro-ethylamino)-ethoxy]-phenyl}-5,7-dimethoxy-3H-quinazolin-4-one;
N-{2-[4-(6,8-Dimethoxy-1-oxo-1,2-dihydro-isoquinolin-3-yl)-2,6-dimethyl-phenoxy]-ethyl}-formamide;
N-(2-(4-(5,7-dimethoxy-4-oxo-3,4-dihydroquinazolin-2-yl)-2,6-dimethylphenoxy)ethyl)methanesulfonamide;
N-(2-(4-(5,7-dimethoxy-4-oxo-3,4-dihydroquinazolin-2-yl)-2,6-dimethylphenoxy)ethyl)-4-methoxybenzamide;
N-(2-(4-(5,7-dimethoxy-4-oxo-3,4-dihydroquinazolin-2-yl)-2,6-dimethylphenoxy)ethyl)acetamide;
N-(2-(4-(5,7-dimethoxy-4-oxo-3,4-dihydroquinazolin-2-yl)-2,6-dimethylphenoxy)ethyl)isobutyramide;
2-(3,5-dimethyl-4-(2-(methylamino)ethoxy)phenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)propane-2-sulfonamide;
2-(4-(2-(isopropylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2-methylphenoxy)ethyl)acetamide;
N-(2-(4-(5,7-dimethoxy-4-oxo-3,4-dihydroquinazolin-2-yl)-2-methylphenoxy)ethyl)isobutyramide;
N-(2-(4-(5,7-dimethoxy-4-oxo-3,4-dihydroquinazolin-2-yl)-2-methylphenoxy)ethyl)methanesulfonamide;
2-(4-(2-(dimethylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)-N-methylacetamide;
N-(2-(4-(5,7-dimethoxy-4-oxo-3,4-dihydroquinazolin-2-yl)-2,6-dimethylphenoxy)ethyl)formamide;
N-(2-(4-(5,7-dimethoxy-4-oxo-3,4-dihydroquinazolin-2-yl)-2,6-dimethylphenoxy)ethyl)-N-methylformamide,
N-(2-(4-(5,7-Dimethoxy-4-oxo-3,4-dihydroquinazolin-2-yl)-2,6-dimethylphenoxy)ethyl)dimethylamino-N-sulfonamide;
N-(2-(4-(5,7-dimethoxy-4-oxo-3,4-dihydroquinazolin-2-yl)-2,6-dimethylphenoxy)ethyl)cyanamide;
2-(3,5-dimethyl-4-(2-(5-methylisoxazol-3-ylamino)ethoxy)phenyl)-5,7-dimethoxyquinazolin-4(3H)-one;
2-(3,5-dimethyl-4-(2-(pyrimidin-2-ylamino)ethoxy)phenyl)-5,7-dimethoxyquinazolin-4(3H)-one,
2-(4-(2-(isoxazol-3-ylamino)ethoxy)-3,5-dimethylphenyl)-5,7-dimethoxyquinazolin-4(3H)-one;
2-(4-(2-(4,6-dimethoxypyrimidin-2-ylamino)ethoxy)-3,5-dimethylphenyl)-5,7-dimethoxyquinazolin-4(3H)-one;
2-[4-(3-hydroxy-propyl)-3,5-dimethoxyphenyl]-5,7-dimethoxy-3H-quinazolin-4-one;
2-[4-(3-hydroxy-propyl)-3-methoxy-phenyl]-5,7-dimethoxy-3H-quinazolin-4-one; and
2-[2-(2-hydroxyethyl)-1H-indol-6-yl]-5,7-dimethoxy-3H-quinazolin-4-one, or a
tautomer, stereoisomer, pharmaceutically acceptable salt, or hydrate thereof.

Another aspect of the invention provides compounds of Formula II selected from:
2-(4-(2-hydroxyethoxy)-3,5-dimethylphenyl)-6-morpholinoquinazolin-4(3H)-one;
2-(4-(2-(benzyloxy)ethoxy)-3,5-dimethylphenyl)-5,7-dimethoxypyrido[2,3-d]pyrimidin-4(3H)-one;
2-(4-(2-hydroxyethoxy)-3,5-dimethylphenyl)-5,7-dimethylpyrido[2,3-d]pyrimidin-4(3H)-one;
5,7-difluoro-2-(4-(2-hydroxyethoxy)-3,5-dimethylphenyl)quinazolin-4(3H)-one;
2-[4-(2-hydroxy-ethoxy)-3,5-dimethyl-phenyl]-5,7-diisopropoxy-3H-quinazolin-4-one;
2-[4-(2-hydroxyethoxy)-3,5-dimethyl-phenyl]-6-morpholin-4-ylmethyl-3H-quinazolin-4-one;
2-[4-(2,3-Dihydroxy-propoxy)-3,5-dimethyl-phenyl]-5,7-dimethoxy-3H-quinazolin-4-one;
2-[4-(2-hydroxy-ethoxy)-3,5-dimethylphenyl]-5,7-dimethoxy-6-morpholin-4-ylmethyl-3H-quinazolin-4-one;
2-[4-(2-hydroxy-ethoxy)-phenyl]-5,7-dimethoxy-3H-quinazolin-4-one;
2-[4-(2-hydroxy-ethoxy)-naphthalen-1-yl]-5,7-dimethoxy-3H-quinazolin-4-one;
2-(2-hydroxymethyl-benzofuran-5-yl)-5,7-dimethoxy-3H-quinazolin-4-one;
7-(2-benzyloxy-ethoxy)-2-[4-(2-hydroxy-ethoxy)-3,5-dimethyl-phenyl]-5-methoxy-3H-quinazolin-4-one;
7-(2-benzyloxy-ethoxy)-2-(2-hydroxymethyl-benzofuran-5-yl)-5-methoxy-3H-quinazolin-4-one;

2-[4-(5,7-dimethoxy-4-oxo-3,4-dihydro-quinazolin-2-yl)-2,
6-dimethyl-phenoxy]-N-methyl-acetamide;
2-[4-(5,7-Dimethoxy-4-oxo-3,4-dihydro-quinazolin-2-yl)-
2,6-dimethyl-phenoxy]-N-(4-methoxy-phenyl)-acetamide;
N-benzyl-2-[4-(5,7-dimethoxy-4-oxo-3,4-dihydroquinazolin-2-yl)-2,6-dimethylphenoxy]acetamide,
2-[4-(4-hydroxy-butoxy)-3,5-dimethyl-phenyl]-5,7-dimethoxy-3H-quinazolin-4-one;
7-chloro-2-(4-(2-hydroxyethoxy)-3,5-dimethylphenyl)quinazolin-4(3H)-one;
8-chloro-2-(4-(2-hydroxyethoxy)-3,5-dimethylphenyl)quinazolin-4(3H)-one;
2-(4-(2-hydroxyethoxy)-3,5-dimethylphenyl)-8-methoxyquinazolin-4(3H)-one;
5-chloro-2-(4-(2-hydroxyethoxy)-3,5-dimethylphenyl)quinazolin-4(3H)-one;
2-(4-(2-hydroxyethoxy)-3,5-dimethylphenyl)-7-methoxyquinazolin-4(3H)-one;
2-(4-(2-hydroxyethoxy)-3,5-dimethylphenyl)-6-(4-methylpiperazin-1-yl)methyl)quinazolin-4(3H)-one;
5,7-Dimethoxy-2-{3-methyl-4-[2-(5-phenyl-4H-[1,2,4]triazol-3-ylamino)-ethoxy]-phenyl}-3H-quinazolin-4-one;
2-{3,5-Dimethyl-4-[2-(3-methyl-[1,2,4]oxadiazol-5-ylamino)-ethoxy]phenyl}-5,7-dimethoxy-3H-quinazolin-4-one;
N-{2-[4-(5,7-dimethoxy-4-oxo-3,4-dihydro-pyrido[2,3-d]pyrimidin-2-yl)-2,6-dimethyl-phenoxy]-ethyl}-acetamide;
N-(4-(5,7-dimethoxy-4-oxo-3,4-dihydroquinazolin-2-yl)-2,6-dimethylbenzyl)acetamide;
N-[4-(5,7-dimethoxy-4-oxo-3,4-dihydro-pyrido[2,3-d]pyrimidin-2-yl)-2,6-dimethyl-benzyl]-acetamide;
2-{3,5-Dimethyl-4-[2-(2,2,2-trifluoro-ethylamino)-ethoxy]-phenyl}-5,7-dimethoxy-3H-quinazolin-4-one;
N-{2-[4-(6,8-Dimethoxy-1-oxo-1,2-dihydro-isoquinolin-3-yl)-2,6-dimethyl-phenoxy]-ethyl}-formamide;
2-(3,5-dimethyl-4-(2-(methylamino)ethoxy)phenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)propane-2-sulfonamide;
2-(4-(2-(isopropylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2-methylphenoxy)ethyl)acetamide;
2-(4-(2-(dimethylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)-N-methylacetamide;
N-(2-(4-(5,7-dimethoxy-4-oxo-3,4-dihydroquinazolin-2-yl)-2,6-dimethylphenoxy)ethyl)formamide,
N-(2-(4-(5,7-dimethoxy-4-oxo-3,4-dihydroquinazolin-2-yl)-2,6-dimethylphenoxy)ethyl)-N-methylformamide;
N-(2-(4-(5,7-Dimethoxy-4-oxo-3,4-dihydroquinazolin-2-yl)-2,6-dimethylphenoxy)ethyl)dimethylamino-N-sulfonamide;
N-(2-(4-(5,7-dimethoxy-4-oxo-3,4-dihydroquinazolin-2-yl)-2,6-dimethylphenoxy)ethyl)cyanamide;
2-(3,5-dimethyl-4-(2-(5-methylisoxazol-3-ylamino)ethoxy)phenyl)-5,7-dimethoxyquinazolin-4(3H)-one;
2-(3,5-dimethyl-4-(2-(pyrimidin-2-ylamino)ethoxy)phenyl)-5,7-dimethoxyquinazolin-4(3H)-one;
2-(4-(2-(isoxazol-3-ylamino)ethoxy)-3,5-dimethylphenyl)-5,7-dimethoxyquinazolin-4(3H)-one;
2-(4-(2-(4,6-dimethoxypyrimidin-2-ylamino)ethoxy)-3,5-dimethylphenyl)-5,7-dimethoxyquinazolin-4(3H)-one;
2-[4-(3-hydroxy-propyl)-3,5-dimethoxyphenyl]-5,7-dimethoxy-3H-quinazolin-4-one;
2-[4-(3-hydroxy-propyl)-3-methoxy-phenyl]-5,7-dimethoxy-3H-quinazolin-4-one; and
2-[2-(2-hydroxyethyl)-1H-indol-6-yl]-5,7-dimethoxy-3H-quinazolin-4-one, and tautomers, stereoisomers, pharmaceutically acceptable salts, and hydrates thereof.

Pharmaceutical Compositions

Pharmaceutical compositions are provided comprising at least one compound of Formula I or II, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the invention as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the invention as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the invention may be prepared by any of the well known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the invention as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the invention with a liquid or finely divided solid carrier, or both, and then, if necessary, shaping the product. For example, a tablet may be prepared by compressing or molding a powder or granules of at least one compound of the invention, which may be optionally combined with one or more accessory ingredients. Compressed tablets may be prepared by compressing, in a suitable machine, at least one compound of the invention in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the invention is moistened with an inert liquid diluent.

Formulations suitable for buccal (sub-lingual) administration include lozenges comprising at least one compound of the invention in a flavored base, usually sucrose and acacia or tragacanth, and pastilles comprising the at least one compound in an inert base such as gelatin and glycerin or sucrose and acacia.

Formulations of the invention suitable for parenteral administration comprise sterile aqueous preparations of at least one compound of Formula I or II, or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the invention may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I or II, or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 μg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and Table 1 for Equivalent Surface Area Dosage Factors).

TABLE 1

Equivalent Surface Area Dosage Factors

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formula I or II, or a tautomer, stereoisomer, pharmaceutically acceptable salt or hydrate thereof, is administered in combination with another therapeutic agent. The other therapeutic agent can provide additive or synergistic value relative to the administration of a compound of the invention alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formula I, II, III, IV, V or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprenisolone (Medrol®), triamcinolone, methotrexate (Rheumatrex®, Trexall®), hydroxychloroquine (Plaquenil®), sulfasalazine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™) ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine.

Therapeutic Methods

The invention provides methods of treating or preventing cardiovascular and inflammatory diseases and related disease states, characterized by altered levels of markers of inflammation such as IL-6 and/or VCAM-1. These methods comprise administering to a subject (e.g., a mammal, such as e.g., a human) a therapeutically effective amount of at least one compound of the invention, i.e., a compound of Formula I or II, or a tautomer, stereoisomer, pharmaceutically acceptable salt or hydrate thereof. In another embodiment, at least one compound of the invention may be administered as a pharmaceutically acceptable composition, comprising one or more compounds of Formula I or II and a pharmaceutically acceptable carrier.

In one embodiment, the inflammatory diseases and related disease states are those where inhibition of IL-6 and/or VCAM-1 is desirable.

In some embodiments, the methods of the invention comprise administering at least one compound of Formula I or Formula II to a subject, such as a human, as a preventative measure against cardiovascular and inflammatory diseases and related disease states, such as, for example, atherosclerosis, asthma, arthritis, cancer, multiple sclerosis, psoriasis, and inflammatory bowel diseases, and autoimmune disease(s).

In one embodiment, at least one compound of Formula I or Formula II is administered as a preventative measure to a subject, such as a human, having a genetic predisposition to cardiovascular and inflammatory diseases and related disease states, such as, for example, familial hypercholesterolemia, familial combined hyperlipidemia, atherosclerosis, a dyslipidemia, a dyslipoproteinemia, arthritis, cancer, multiple sclerosis, or Alzheimer's disease.

In another embodiment, at least one compound of Formula I or Formula II is administered as a preventative measure to a subject, such as a human, having a non-genetic predisposition to a disease including a cardiovascular disease or an inflammatory disorder. Examples of such non-genetic predispositions include cardiac bypass surgery and PTCA (which can lead to restenosis), an accelerated form of atherosclerosis, diabetes in women, (which can lead to polycystic ovarian disease), and cardiovascular disease (which can lead to impotence). Accordingly, compositions of the invention may be used for the prevention of one disease or disorder and concurrently treating another (e.g., prevention of polycystic ovarian disease while treating diabetes; prevention of impotence while treating a cardiovascular disease).

Angioplasty and open heart surgery, such as coronary bypass surgery, may be required to treat cardiovascular diseases, such as atherosclerosis. These surgical procedures entail using invasive surgical devices and/or implants, and are associated with a high risk of restenosis and thrombosis. Accordingly, the compounds of Formula I or Formula II may be used as coatings on surgical devices (e.g., catheters) and implants (e.g., stents) to reduce the risk of restenosis and thrombosis associated with invasive procedures used in the treatment of cardiovascular diseases.

In another embodiment, the compounds of Formula I or Formula II may be used for the prevention of one disease or disorder while concurrently treating another (e.g., prevention of polycystic ovarian disease while treating diabetes; prevention of impotence while treating a cardiovascular disease).

EXAMPLES

The invention is further illustrated by the following non-limiting examples, wherein the following abbreviations have the following meanings. If an abbreviation is not defined, it has its generally accepted meaning.

AcOH=acetic acid
BINAP=2,2'-bis(diphenylphosphino)-1,1'-binaphthyl
Boc=N-tert-butoxycarbonyl
TBDMS=tert-butyldimethylsilyl
dba=dibenzylidene acetone
DCM=dichloromethane
DMAP=dimethylaminopyridine
DMF=dimethylformamide
DMSO=dimethylsulfoxide
EDCI=1-ethyl-3-(3'-dimethylaminopropyl)carbodiimide
EtOH=ethanol
EtOAc=ethyl acetate
IBX=2-Iodoxybenzoic acid
MeOH=methanol
HOBt=N-hydroxybenzotriazole
THF=tetrahydrofuran
TEA=triethylamine
p-TSA=p-toluenesulfonic acid
TBAF=tetrabutylammonium fluoride
DMA=N,N-dimethylacetamide
DIBAL-H=diisobutylaluminum hydride
TPAP=tetrapropylammonium perruthenate
NMO=N-methylmorpholine N-oxide
DDQ=2,3-dicyano-5,6-dichloro-parabenzoquinone
DME=1,2-dimethoxyethane
TFA=trifluoroacetic acid
DPPF=1,1'-bis(diphenylphosphino)ferrocene
Pd(OAc)$_2$=palladium(II) acetate
Pd(PPh$_3$)$_4$=tetrakis(triphenylphosphine)palladium(0)

Example 1. Preparation of 5-(2-dimethylaminoethoxy)-2(4-hydroxy-3,5-dimethylphenyl)-7-methoxy-3H-quinazolin-4-one

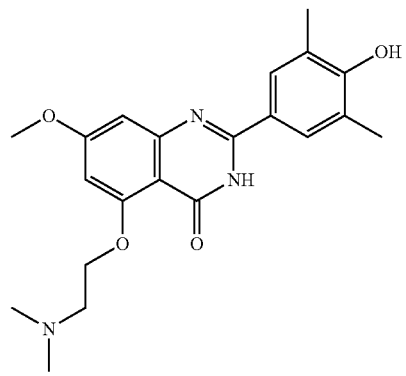

To a solution of 3,5-dimethyl-4-hydroxybenzaldehyde (10.0 g, 66.6 mmol) in anhydrous DMF (20 mL) was added NaH (4.00 g, 99.9 mmol) in portions and the mixture was stirred for 1 hour at room temperature. Benzyl bromide (9.5 mL, 80 mmol) was added dropwise and stirred for 16 hours at room temperature. Water was added, the mixture was acidified with acetic acid to pH approximately 4-5, and the product was isolated by extraction with ethyl acetate. The solvent was evaporated in vacuo and the residue was purified by column chromatography (silica gel 230-400 mesh; 2-5% ethyl acetate/hexane as eluent) to give 4-benzyloxy-3,5-dimethyl-benzaldehyde as white solid. Yield: 15.2 g (95%).

A mixture of 2-amino-4,6-difluorobenzamide (2.13 g, 12.4 mmol), 4-benzyloxy-3,5-dimethylbenzaldehyde (2.98 g, 12.4 mmol), NaHSO$_3$ (2.50 g, 13.6 mmol) and p-toluene sulfonic acid (0.236 g, 1.24 mmol) in N,N-dimethylacetamide (20 mL) was stirred at 110-120° C. for 16 hours. The solvent was evaporated in vacuo, water was added and the precipitated solid was filtered off, washed with water and ether to give 2-(4-benzyloxy-3,5-dimethylphenyl)-5,7-difluoro-3H-quinazolin-4-one as a light yellow solid. Yield: 1.99 g (41%).

To a solution of 2-dimethylaminoethanol (180 mg, 2.03 mmol) in DMF (2 mL) was added NaH (61 mg, 1.5 mmol) at 0° C. The reaction mixture was stirred at room temperature for 30 minutes. Then, 2-(4-benzyloxy-3,5-dimethylphenyl)-5,7-difluoro-3H-quinazolin-4-one (200 mg, 0.510 mmol) was added and the reaction mixture was stirred at room temperature for 16 hours. The reaction mixture was diluted with water and extracted with ethyl acetate. The combined organic layers were washed with water, brine, dried over Na$_2$SO$_4$, and concentrated in vacuo to give product 2-(4-benzyloxy-3,5-dimethyl phenyl)-5-(2-dimethylamino-ethoxy)-7-fluoro-3H-quinazolin-4-one. Yield: 220 mg (93%).

To a solution of 2-(4-benzyloxy-3,5-dimethylphenyl)-5-(2-dimethylaminoethoxy)-7-fluoro-3H-quinazolin-4-one (220 mg, 0.470 mmol) in DMF (3 mL) was added 25% (w/w) sodium methoxide in methanol (205 mg, 3.81 mmol). The reaction mixture was heated at 95° C. for 4 hours. The reaction mixture was cooled to the room temperature, diluted with water, and extracted with ethyl acetate. The combined organic layer was washed with water, brine, dried over anhydrous Na$_2$SO$_4$, and concentrated in vacuo to give crude product, which was purified by column chromatography (silica gel 230-400 mesh; 5% NH$_3$ in methanol/CH$_2$Cl$_2$ as eluent) to give pure product 2-(4-benzyloxy-3,5-dimethylphenyl)-5-(2-dimethylamino-ethoxy)-7-methoxy-3H-quinazolin-4-one. Yield: 110 mg (49%).

To a solution of 2-(4-benzyloxy-3,5-dimethylphenyl)-5-(2-dimethylaminoethoxy)-7-methoxy-3H-quinazolin-4-one (110 mg, 0.23 mmol) in methanol (5 mL) and THF (5 mL) was added Pd/C (50 mg, 10% on charcoal). The reaction mixture was hydrogenated for 2 hours at 50 psi at room temperature. The mixture was filtered through celite and solvent was evaporated in vacuo to give crude product, which was purified by column chromatography (silica gel 230-400 mesh; 5% NH$_3$ in methanol/CH$_2$Cl$_2$ as eluent) to give the title compound as a light brown solid. Yield: 70 mg (78%). $^1$H NMR (400 MHz, CDCl$_3$): δ 7.58 (s, 2H), 6.80 (s, 1H), 6.40 (s, 1H), 4.20 (t, 2H), 3.90 (s, 3H), 2.90 (t, 2H), 2.40 (s, 3H), 2.25 (s, 3H). MS (ES$^+$) m/z: 384.09 (M+1).

Example 2. Preparation of 2-(4-hydroxy-3,5-dimethyl-phenyl)-7-methoxy-5-(2-methoxy-ethoxy)-3H-quinazolin-4-one

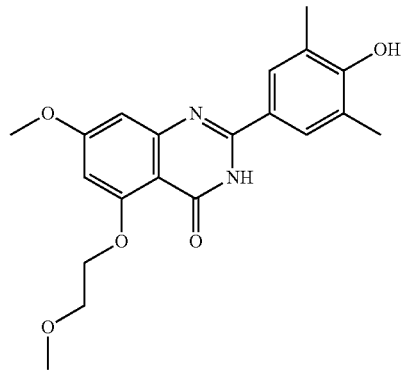

To a solution of 2-methoxy-ethanol (2 mL) in anhydrous DMF (2 mL) was added NaH (0.276 g, 6.90 mmol) in portions at 0° C. The reaction mixture was allowed to warm to room temperature and stirred for 30 minutes. The compound 2-(4-benzyloxy-3,5-dimethyl-phenyl)-5,7-difluoro-3H-quinazolin-4-one (0.25 g, 0.64 mmol) was added and the reaction mixture was stirred at room temperature for 16 hours. Water was added and the mixture was acidified with acetic acid to pH approximately 4-5. The precipitated solid was filtered off and washed with water and dried over anhydrous Na$_2$SO$_4$ to give 2-(4-benzyloxy-3,5-dimethyl-phenyl)-7-fluoro-5-(2-methoxy-ethoxy)-3H-quinazolin-4-one as a white solid. Yield: 0.28 g (98%).

To a solution of 2-(4-benzyloxy-3,5-dimethyl-phenyl)-7-fluoro-5-(2-methoxy-ethoxy)-3H-quinazolin-4-one (0.28 g, 0.62 mmol) in anhydrous DMF (3 mL) was added a 25% solution of sodium methoxide in methanol (1.5 mL, 7.0 mmol) and the reaction mixture was heated to 80-90° C. for 6 hours. Water was added and the mixture was acidified with acetic acid, to pH approximately 4-5. The precipitated solid was filtered off and purified by column chromatography (silica gel 230-400 mesh; 20-50% ethyl acetate/CH$_2$Cl$_2$ as eluent) to give 2-(4-benzyloxy-3,5-dimethyl-phenyl)-7-methoxy-5-(2-methoxy-ethoxy)-3H-quinazolin-4-one as a white solid. Yield: 0.1 g (35%).

The compound 2-(4-benzyloxy-3,5-dimethyl-phenyl)-7-methoxy-5-(2-methoxy-ethoxy)-3H-quinazolin-4-one (0.1 g, 0.22 mmol) was hydrogenated in THF/methanol (20/20 mL) at room temperature using Pd/C (10 wt %, 0.05 g) for 4 hours. After filtering through celite, the solvent was evaporated in vacuo and the crude material was purified by column chromatography (silica gel 230-400 mesh; 20-50% ethyl acetate/CH$_2$Cl$_2$ as eluent) to give the title compound as a white solid. Yield: 0.05 g (61.7%). $^1$H NMR (400 MHz, DMSO-d$_6$): δ 7.81 (s, 2H), 6.70 (s, 1H), 6.51 (s, 1H), 4.19 (t, 2H), 3.87 (s, 3H), 3.70 (t, 2H), 3.40 (s, 3H), 2.21 (s, 6H). MS (ES$^+$) m/z: 371.11 (M+1).

Example 3. Preparation of 7-(2-amino-ethoxy)-2-(4-hydroxy-3,5-dimethyl-phenyl)-5-methoxy-3H-quinazolin-4-one

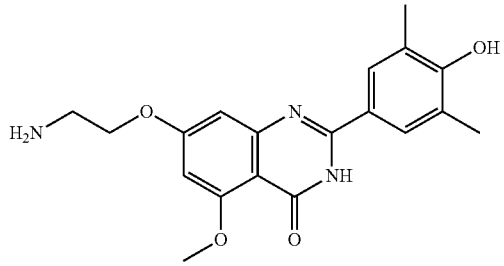 [SMILES: COc1cc(OCCN)cc2nc(-c3cc(C)c(O)c(C)c3)[nH]c(=O)c12]

To a solution of 2-amino-4,6-difluoro-benzamide (0.400 g, 2.32 mmol) and 4-benzyloxy-3,5-dimethylbenzaldehyde (0.560 g, 2.32 mmol) in N,N-dimethylacetamide (5 mL) were added NaHSO$_3$ (0.450 g, 2.55 mmol) and p-TSA (44 mg, 0.23 mmol) and the reaction mixture was heated at 115-120° C. for 16 hours. The reaction mixture was cooled to room temperature. N,N-Dimethylacetamide was removed under reduced pressure. The residue was diluted with water and the solid was collected and mixed and stirred for 0.5 hours with methanol (20 mL). The solid was filtered to give 2-(4-benzyloxy-3,5-dimethylphenyl)-5,7-difluoro-3H-quinazolin-4-one. Yield: 0.41 g (45%).

A solution of 2-(4-benzyloxy-3,5-dimethyl-phenyl)-5,7-difluoro-3H-quinazolin-4-one (0.39 g, 1.0 mmol) and 25% sodium methoxide in methanol (0.70 g, 3.2 mmol) in DMF (1.5 mL) was stirred at room temperature for 16 hours. Acetic acid (1.0 mL) was added and the mixture was poured into water (20 mL) and stirred for 0.5 hours. The solid was filtered and further rinsed with water (30 mL), and dried to give 2-(4-benzyloxy-3,5-dimethyl-phenyl)-7-fluoro-5-methoxy-3H-quinazolin-4-one. Yield: 0.39 g (92%).

To a solution of 2-(4-benzyloxy-3,5-dimethyl-phenyl)-7-fluoro-5-methoxy-3H-quinazolin-4-one (0.390 g, 0.960 mmol) and 2-dimethylamine-ethanol (0.258 g, 2.89 mmol) in DMF (1.5 mL) was added sodium hydride (0.135 g, 2.97 mmol). The reaction mixture was kept at 80° C. for 16 hours and then poured into water (20 mL). The aqueous layer was adjusted to pH 9.0, and extracted with dichloromethane. The crude product was purified by column chromatography on silica gel (230-400 mesh) using 10% methanol in dichloromethane with 1% triethylamine as eluent to give 7-(2-amino-ethoxy)-2-(4-benzyloxy-3,5-dimethyl-phenyl)-5-methoxy-3H-quinazolin-4-one. Yield: 0.25 g (58%).

To a solution of 7-(2-amino-ethoxy)-2-(4-benzyloxy-3,5-dimethyl-phenyl)-5-methoxy-3H-quinazolin-4-one (0.25 g, 0.56 mmol) in methanol (15 mL) was added 10% palladium charcoal wet (0.17 g) and the reaction mixture was subjected to hydrogenation under hydrogen balloon at room temperature for 16 hours. The catalyst was filtered through celite and methanol was removed. The resulting material was further washed with an ethyl acetate and ether mixture (20 mL/20 mL) to give the title compound. Yield: 0.13 g (75%). $^1$H NMR (400 Hz, DMSO-d$_6$): δ 11.70 (s, 1H), 8.98 (s, 1H), 7.83 (s, 2H), 6.78 (s, 1H), 6.48 (s, 1H), 4.25 (t, 2H), 3.82 (s, 3H), 2.81 (t, 2H), 2.35 (s, 6H), 2.24 (s, 6H). MS (ES$^+$) m/z: 384.14 (M+1).

Example 4. Preparation of 2-(4-hydroxy-3,5-dimethyl-phenyl)-5-methoxy-7-(2-methoxy-ethoxy)-3H-quinazolin-4-one

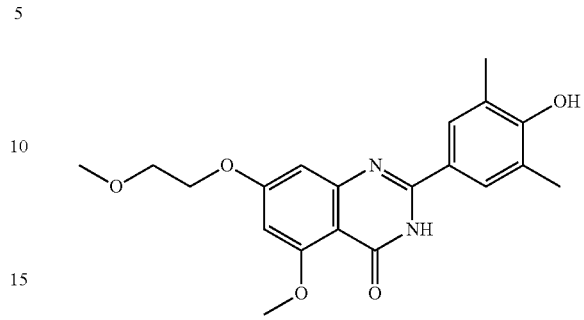

Sodium hydride (0.340 g, 8.62 mmol) was taken in anhydrous DMF (5 mL). Anhydrous 2-methoxy-ethanol (1.64 g, 21.6 mmol) was added dropwise at 0° C. under nitrogen over a period of 15 minutes. Stirring was continued at 0° C. for 5 minutes. The ice-bath was removed and stirring continued at room temperature for 10 minutes. Then, 2-(4-benzyloxy-3,5-dimethyl-phenyl)-7-fluoro-5-methoxy-3H-quinazolin-4-one (0.436 g, 1.08 mmol) was added. The color changed to green and stirring continued at 100° C. for 4 hours (progress of the reaction was monitored by TLC). The reaction mixture was cooled to room temperature, then quenched with glacial acetic acid (2 mL). Water (75 mL) was added. A white precipitate formed, which was filtered, washed with water, and dried under vacuum. Crude compound was purified by column chromatography (silica gel 230-400 mesh; 0-3% methanol in CH$_2$Cl$_2$ as eluent) to give 2-(4-benzyloxy-3,5-dimethyl-phenyl)-5-methoxy-7-(2-methoxy-ethoxy)-3H-quinazolin-4-one as a white solid. Yield: 0.09 g (18%).

To a solution of 2-(4-benzyloxy-3,5-dimethyl-phenyl)-5-methoxy-7-(2-methoxy-ethoxy)-3H-quinazolin-4-one (0.083 g, 0.18 mmol) in methanol (15 mL) and THF (5 mL) was added palladium on charcoal (75 mg). The reaction mixture was hydrogenated at 50 psi for 16 hours at room temperature then filtered through celite. The filtrate was concentrated under reduced pressure and the crude compound was purified by preparative HPLC to give the title compound as a white solid. Yield: 0.043 g (45%). $^1$H NMR (400 MHz, CDCl$_3$): δ 7.80 (s, 2H), 7.00 (s, 1H), 6.52 (s, 1H), 4.20 (m, 2H), 3.80 (m, 5H), 3.48 (s, 3H), 2.22 (s, 6H).

Example 5. Preparation of 7-(2-benzyloxy-ethoxy)-2-(4-hydroxy-3,5-dimethyl-phenyl)-5-methoxy-3H-quinazolin-4-one

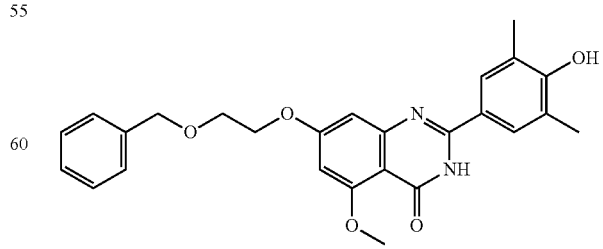

To a suspension of sodium hydride (2.00 g, 50.0 mmol) in anhydrous DMF (30 mL) at 0° C. was added a solution of 4-hydroxy-3,5-dimethyl-benzaldehyde (5.00 g, 33.3 mmol) in anhydrous DMF (20 mL), dropwise over a period of 30 minutes, under nitrogen. Stirring continued at room temperature for 30 minutes and the mixture was cooled to 0° C. Chloromethoxymethane (5.06 mL, 66.6 mmol) was added and the reaction mixture was stirred at room temperature for 16 hours under nitrogen. The reaction mixture was poured into water (200 mL), extracted with ethyl acetate (2×50 mL), dried over anhydrous Na$_2$SO$_4$, and concentrated. The crude compound was purified by column chromatography (SiO$_2$, ethyl acetate/hexanes=1:3) to afford 4-methoxymethoxy-3,5-dimethyl-benzaldehyde as colorless oil. Yield: 5.97 g (92%).

To a solution of 4-methoxymethoxy-3,5-dimethyl-benzaldehyde (4.00 g, 20.6 mmol) and 2-amino-4,6-difluoro-benzamide (3.55 g, 20.6 mmol) in N,N-dimethylacetamide (20 mL) were added sodium hydrogen sulfite (58.5 wt %) (5.45 g, 30.9 mmol) and p-toluenesulfonic acid (0.20 g, 1.0 mmol). The reaction mixture was stirred at 120° C. for 16 hours under nitrogen and cooled to room temperature. The solvent was evaporated under reduced pressure. Methanol (50 mL) and water (200 mL) were added, the separated solid was filtered, washed with water (30 mL), methanol (30 mL), hexanes (100 mL), and dried under vacuum, to afford 5,7-difluoro-2-(4-methoxymethoxy-3,5-dimethyl-phenyl)-3H-quinazolin-4-one as a white solid. Yield: 1.40 g (20%).

To a solution of 5,7-difluoro-2-(4-methoxymethoxy-3,5-dimethyl-phenyl)-3H-quinazolin-4-one (1.40 g, 4.04 mmol) in anhydrous DMF (20 mL) was added a solution of sodium methoxide in methanol (25 wt %, 5.0 mL, 24 mmol). The reaction mixture was stirred at room temperature for 16 hours under nitrogen, diluted with water (100 mL), extracted with ethyl acetate, dried over sodium sulfate, and concentrated on a rotary evaporator to afford 7-fluoro-5-methoxy-2-(4-methoxymethoxy-3,5-dimethyl-phenyl)-3H-quinazolin-4-one as a white solid. Yield: 1.1 g (76%).

To a suspension of sodium hydride (0.176 g, 4.40 mmol) in anhydrous DMF (20 mL) was added benzyloxyethanol (1.02 g, 6.70 mmol) at room temperature under nitrogen. The reaction mixture was stirred 60° C. for 30 minutes to get a clear solution. Then, 7-fluoro-5-methoxy-2-(4-methoxymethoxy-3,5-dimethyl-phenyl)-3H-quinazolin-4-one (0.200 g, 0.559 mmol) was added and the reaction mixture was stirred at 105° C. for 16 hours under nitrogen. The reaction was diluted with water (100 mL), extracted with ethyl acetate (100 mL), and concentrated on a rotary evaporator. The oily residue was subjected to column chromatography (SiO$_2$, hexanes/ethyl acetate/methanol=6:2:1) to afford a mixture of two components of very similar polarity. The mixture was dissolved in 50% aqueous acetic acid (60 mL) and mixed with concentrated HCl (3 mL). The resulting mixture was stirred at 70° C. for 1 hour and concentrated to dryness on a rotary evaporator. The residue was diluted with saturated sodium bicarbonate aqueous solution (50 mL), extracted with ethyl acetate (150 mL), and concentrated. The residue was purified by column chromatography (SiO$_2$, hexanes/ethyl acetate/methanol=7:2:1) to afford the title compound as a light yellow solid. Yield: 45 mg (18%). $^1$H NMR (400 MHz, CDCl$_3$): δ 9.68 (br s, 1H), 7.69 (s, 2H), 7.40-7.30 (m, 5H), 6.79 (d, 1H), 6.50 (d, 1H), 4.66 (s, 2H), 4.27 (t, 2H), 3.96 (s, 3H), 3.88 (t, 2H), 2.33 (s, 6H). MS (ES$^+$) m/z: 447.59 (M+1).

Example 6. Preparation of 2-(4-hydroxy-3,5-dimethylphenyl)-5-methoxy-7-[2-(pyridin-3-ylmethoxy)ethoxy]-3H-quinazolin-4-one

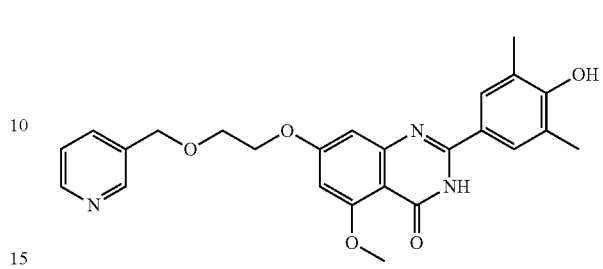

To a stirred solution of 5,7-difluoro-2-(4-methoxymethoxy-3,5-dimethylphenyl)-3H-quinazolin-4-one (1.04 g, 3.00 mmol) in anhydrous DMF (10 mL) was added a solution of sodium methoxide (25 wt %) in methanol (3.9 mL, 18.0 mmol) at room temperature. The reaction mixture was stirred at room temperature for 16 hours under nitrogen. Water (100 mL) was added, the white precipitated solid was filtered off, washed with water and dried under vacuum. The solid was further washed with 10% methanol in ether (20 mL), then ether (20 mL), and dried under vacuum. Yield 0.95 g (88%).

Sodium hydride (60% in mineral oil; 1.00 g, 25.0 mmol) was added slowly to ethylene glycol (1.48 g, 239 mmol), cooled to 0° C. under nitrogen. The cooling bath was removed, and the mixture was stirred for a further 15 minutes at room temperature, before 3-(bromomethyl)pyridine hydrobromide (2.53 g, 10.0 mmol) was added. Then, the mixture was stirred at room temperature for 2.5 days. Water was added, the mixture was extracted with EtOAc (5×100 mL), the extracts were washed with brine, dried over anhydrous Na$_2$SO$_4$, and concentrated under vacuum. Purification by column chromatography on silica gel, with CH$_2$Cl$_2$/MeOH (95:5) as the eluent, gave 2-(pyridin-3-ylmethoxy)-ethanol as a colorless liquid. Yield 0.90 g, 59%.

To a solution of 7-fluoro-5-methoxy-2-(4-methoxymethoxy-3,5-dimethyl-phenyl)-3H-quinazolin-4-one (0.30 g, 0.86 mmol) and 2-(pyridin-3-ylmethoxy)ethanol (0.20 g, 1.3 mmol) in DMF (2.0 mL), was added sodium hydride (60% in mineral oil) (0.30 g, 6.9 mmol). The mixture was stirred at room temperature under nitrogen for 3 h, then in an oil bath at 95° C. for 2.5 days. The mixture was concentrated under vacuum, water (approximately 50 mL) was added, and the mixture extracted with dichloromethane (3×50 mL). The dichloromethane solution was dried over anhydrous Na$_2$SO$_4$, concentrated under vacuum, and purified by column chromatography on silica gel, with CH$_2$Cl$_2$/MeOH (95:5) as eluent, to give 5-methoxy-2-(4-methoxymethoxy-3,5-dimethylphenyl)-7-[2-(pyridin-3-ylmethoxy)-ethoxy]-3H-quinazolin-4-one. Yield 150 mg (35%).

To a solution of 5-methoxy-2-(4-methoxymethoxy-3,5-dimethylphenyl)-7-[2-(pyridin-3-ylmethoxy)ethoxy]-3H-quinazolin-4-one (0.10 g, 0.20 mmol) in acetic acid (10 mL) and water (10 mL), sulphuric acid (0.5 mL) was added. The solution was stirred in a 75° C. oil bath for 5 hours. The mixture was then concentrated under reduced pressure. The residue was dissolved in methanol, and 2 M Na$_2$CO$_3$ was added until the pH reached 8. The mixture was concentrated under reduced pressure. The resulting precipitate was filtered, washed with water, and dried in air. The precipitate was washed further with methanol to give the title compound. Yield: 67 mg (74%). ¹H NMR (400 MHz, DMSO-$d_6$): δ 11.69 (s, 1H), 8.95 (s, 1H), 8.59 (s, 1H), 8.51 (d, J=3.2 Hz, 1H), 7.84 (s, 2H), 7.79 (dt, J=7.6 and 2.0 Hz, 1H), 7.41-7.38 (m, 1H), 6.72 (d, J=2.0 Hz, 1H), 6.49 (d, J=2.4 Hz, 1H), 4.63 (s, 2H), 4.30 (m, 2H), 3.86 (m, 2H), 3.83 (s, 3H), 2.23 (s, 6H). MS (ES) m/z: 446.52 (M−1).

Example 7. Preparation of 7-(2-dimethylamino-ethoxy)-2-(4-hydroxy-3,5-dimethylphenyl)-3H-quinazolin-4-one

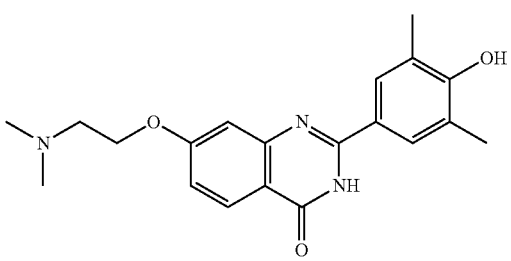

To a solution of 2-amino-4-fluoro-benzamide (0.77 g, 5.00 mmol) and 4-benzyloxy-3,5-dimethyl-benzaldehyde (1.20 g, 5.00 mmol) in N,N-dimethyl acetamide (20 mL) were added sodium hydrogen sulfite (58.5 wt %, 1.10 g, 6.00 mmol) and p-toluenesulfonic acid monohydrate (0.19 g, 1.00 mmol). The reaction mixture was stirred at 120° C. for 16 hours under nitrogen, and then cooled to room temperature. Solvent was evaporated under reduced pressure, and water (100 mL) was added. The separated solid was filtered, washed with water (50 mL), and dried under vacuum to give a white solid. Yield: 0.74 g (39%).

Sodium hydride (60% suspension in mineral oil; 0.36 g, 9.00 mmol) was taken in anhydrous DMF (20 mL). Then, 2-dimethylamino-ethanol (1.07 g, 12.0 mmol) was added drop-wise at room temperature under nitrogen. After the addition, the reaction mixture was stirred at room temperature for 20 minutes. Then, 2-(4-benzyloxy-3,5-dimethylphenyl)-7-fluoro-3H-quinazolin-4-one (0.56 g, 1.50 mmol) was added and the reaction mixture was stirred at 80° C. for 16 hours. The reaction mixture was cooled to room temperature. Water (100 mL) was added and the mixture was neutralized to pH approximately 8 with aqueous 2 N HCl. The separated solid was filtered, washed with water, and dried under vacuum. The crude compound was purified by the Simpliflash system (0-5% methanol in $CH_2Cl_2$ and 7 N ammonia in methanol 5% in $CH_2Cl_2$ as eluent) to give 2-(4-benzyloxy-3,5-dimethylphenyl)-7-(2-dimethylamino-ethoxy)-3H-quinazolin-4-one as a white solid. Yield: 0.32 g (48%).

2-(4-Benzyloxy-3,5-dimethylphenyl)-7-(2-dimethyl-amino-ethoxy)-3H-quinazolin-4-one (0.30 g, 11.2 mmol) was dissolved in a mixture of methanol and THF (1:1, 60 mL). Palladium on carbon (10 wt %, 0.20 g) was added and the reaction mixture was hydrogenated at 45 psi for 6 hours. The reaction mixture was filtered, and the filtrate was concentrated. The residue was washed with 10% methanol in ether, then ether, and dried under vacuum to give the title compound as a white solid. Yield: 0.18 g (75%). ¹H NMR (400 MHz, DMSO-$d_6$): δ 11.98 (br s, 1H), 8.94 (br s, 1H), 7.99 (d, J=8.59 Hz, 1H), 7.86 (s, 2H), 7.13 (s, 1H), 7.01 (d, J=8.98 Hz, 1H), 4.21 (t, J=5.46 Hz, 2H), 2.68 (t, J=5.27 Hz, 2H), 2.24 (s, 12H). MS (ES+) m/z 354.16 (100%).

Example 8. Preparation of 2-(4-hydroxy-3,5-dimethyl-phenyl)-6-(pyridin-4-ylamino)-3H-quinazolin-4-one

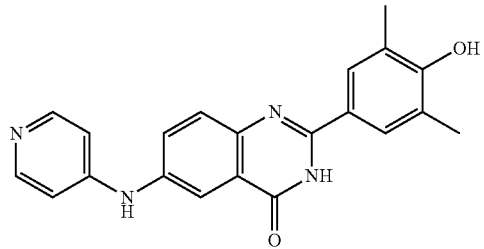 [SMILES: Cc1cc(-c2nc3ccc(Nc4ccncc4)cc3c(=O)[nH]2)cc(C)c1O]

To a solution of 6-amino-2-(4-hydroxy-3,5-dimethyl-phenyl)-3H-quinazolin-4-one (300 mg, 1.07 mmol) in pyridine (3 mL), were added 4-bromopyridinium hydrochloride (207 mg, 1.07 mmol), $Pd_2(dba)_3$ (19 mg, 0.02 mmol), dppf (18 mg, 0.03 mmol) and NaO-t-Bu (328 mg, 3.41 mmol). The reaction mixture was heated at 140° C. for 1 hour in a microwave oven. Solvent was removed under reduced pressure. The crude compound was purified by the Simpliflash system (5% 7 N ammonia in methanol and dichloromethane as eluent) to give the title compound as a yellow solid. Yield: 58 mg (15%). ¹H NMR (400 MHz, DMSO-$d_6$): δ 12.13 (s, 1H), 9.16 (s, 1H), 8.92 (s, 1H), 8.25 (br s, 2H), 7.84 (d, J=2.0 Hz, 1H), 7.81 (s, 2H), 7.65 (m, 2H), 6.99 (d, J=5.2 Hz, 2H), 2.22 (s, 6H). MS (ES) m/z: 359.26 (M+1) (100%).

Example 9. Preparation of 2-(4-hydroxy-3,5-dimethyl-phenyl)-6-(pyridin-2-ylamino)-3H-quinazolin-4-one

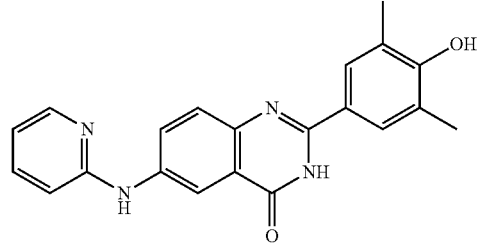 [SMILES: Cc1cc(-c2nc3ccc(Nc4ccccn4)cc3c(=O)[nH]2)cc(C)c1O]

To a solution of 6-amino-2-(4-hydroxy-3,5-dimethyl-phenyl)-3H-quinazolin-4-one (300 mg, 1.07 mmol) in pyridine (3.5 mL), were added 2-bromopyridine (202 mg, 1.28 mmol), $Pd_2(dba)_3$ (20 mg, 0.02 mmol), dppf (18 mg, 0.03 mmol) and NaO-t-Bu (329 mg, 3.42 mmol). The reaction mixture was heated at 125° C. for 1 hour in a microwave oven (100 W). Solvent was removed under reduced pressure. The crude compound was purified by column chromatography (silica gel 230-400 mesh; 3% methanol, 37% ethyl acetate and 60% $CH_2Cl_2$ as eluent). The compound was further purified by preparative HPLC to give the title compound as a beige-colored solid. Yield: 35 mg (9%). ¹H NMR (400 MHz, DMSO-$d_6$): δ 12.01 (br s, 1H), 9.40 (s, 1H), 8.87 (br s, 1H), 8.60 (d, J=2.34 Hz, 1H), 8.23 (d, J=3.91 Hz, 1H), 7.97 (dd, J=8.99 and 2.74 Hz, 1H), 7.82 (s, 2H), 7.72-7.44

(m, 2H), 6.87 (d, J=8.60 Hz, 1H), 6.83-6.78 (m, 1H), 2.23 (s, 6H). MS (ES) m/z: 359.01 (M+1) (100%).

Example 10. Preparation of 2-(4-hydroxy-3,5-dimethylphenyl)-6-((4-methylpiperazin-1-yl)methyl)quinazolin-4(3H)-one

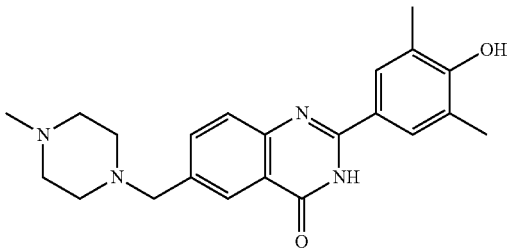

A solution of 2-amino-5-bromobenzamide (12.0 g, 55.8 mmol) and 4-hydroxy-3,5-dimethylbenzaldehyde (8.4 g, 55.8 mmol) in DMA (200 mL) was treated with NaHSO$_3$ (7.7 g, 72.5 mmol) and p-TsOH (1.1 g, 5.6 mmol). The reaction was heated at 135° C. for 2.5 hours, at which time, H$_2$O (10 mL) and CH$_2$Cl$_2$ (100 mL) were added and the solids were collected by filtration. The solids were washed with CH$_2$Cl$_2$ and dried in vacuo to afford 6-bromo-2-(4-hydroxy-3,5-dimethylphenyl)quinazolin-4(3H)-one (13.1 g, 68%).

A solution of 6-bromo-2-(4-hydroxy-3,5-dimethylphenyl)quinazolin-4(3H)-one (2.0 g, 5.8 mmol) in DMF (20 mL) was treated with vinyltributyltin (2.6 mL, 8.70 mmol), Pd(PPh$_3$)$_4$ (0.670 g, 0.58 mmol), and LiCl (0.730 g, 17.4 mmol). The reaction was stirred at reflux for 30 minutes, then concentrated in vacuo. The residue was purified by flash chromatography on silica gel, eluting with 30% to 100% of 92:7:1 CHCl$_3$/MeOH/concentrated NH$_4$OH in CH$_2$Cl$_2$, to afford 2-(4-hydroxy-3,5-dimethylphenyl)-6-vinylquinazolin-4(3H)-one (0.780 g, 46%).

To a suspension of 2-(4-hydroxy-3,5-dimethylphenyl)-6-vinylquinazolin-4(3H)-one (0.500 g, 1.70 mmol) in THF (30 mL) and H$_2$O (10 mL) was added NaIO$_4$ (1.09 g, 5.10 mmol), followed by OsO$_4$ (0.2 mL, 0.017 mmol). The reaction was stirred overnight, then concentrated in vacuo. The residue was purified by flash chromatography on silica gel, eluting with 92:7:1 to 6:3:1 CHCl$_3$/MeOH/concentrated NH$_4$OH to afford 2-(4-hydroxy-3,5-dimethylphenyl)-4-oxo-3,4-dihydroquinazoline-6-carbaldehyde (0.475 g, 95%).

To a solution of 2-(4-hydroxy-3,5-dimethylphenyl)-4-oxo-3,4-dihydroquinazoline-6-carbaldehyde (0.115 g, 0.40 mmol) in DCE/CH$_2$Cl$_2$ (1:1, 15 mL) was added 1-methylpiperazine (0.13 mL, 1.20 mmol) and NaBH(OAc)$_3$ (0.250 g, 1.20 mmol). The reaction stirred at room temperature overnight. After this time, the mixture was concentrated in vacuo and purified by flash chromatography on silica gel eluting with 92:7:1 CHCl$_3$/MeOH/concentrated NH$_4$OH to afford the title compound (0.036 g, 25%) as a white solid: $^1$H NMR (300 MHz, DMSO-d$_6$): δ 11.63 (br s, 1H), 8.77 (br s, 1H), 8.00 (s, 1H), 7.85 (s, 2H), 7.65-7.69 (m, 2H), 3.57 (s, 2H), 2.15-2.39 (m, 17H); APCI MS m/z 377 [M–H]$^−$.

Example 11. Preparation of N-((2-(4-hydroxy-3,5-dimethylphenyl)-4-oxo-3,4-dihydroquinazolin-6-yl)methyl)methanesulfonamide

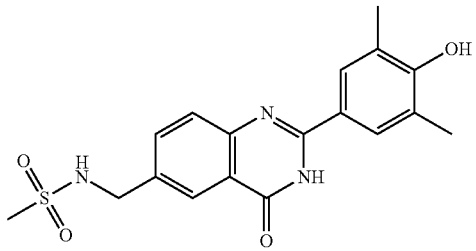

To a solution of methyl-5-methyl-2-nitrobenzoate (2.3 g, 11.8 mmol) in CHCl$_3$ (150 mL) was added NBS (5.3 g, 30.0 mmol) and benzoyl peroxide (0.285 g, 1.2 mmol). The reaction was heated at reflux temperature overnight. Then, the resulting mixture was washed sequentially with H$_2$O, Na$_2$CO$_3$, and brine. The organic layer was then dried (Na$_2$SO$_4$), filtered, and concentrated in vacuo. Purification by flash chromatography on silica gel, eluting with 5% to 20% ethyl acetate/heptane, afforded methyl 5-(bromomethyl)-2-nitrobenzoate (1.3 g, 40%).

To a solution of methyl 5-(bromomethyl)-2-nitrobenzoate (1.3 g, 4.7 mmol) in DMF (15 mL) was added potassium phthalimide (1.0 g, 5.2 mmol) and the reaction was stirred at room temperature for 1 hour and concentrated in vacuo. Purification by flash chromatography, eluting with 15% to 70% ethyl acetate/heptane, afforded methyl 5-((1,3-dioxoisoindolin-2-yl)methyl)-2-nitrobenzoate (1.4 g, 88%).

A solution of methyl 5-((1,3-dioxoisoindolin-2-yl)methyl)-2-nitrobenzoate (0.50 g, 1.4 mmol) in EtOH (10 mL) was treated with hydrazine (0.14 mL, 4.4 mol) and the reaction was stirred at room temperature overnight. After this time, the mixture was concentrated in vacuo and purified by flash chromatography on silica gel, eluting with 30% to 100% of 92:7:1 CHCl$_3$/MeOH/concentrate NH$_4$OH in CH$_2$Cl$_2$, to afford methyl 5-(aminomethyl)-2-nitrobenzoate (0.23 g, 78%).

To a solution of methyl 5-(aminomethyl)-2-nitrobenzoate (0.23 g, 1.1 mmol) in CH$_2$Cl$_2$ (5 mL) was added Et$_3$N (0.31 mL, 2.2 mmol) and methanesulfonyl chloride (0.08 mL, 1.1 mmol). The reaction was stirred for 15 minutes at room temperature, concentrated in vacuo, and purified by flash chromatography on silica gel, eluting with 2% to 20% MeOH/CH$_2$Cl$_2$, to afford methyl 5-(methylsulfonamidomethyl)-2-nitrobenzoate (0.18 g, 57%).

A mixture of methyl 5-(methylsulfonamidomethyl)-2-nitrobenzoate (0.18 g, 0.62 mmol) in EtOH (10 mL) was flushed with N$_2$. Pd/C (0.018 g) was added and the reaction was flushed with H$_2$ for 2 hours. Then, the resulting mixture was filtered through celite and the filtrate was concentrated. Purification by flash chromatography, eluting with 15% to 60% of 92:7:1 CHCl$_3$/MeOH/concentrate NH$_4$OH in CH$_2$Cl$_2$, afforded methyl 2-amino-5-(methylsulfonamidomethyl)-benzoate (0.085 g, 53%).

To a solution of methyl 2-amino-5-(methylsulfonamidomethyl)benzoate (0.085 g, 0.33 mmol) in THF (7 mL) and H$_2$O (3 mL) was added LiOH.H$_2$O (0.028 g, 0.65 mol). The reaction was stirred at room temperature for 2 hours and then neutralized with 1 N HCl. The resulting aqueous solution was extracted with EtOAc. The organics were washed with brine, dried (Na$_2$SO$_4$), filtered, and concentrated, to afford 2-amino-5-(methylsulfonamidomethyl)benzoic acid (0.066 g, 82%).

A solution of 2-amino-5-(methylsulfonamidomethyl)benzoic acid (0.066 g, 0.27 mol) in THF (5 mL) was treated with EDCI (0.062 g, 0.32 mmol), HOBT (0.044 g, 0.32 mol) and NMM (0.035 mL, 0.32 mmol.) The reaction was stirred at room temperature for 1.5 hours. Then, NH$_4$OH (0.03 mL, 0.35 mmol) in H$_2$O (0.03 mL) was added. The mixture was stirred at room temperature for 5 hours and then concentrated. Purification by flash chromatography, eluting with 92:7:1 to 7:2.5:0.5 CHCl$_3$/MeOH/concentrated NH$_4$OH, afforded 2-amino-5-(methylsulfonamidomethyl)benzamide (0.035 g, 53%).

A mixture of 2-amino-5-(methylsulfonamidomethyl)benzamide (0.035 g, 0.14 mmol), 4-hydroxy-3,5-dimethyl benzaldehyde (0.022 g, 0.14 mmol) and CuCl$_2$ (0.039 g, 0.28 mmol) in EtOH (5 mL) was refluxed for 3 h, then concentrated in vacuo. Purification by flash chromatography on silica gel, eluting with 92/7/1 CHCl$_3$:MeOH:concentrated NH$_4$OH, followed by reverse-phase chromatography, eluting with 10% to 50% CH$_3$CN in H$_2$O with 0.1% TFA, and finally flash chromatography on silica gel, eluting with 7:2.5:0.5 CHCl$_3$/MeOH/concentrated NH$_4$OH, afforded the title compound (0.030 g, 57%) as a white solid. $^1$H NMR (300 MHz, DMSO-d$_6$): δ 8.09 (s, 1H), 7.83-7.90 (m, 2H), 7.65-7.78 (m, 3H), 6.81-7.54 (m, 2H), 4.30 (d, J=6.2 Hz, 2H), 2.91 (s, 3H), 2.24 (s, 6H). ESI MS m/z 374 [M+H]$^+$.

Example 12. Preparation of 2-(4-(2-hydroxyethoxy)-3,5-dimethylphenyl)-6-morpholinoquinazolin-4(3H)-one

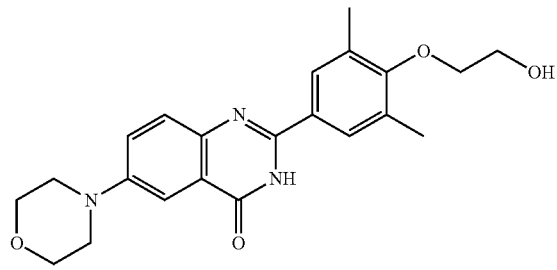 [SMILES: Cc1cc(-c2nc3ccc(N4CCOCC4)cc3c(=O)[nH]2)cc(C)c1OCCO]

A mixture of 3,5-dimethoxy-4-hydroxybenzaldehyde (10 g, 66.67 mmol), (2-bromoethoxy)-dimethyl-tert-butylsilane (15 mL, 70 mmol), potassium iodide (1.1 g, 6.67 mmol), and sodium hydride (4 g, 100 mmol) in DMF (150 mL) was heated and stirred at 70° C. for 14 hours. The reaction was then cooled and quenched by adding water (100 mL). The mixture was extracted with EtOAc (3×100 mL) and concentrated on a rotary evaporator. The resulting residue was purified by column (SiO$_2$, hexanes/EtOAc, 6:1) to yield 4-[2-(tert-butyl-dimethyl-silanyloxy)-ethoxy]-3,5-dimethyl-benzaldehyde (15.4 g, 75%).

A solution of 5-morpholin-4-yl-2-nitro-benzamide (2 g, 7.96 mmol) in MeOH (50 mL) and DMF (150 mL) in a Parr bottle was mixed with Pd/C (0.5 g) and was subjected to hydrogenation (35 psi) at room temperature for 14 hours. The suspension was then passed through a celite pad and the filtrated was concentrated on a rotary evaporator, to provide 2-amino-5-morpholin-4-yl-benzamide (1.69 g, 96%).

A mixture of 2-amino-5-morpholin-4-yl-benzamide (0.2 g, 0.905 mmol), 4-[2-(tert-butyl-dimethyl-silanyloxy)-ethoxy]-3,5-dimethyl-benzaldehyde (0.28 g, 0.905 mol), sodium hydrogensulfite (0.162 g, 0.905 mmol) and p-toluenesulfonic acid (0.224 g, 1.177 mol) in N,N-dimethyl acetamide (10 mL) was stirred at 150° C. for 4 hours. The reaction mixture was cooled to room temperature, diluted with water (50 L), basified with sodium bicarbonate to pH approximately 8-9, extracted with EtOAc (3×100 mL), and concentrated on a rotary evaporator, affording a solid residue. Further purification on a column (SiO$_2$, DCM/MeOH/EtOAc=6:1:2) yielded 2-{4-[2-(tert-butyl-dimethyl-silanyloxy)-ethoxy]-3,5-dimethyl-phenyl}-6-morpholin-4-yl-3H-quinazolin-4-one (66 mg, 14%).

The above compound (66 mg, 0.129 mmol) in THF (10 mL) was mixed with TBAF in THF (2 mL, 2 mmol) and stirred at room temperature for 5 hours. The mixture was then concentrated on a rotary evaporator and subjected to column chromatography (SiO$_2$, DCM/MeOH/EtOAc=6:1:2) to yield the title compound as a light yellow solid (35 mg, 68%). MP 279.5-281° C.

Example 13. Preparation of 2-(4-(2-(benzyloxy)ethoxy)-3,5-dimethylphenyl)-5,7-dimethoxypyrido[2,3-d]pyrimidin-4(3H)-one

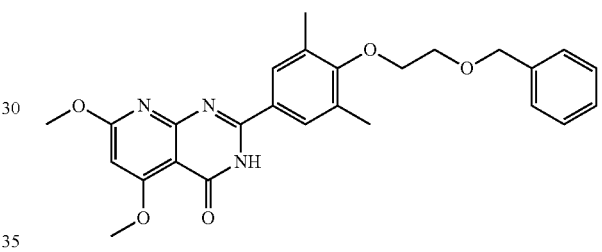

A mixture of dimethyl acetone-1,3-dicarboxylate (200 g 1.148 mol), cyanamide (48.3 g, 1.148 mol), and Ni(acac)$_2$ (14.75 g, 0.0574 mol) in dioxane (200 mL) was heated to reflux in a 1-L flask with a reflux condenser. The reaction mixture was heated at reflux for 16 hours and then cooled to room temperature. The precipitate was filtered off, and the solid was mixed with methanol (200 mL), stirred for 30 minutes, and filtered again to give methyl 2-amino-4-hydroxy-6-oxo-1,6-dihydropyridine-3-carboxylate (93 g, 44%).

In a 1-L flask with a reflux condenser was added methyl 2-amino-4-hydroxy-6-oxo-1,6-dihydropyridine-3-carboxylate (93.0 g, 0.505 mol) and POCl$_3$ (425 mL) and the reaction mixture was heated to reflux for 35 minutes. About 300 mL POCl$_3$ was evaporated under vacuum. The residue was poured into ice and water (400 mL), which was further neutralized with KOH to pH approximately 6-7. The precipitate was filtered off and extracted with ethyl acetate (2×300 mL). The organic solution was concentrated and passed through a column, eluting with hexane:ethyl acetate 4:1, to give methyl 2-amino-4,6-dichloropyridine-3-carboxylate (22.5 g, 20.1%).

In a 500-mL flask with a reflux condenser was added methyl 2-amino-4,6-dichloropyridine-3-carboxylate (22.5 g, 0.101 mol) and 25 wt % sodium methoxide in methanol (88 mL, 0.407 mol), together with methanol (20 mL). The mixture was heated to reflux for 5 hours, then cooled to room temperature. Acetic acid (15 mL) was added to the mixture and pH was adjusted to approximately 7. Methanol was removed and the residue was poured into water (100 mL). The precipitated solid was filtered and further rinsed with water (3×200 mL) to give methyl 2-amino-4,6-dimethoxy-pyridine-3-carboxylate (18.5 g, 86.4%).

In a 500-mL flask with a reflux condenser was added methyl 2-amino-4,6-dimethoxypyridine-3-carboxylate (18.5 g, 0.0872 mol), potassium hydroxide (19.5 g, 0.349 mol) in water (80 mL) and ethanol (100 mL). The mixture was heated to 80° C. for 16 hours. The solvent was removed and aqueous HCl was used to adjust the pH to 6. The water was removed by freeze drying. The obtained solid was extracted with methanol to yield 2-amino-4,6-dimethoxy-nicotinic acid (17.2 g, 100%).

2-Amino-4,6-dimethoxy-nicotinic acid (17.2 g, 0.0872 mol) was added to THF (110 mL). 1-[3-(Dimethylamino) propyl]-3-ethylcarbodiimide hydrochloride (21.73 g, 0.113 mol), 1-hydroxybenzotriazole hydrate (12.96 g, 0.0959 mol) and 4-methyl morpholine (9.7 g, 0.0959 mol) were then added to the suspension. After stirring for 10 minutes at room temperature, 50% v/v ammonium hydroxide (18.3 g, 0.262 mol) was added. The reaction mixture was kept at room temperature for 16 hours. THF was removed and the residue was poured into cold water (100 mL). The precipitate was filtered off and washed with cold water to yield 2-amino-4,6-dimethoxy-nicotinamide (10.8 g, 62.3%).

To a solution of 4-hydroxy-3,5-dimethylbenzaldehyde (6.84 g, 0.0455 mol) in anhydrous DMF (15 mL) was added NaH in mineral oil (60%, 2.23 g, 0.0558 mol). (2-Bromo-ethoxymethyl)-benzene (10.0 g, 0.0465 mol) was added and the reaction was kept at 65° C. overnight. The reaction mixture was poured into water and extracted with dichloromethane to yield (4-(2-benzyloxy-ethoxy)-3,5-dimethyl-benzaldehyde (10.5 g, 81%), which was used for next step reaction without further purification.

To a solution of 2-amino-4,6-dimethoxy-nicotinamide (2.55 g, 12.9 mmol) and 4-(2-benzyloxy-ethoxy)-3,5-dimethylbenzaldehyde (3.68 g, 12.9 mmol) in N,N-dimethyl acetamide (20 mL), were added NaHSO₃ (2.52 g, 14.2 mmol) and p-TSA (1.98 g, 10.4 mmol). The reaction mixture was heated at 150° C. for 14 hours. The reaction mixture was cooled to room temperature. The solvent was removed under reduced pressure. The residue was diluted with water and the solid was collected and further washed with methanol. The crude product was purified by column chromatography (silica gel 230-400 mesh; 2% methanol in CH₂Cl₂ as eluent) to give the title compound as an off-white solid (0.88 g, 14.7%). MP 204.5-205.9° C.

Example 14. Preparation of 2-(4-(2-hydroxy-ethoxy)-3,5-dimethylphenyl)-5,7-dimethylpyrido[2,3-d]pyrimidin-4(3H)-one

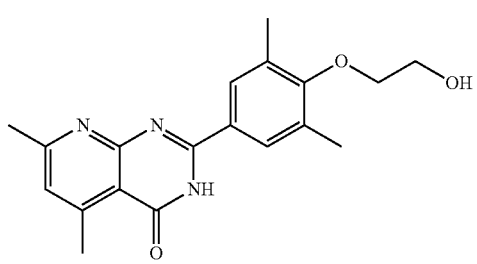 [SMILES: Cc1cc(C)c2c(=O)[nH]c(-c3cc(C)c(OCCO)c(C)c3)nc2n1]

A mixture of 3,5-dimethoxy-4-hydroxybenzaldehyde (10 g, 67 mmol), (2-bromoethoxy)-dimethyl-tert-butylsilane (15 mL, 70 mmol), potassium iodide (1.1 g, 6.7 mmol), and sodium hydride (4 g, 100 mmol) in DMF (150 mL) was heated and stirred at 70° C. for 14 hours. The reaction was then cooled and quenched by adding water (100 mL). The mixture was extracted with EtOAc (3×100 mL) and concentrated on a rotary evaporator. The resulting residue was purified by column (SiO₂, hexanes/EtOAc=6:1) to yield 4-[2-(tert-butyl-dimethyl-silanyloxy)-ethoxy]-3,5-dimethyl-benzaldehyde (15.4 g, 75%).

A mixture of 2-amino-4,6-dimethyl-nicotinamide (0.25 g, 1.5 mmol), 4-[2-(tert-butyl-dimethyl-silanyloxy)-ethoxy]-3,5-dimethyl-benzaldehyde (0.468 g, 1.5 mmol), sodium hydrogensulfite (0.271 g, 1.51 mmol) and p-toluenesulfonic acid (0.358 g, 1.82 mmol) in N,N-dimethyl acetamide (10 mL) was stirred at 150° C. for 4 hours. The reaction mixture was cooled to room temperature, diluted with water (50 mL), basified with sodium bicarbonate, to pH approximately 8-9, extracted with EtOAc (3×100 mL), and concentrated on a rotary evaporator, to afford a solid residue, which was purified by column chromatography (SiO₂, DCM/MeOH/EtOAc=6:1:2) to yield 2-{4-[2-(tert-butyl-dimethyl-silanyloxy)-ethoxy]-3,5-dimethyl-phenyl}-5,7-dimethyl-3H-pyrido[2,3-d]pyrimidin-4-one (56 mg, 8%).

To a solution of 2-{4-[2-(tert-butyl-dimethyl-silanyloxy)-ethoxy]-3,5-dimethyl-phenyl}-5,7-dimethyl-3H-pyrido[2,3-d]pyrimidin-4-one (107 mg, 0.234 mmol) in THF (10 mL) was added TBAF in THF (3 mL, 3 mmol) and the mixture was stirred at room temperature for 15 hours. The mixture was then concentrated on a rotary evaporator and subjected to column chromatography (SiO₂, DCM/MeOH/EtOAc=6:1:2) to yield 2-[4-(2-hydroxy-ethoxy)-3,5-dimethyl-phenyl]-5,7-dimethyl-3H-pyrido[2,3-d]pyrimidin-4-one (36 mg, 45%).

A solution of 2-[4-(2-hydroxy-ethoxy)-3,5-dimethyl-phenyl]-5,7-dimethyl-3H-pyrido-[2,3-d]pyrimidin-4-one (36 mg, 0.105 mmol) in MeOH (5 mL) and DCM (5 mL) was mixed with HCl in ether (2 mL, 2 mmol) and stirred at room temperature for 30 minutes. The reaction mixture was then concentrated on a rotary evaporator. The resulting solid residue was re-dissolved in minimal volume of MeOH-DCM (1:1) and triturated with hexanes. The solid was collected by filtration and washed with MeOH-DCM (1:20) to yield the title compound as a yellow solid (16.6 mg, 41%).

Example 15. Preparation of 5,7-difluoro-2-(4-(2-hydroxyethoxy)-3,5-dimethylphenyl)quinazolin-4(3H)-one

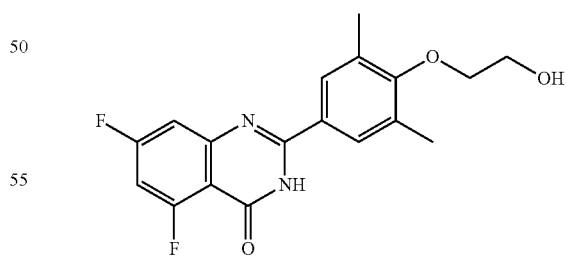

A mixture of 3,5-dimethoxy-4-hydroxybenzaldehyde (10 g, 66.67 mmol), (2-bromoethoxy)-dimethyl-tert-butylsilane (15 mL, 70 mmol), potassium iodide (1.1 g, 6.67 mmol), and sodium hydride (4.00 g, 100 mmol) in DMF (150 mL) was heated and stirred at 70° C. for 14 hours. The reaction was then cooled and quenched by addition of water (100 mL). The mixture was extracted with EtOAc (3×100 mL) and concentrated on a rotary evaporator. The resulting residue was purified by column (SiO$_2$, hexanes/EtOAc=6:1) to yield 4-[2-(tert-butyl-dimethyl-silanyloxy)-ethoxy]-3,5-dimethyl-benzaldehyde (15.4 g, 75%).

A solution of 2-amino-4,6-difluorobenzoic acid (0.5 g, 2.9 mmol), EDCI.HCl (0.887 g, 4.62 mmol), HOBt (0.975 g, 7.22 mmol), and triethylamine (1.6 mL, 11.552 mmol) in THF (50 mL) was stirred at room temperature for 1 hour. Ammonium hydroxide (50% aqueous, 10 mL) was then added to the reaction mixture. The resulting mixture was stirred at room temperature for 6 hours. The reaction was quenched by adding water (50 mL), extracted with DCM (3×100 mL), and concentrated on a rotary evaporator to afford 2-amino-4,6-difluorobenzamide (0.25 g, 50%).

A mixture of 2-amino-4,6-difluoro benzamide (0.25 g, 1.45 mmol), 4-[2-(tert-butyl-dimethyl-silanyloxy)-ethoxy]-3,5-dimethyl-benzaldehyde (0.448 g, 1.45 mmol), sodium hydrogensulfite (0.26 g, 1.45 mmol) and p-toluenesulfonic acid (0.276 g, 1.45 mmol) in N,N-dimethyl acetamide (10 mL) was stirred at 155° C. for 14 hours. The reaction mixture was cooled to room temperature, diluted with water (50 mL), extracted with EtOAc (3×100 mL), and concentrated on a rotary evaporator, to afford impure product. The residue was re-dissolved in THF (20 mL) and mixed with TBAF in THF (10 mL, 10 mmol). The reaction mixture was stirred at room temperature for 3 hours and concentrated on a rotary evaporator to afford an oily residue. Further purification by column (SiO$_2$, EtOAc/DCM=3:1) yielded a light yellow solid. This solid was diluted with MeOH (10 mL) to make a slurry. The solid was collected by filtration and washed with MeOH to afford the title compound as a light yellow solid (49 mg, 5% overall yield).

Example 16. Preparation of 2-[4-(2-hydroxy-ethoxy)-3,5-dimethyl-phenyl]-5,7-diisopropoxy-3H-quinazolin-4-one

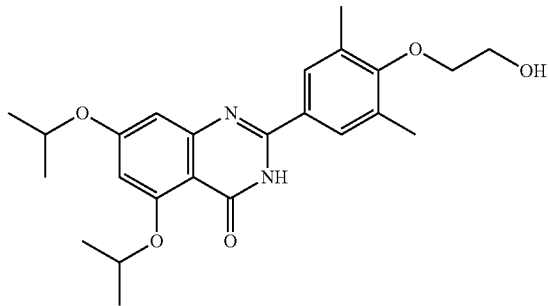 [SMILES: Cc1cc(-c2nc3cc(OC(C)C)cc(OC(C)C)c3c(=O)[nH]2)cc(C)c1OCCO]

To a solution of 3,5-dihydroxybenzoic acid (10.0 g, 64.9 mmol) in anhydrous ethanol (100 mL) at room temperature was slowly added concentrated sulfuric acid (10 mL). The resulting mixture was stirred at reflux for 36 hours. The reaction was cooled to room temperature, diluted with water (200 mL), extracted with CH$_2$Cl$_2$ (3×100 mL), and concentrated on a rotary evaporator, to afford 3,5-dihydroxybenzoic acid ethyl ester as a colorless oil. Yield: 8.2 g (69%).

A solution of 3,5-dihydroxybenzoic acid ethyl ester (6.0 g, 33 mmol) and 2-iodo-propane (9.9 mL, 99 mmol) in DMF (200 mL) was mixed with potassium carbonate (13.7 g, 98.9 mmol) and the mixture was stirred at room temperature for 14 hours. The reaction mixture was then diluted with water (300 mL), and extracted with ethyl acetate (3×100 mL). The residue obtained upon concentration was subjected to column chromatography (SiO$_2$, hexanes/ethyl acetate=3:1) to afford 3,5-diisopropoxybenzoic acid ethyl ester. Yield: 8.80 g (100%).

A solution of 3,5-diisopropoxybenzoic acid ethyl ester (8.80 g, 33.1 mmol) and lithium hydroxide (3.18 g, 132 mmol) in water (100 mL), methanol (50 mL), and THF (50 mL) was stirred at reflux for 3 hours. It was then cooled to room temperature, diluted with water (200 mL), acidified with 2 N hydrochloric acid, to pH approximately 2, extracted with CH$_2$Cl$_2$ (3×100 mL), and concentrated on a rotary evaporator, to afford 3,5-diisopropoxybenzoic acid as a white solid. Yield: 7.60 g (97%).

A solution of 3,5-diisopropoxybenzoic acid (7.60 g, 31.9 mmol), triethylamine (5.3 mL, 38 mmol), and diphenylphosphoryl azide (8.3 mL, 38 mmol) in 1,4-dioxane (120 mL) and tert-butanol (30 mL) was stirred at reflux for 16 hours. The reaction mixture was then cooled to room temperature, diluted with 0.2 N sodium bicarbonate aqueous (200 mL), extracted with CH$_2$Cl$_2$ (3×100 mL), and concentrated on a rotary evaporator. The residue obtained was subjected to column chromatography (SiO$_2$, hexanes/ethyl acetate=3:1) to afford 3,5-diisopropoxyphenyl)-carbamic acid tert-butyl ester as a white solid. Yield: 5.60 g (57%).

A solution of 3,5-diisopropoxyphenyl)-carbamic acid tert-butyl ester (5.60 g, 18.2 mmol) in trifluoroacetic acid (30 mL) was stirred at reflux for 30 minutes and concentrated on a rotary evaporator to dryness to afford 3,5-diisopropoxyphenylamine trifluoroacetic acid salt as an oil. Yield: 5.27 g (90%).

To a round-bottomed flask contained 3,5-diisopropoxyphenylamine trifluoroacetic acid salt (5.27 g, 16.4 mmol) was slowly added oxalyl chloride (20 mL) and the mixture was stirred at reflux for 1 hour. Extra oxalyl chloride was removed by distillation and methanol (100 mL) was added to the residue. It was then stirred at room temperature for 30 minutes and concentrated to dryness on a rotary evaporator to afford 4,6-diisopropoxy-1H-indole-2,3-dione as a semi-solid. Yield: 4.33 g (100%).

A solution of potassium hydroxide (15.3 g, 273 mmol) in water (60 mL) was mixed with 4,6-diisopropoxy-1H-indole-2,3-dione (4.33 g, 16.4 mmol). To this mixture was slowly added hydrogen peroxide. The resulting mixture was stirred at 70° C. for 30 minutes and cooled to 0° C. The mixture was acidified at 0° C. with 2 N hydrochloric acid to pH approximately 4, extracted with CH$_2$Cl$_2$ (3×100 mL), and concentrated on a rotary evaporator to afford 2-amino-4,6-diisopropoxy-benzoic acid as a semi-solid. Yield: 2.91 g (70%).

A solution of 2-amino-4,6-diisopropoxybenzoic acid (2.91 g, 11.5 mmol), N-(3-dimethylaminopropyl)-N'-ethyl-carbodiimide hydrochloride (3.20 g, 16.7 mmol), HOBt (3.10 g, 23.0 mmol), and triethylamine (4.2 mL, 30 mmol) in THF (200 mL) was stirred at room temperature for 20 minutes. 50% (v/v) ammonia aqueous (20 mL) was then added. The resulting solution was stirred at room temperature for 14 hours, diluted with water (200 mL), extracted with CH$_2$Cl$_2$ (3×100 mL), and concentrated on a rotary evaporator. The residue obtained was subjected to column chromatography (SiO$_2$, ethyl acetate/dichloromethane/methanol=6:2:1) to afford 2-amino-4,6-diisopropoxybenzamide. Yield: 1.2 g (41%).

A solution of 2-amino-4,6-diisopropoxybenzamide (0.30 g, 1.2 mmol), 4-(2-hydroxy-ethoxy)-3,5-dimethylbenzaldehyde (0.28 g, 1.4 mmol), sodium bisulfite (0.25 g, 1.4 mmol), and p-toluenesulfonic acid (20 mg, 0.11 mmol) in dimethyl acetamide (10 mL) was stirred at 150° C. for 12 hours. Extra solvent was evaporated on a rotary evaporator and the residue was diluted with saturated sodium bicarbonate aqueous solution (100 mL) and extracted with CH$_2$Cl$_2$ (3×100 mL). The residue obtained upon concentration was subjected to column chromatography (SiO$_2$, ethyl acetate/dichloromethane/hexanes/methanol=4:4:4:1) to afford the title compound as a light yellow solid. Yield: 35 mg (6.9%). $^1$H NMR (400 MHz, CDCl$_3$): δ 9.78 (br s, 1H), 7.66 (s, 2H), 6.78 (d, 1H), 6.42 (d, 1H), 4.72 (m, 1H), 4.63 (m, 1H), 3.97 (t, 3H), 3.92 (t, 2H), 2.33 (s, 6H), 1.45 (d, 3H), 1.41 (d, 3H). MS (ES$^+$) m/z: 427.13 (M+1).

Example 17. Preparation of 2-[4-(2-hydroxy-ethoxy)-3,5-dimethyl-phenyl]-6-morpholin-4-ylmethyl-3H-quinazolin-4-one

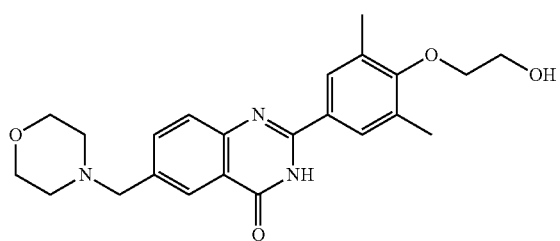 [SMILES: Cc1cc(-c2nc3ccc(CN4CCOCC4)cc3c(=O)[nH]2)cc(C)c1OCCO]

To a solution of 5-methyl-2-nitrobenzoic acid (25.0 g, 138 mmol) in ethanol (200 mL) was slowly added concentrated sulfuric acid (30 mL). The resulting solution was stirred at reflux for 48 hours. The reaction mixture was then poured into icy water (300 mL), extracted with CH$_2$Cl$_2$ (3×100 mL), and concentrated on a rotary evaporator, to afford 5-methyl-2-nitrobenzoic acid ethyl ester. Yield: 28.9 g (100%).

A solution of 5-methyl-2-nitrobenzoic acid ethyl ester (28.9 g, 138 mmol), N-bromosuccinimide (24.6 g, 138 mmol), and benzoyl peroxide (7.41 g, 30.6 mmol) in carbon tetrachloride (400 mL) was stirred at 80° C. under irradiation from a medium pressure mercury lamp for 3 hours. The lamp was then removed and the reaction was cooled to 40° C. To this solution was slowly added morpholine (14.6 mL, 168 mmol) and triethylamine (43.0 mL, 306 mmol). The resulting mixture was stirred at 40° C. for 14 hours, diluted with saturated sodium bicarbonate aqueous (300 mL), extracted with CH$_2$Cl$_2$ (3×100 mL), and concentrated on a rotary evaporator. The residue was subjected to column chromatography (SiO$_2$, hexanes/ethyl ether=1:2) to afford 5-morpholin-4-ylmethyl-2-nitrobenzoic acid ethyl ester as an oil. Yield: 20 g (49%).

To a solution of 5-morpholin-4-ylmethyl-2-nitrobenzoic acid ethyl ester (20 g, 68 mmol) in acetic acid (100 mL) was added iron powder (13.0 g, 231 mmol). The resulting suspension was stirred at 60° C. for 3 hours, cooled to room temperature, and diluted with water (200 mL) and CH$_2$Cl$_2$ (200 mL). The solid was filtered off, and the filtrate was extracted with CH$_2$Cl$_2$ (3×100 mL) and concentrated on a rotary evaporator to remove all solvent. The residue was re-dissolved in CH$_2$Cl$_2$ (400 mL), and backwashed with 2 N potassium hydroxide aqueous (2×200 mL). The organic layer was dried over anhydrous sodium sulfate and concentrated, to afford 2-amino-5-morpholin-4-ylmethylbenzoic acid ethyl ester as an oil. Yield: 17.7 g (100%).

A solution of 2-amino-5-morpholin-4-ylmethylbenzoic acid ethyl ester (3.82 g, 15.3 mmol) and lithium hydroxide (0.733 g, 30.6 mmol) in THF (25 mL), methanol (15 mL), and water (10 mL) was stirred at reflux for 2.5 hours. The reaction mixture was then concentrated to dryness on a rotary evaporator and further dried under high vacuum for 24 hours to afford lithium 2-amino-5-morpholin-4-ylmethylbenzoate. Complete conversion was assumed and the solid obtained was used in the next step without further purification.

A solution of lithium 2-amino-5-morpholin-4-ylmethylbenzoate (3.70 g, 15.3 mmol), N-(3-dimethylaminopropyl)-N'-ethylcarbodiimide hydrochloride (5.87 g, 30.6 mmol), HOBt (4.54 g, 33.6 mmol), and 4-methylmorpholine (5.0 mL, 46 mmol) in THF (200 mL) was stirred at room temperature for 40 minutes. 50% (v/v) aqueous ammonia (20 mL) was then added. The resulting solution was stirred at room temperature for 14 hours, diluted with water (200 mL), extracted with CH$_2$Cl$_2$ (3×100 mL), and concentrated on a rotary evaporator, to afford 2-amino-5-morpholin-4-ylmethylbenzamide as a light yellow solid. Yield: 1.2 g (33%).

A solution of 2-amino-5-morpholin-4-ylmethylbenzamide (0.60 g, 2.6 mmol), 4-(2-hydroxyethoxy)-3,5-dimethylbenzaldehyde (0.58 g, 3.9 mmol), sodium bisulfite (1.14 g, 6.44 mmol), and p-toluenesulfonic acid (0.88 g, 4.6 mmol) in dimethyl acetamide (10 mL) was stirred at 150° C. for 12 hours. Extra solvent was evaporated on a rotary evaporator and the residue was diluted with saturated sodium bicarbonate aqueous solution (100 mL) and extracted with CH$_2$Cl$_2$ (3×100 mL). The residue obtained on concentration was subjected to column chromatography (SiO$_2$, hexanes/ethyl acetate/dichloromethane/methanol=4:4:8:1) to afford 2-[4-(2-hydroxyethoxy)-3,5-dimethylphenyl]-6-morpholin-4-ylmethyl-3H-quinazolin-4-one as a light yellow solid. Yield: 0.15 g (14%).

A solution of 2-[4-(2-hydroxyethoxy)-3,5-dimethylphenyl]-6-morpholin-4-ylmethyl-3H-quinazolin-4-one (0.15 g, 0.37 mmol) in CH$_2$Cl$_2$ (10 mL) was mixed with 1 N HCl in ethyl ether (3 mL, 3 mmol) and was stirred at room temperature for 10 minutes to form a suspension. The solid was filtered, and washed with CH$_2$Cl$_2$ to afford the title compound as a light yellow solid. Yield: 52 mg (29%). $^1$H NMR (400 MHz, CD$_3$OD): δ 8.49 (s, 1H), 8.13 (d, 1H), 7.93 (d, 1H), 7.77 (s, 2H), 4.58 (s, 2H), 4.05 (m, 2H), 3.98 (t, 2H), 3.91 (t, 2H), 3.80 (m, 2H), 3.41 (m, 2H), 3.30 (m, 2H), 2.44 (s, 6H). MS (ES$^+$) m/z: 410.05 (M+1).

Example 18. Preparation of 2-[4-(2,3-Dihydroxypropoxy)-3,5-dimethyl-phenyl]-5,7-dimethoxy-3H-quinazolin-4-one

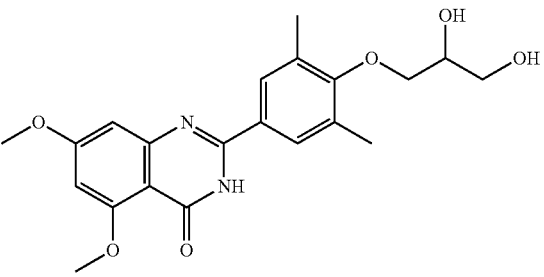 [SMILES: COc1cc(OC)c2c(=O)[nH]c(-c3cc(C)c(OCC(O)CO)c(C)c3)nc2c1]

To a solution of 4-hydroxy-3,5-dimethylbenzaldehyde (1.50 g, 10.0 mmol) in anhydrous DMF (20 mL) were added cesium carbonate (6.52 g, 20.0 mmol) and 4-chloromethyl-2,2-dimethyl-[1,3]dioxolane (1.50 g, 10.0 mmol). The reaction mixture was stirred at 80° C. for 4 days under nitrogen, then cooled to room temperature. Water (100 mL) was added, and the mixture extracted with ethyl acetate (200 mL). The organic phase was separated, washed with 1 N aqueous NaOH solution (100 mL), water (2×100 mL), brine (100 mL), and dried over anhydrous $Na_2SO_4$. Solvent was removed under reduced pressure, and the crude compound was purified using the Simpliflash system (20% ethyl acetate in hexanes as eluent) to give 4-(2,2-dimethyl-[1,3]dioxolane-4-ylmethoxy)-3,5-dimethyl-benzaldehyde as a yellow oil. Yield: 0.95 g (36%).

To a solution of 2-amino-4,6-dimethoxybenzamide (0.35 g, 1.8 mmol) in N,N-dimethyl acetamide (10 mL) were added 4-(2,2-dimethyl-[1,3]dioxolane-4-ylmethoxy)-3,5-dimethyl-benzaldehyde (0.520 g, 1.98 mmol), sodium hydrogensulfite (58.5 wt %) (0.350 g, 1.98 mmol) and p-toluenesulfonic acid (0.17 g, 0.90 mmol). The reaction mixture was stirred at 120° C. for 16 hours under nitrogen, then cooled to room temperature. Solvent was evaporated under reduced pressure, water (50 mL) was added, the separated solid was filtered, washed with water, then dichloromethane (10 mL), and dried under vacuum to give the title compound as a yellow solid. Yield: 0.34 g (47%). $^1$H NMR (400 MHz, DMSO-$d_6$): δ 11.8 (s, 1H), 7.83 (s, 2H), 6.64 (s, 1H), 6.44 (s, 1H), 4.95 (d, 1H), 4.40 (t, 1H), 3.88 (s, 3H), 3.84-3.66 (m, 6H), 3.46 (t, 2H), 2.28 (s, 6H). MS (ES) m/z: 401.04 (M+1) (100%).

Example 19. Preparation of 2-[4-(2-hydroxyethoxy)-3,5-dimethylphenyl]-5,7-dimethoxy-6-morpholin-4-ylmethyl-3H-quinazolin-4-one hydrochloride

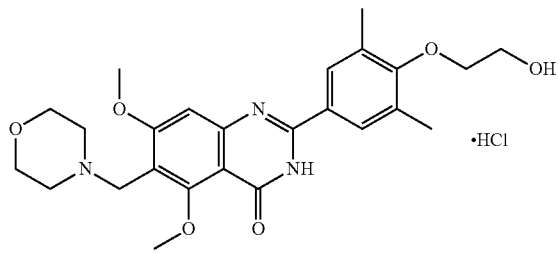 [SMILES: COc1cc2nc(-c3cc(C)c(OCCO)c(C)c3)[nH]c(=O)c2c(OC)c1CN1CCOCC1 ; Cl]

Bromine (33.7 mL, 657 mmol) and 1,4-dioxane (56.0 mL, 657 mmol) was mixed at room temperature to provide fresh dioxane dibromide, which was then diluted with ethyl ether (900 mL). To a solution of 2,6-dimethoxytoluene (50.0 g, 328 mmol) in ether (450 mL) was added the freshly prepared dioxane dibromide in ether (900 mL) over 30 minutes while stirring at room temperature. After the addition, the mixture was stirred at room temperature for an additional 1.5 hours, and was poured into a beaker containing water (500 mL) and partitioned. The aqueous was discarded and the ethereal layer was washed sequentially with water (2×500 mL), saturated sodium bicarbonate aqueous (2×500 mL), dried over anhydrous sodium sulfate, and concentrated on a rotary evaporator, to afford 3-bromo-2,6-dimethoxytoluene as a colorless oil. Yield: 76 g, (100%).

A cooling well was used to collect 300 mL of ammonia at −78° C., which was then mixed with 0.5 g potassium and 0.5 g ferric nitrate. After the initial blue color discharged, potassium (14.2 g, 364 mmol) was added at −78° C., portion-wise so that the blue color discharged before to each addition. After complete addition of potassium, the solution was stirred at −78° C. for 15 minutes. To this solution was slowly added 3-bromo-2,6-dimethoxytoluene (42.0 g, 182 mmol) in THF (100 mL). The resulting mixture was stirred at −78° C. for 3 hours and then 0° C. for 1 hour. The reaction was quenched by adding water (150 mL) and was extracted with $CH_2Cl_2$ (3×200 mL) to afford a brown oil as the crude product. The product was further purified by column chromatography ($SiO_2$, hexanes/ethyl acetate=1:1) to yield 3,5-dimethoxy-4-methylaniline. Yield: 22.1 g (73%).

A solution of 3,5-dimethoxy-4-methylaniline (22.1 g, 132 mmol) in 1,4-dioxane (380 mL) and water (380 mL) was mixed with potassium carbonate (45.6 g, 331 mmol) and $(Boc)_2O$ (34.6 g 159 mmol) and stirred at room temperature for 14 hours. The reaction mixture was then extracted with $CH_2Cl_2$ (3×100 mL) and concentrated on a rotary evaporator. The resulting solid residue was purified by column chromatography ($SiO_2$, hexanes/ethyl acetate=2:1) to yield a solid. A mixed solvent of $CH_2Cl_2$-hexanes (20 mL/300 mL) was used to make a slurry and the solid was collected by filtration and washed with hexanes to provide (3,5-dimethoxy-4-methylphenyl)-carbamic acid tert-butyl ester as a light yellow needle-like solid. Yield: 28.6 g (81%).

A solution of (3,5-dimethoxy-4-methylphenyl)-carbamic acid tert-butyl ester (28.6 g, 107 mmol) in carbon tetrachloride (450 mL) was mixed with NBS (19.05 g, 107.1 mmol) and AIBN (1.55 g, 9.37 mmol) and was stirred at 80° C. under irradiation from a medium-pressure mercury lamp for 2 hours. The reaction was then quenched by adding water (150 mL) and extracted with $CH_2Cl_2$ (3×100 mL), and concentrated on a rotary evaporator to afford a solid residue. Further purification on column ($SiO_2$, hexanes/ethyl acetate=2:1) yielded (2-bromo-3,5-dimethoxy-4-methylphenyl)-carbamic acid tert-butyl ester. Yield: 34.9 g (94%).

solution of (2-bromo-3,5-dimethoxy-4-methylphenyl)-carbamic acid tert-butyl ester (34.9 g, 101 mmol) in carbon tetrachloride (450 mL) was mixed with N-bromosuccinimide (21.5 g, 121 mmol) and AIBN (1.55 g, 9.37 mmol) and was stirred at 80° C. under irradiation from a medium-pressure mercury lamp for 4 hours. The reaction was then quenched by adding water (150 mL) and extracted with $CH_2Cl_2$ (3×100 mL), and concentrated on a rotary evaporator to afford a solid residue. Further purification on a column ($SiO_2$, hexanes/ethyl acetate=2:1) yielded (2-bromo-4-bromomethyl-3,5-dimethoxyphenyl)-carbamic acid tert-butyl ester. Yield: 39.0 g (91%).

A solution of (2-bromo-4-bromomethyl-3,5-dimethoxyphenyl)-carbamic acid tert-butyl ester (39.0 g, 91.8 mmol) in THF (600 mL) was mixed with morpholine (45.0 mL, 515 mmol) and stirred at room temperature for 7 hours. The reaction was diluted with water (300 mL), extracted with $CH_2Cl_2$ (3×200 mL), and concentrated on a rotary evaporator. The residue was further purified by column ($SiO_2$, dichloromethane/methanol=20:1) to provide (2-bromo-3,5-dimethoxy-4-morpholin-4-ylmethylphenyl)-carbamic acid tert-butyl ester. Yield: 35 g (88%).

A solution of (2-bromo-3,5-dimethoxy-4-morpholin-4-ylmethylphenyl)-carbamic acid tert-butyl ester (3.0 g, 6.9 mmol) in THF (150 mL) was mixed with sodium hydride (0.333 g, 8.33 mmol) and stirred at room temperature for 1.5 hours. The resulting mixture was then cooled to −78° C. and mixed with nBuLi (3.33 mL, 8.33 mmol). The reaction was stirred for 1.5 hours at −78° C. before addition of tBuLi (8.16 mL, 13.9 mmol). After addition of tBuLi, the reaction was stirred at −78° C. for 1 hour and carbon dioxide gas was then bubbled through for 8 hours, allowing the temperature to rise gradually to room temperature. The reaction was quenched by adding water (0.50 mL, 28 mmol) and concentrated on a rotary evaporator. The solid residue was made into a slurry in a minimal amount of methanol and the solid was filtered off. The filtrate was then concentrated on a rotary evaporator and the solid was made into a slurry again in methanol and filtered. After repeating three times, the filtrate was concentrated to yield impure 6-tert-butoxycarbonylamino-2,4-dimethoxy-3-morpholin-4-ylmethyl-benzoic acid. Crude yield: 1.80 g (40%).

A solution of crude 6-tert-butoxycarbonylamino-2,4-dimethoxy-3-morpholin-4-ylmethyl-benzoic acid (1.80 g, 4.54 mmol), N-(3-dimethylaminopropyl)-N'-ethylcarbodiimide hydrochloride (1.31 g, 6.82 mmol), HOBt (1.23 g, 9.09 mmol), and triethylamine (3.3 mL, 24 mmol) in THF (50 mL) was stirred at room temperature for 1 hour. 50% (v/v) aqueous ammonia (20 mL) was then added. The resulting solution was stirred at room temperature for 14 hours, diluted with water (100 mL), extracted with $CH_2Cl_2$ (3×100 mL), and concentrated on a rotary evaporator. The residue was further purified by column chromatography ($SiO_2$, dichloromethane/methanol/ethyl acetate=2:1:4) to provide (2-carbamoyl-3,5-dimethoxy-4-morpholin-4-ylmethyl-phenyl)-carbamic acid tert-butyl ester. Yield: 0.90 g (50%).

A solution of (2-carbamoyl-3,5-dimethoxy-4-morpholin-4-ylmethylphenyl)-carbamic acid tert-butyl ester (0.90 g, 2.7 mmol) in acetic acid (20 mL) and 12 N HCl aqueous (20 mL) was stirred at 50° C. for 1 hour, and then concentrated to dryness on a rotary evaporator. The residue was mixed with saturated sodium bicarbonate aqueous (40 mL), extracted with $CH_2Cl_2$ (3×100 mL), and concentrated on a rotary evaporator. The residue was further purified on a column ($SiO_2$, dichloromethane/methanol/ethyl acetate=3:2:3), to provide 6-amino-2,4-dimethoxy-3-morpholin-4-ylmethylbenzamide. Yield: 0.6 g (89%).

A solution of 6-amino-2,4-dimethoxy-3-morpholin-4-ylmethylbenzamide (0.50 g, 1.7 mmol), 4-(2-hydroxyethoxy)-3,5-dimethylbenzaldehyde (0.50 g, 2.5 mmol), sodium bisulfite (0.90 g, 5.1 mmol), and p-toluenesulfonic acid (0.80 g, 4.2 mmol) in dimethyl acetamide (15 mL) was stirred at 150° C. for 14 hours. Extra solvent was evaporated on a rotary evaporator and the residue was diluted with saturated sodium bicarbonate aqueous solution (100 mL) and extracted with $CH_2Cl_2$ (3×100 mL). The residue obtained upon concentration was subjected to column chromatography ($SiO_2$, hexanes/ethyl acetate/dichloromethane/methanol=1:2:5:1) to afford 2-[4-(2-hydroxy-ethoxy)-3,5-dimethylphenyl]-5,7-dimethoxy-6-morpholin-4-ylmethyl-3H-quinazolin-4-one as a light yellow solid. Yield: 0.12 g (15%).

A solution of 2-[4-(2-hydroxy-ethoxy)-3,5-dimethylphenyl]-5,7-dimethoxy-6-morpholin-4-ylmethyl-3H-quinazolin-4-one (0.12 g, 0.26 mmol) in $CH_2Cl_2$ (10 mL) was mixed with 1 N HCl in ethyl ether (3 mL, 3 mmol) and was stirred at room temperature for 10 minutes to form a suspension. The solid was filtered, and washed with $CH_2Cl_2$ to afford the title compound as a light yellow solid. Yield: 32 mg (23%). $^1$H NMR (400 MHz, $CDCl_3$): δ 7.62 (s, 2H), 7.08 (s, 1H), 4.00 (m, 4H), 3.96 (s, 3H), 3.87 (s, 3H), 3.80 (br s, 2H), 3.70 (br s, 4H), 2.67 (br s, 4H), 2.40 (s, 6H). MS ($ES^+$) m/z: 470.17 (M+1).

Example 20. Preparation of 2-[4-(2-hydroxy-ethoxy)-phenyl]-5,7-dimethoxy-3H-quinazolin-4-one

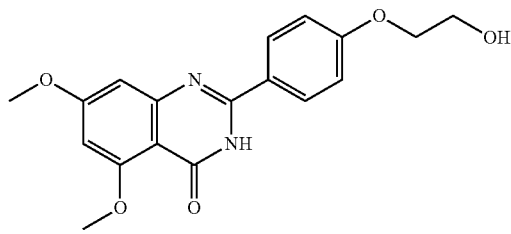 [SMILES: COc1cc(OC)c2c(=O)[nH]c(-c3ccc(OCCO)cc3)nc2c1]

To a flask (250 mL) with a magnetic stirrer were added 4-hydroxybenzaldehyde (10.0 g, 81.8 mmol), 2-chloroethanol (26.3 g, 327 mmol), potassium carbonate (22.6 g, 163 mmol), and ethanol (80 mL). The reaction mixture was stirred at 70° C. for 16 hours. Potassium carbonate was filtered and ethanol was removed. The residue was diluted with ethyl acetate (200 mL) and washed with 5% sodium hydroxide (100 mL), water (100 mL), and brine (100 mL). The crude product was purified by column chromatography (silica gel, 230-400 mesh), using hexane/ethyl acetate (1:1) as eluent, to afford 4-(2-hydroxy-ethoxy)-benzaldehyde. Yield: 10.0 g (73%).

To a solution of 2-amino-4,6-dimethoxy-benzamide (0.400 g, 2.00 mmol) and 4-(2-hydroxy-ethoxy)-benzaldehyde (0.340 g, 2.00 mmol) in N,N-dimethylacetamide (8 mL) were added $NaHSO_3$ (0.390 g, 2.20 mmol) and p-TSA (38 mg, 0.20 mmol). The reaction mixture was stirred at 115-120° C. for 5 hours and cooled to room temperature. The solvent was removed under reduced pressure. The residue was diluted with water (40 mL) and the solid was collected, mixed with methanol (50 mL), and stirred for 30 min. The solid was filtered and rinsed with ether (30 mL) to give the title compound as white solid. Yield: 0.42 g (61%). $^1$H NMR (400 Hz, $DMSO-d_6$): δ 11.98 (s, 1H), 8.18 (d, 2H), 7.08 (d, 2H), 6.78 (s, 1H), 6.52 (s, 1H), 4.98 (s, 1H), 4.10 (t, 2H), 3.90 (s, 3H), 3.84 (s, 3H), 3.74 (t, 2H). MS ($ES^+$) m/z: 343.13 (M+1).

Example 21. Preparation of 2-[4-(2-hydroxy-ethoxy)-naphthalen-1-yl]-5,7-dimethoxy-3H-quinazolin-4-one

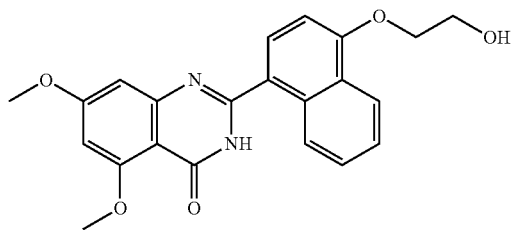 [SMILES: COc1cc(OC)c2c(=O)[nH]c(-c3ccc(OCCO)c4ccccc34)nc2c1]

To a mixture of 4-hydroxy-naphthalene-1-carbaldehyde (1.0 g, 5.8 mmol) and potassium carbonate (2.40 g, 17.4 mmol) in N,N-dimethylformamide (3 mL) under nitrogen was added 2-chloroethanol (0.80 mL, 12 mmol). The reaction mixture was heated at reflux for 20 hours and the solvent was then removed under reduced pressure. The residue was diluted with ethyl acetate, washed with water, 0.2 N aqueous sodium hydroxide, brine, and dried over anhydrous sodium sulfate. The crude oil (1.03 g) was purified by column chromatography (silica gel 230-400 mesh; methylene chloride/EtOAc=3/7), to give 4-(2-hydroxy-ethoxy)-naphthalene-1-carbaldehyde as a colorless oil. Yield: 0.6 g (48%).

To a solution of 2-amino-4,6-dimethoxy-benzamide (0.45 g, 2.3 mmol) in N,N-dimethylacetamide (25 mL) under nitrogen was added 4-(2-hydroxy-ethoxy)-naphthalene-1-carbaldehyde (0.50 g, 2.3 mmol) followed by sodium hydrogensulfite (0.26 g, 2.5 mmol) and p-toluenesulfonic acid (0.22 g, 1.1 mmol). The resulting mixture was heated at 130° C. for 15 hours and the solvent was removed under reduced pressure. The residue was diluted with ethyl acetate, washed with water, and dried over sodium sulfate. The crude orange solid (0.37 g) was purified by column chromatography (silica gel, 230-400 mesh; 3/7 methylene chloride/EtOAc then 9/1 methylene chloride/MeOH as eluent) and by triturating with methylene chloride and ether to afford the title compound as a light orange solid. Yield: 0.16 g (36%). $^1$H NMR (400 MHz, CDCl$_3$+CD$_3$OD): δ 8.34 (d, 1H), 8.19 (d, 1H), 7.62 (d, 1H), 7.44-7.53 (m, 2H), 6.84 (d, 1H), 6.75 (s, 1H), 6.43 (s, 1H), 4.22-4.24 (m, 2H), 4.01-4.03 (m, 2H), 9.90 (s, 3H), 3.85 (s, 3H). MS (ES$^+$) m/z: 393.27 (M+1).

Example 22. Preparation of 2-(2-hydroxymethyl-benzofuran-5-yl)-5,7-dimethoxy-3H-quinazolin-4-one

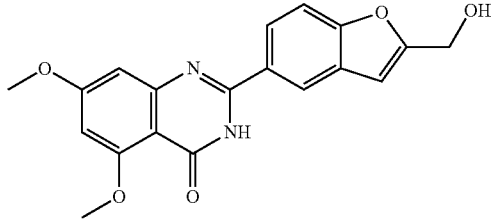 [SMILES: COc1cc(OC)c2c(=O)[nH]c(-c3ccc4oc(CO)cc4c3)nc2c1]

To a solution of 4-hydroxy-benzaldehyde (3.66 g, 30.0 mmol) in 50% (v/v) aqueous ammonium hydroxide (250 mL) was quickly added a solution of potassium iodide (24.9 g, 150 mmol) and iodine (7.62 g, 30.0 mmol) in water (60 mL). The dark colored solution was stirred at room temperature for 1 hour and the color changed to yellow. Stirring was continued at room temperature for 16 hours. The color changed to gray. Then, the reaction mixture was filtered through a celite pad. The filtrate was acidified with concentrated HCl to pH approximately 1 and extracted with ethyl acetate (1×300 mL). The organic phase was washed with water (150 mL) and brine (150 mL), dried over anhydrous Na$_2$SO$_4$, and concentrated to give 4-hydroxy-3-iodo-benzaldehyde as an off-white solid (1:1 mixture of starting material and product). Yield: 5.34 g (crude).

To a degassed solution of 4-hydroxy-3-iodo-benzaldehyde (5.34 g, 15.0 mmol) in anhydrous DMF (100 mL) were added bis(triphenylphosphine)palladium(II) dichloride (0.53 g, 0.75 mmol), copper (I) iodide (0.14 g, 0.75 mmol), 1,1,3,3-tetramethyl guanidine (8.64 g, 75.0 mmol), and propargyl alcohol (1.18 g, 21.0 mmol). The reaction mixture was stirred at room temperature for 24 hours under nitrogen and then concentrated to dryness under reduced pressure. The residue was diluted with 2 N aqueous HCl (150 mL) and extracted with ethyl acetate (1×200 mL). Organic phase was washed with water (2×100 mL), brine (100 mL), and dried over anhydrous Na$_2$SO$_4$. Solvent was evaporated and crude compound was purified using the Simpliflash system (30% ethyl acetate in hexanes as eluent) to give 2-hydroxymethyl-benzofuran-5-carbaldehyde as a pale yellow solid. Yield: 1.36 g (26% for two steps).

To a solution of 2-hydroxymethyl-benzofuran-5-carbaldehyde (0.450 g, 2.55 mmol) and 2-amino-4,6-dimethoxy-benzamide (0.500 g, 2.55 mmol) in N,N-dimethylacetamide (5 mL) were added sodium hydrogen sulfite (58.5 wt %; 0.510 g, 2.80 mmol) and p-toluenesulfonic acid (50 mg, 0.25 mmol). The reaction mixture was stirred at 120° C. for 6 hours under nitrogen and cooled to room temperature. The separated solid was filtered, washed with ether (30 mL), water (30 mL), and ethyl acetate (20 mL), and then dried under vacuum to give the title compound as a yellow solid. Yield: 0.572 g (64%). $^1$H NMR (400 MHz, DMSO-d$_6$): δ 12.07 (br s, 1H), 8.44 (d, J=2.0 Hz, 1H), 8.10 (dd, J=8.8 and 1.6 Hz, 1H), 7.67 (d, J=8.8 Hz, 1H), 6.89 (s, 1H), 6.76 (d, J=2.4 Hz, 1H), 6.54 (d, J=2.4 Hz, 1H), 4.61 (s, 2H), 3.90 (s, 3H), 3.86 (s, 3H). MS (ES$^+$) m/z: 353.20 (M+1).

Example 23. Preparation of 7-(2-benzyloxy-ethoxy)-2-[4-(2-hydroxy-ethoxy)-3,5-dimethyl-phenyl]-5-methoxy-3H-quinazolin-4-one

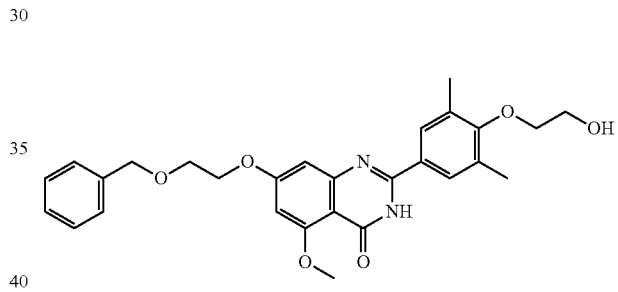

To a solution of 4-hydroxy-3,5-dimethyl-benzaldehyde (1.00 g, 6.70 mmol) in DMF (20 mL) was added cesium carbonate (8.70 g, 26.6 mmol) followed by (2-bromo-ethoxy)-tert-butyl-dimethyl-silane (2.9 mL, 13 mmol). The reaction mixture was stirred at room temperature for 16 hours. Water was added and the product was extracted with ethyl acetate. The solvent was evaporated in vacuo to obtain 4-[2-(tert-butyl-dimethyl-silanyloxy)-ethoxy]-3,5-dimethyl-benzaldehyde as a colorless oil. It was contaminated with (2-bromo-ethoxy)-tert-butyl-dimethyl-silane, but was used in the next step without further purification. Yield: 2.5 g (71%).

To a stirred solution of 2-amino-4,6-difluoro-benzamide (0.50 g, 2.9 mmol) and 4-[2-(tert-butyl-dimethyl-silanyloxy)-ethoxy]-3,5-dimethyl-benzaldehyde (1.3 g, 2.9 mmol) in N,N-dimethylacetamide (10 mL) were added sodium hydrogen sulfite (0.60 g, 3.5 mmol) and p-toluenesulfonic acid (0.1 g, 0.6 mmol) and the reaction mixture was stirred at 120° C. for 16 hours. The solvent was evaporated in vacuo, water was added, and the precipitated solid was filtered off to obtain 2-{4-[2-(tert-butyl-dimethyl-silanyloxy)-ethoxy]-3,5-dimethyl-phenyl}-5,7-difluoro-3H-quinazolin-4-one as a yellow solid, which was used in the next step without further purification. Yield: 0.490 g (36%).

To a suspension of 2-{4-[2-(tert-butyl-dimethyl-silanyloxy)-ethoxy]-3,5-dimethyl-phenyl}-5,7-difluoro-3H-quinazolin-4-one (0.490 g, 1.06 mmol) in DMF (3 mL) was added sodium methoxide in methanol (2.3 mL, 11 mmol) and the reaction mixture was stirred at room temperature for 16 hours. Water was added, the mixture was acidified with acetic acid, to pH approximately 4-5, and the precipitated solid was filtered off to obtain 7-fluoro-2-[4-(2-hydroxy-ethoxy)-3,5-dimethyl-phenyl]-5-methoxy-3H-quinazolin-4-one as a white solid. Yield: 0.21 g (55%).

To a solution of 7-fluoro-2-[4-(2-hydroxy-ethoxy)-3,5-dimethyl-phenyl]-5-methoxy-3H-quinazolin-4-one (0.21 g, 0.59 mmol) in THF (12 mL) was added imidazole (80 mg, 1.2 mmol), followed by tert-butyldiphenylsilyl chloride (0.20 mL, 0.65 mmol). The reaction mixture was stirred at room temperature for 16 hours. Saturated NH$_4$Cl aqueous solution was added and the product was extracted with ethyl acetate. The solvent was evaporated in vacuo and the residue was purified by column chromatography (silica gel; 230-400 mesh; eluting with 5-10% ethyl acetate/CH$_2$Cl$_2$) to afford 2-{-4-[2-(tert-butyl-diphenyl-silanyloxy)-ethoxy]-3,5-dimethyl-phenyl}-7-fluoro-5-methoxy-3H-quinazolin-4-one. Yield: 0.36 g (quantitative).

To a solution of 2-benzyloxy-ethanol (3 mL) in dimethyl sulfoxide (3 mL) was added sodium hydride (0.24 g, 6.0 mmol) in portions and the reaction mixture was stirred at room temperature for 45 minutes. To this mixture was added 2-{-4-[2-(tert-butyl-diphenyl-silanyloxy)-ethoxy]-3,5-dimethyl-phenyl}-7-fluoro-5-methoxy-3H-quinazolin-4-one (0.36 g, 0.60 mmol) and the reaction mixture was heated at 70° C. for 16 hours. Water was added, and the mixture was acidified with acetic acid, to pH approximately 4-5, and the precipitated solid was filtered off to obtain a crude product, which was purified by preparative HPLC to obtain the title compound as a white solid. Yield: 0.12 g (42%). $^1$H NMR (400 MHz, DMSO-d$_6$): δ 11.83 (s, 1H), 7.89 (s, 2H), 7.37 (m, 5H), 6.75 (s, 1H), 6.53 (s, 1H), 4.91 (s, 1H), 4.58 (s, 2H), 4.30 (s, 2H), 3.84-3.73 (m, 9H), 2.31 (s, 6H). MS (ES$^+$) m/z: 491.55 (M+1).

Example 24. Preparation of 7-(2-benzyloxy-ethoxy)-2-(2-hydroxymethyl-benzofuran-5-yl)-5-methoxy-3H-quinazolin-4-one

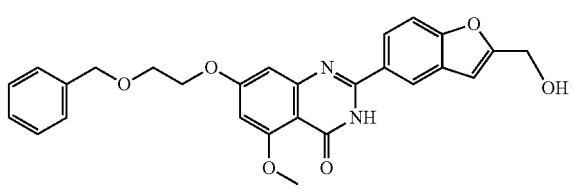 [SMILES: COc1cc(OCCOCc2ccccc2)cc2nc(-c3ccc4oc(CO)cc4c3)[nH]c(=O)c12]

To a stirred solution of 2-hydroxymethyl-benzofuran-5-carbaldehyde (2.00 g, 11.4 mmol) in anhydrous CH$_2$Cl$_2$ (25 mL) were added N,N-diisopropylethyl amine (5.17 g, 40.0 mmol) and chloromethyl methyl ether (2.76 g, 34.3 mmol) at room temperature. The reaction mixture was stirred at room temperature for 16 hours under nitrogen. Phosphate buffer (pH 7, 100 mL) was added and the mixture was extracted with dichloromethane (100 mL). The organic phase was separated, washed with brine, and dried over anhydrous Na$_2$SO$_4$. Removal of solvent gave 2-methoxymethoxymethyl-benzofuran-5-carbaldehyde as an orange oil. Yield 2.41 g (96%).

To a solution of 2-methoxymethoxymethyl-benzofuran-5-carbaldehyde (2.31 g, 10.5 mmol) and 2-amino-4,6-difluoro-benzamide (1.20 g, 7.00 mmol) in N,N-dimethyl acetamide (15 mL) were added sodium hydrogen sulfite (58.5 wt %; 1.54 g, 8.40 mmol) and p-toluenesulfonic acid monohydrate (0.26 g, 1.40 mmol). The reaction mixture was stirred at 120° C. for 4 hours under nitrogen, then cooled to room temperature. Solvent was evaporated under reduced pressure and water (100 mL) was added. The separated solid was filtered, washed with water (50 mL), and dried under vacuum, to give 5,7-difluoro-2-(2-methoxymethoxymethyl-benzofuran-5-yl)-3H-quinazolin-4-one as a white solid. Yield 0.96 g (37%).

To a suspension of 5,7-difluoro-2-(2-methoxymethoxymethyl-benzofuran-5-yl)-3H-quinazolin-4-one (0.95 g, 2.56 mmol) in anhydrous DMF (5 mL) was added a solution of sodium methoxide (25 wt %) in methanol at 0° C. under nitrogen. Then, the reaction mixture was stirred at 0° C. for 6 hours. Water (20 mL) was added, the mixture was acidified to pH approximately 6 with glacial acetic acid. The separated solid was filtered, washed with water (20 mL), and dried under vacuum to give 7-fluoro-5-methoxy-2-(2-methoxymethoxymethyl-benzofuran-5-yl)-3H-quinazolin-4-one as a white solid. Yield 0.94 g (95%).

Sodium hydride (60% suspension in mineral oil; 0.48 g, 12.0 mmol) was taken in anhydrous DMF (5 mL). 2-Benzyloxyethanol (3.65 g, 24.0 mmol) was added dropwise at room temperature under nitrogen. After the addition, the reaction mixture was stirred at room temperature for 30 minutes. Then, 7-fluoro-5-methoxy-2-(2-methoxymethoxymethyl-benzofuran-5-yl)-3H-quinazolin-4-one (0.46 g, 1.2 mmol) was added and the reaction mixture was stirred at 80° C. for 16 hours. The reaction mixture was then cooled to room temperature. Water (50 mL) was added, the mixture was acidified to pH approximately 6 with glacial acetic acid and extracted with CH$_2$Cl$_2$ (2×100 mL). The organic phase was washed with brine (100 mL) and then dried over anhydrous Na$_2$SO$_4$. Removal of solvent, followed by purification, by the Simpliflash system (0-2% methanol in CH$_2$Cl$_2$ as eluent) gave 7-(2-benzyloxy-ethoxy)-5-methoxy-2-(2-methoxymethoxymethyl-benzofuran-5-yl)-3H-quinazolin-4-one as a white solid. Yield 0.28 g (45%).

To a solution of 7-(2-benzyloxy-ethoxy)-5-methoxy-2-(2-methoxymethoxymethyl-benzo-furan-5-yl)-3H-quinazolin-4-one (0.27 g, 0.53 mmol) in 50% aqueous acetic acid (15 mL), conc. H$_2$SO$_4$ (0.3 mL) was added. The reaction mixture was stirred at 75° C. for 2 hours, then cooled to room temperature. Water (50 mL) was added, and the mixture was neutralized to pH approximately 7 with 4 N aqueous NaOH solution. The separated solid was filtered, washed with water (20 mL), and dried under vacuum. Crude compound was purified by column chromatography (silica gel 230-400 mesh; 2:20:78 methanol/ethyl acetate/CH$_2$Cl$_2$ as eluent) to give the title compound as a white solid. Yield 0.13 g (52%).

$^1$H NMR (400 MHz, DMSO-d$_6$): δ 12.03 (bs, 1H), 8.43 (s, 1H), 8.09 (dd, J=8.58 and 1.95 Hz, 1H), 7.65 (d, J=8.58 Hz, 1H), 7.37-7.29 (m, 5H), 6.88 (s, 1H), 6.77 (d, J=1.95 Hz, 1H), 6.55 (d, J=1.56 Hz, 1H), 5.51 (s, 1H), 4.60 (t, J=4.68 Hz, 4H), 4.31 (s, 2H), 3.90-3.83 (m, 5H). MS (ES+) m/z 473.48 (100%).

Example 25. Preparation of 2-[4-(5,7-dimethoxy-4-oxo-3,4-dihydro-quinazolin-2-yl)-2,6-dimethyl-phenoxy]-N-methyl-acetamide

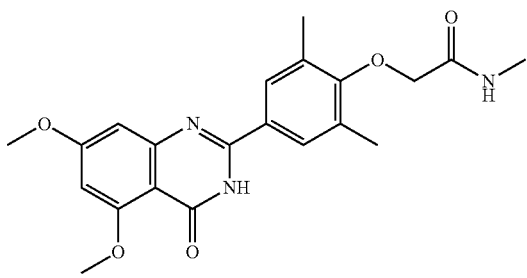

To a solution of [4-(5,7-dimethoxy-4-oxo-3,4-dihydro-quinazolin-2-yl)-2,6-dimethyl-phenoxy]-acetic acid (0.20 g, 0.52 mmol) in anhydrous DMF (8 mL) were added EDCI (0.12 g, 0.62 mmol) and HOBt (0.084 g, 0.62 mmol). Then, a solution of N-methyl amine (2.0 M solution in THF, 1.3 mL, 2.60 mmol) was added and the reaction mixture was stirred at room temperature for 16 hours under nitrogen. Solvent was evaporated under reduced pressure, water (20 mL) was added, and the separated solid was filtered, washed with water (30 mL), ether (20 mL) and dried under vacuum to give the title compound as a white solid. Yield: 0.13 g (63%). $^1$H NMR (400 MHz, DMSO-$d_6$): δ11.86 (br s, 1H), 8.19 (br s, 1H), 7.91 (s, 2H), 6.74 (d, J=1.95 Hz, 1H), 6.52 (d, J=1.95 Hz, 1H), 4.26 (s, 2H), 3.89 (s, 3H), 3.85 (s, 3H), 2.72 (d, J=4.30 Hz, 3H), 2.30 (s, 6H). MS (ES) m/z: 398.53 (M+1) (100%).

Example 26. Preparation of 2-[4-(5,7-Dimethoxy-4-oxo-3,4-dihydro-quinazolin-2-yl)-2,6-dimethyl-phenoxy]-N-(4-methoxy-phenyl)-acetamide

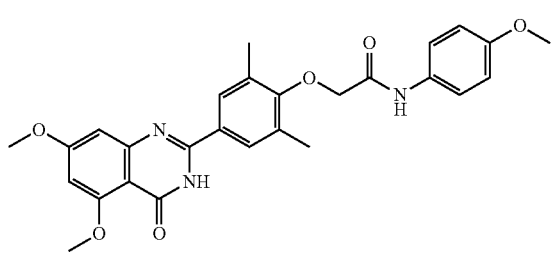

To a solution of 4-hydroxy-3,5-dimethyl-benzaldehyde (9.00 g, 60.0 mmol) in ethanol (300 mL) were added potassium carbonate (24.9 g, 180 mmol) and methyl bromoacetate (11.4 mL, 120 mmol). The reaction mixture was stirred at 95° C. under nitrogen for 16 hours. The mixture was concentrated to dryness under reduced pressure. Water (150 mL) and 1 N NaOH solution (90 mL) were added to the residue. The mixture was stirred at room temperature for 30 minutes, then washed with ether. Concentrated HCl was added slowly to the aqueous solution until a large amount of white precipitate formed. The solid was filtered, washed with water, and air-dried, to give (4-formyl-2,6-dimethyl-phenoxy)-acetic acid as a white solid. Yield: 11.1 g (89%).

To a solution of (4-formyl-2,6-dimethyl-phenoxy)-acetic acid (3.12 g, 15.0 mmol) and 2-amino-4,6-dimethoxy-benzamide (2.94 g, 15.0 mmol) in N,N-dimethylacetamide (50 mL) were added sodium hydrogen sulfite (58.5 wt %, 3.02 g, 16.5 mmol) and p-toluenesulfonic acid monohydrate (0.285 g, 1.50 mmol). The reaction mixture was stirred at 120° C. for 17 hours under nitrogen and cooled to room temperature. The precipitate was filtered, washed with water, then methanol, and air-dried to give 1.29 g [4-(5,7-dimethoxy-4-oxo-3,4-dihydro-quinazolin-2-yl)-2,6-dimethyl-phenoxy]-acetic acid. The filtrate was concentrated to dryness and water was added. The suspension was stirred for 30 minutes and filtered. The solid was washed with water, then methanol. After air drying, 3.78 g more [4-(5,7-dimethoxy-4-oxo-3,4-dihydro-quinazolin-2-yl)-2,6-dimethyl-phenoxy]-acetic acid was obtained. Yield: 5.07 g (88%).

To a mixture of [4-(5,7-dimethoxy-4-oxo-3,4-dihydro-quinazolin-2-yl)-2,6-dimethyl-phenoxy]-acetic acid (0.400 g, 1.04 mmol), 1-ethyl-3-(3'-dimethylaminopropyl)carbodiimide hydrochloride (EDCI; 0.240 g, 1.24 mmol), 1-hydroxybenzotriazole hydrate (HOBt; 0.17 g, 1.24 mmol) in DMF (10 mL) was added 4-methylmorpholine (0.20 mL, 1.8 mmol). After 10 minutes, p-anisidine (0.26 g, 2.08 mmol) was added. The mixture was stirred at room temperature under nitrogen for 2.5 days. The solvent was removed under reduced pressure. Water was added, stirred for 30 minutes. The solid was filtered, washed with water, and dried in air. The crude product was purified by column chromatography (silica gel, 230-400 mesh; 5% MeOH in CH$_2$Cl$_2$ as eluent). The product fractions were combined, concentrated to dryness. The solid was dissolved in small amount of dichloromethane, precipitate out by adding ether. The precipitate was filtered, washed with ether, dried under vacuum to afford the title compound as a white solid. Yield: 0.26 g (51%). $^1$H NMR (400 MHz, CDCl$_3$): δ 10.30 (br s, 1H), 8.52 (s, 1H), 7.83 (s, 2H), 7.58 (dd, J=6.8 and 2.0 Hz, 2H), 6.93 (dd, J=6.8 and 2.0 Hz, 2H), 6.84 (d, J=2.4 Hz, 1H), 6.48 (d, J=2.0 Hz, 1H), 4.44 (s, 2H), 3.97 (s, 3H), 3.94 (s, 3H), 3.83 (s, 3H), 2.42 (s, 3H). MS (ES$^+$) m/z: 490.55 (M+1).

Example 27. Preparation of N-benzyl-2-[4-(5,7-dimethoxy-4-oxo-3,4-dihydroquinazolin-2-yl)-2,6-dimethylphenoxy]acetamide

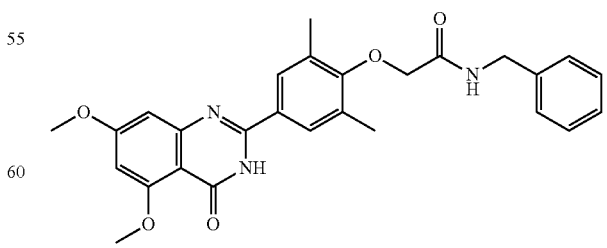

To a mixture of [4-(5,7-dimethoxy-4-oxo-3,4-dihydroquinazolin-2-yl)-2,6-dimethylphenoxy]acetic acid (0.25 g, 0.65 mmol), 1-ethyl-3-(3'-dimethylaminopropyl)carbodiimide hydrochloride (EDCI; 0.137 g, 0.715 mmol), 1-hydroxybenzotriazole hydrate (HOBT; 0.110 g, 0.715 mmol) in DMF (3 mL) was added 4-methylmorpholine (0.08 mL, 0.715 mmol) at room temperature. After 10 minutes, benzylamine (0.142 mL, 1.30 mmol) was added. The mixture was stirred at room temperature under nitrogen for 15 hours. The solvent was removed under reduced pressure. The crude compound was purified by column chromatography (silica gel 230-400 mesh; 3% methanol in dichloromethane as eluent), followed by triturating with an ether-hexane mixture to afford the title compound as a white solid. Yield: 60 mg (39%). $^1$H NMR (400 MHz, DMSO-d$_6$): δ 11.86 (s, 1H), 8.79 (t, J=6.2 Hz, 1H), 7.89 (s, 2H), 7.34-7.21 (m, 5H), 6.72 (d, J=2.0 Hz, 1H), 6.50 (d, J=2.0 Hz, 1H), 4.38 (d, J=6.0 Hz, 2H), 4.33 (s, 2H), 3.87 (s, 3H), 3.82 (s, 3H), 2.30 (s, 6H). MS (ES$^+$) m/z: 474.49 (M+1).

Example 28. Preparation of 2-[4-(4-hydroxy-butoxy)-3,5-dimethyl-phenyl]-5,7-dimethoxy-3H-quinazolin-4-one

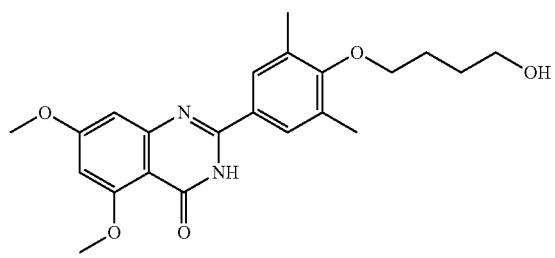 [SMILES: COc1cc(OC)c2c(=O)[nH]c(-c3cc(C)c(OCCCCO)c(C)c3)nc2c1]

To a solution of 4-hydroxy-3,5-dimethyl benzaldehyde (5.00 g, 33.3 mmol) in DMF (30 mL) were added 4-bromo butan-1-ol (6.11 g, 39.9 mmol) and Cs$_2$CO$_3$ (16.24 g, 50.0 mmol). The reaction mixture was stirred at room temperature for 48 hours. Water was added and the products were extracted with ethyl acetate (2×200 mL). The combined organic phase was washed with water (100 mL), brine (100 mL), and dried over anhydrous Na$_2$SO$_4$. Solvent was removed and the crude compound was purified using the Simpliflash system (40% ethyl acetate in hexane as eluent) to give 4-(4-hydroxybutoxy)-3,5-dimethyl benzaldehyde as a colorless liquid. Yield: 0.66 g (7%).

To a solution of 2-amino-4,6-dimethoxy-benzamide (0.50 g, 2.53 mmol) and 4-(4-hydroxybutoxy)-3,5-dimethyl benzaldehyde (0.66 g, 2.53 mmol) in N,N-dimethyl acetamide (10 mL), NaHSO$_3$ (0.50 g, 2.79 mmol) and p-TSA (96 mg, 0.50 mmol) were added and the reaction mixture was heated at 115° C. for 16 hours, then cooled to room temperature. Solvent was removed under reduced pressure. Water (100 mL) was added and the mixture was stirred for 1 hour. The solid separated was filtered and dried. The solid was again washed with diethyl ether to give the title compound as a white solid. Yield: 1.69 g (82%). $^1$H NMR (400 MHz, CDCl$_3$): δ 9.10 (s, 1H), 7.66 (s, 2H), 6.83 (d, J=2.4 Hz, 1H), 6.46 (d, J=2.0 Hz, 1H), 3.98 (s, 3H), 3.93 (s, 3H), 3.85 (t, J=6.0 Hz, 2H), 3.78 (m, 2H), 2.36 (s, 6H), 1.94 (m, 2H), 1.85 (m, 2H). MS (ES) m/z: 399.12 (M+1) (100%).

Example 29. Preparation of 7-chloro-2-(4-(2-hydroxyethoxy)-3,5-dimethylphenyl)quinazolin-4(3H)-one

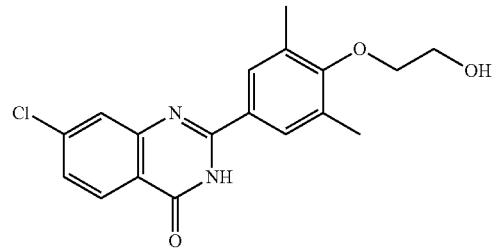 [SMILES: Cc1cc(-c2nc3cc(Cl)ccc3c(=O)[nH]2)cc(C)c1OCCO]

Following the method described in Example 33, the title compound was made starting from 2-amino-4-chlorobenzoic acid and isolated as a white solid. $^1$H NMR (300 MHz, DMSO-d$_6$): δ 12.46 (s, 1H), 8.12 (d, J=8.49 Hz, 1H), 7.90 (s, 2H), 7.77 (d, J=2.00 Hz, 1H), 7.52 (dd, J=8.49, 2.00 Hz, 1H), 4.90 (t, J=5.51 Hz, 1H), 3.86 (t, J=4.88 Hz, 2H), 3.76-3.69 (m, 2H), 2.32 (s, 6H). MS (APCI) m/z 345 [C$_{18}$H$_{17}$ClN$_2$O$_3$+H]$^+$.

Example 30. Preparation of 8-chloro-2-(4-(2-hydroxyethoxy)-3,5-dimethylphenyl)quinazolin-4(3H)-one

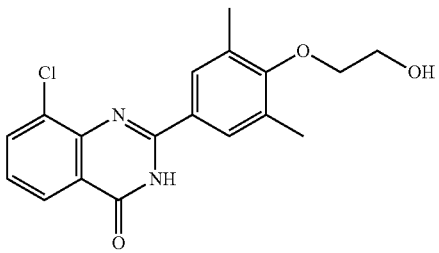 [SMILES: Cc1cc(-c2nc3c(Cl)cccc3c(=O)[nH]2)cc(C)c1OCCO]

Following the procedure described in Example 33, the title compound was made starting from 2-amino-3-chlorobenzoic acid and isolated as a white solid. $^1$H NMR (300 MHz, DMSO-d$_6$): δ 12.55 (s, 1H), 8.09 (dd, J=7.88, 1.37 Hz, 1H), 8.00-7.93 (m, 3H), 7.46 (t, J=7.88 Hz, 1H), 4.91 (t, J=5.54 Hz, 1H), 3.86 (t, J=4.90 Hz, 2H), 3.77-3.69 (m, 2H), 2.33 (s, 6H). MS (APCI) m/z 345 [C$_{18}$H$_{17}$ClN$_2$O$_3$+H]$^+$.

Example 31. Preparation of 2-(4-(2-hydroxyethoxy)-3,5-dimethylphenyl)-8-methoxyquinazolin-4(3H)-one

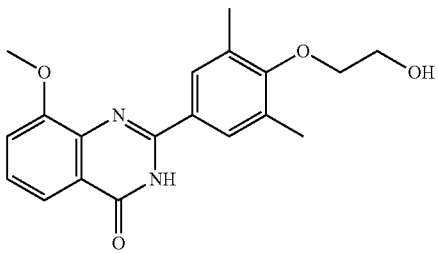 [SMILES: COc1cccc2c(=O)[nH]c(-c3cc(C)c(OCCO)c(C)c3)nc12]

Following the procedure described in Example 33, the title compound was made starting from 2-amino-3-methoxybenzoic acid and isolated as a white solid. ¹H NMR (300 MHz, DMSO-d₆): δ 12.34 (s, 1H), 7.87 (s, 2H), 7.69 (dd, J=7.63, 1.59 Hz, 1H), 7.45-7.34 (m, 2H), 4.90 (t, J=5.53 Hz, 1H), 3.94 (s, 3H), 3.85 (t, J=4.92 Hz, 2H), 3.77-3.69 (m, 2H), 2.33 (s, 6H). MS (APCI) m/z 341 [$C_{19}H_{20}N_2O_4$+H]⁺.

Example 32. Preparation of 5-chloro-2-(4-(2-hydroxyethoxy)-3,5-dimethylphenyl)quinazolin-4(3H)-one

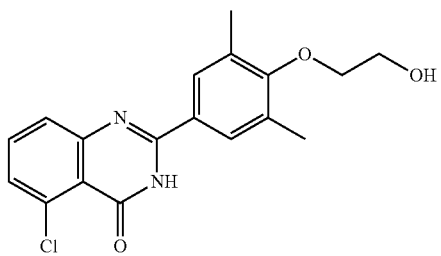 [SMILES: Cc1cc(-c2nc3cccc(Cl)c3c(=O)[nH]2)cc(C)c1OCCO]

A mixture of 2-amino-6-chlorobenzoic acid (5.00 g, 29.1 mmol) in acetonitrile (50.0 mL) was stirred at room temperature under nitrogen. Pyridine (4.72 mL, 58.3 mmol) was added, followed by drop-wise addition of triphosgene (2.85 g, 9.60 mmol) in CH₂Cl₂ (20.0 mL). After the addition, the mixture was heated at 55° C. for 2 hours, then cooled to 25° C. and stirred overnight. Water (100 mL) was added to quench, the mixture was filtered, and washed with cold CH₂Cl₂, to provide 5-chloro-1H-benzo[d][1,3]oxazine-2,4-dione (3.54 g, 62%) as a white solid.

A mixture of 5-chloro-1H-benzo[d][1,3]oxazine-2,4-dione (3.50 g, 17.7 mmol) and 2 M NH₃ in EtOH (11.5 mL, 23.0 mmol) and EtOH (10.0 mL) was stirred at room temperature for 2 hours. The volatiles were removed under reduced pressure, the residue was triturated with water (50 mL), and the solid was filtered, to provide 2-amino-6-chlorobenzamide (1.60 g, 49%) as a tan solid.

A mixture of 2-amino-6-chlorobenzamide (0.490 g, 3.00 mmol), 4-(2-(tert-butyldimethylsilyloxy)ethoxy)-3,5-dimethylbenzaldehyde (0.925 g, 3.00 mmol), NaHSO₃ (94%, 0.468 g, 4.50 mmol), and p-TsOH.H₂O (0.171 g, 0.900 mmol) in DMA (10.0 mL) was heated at 140° C. for 16 hours. The mixture was cooled to room temperature and the solvent was removed under reduced pressure. The residue was diluted with EtOAc (50 mL), washed with water (50 mL), then brine (50 mL), dried over anhydrous Na₂SO₄, filtered, and the solvent was removed under reduced pressure, to provide 2-(4-(2-(tert-butyldimethylsilyloxy)ethoxy)-3,5-dimethylphenyl)-5-chloroquinazolin-4(3H)-one as an off-white solid. The crude material was used directly in the next step without characterization.

Following the method described for desilylation using TBAF in Example 33 below, the title compound was made from 2-(4-(2-(tert-butyldimethylsilyloxy)ethoxy)-3,5-dimethylphenyl)-5-chloroquinazolin-4(3H)-one in 21% yield and was isolated as a white solid. ¹H NMR (300 MHz, DMSO-d₆): δ 12.32 (s, 1H), 7.90 (s, 2H), 7.82-7.55 (m, 2H), 7.48 (dd, J=7.54, 1.35 Hz, 1H), 4.90 (t, J=5.51 Hz, 1H), 3.86 (t, J=4.90 Hz, 2H), 3.77-3.68 (m, 2H), 2.32 (s, 6H). MS (APCI) m/z 345 [$C_{18}H_{17}ClN_2O_3$+H]⁺.

Example 33. Preparation of 2-(4-(2-hydroxyethoxy)-3,5-dimethylphenyl)-7-methoxyquinazolin-4(3H)-one

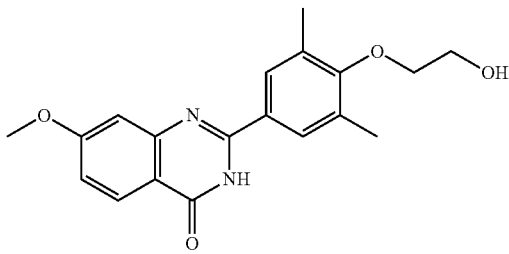 [SMILES: COc1ccc2c(=O)[nH]c(-c3cc(C)c(OCCO)c(C)c3)nc2c1]

A mixture of 2-nitro-4-methoxybenzoic acid (1.00 g, 5.10 mmol) in methanol (10.0 mL) was stirred at room temperature under nitrogen. Palladium on carbon (10% wt, 50% wet, 0.559 g, 0.255 mmol) was added. The round-bottomed flask was capped with a new septa and degassed under vacuum. The flask was charged with hydrogen and degassed again. This was repeated twice and a hydrogen-filled balloon was attached to the flask. The mixture was stirred at room temperature for 4 hours. Nitrogen was then bubbled through the mixture to displace any excess hydrogen. The mixture was filtered through celite 521 and the filtrate was concentrated under reduced pressure to provide 2-amino-4-methoxybenzoic acid (0.890 g, >99%) as an off-white solid. The crude material was used directly in the next step without characterization.

A mixture of 2-amino-4-methoxybenzoic acid (0.490 g, 3.00 mmol), EDCI (1.12 g, 5.83 mmol), HOBt (0.788 g, 5.83 mmol), N-methylmorpholine (0.590 g, 5.83 mmol) and 14.8 N NH₄OH (0.781 mL, 10.6 mmol) in THF was stirred at room temperature for 16 hours. The solvent was removed under reduced pressure, then the residue was diluted with EtOAc (100 mL), washed with water (2×100 mL), then brine (100 mL), dried over anhydrous Na₂SO₄, filtered, and the solvent was removed under reduced pressure to provide 2-amino-4-methoxybenzamide as a tan solid.

A mixture of 2-amino-4-methoxybenzamide (0.490 g, 3.00 mmol), 4-(2-(tert-butyldimethylsilyloxy)ethoxy)-3,5-dimethylbenzaldehyde (0.925 g, 3.00 mmol), NaHSO₃ (94%, 0.468 g, 4.50 mmol), and p-TsOH.H₂O (0.171 g, 0.900 mmol) in benzene (10.0 mL) was heated at 80° C. for 36 hours. The mixture was cooled to room temperature and the solvent was removed under reduced pressure. The residue was diluted with EtOAc (50 mL), washed with water (50 mL) then brine (50 mL), dried over anhydrous Na₂SO₄, filtered, and the solvent was removed under reduced pressure to provide 2-(4-(2-(tert-butyldimethylsilyloxy)ethoxy)-3,5-dimethylphenyl)-7-methoxyquinazolin-4(3H)-one as a pink solid. The crude material was used directly in the next step without characterization.

A mixture of 2-(4-(2-(tert-butyldimethylsilyloxy)ethoxy)-3,5-dimethylphenyl)-7-methoxyquinazolin-4(3H)-one (1.09 g, 2.30 mmol) in 1 M TBAF (11.6 mL, 11.6 mmol) was stirred at room temperature for 3 hours. The mixture was diluted with water (100 mL) and extracted with EtOAc (2×100 mL). The organic layers were combined, washed with saturated aqueous NH₄Cl (2×75 mL), then brine (100 mL), dried over anhydrous Na₂SO₄, filtered, and the solvent was removed under reduced pressure. The residue was purified over silica gel (12 g, EtOAc/hexanes), triturated in ether, and the product was freeze-dried from MeCN/H₂O to yield the title compound (0.0960 g, 12%) as a white solid. $^1$H NMR (300 MHz, DMSO-$d_6$): δ 12.18 (s, 1H), 8.02 (d, J=8.79 Hz, 1H), 7.91 (s, 2H), 7.16 (d, J=2.46 Hz, 1H), 7.07 (dd, J=8.79, 2.46 Hz, 1H), 4.90 (t, J=5.53 Hz, 1H), 3.91 (s, 3H), 3.89-3.82 (m, 2H), 3.77-3.67 (m, 2H), 2.32 (s, 6H), 2.22 (d, J=6.92 Hz, 1H). MS (APCI) m/z 341 [$C_{19}H_{20}N_2O_4$+H]$^+$.

Example 34. Preparation of 2-(4-(2-hydroxyethoxy)-3,5-dimethylphenyl)-6-((4-methylpiperazin-1-yl)methyl)quinazolin-4(3H)-one

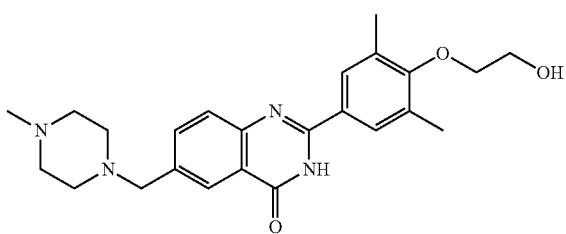 [SMILES: Cc1cc(-c2nc3ccc(CN4CCN(C)CC4)cc3c(=O)[nH]2)cc(C)c1OCCO]

To a solution of 4-(2-(tert-butyldimethylsilyloxy)ethoxy)-3,5-dimethylbenzaldehyde (7.5 g, 24.4 mmol) in DMA (50 mL) was added 2-amino-5-bromobenzamide (5.2 g, 24.4 mmol), NaHSO3 (3.9 g, 36.5 mmol) and p-TsOH (0.46 g, 2.4 mmol), and the reaction was heated at 160° C. After 1 hour, the resulting mixture was cooled to room temperature, diluted with water, and filtered to afford 6-bromo-2-(4-(2-(tert-butyldimethylsilyloxy)ethoxy)-3,5-dimethylphenyl)quinazolin-4(3H)-one (6.7 g, 55%) as a white solid (6.7 g, 55%).

A mixture of 6-bromo-2-(4-(2-(tert-butyldimethylsilyloxy)ethoxy)-3,5-dimethylphenyl)quinazolin-4(3H)-one (5.0 g, 9.9 mmol), vinyltributyltin (4.3 mL, 14.9 mmol) and PdCl$_2$(PPh$_3$)$_2$ (0.70 g, 1.0 mmol) in CH$_3$CN (150 mL) was stirred at reflux overnight. Then, additional PdCl$_2$(PPh$_3$)$_2$ (0.10 g, 0.14 mmol) and vinyltributyltin (2.0 mL, 6.8 mmol) were added and the reaction continued to reflux overnight. The resulting mixture was cooled to room temperature, filtered through celite, and the filtrate concentrated. The residue was purified by flash chromatography (silica, eluting with 98:2 CH$_2$Cl$_2$/MeOH) to afford 2-(4-(2-(tert-butyldimethylsilyloxy)ethoxy)-3,5-dimethylphenyl)-6-vinylquinazolin-4(3H)-one (2.0 g, 45%).

To a solution of 2-(4-(2-(tert-butyldimethylsilyloxy)ethoxy)-3,5-dimethylphenyl)-6-vinylquinazolin-4(3H)-one (0.63 g, 1.4 mmol) in THF (50 mL) and H$_2$O (5 mL) was added NaIO$_4$ (0.90 g, 4.2 mmol) and OsO$_4$ (0.11 mL, 0.014 mmol), and the reaction was stirred overnight at room temperature. Then, the mixture was concentrated in vacuo and the residue was purified by flash chromatography (silica gel, eluting with 98:2 to 95:5 CH$_2$Cl$_2$/MeOH) to afford 2-(4-(2-(tert-butyldimethylsilyloxy)ethoxy)-3,5-dimethylphenyl)-4-oxo-3,4-dihydroquinazoline-6-carbaldehyde (0.52 g, 82%).

A solution of 2-(4-(2-(tert-butyldimethylsilyloxy)ethoxy)-3,5-dimethylphenyl)-4-oxo-3,4-dihydroquinazoline-6-carbaldehyde (0.11 g, 0.24 mmol) in DCE/CH$_2$Cl$_2$ (1:1, 15 mL) was treated with 1-methylpiperazine (0.05 mL, 0.48 mmol) and NaBH(OAc)$_3$ (0.103 g, 0.48 mmol) and the reaction mixture was stirred at room temperature overnight. Then, the mixture was concentrated in vacuo and the residue was purified by flash chromatography (silica gel, eluting with 60% of 92:7:1 CHCl$_3$/MeOH/concentrated NH$_4$OH in CH$_2$Cl$_2$) to afford 2-(4-(2-(tert-butyldimethylsilyloxy)ethoxy)-3,5-dimethylphenyl)-6-((4-methylpiperazin-1-yl)methyl)quinazolin-4(3H)-one (0.14 g, 98%).

A solution of 2-(4-(2-(tert-butyldimethylsilyloxy)ethoxy)-3,5-dimethylphenyl)-6-((4-methylpiperazin-1-yl)methyl)quinazolin-4(3H)-one (0.087 g, 0.16 mmol) in a 1 M TBAF/THF solution (1.3 mL, 1.3 mmol) was stirred for 2 hours at room temperature. Then, the resulting mixture was concentrated in vacuo and purified by flash chromatography (silica gel, eluting with 70% of 92:7:1 CHCl$_3$/MeOH/concentrated NH$_4$OH in CH$_2$Cl$_2$) to afford the title compound (0.070 g, 100%): $^1$H NMR (300 MHz, DMSO-$d_6$): δ 12.31 (s, 1H), 8.02 (s, 1H), 7.89 (s, 2H), 7.56-7.79 (m, 2H), 4.92 (t, J=5.3 Hz, 1H), 3.77-3.93 (m, 2H), 3.64-3.75 (m, 2H), 3.58 (s, 2H), 2.21-2.45 (m, 14H), 2.15 (s, 3H). APCI MS m/z 423 [M+H]$^+$.

Example 35. Preparation of 5,7-Dimethoxy-2-{3-methyl-4-[2-(5-phenyl-4H-[1,2,4]triazol-3-ylamino)-ethoxy]-phenyl}-3H-quinazolin-4-one

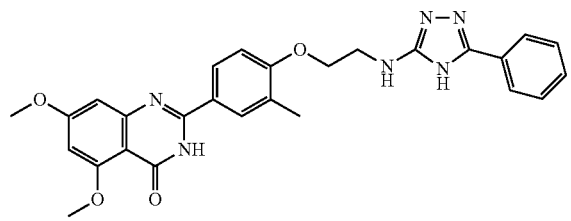 [SMILES: COc1cc(OC)c2c(=O)[nH]c(-c3ccc(OCCNc4nnc(-c5ccccc5)[nH]4)c(C)c3)nc2c1]

To a solution of 2-[4-(2-amino-ethoxy)-3,5-dimethyl-phenyl]-5,7-dimethoxy-3H-quinazolin-4-one (0.37 g, 1.00 mmol) in anhydrous dichloroethane (20 mL) was added benzoyl isothiocyanate (0.18 g 1.10 mmol). The reaction mixture was stirred at room temperature for 3 hours. The solvent was removed and ether (30 mL) was added. The mixture was stirred for 30 minutes and the solid was filtered and dried to give 1-benzoyl-3-{2-[4-(5,7-dimethoxy-4-oxo-3,4-dihydro-quinazolin-2-yl)-2-methyl-phenoxy]-ethyl}-thiourea as a white solid. Yield: 0.53 g (99%).

To a solution of 1-benzoyl-3-{2-[4-(5,7-dimethoxy-4-oxo-3,4-dihydro-quinazolin-2-yl)-2-methyl-phenoxy]-ethyl}-thiourea (0.42 g, 0.785 mmol) in chloroform (20 mL) was added hydrazine hydrate (1.30 mL, 26.5 mmol). The reaction mixture was stirred at reflux for 16 hours. After the solvent was removed, the residue was purified by preparative HPLC to afford the title compound as a white solid. Yield: 35 mg (29%). $^1$H NMR (400 MHz, CDCl$_3$): δ 12.26 (s, 1H), 11.82 (s, 1H), 7.91 (m, 2H), 7.89 (s, 2H), 7.40 (m, 3H), 6.84 (s, 1H), 6.73 (d, J=2.0 Hz, 1H), 6.51 (d, J=2.0 Hz, 1H), 3.98 (t, J=5.6 Hz, 2H), 3.88 (s, 3H), 3.84 (s, 3H), 3.62 (m, 2H), 2.29 (s, 6H). MS (ES$^+$) m/z 513.53 (M+1).

Example 36. Preparation of 2-{3,5-Dimethyl-4-[2-(3-methyl-[1,2,4]oxadiazol-5-ylamino)-ethoxy]-phenyl}-5,7-dimethoxy-3H-quinazolin-4-one

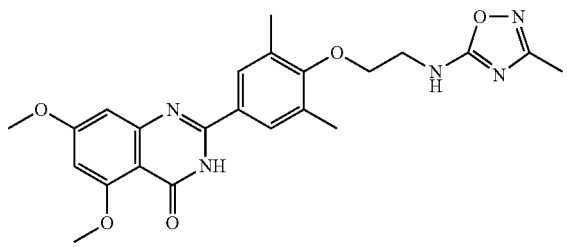

Acetamide oxime (5.00 g, 67.5 mmol) and trichloroacetic anhydride (49.3 mL, 270 mmol) were stirred at 120-130° C. for 3 hours. The mixture was then distilled under vacuum. The fraction at approximately 50-70° C./approximately 5 mmHg was collected. The collected fraction was added to cold saturated aqueous $NaHCO_3$ and extracted with ethyl acetate. The organic phase was washed with saturated aqueous $NaHCO_3$ solution and dried over $Na_2SO_4$. The solvent was evaporated to give 3-methyl-5-trichloromethyl-[1,2,4]oxadiazole as a colorless liquid. Yield: 7.69 g (52%)

A mixture of 3-methyl-5-trichloromethyl-[1,2,4]oxadiazole (56 mg, 0.28 mmol), 2-[4-(2-amino-ethoxy)-3,5-dimethyl-phenyl]-5,7-dimethoxy-3H-quinazolin-4-one (92 mg, 0.25 mmol), and cesium carbonate (179 mg, 0.55 mmol) in DMF (3 mL) was stirred at room temperature under nitrogen for 3.5 days. Water was added, and the mixture was extracted with MeOH/$CH_2Cl_2$. The organic phase was washed with brine, dried over anhydrous $Na_2SO_4$, purified by column chromatography (silica gel; 5% MeOH in $CH_2Cl_2$ as eluent) to give the title compound as a beige solid. Yield: 75 mg (60%). $^1$H NMR (400 MHz, $CDCl_3$): δ 9.68 (s, 1H), 7.71 (s, 2H), 6.82 (d, J=2.4 Hz, 1H), 6.46 (d, J=2.4 Hz, 1H), 5.80 (t, J=5.6 Hz, 1H), 4.00-3.97 (m, 5H), 3.93 (s, 3H), 3.83 (m, 2H), 2.34 (s, 6H), 2.24 (s, 3H). MS ($ES^+$) m/z: 452.57 (M+1).

Example 37. Preparation of N-{2-[4-(5,7-dimethoxy-4-oxo-3,4-dihydro-pyrido[2,3-d]pyrimidin-2-yl)-2,6-dimethyl-phenoxy]-ethyl}-acetamide

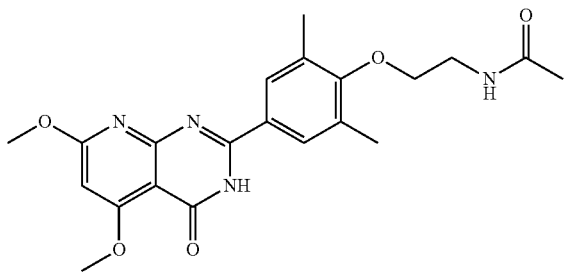 [SMILES: COc1cc(OC)c2c(=O)[nH]c(-c3cc(C)c(OCCNC(C)=O)c(C)c3)nc2n1]

To a solution of 4-hydroxy-3,5-dimethyl-benzaldehyde (15.0 g, 0.10 mol) in anhydrous DMF (30 mL) was added 60% sodium hydride (4.80 g, 0.12 mol) and the reaction mixture was kept stirring for 20 minutes. 2-(2-Bromoethyl)-isoindole-1,3-dione (25.4 g, 0.10 mol) in anhydrous DMF (30 mL) was added drop-wise. The reaction mixture was heated to 65° C. for 5 hours. Acetic acid (3 mL) was added, DMF was removed, and the residue was poured into water (150 mL), and extracted with dichloromethane (200 mL). The crude compound was purified by column chromatography (silica gel 230-400 mesh; eluting with ethyl acetate and hexane 1:1) to give 4-[2-(1,3-dioxo-1,3-dihydro-isoindol-2-yl)-ethoxy]-3,5-dimethyl-benzaldehyde. Yield: 11.0 g (34%).

To a solution of 2-amino-4,6-dimethoxy-nicotinamide (0.40 g, 2.02 mmol, and 4-[2-(1,3-dioxo-1,3-dihydro-isoindol-2-yl)-ethoxy]-3,5-dimethyl-benzaldehyde (0.65 g, 2.02 mmol) in N,N-dimethylacetamide (30 mL) was added $NaHSO_3$ (58.5 wt %, 0.40 g, 2.20 mol) and p-TSA (0.12 g, 6.00 mmol). The reaction mixture was heated to 145° C. for 16 hours, and then cooled to room temperature. Solvent was removed under reduced pressure. Aqueous sodium bicarbonate solution (50 mL) was added and the solid separated was filtered and washed with ether (50 mL). Crude compound was purified by column chromatography (silica gel, 230-400 mesh; methanol, ethyl acetate and dichloromethane 5:20:75) to give 2-{2-[4-(5,7-dimethoxy-4-oxo-3,4-dihydro-pyrido[2,3-d]pyrimidin-2-yl)-2,6-dimethyl-phenoxy]-ethyl}-isoindole-1,3-dione as a light yellow solid. Yield: 0.43 g (43%).

Hydrazine hydrate (0.2 mL, 4.1 mmol) was added to a solution of 2-{2-[4-(5,7-dimethoxy-4-oxo-3,4-dihydro-pyrido[2,3-d]pyrimidin-2-yl)-2,6-dimethyl-phenoxy]-ethyl}-isoindole-1,3-dione (0.43 g, 0.86 mmol) in ethanol (10 mL). The reaction mixture was heated to 70° C. for 4 hours, solvent was removed, and the residue was purified by column chromatography (silica gel, 230-400 mesh; eluting with 5% 7 N ammonia in methanol and dichloromethane) to give 2-[4-(2-amino-ethoxy)-3,5-dimethyl-phenyl]-5,7-dimethoxy-3H-pyrido[2,3-d]pyrimidin-4-one as a white solid. Yield: 0.22 g (69%).

To a solution of 2-[4-(2-amino-ethoxy)-3,5-dimethyl-phenyl]-5,7-dimethoxy-3H-pyrido[2,3-d]pyrimidin-4-one (0.21 g, 0.56 mmol) in pyridine (4 mL) and dichloromethane (10 mL) was added acetyl chloride (51 mg, 0.65 mmol), and the reaction mixture was stirred at room temperature for 3 hours. The solvent was removed under reduced pressure, the residue was poured into water (50 mL) and stirred for 30 minutes. The solid separated was filtered and washed with cold water and ether, and then dried under vacuum to give the title compound as a white solid. Yield: 0.19 g (81%). $^1$H NMR (400 MHz, DMSO-$d_6$): δ 8.15 (s, 1H), 7.90 (s, 2H), 6.36 (s, 1H), 3.93 (s, 3H), 3.88 (s, 3H), 3.79 (t, J=5.6 Hz, 3H), 3.42 (q, J=5.6 Hz, 2H), 2.28 (s, 6H), 1.84 (s, 3H). MS (ES) m/z: 411.15 (M−1).

Example 38. Preparation of N-(4-(5,7-dimethoxy-4-oxo-3,4-dihydroquinazolin-2-yl)-2,6-dimethylbenzyl)acetamide

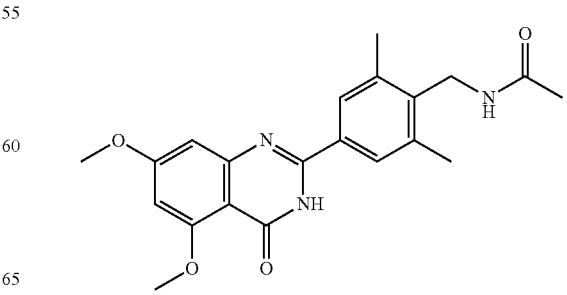

4-Bromo-2,6-dimethylaniline (4.49 g, 22.4 mmol), water (25 mL) and concentrated HCl (8.0 mL) were sonicated and cooled to 0° C. Sodium nitrite (1.67 g, 24.2 mmol) in water (5 mL) was added over 20 minutes. The mixture was stirred at 0° C. for 30 minutes, and solid $Na_2CO_3$ was added to adjust the pH to approximately 7. The liquid portion was added, in portions, to copper (I) cyanide (2.42 g, 27.0 mmol) and potassium cyanide (3.65 g, 56.1 mmol) in water (25 mL) at 70° C. over a period of 25 minutes and the mixture was heated at 70° C. for 45 minutes. The mixture was cooled and extracted with toluene (2×150 mL). The organic phase was washed with water (100 mL), then brine (100 mL), dried ($Na_2SO_4$), filtered, and evaporated to afford a brown oil. Purification by column chromatography (silica gel 230-400 mesh; 25% dichloromethane in hexanes as the eluent) gave 4-bromo-2,6-dimethylbenzonitrile as an orange solid. Yield: 2.3 g (49%).

To 4-bromo-2,6-dimethylbenzonitrile (1.84 g, 8.75 mmol) in anhydrous THF (95 mL), at −78° C. under nitrogen, was added n-butyllithium (2.5 M in hexanes; 3.85 mL, 9.63 mmol) dropwise over 10 minutes. The solution was stirred at −78° C. for 1 hour, and anhydrous DMF (1.00 mL, 12.91 mmol) was added dropwise. The mixture was stirred at −78° C. for 1 hour and at 0° C. for 25 minutes. The reaction was quenched with 1 M HCl, to pH approximately 3. The solution was poured into water (370 mL) and extracted with $CHCl_3$ (7×100 mL). The organic phase was dried over anhydrous $Na_2SO_4$, filtered, and evaporated, to give 4-formyl-2,6-dimethylbenzonitrile as a yellow-orange solid (1.20 g, 86%).

4-Formyl-2,6-dimethylbenzonitrile (1.20 g, 7.53 mmol), anhydrous MeOH (80 mL), trimethylorthoformate (18.0 mL, 164.5 mmol), and camphorsulfonic acid (0.050 g, 0.215 mmol) were stirred at room temperature under nitrogen for 23 hours. Triethylamine (7.5 mL) was added and the solution was evaporated to an oil. The oil was diluted with $NaHCO_3$ (100 mL) and extracted with $CHCl_3$ (5×75 mL). The organic phase was dried over anhydrous $Na_2SO_4$, filtered, and evaporated to afford 4-(dimethoxymethyl)-2,6-dimethylbenzonitrile as a golden-red oil. Yield: 1.40 g (90%).

To 4-(dimethoxymethyl)-2,6-dimethylbenzonitrile (0.86 g, 4.18 mmol) in anhydrous THF (40 mL), at 0° C. under nitrogen, was added solid lithium aluminum hydride (0.34 g, 8.94 mmol) in portions over 15 minutes. The mixture was stirred at 0° C. for 30 minutes and at room temperature for 20 hours. The mixture was cooled to 0° C. and quenched with solid $Na_2SO_4·10H_2O$, stirred for 10 minutes, and then stirred at room temperature for 15 minutes. Solids were removed by filtration and washed with THF (100 mL). The filtrate was evaporated to give (4-(dimethoxymethyl)-2,6-dimethylphenyl)methanamine as a golden-brown semi-solid. Yield: 0.87 g (100%)

To (4-(dimethoxymethyl)-2,6-dimethylphenyl)methanamine (0.87 g, 4.18 mmol), anhydrous $CH_2Cl_2$ (20 mL), $Et_3N$ (5.84 mL, 41.89 mmol), at 0° C. under nitrogen, was added acetic anhydride (0.44 mL, 4.65 mmol), followed by DMAP (0.018 g, 0.147 mmol). The mixture was stirred at 0° C. for 15 minutes and then at room temperature for 23 hours. The mixture was evaporated to a solid. The solid was stirred with $NaHCO_3$ (100 mL) and $CHCl_3$ (50 mL) for 15 minutes. The organic phase was separated and the aqueous phase extracted with $CHCl_3$ (4×50 mL). The combined organic phase was washed with brine (75 mL), dried over anhydrous $Na_2SO_4$, filtered, and evaporated to afford N-(4-(dimethoxymethyl)-2,6-dimethylbenzyl)acetamide as a light orange solid (1.00 g, 95%).

To N-(4-(dimethoxymethyl)-2,6-dimethylbenzyl)acetamide (0.83 g, 3.30 mmol) in $CHCl_3$ (65 mL), at 0° C. was added trifluoroacetic acid/water (1:1, 10 mL) added dropwise. The solution was stirred at 0° C. for 1.75 hours. The solution was diluted with water (200 mL) and the organic phase separated. The aqueous phase was extracted with $CHCl_3$ (4×75 mL). The combined organic phase was washed with $NaHCO_3$ (200 mL). The aqueous phase was back-extracted with $CHCl_3$ (3×30 mL). The combined organic phase was dried ($Na_2SO_4$), filtered, and evaporated to give a N-(4-formyl-2,6-dimethylbenzyl)acetamide as a brown solid. Yield: 0.56 g (82%)

2-Amino-4,6-dimethoxybenzamide (0.334 g, 1.70 mmol), N-(4-formyl-2,6-dimethylbenzyl)acetamide (0.35 g, 1.70 mmol), anhydrous N,N-dimethylacetamide (10 mL), sodium bisulfite (58.5 wt %, 0.343 g, 1.87 mmol) and p-TsOH·$H_2O$ (0.065 g, 0.341 mmol) were heated at 120° C. for 19.5 hours. The solution was evaporated in vacuo and the residue was triturated with water (50 mL). The yellow solid was filtered off and washed with water (50 mL). The product was purified by column chromatography (silica gel, 230-400 mesh; 6% methanol in dichloromethane as the eluent) and triturated with $Et_2O$ (6 mL) to afford the title compound as a white solid. Yield: 0.202 g (31%). $^1$H NMR (400 MHz, DMSO-$d_6$): δ 11.89 (s, 1H), 7.93 (t, J=4.49 Hz, 1H), 7.85 (s, 2H), 6.74 (d, J=1.95 Hz, 1H), 6.51 (d, J=1.95 Hz, 1H), 4.28 (d, J=4.69 Hz, 2H), 3.87 (s, 3H), 3.83 (s, 3H), 2.37 (s, 6H), 1.80 (s, 3H). MS (ES+) m/z: 382.18 (100%), 383.19.

Example 39. Preparation of N-[4-(5,7-dimethoxy-4-oxo-3,4-dihydro-pyrido[2,3-d]pyrimidin-2-yl)-2,6-dimethyl-benzyl]-acetamide

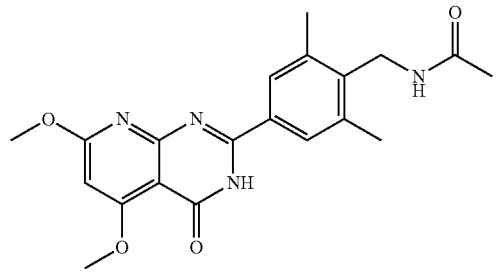 [SMILES: COc1cc(OC)c2c(=O)[nH]c(-c3cc(C)c(CNC(C)=O)c(C)c3)nc2n1]

To a solution of 2-amino-4,6-dimethoxy-nicotinamide (300 mg, 1.52 mmol), N-(4-formyl-2,6-dimethyl-benzyl)-acetamide (342 mg, 1.67 mmol) in N,N-dimethylacetamide (5 mL) were added sodium hydrogen sulfite (58.5 wt %, 300 mg, 1.68 mmol) and p-toluenesulfonic acid monohydrate (60 mg, 0.32 mmol). The reaction mixture was stirred at 150° C. for 17 hours under nitrogen and then cooled to room temperature. The solvent was evaporated under reduced pressure to dryness. Water (50 mL) was added, and extracted with dichloromethane. The organic phase was dried over anhydrous anhydrous sodium sulfate. Solvent was evaporated and the crude compound was purified by column chromatography (silica gel 230-400 mesh; eluting with 5% methanol in dichloromethane) to give the title compound as a white solid. Yield: 78 mg (13%). $^1$H NMR (400 MHz, $CD_3OD$): δ 7.79 (s, 2H), 6.40 (s, 1H), 4.46 (s, 2H), 4.05 (s, 3H), 3.98 (s, 3H), 2.46 (s, 6H), 1.95 (s, 3H). MS (ES$^+$) m/z: 383.13 (M+1).

Example 40. Preparation of 2-{3,5-dimethyl-4-[2-(2,2,2-trifluoro-ethylamino)-ethoxy]-phenyl}-5,7-dimethoxy-3H-quinazolin-4-one

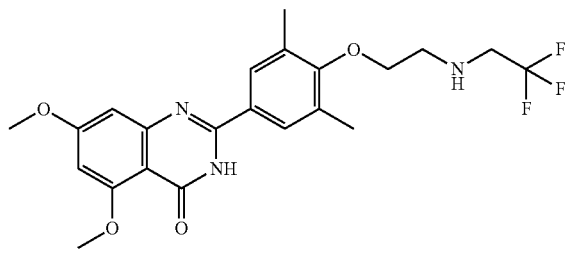 [SMILES: COc1cc(OC)c2c(=O)[nH]c(-c3cc(C)c(OCCNCC(F)(F)F)c(C)c3)nc2c1]

A solution of 2-[4-(2-bromo-ethoxy)-3,5-dimethyl-phenyl]-5,7-dimethoxy-3H-quinazolin-4-one (500 mg, 1.15 mmol) and 2,2,2-trifluoro ethyl amine (1.14 g, 11.53 mmol) and TEA (5 mL) in DMF:THF (10:5 ml) was heated at 40° C. for 24 hours. Then, water (100 mL) was added and product was extracted with ethyl acetate (2×250 mL). The combined organic layer was washed with water, then brine, dried over $Na_2SO_4$, and evaporated, to give crude product. The crude product was purified by the Simpliflash system, using 2% methanol in dichloromethane as eluent, to give the title compound as a white solid. Yield: 81 mg (15%). $^1$H NMR (400 MHz, $CDCl_3$) δ 9.44 (s, 1H), 7.69 (s, 2H), 6.83 (d, J=2.4 Hz, 1H), 6.46 (d, J=2.4 Hz, 1H), 3.97 (s, 3H), 3.93 (s, 3H), 3.91 (s, br, 2H), 3.33 (d, J=4.4 Hz, 2H), 3.14 (d, J=1.2 Hz, 2H), 2.37 (s, 6H). MS (ES) m/z: 450.07 (M−1) (100%).

Example 41. Preparation of N-{2-[4-(6,8-dimethoxy-1-oxo-1,2-dihydro-isoquinolin-3-yl)-2,6-dimethyl-phenoxy]-ethyl}-formamide

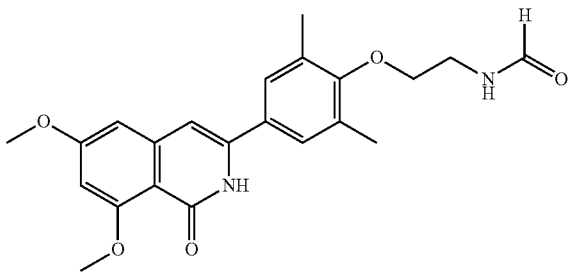 [SMILES: COc1cc(OC)c2c(=O)[nH]c(-c3cc(C)c(OCCNC=O)c(C)c3)cc2c1]

To a suspension of 3-[4-(2-Hydroxy-ethoxy)-3,5-dimethyl-phenyl]-6,8-dimethoxy-2H-isoquinolin-1-one (0.80 g, 2.16 mmol), isoindole-1,3-dione (0.35 g, 2.38 mmol), and triphenyl phosphine (0.85 g, 3.25 mmol) in THF (30 mL), was added diethyl azodicarboxylate (0.56 g, 3.25 mmol), and the reaction mixture was stirred at room temperature for 16 hours. The solvent was evaporated in vacuo and the residue was washed with ether to give 2-{2-[4-(6,8-dimethoxy-1-oxo-1,2-dihydro-isoquinolin-3-yl)-2,6-dimethyl-phenoxy]-ethyl}-isoindole-1,3-dione as an off-white solid. Yield: 1.11 g (crude).

Hydrazine hydrate (0.29 mL, 6.07 mmol) was added to the solution of 2-{2-[4-(6,8-dimethoxy-1-oxo-1,2-dihydro-isoquinolin-3-yl)-2,6-dimethyl-phenoxy]-ethyl}-isoindole-1,3-dione (1.01 g, 2.03 mmol) in ethanol (20 mL). The reaction mixture was heated to 70° C. for 5 hours. The solvent was removed and the residue was purified by the Simpliflash system, using 5% 7 N ammonia in methanol with dichloromethane as eluent, to give 3-[4-(2-amino-ethoxy)-3,5-dimethyl-phenyl]-6,8-dimethoxy-2H-isoquinolin-1-one as a white solid. Yield: 0.59 g (80.2%).

To a solution of 3-[4-(2-amino-ethoxy)-3,5-dimethyl-phenyl]-6,8-dimethoxy-2H-isoquinolin-1-one (0.30 g, 0.8 mmol) in formic acid (20 mL), was heated at reflux for 72 hours. The reaction mixture was cooled to room temperature and solvent was removed under reduced pressure. Water (100 mL) was added to the residue and neutralized with solid $NaHCO_3$. The product was extracted with dichloromethane (2×200 mL). The combined organic layer was washed with water, then brine, dried over $Na_2SO_4$, and evaporated to give crude product. The crude product was purified by the Simpliflash system, using 5% 7 N ammonia in methanol with dichloromethane as eluent, to give the title compound as a white solid. Yield: 97 mg (30%). $^1$H NMR (400 MHz, DMSO): δ 10.70 (s, 1H), 8.31 (br s, 1H), 8.09 (s, 1H), 7.45 (s, 2H), 6.67 (d, J=2.0 Hz, 1H), 6.64 (s, 1H), 6.45 (d, J=2.0 Hz, 1H), 3.83 (s, 3H), 3.79 (s, 3H), 3.77 (m, 2H), 3.48 (m, 3H), 2.25 (s, 6H). MS (ES) m/z: 397.11 (M+1) (100%).

Example 42. Preparation of 2-(3,5-dimethyl-4-(2-(methylamino)ethoxy)phenyl)-5,7-dimethoxyquinazolin-4(3H)-one

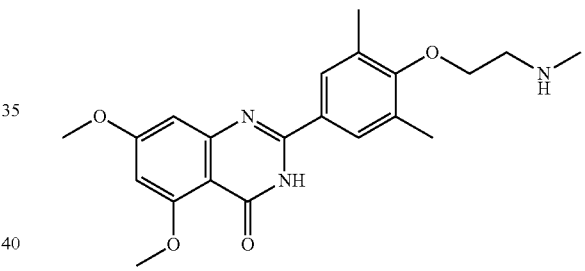

To a mixture of 2-(4-(2-hydroxyethoxy)-3,5-dimethylphenyl)-5,7-dimethoxyquinazolin-4(3H)-one (2.00 g, 5.40 mmol) and $Et_3N$ (0.977 mL, 7.02 mmol) in $CH_2Cl_2$ (27.0 mL) was added slowly MsCl (0.543 mL, 7.02 mmol) at room temperature. After 1 day, additional $Et_3N$ (0.977 mL, 7.02 mmol) and MsCl (0.543 mL, 7.02 mmol) was added and the mixture was stirred for 2 hours, then diluted with EtOAc (300 mL) and washed with 10% aqueous citric acid (3×75 mL), saturated aqueous $NaHCO_3$ (75 mL), and brine (75 mL). An insoluble white solid was collected by filtration to provide 2-(4-(5,7-dimethoxy-4-oxo-3,4-dihydroquinazolin-2-yl)-2,6-dimethyl-phenoxy)ethyl methanesulfonate (0.890 g, 37%).

A mixture of compound 2-(4-(5,7-dimethoxy-4-oxo-3,4-dihydroquinazolin-2-yl)-2,6-dimethyl-phenoxy)ethyl methanesulfonate (0.200 g, 0.446 mmol) and 33% $CH_3NH_2$ in EtOH (5.00 mL) was heated at reflux overnight. The solvent was removed under vacuum and the residue was purified on silica gel (12 g, $CH_2Cl_2/CH_3OH$) and the product freeze-dried from $MeCN/H_2O$ to provide the title compound (0.0968 g, 57%) as a light yellow solid. $^1$H NMR (300 MHz, DMSO-$d_6$: δ 7.90 (s, 2H), 6.73 (d, J=2.29 Hz, 1H), 6.52 (d, J=2.29 Hz, 1H), 3.94-3.80 (m, 8H), 2.98 (t, J=5.46 Hz, 2H), 2.45 (s, 3H), 2.33-2.28 (m, 8H). MS (APCI) m/z 384 $[C_{21}H_{25}N_3O_4+H]^+$.

Example 43. Preparation of N-(2-(4-(5,7-dimethoxy-4-oxo-3,4-dihydroquinazolin-2-yl)-2,6-dimethylphenoxy)ethyl)propane-2-sulfonamide

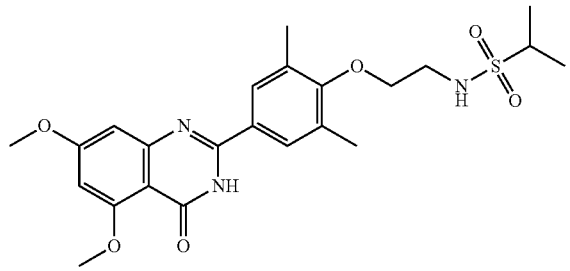 [SMILES: COc1cc(OC)c2c(=O)[nH]c(-c3cc(C)c(OCCNS(=O)(=O)C(C)C)c(C)c3)nc2c1]

A mixture of 3,5-dimethyl-4-hydroxybenzaldehyde (0.600 g, 4.00 mmol), N-(2-bromoethyl)-phthalimide (1.22 g, 4.80 mmol), K$_2$CO$_3$ (0.829 g, 6.00 mmol), NaI (3.00 g, 20.0 mmol) in DMF (40.0 mL) was heated at 80° C. for 2.5 hours. The reaction was cooled to room temperature, diluted with EtOAc (200 mL), washed with 1 M NaOH (2×100 mL), 1 M HCl (2×100 mL), brine (75 mL), dried over sodium sulfate, filtered, and concentrated under vacuum. The residue was chromatographed on silica gel (40 g, hexanes/EtOAc) to provide the expected ether (0.300 g, 23%) as a yellow solid. A mixture of this ether (0.293 g, 0.907 mmol), 2-amino-4,6-dimethoxybenzamide (0.178 g, 0.907 mmol), NaHSO$_3$ (94%, 0.100 g, 0.907 mmol), and p-TsOH.H$_2$O (0.0173 g, 0.0907 mmol) in DMA (11.3 mL) was stirred at reflux for 1.5 hours, then cooled to room temperature. The mixture was diluted with EtOAc (250 mL), washed with saturated aqueous ammonium chloride (3×75 mL), them brine (75 mL), dried over sodium sulfate, filtered, and concentrated under vacuum. The residue was chromatographed on silica gel (40 g, CH$_2$Cl$_2$/CH$_3$OH) to provide the expected product (0.075 g, 17%) as a light yellow solid. A mixture of the above compound (0.213 g, 0.426 mmol) and 2 M methylamine in THF (25.0 mL) was stirred at room temperature for 17 hours. The volatiles were removed under vacuum and 2-(4-(2-aminoethoxy)-3,5-dimethylphenyl)-5,7-dimethoxyquinazolin-4(3H)-one was isolated (0.036 g, 23%) as a white solid.

A mixture of 2-(4-(2-aminoethoxy)-3,5-dimethylphenyl)-5,7-dimethoxyquinazolin-4(3H)-one (0.125 g, 0.338 mmol), 2-propylsulfonyl chloride (0.040 mL, 0.36 mmol), and DBU (0.100 mL, 0.67 mmol) in THF (2.5 mL) was stirred at 60° C. for 18 hours. Then, the mixture was cooled to room temperature and purified by silica gel chromatography, eluting with 92:7:1 CHCl$_3$/MeOH/concentrated NH$_4$OH. The mixture was further purified by reverse-phase HPLC, eluting with 10% to 90% CH$_3$CN in H$_2$O with 0.1% TFA, to afford the desired product. The product was freeze-dried from CH$_3$CN/H$_2$O to afford the title compound (0.080 g, 50%) as a white solid. $^1$H NMR (300 MHz, DMSO-d$_6$: δ 11.85 (s, 1H), 8.09 (s, 2H), 7.33 (t, J=6.0 Hz, 1H), 6.74 (d, J=2.3 Hz, 1H), 6.52 (d, J=2.3 Hz, 1H), 3.89 (s, 3H), 3.82-3.86 (m, 5H), 3.21-3.39 (m, 3H), 2.31 (s, 6H), 1.26 (d, J=6.8 Hz, 6H). APCI MS m/z 476 [M+H]$^+$.

Example 44. Preparation of 2-(4-(2-(isopropylamino)ethoxy)-3,5-dimethylphenyl)-5,7-dimethoxyquinazolin-4(3H)-one

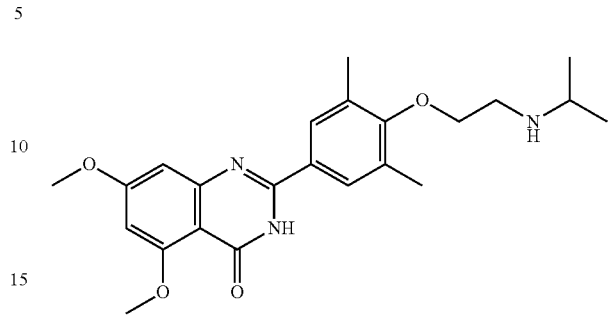

A solution of 2-(4-(2-aminoethoxy)-3,5-dimethylphenyl)-5,7-dimethoxyquinazolin-4(3H)-one (0.200 g, 0.54 mmol) in EtOH (10 mL) and acetone (0.198 mL, 2.71 mmol) was treated with PtO$_2$ (0.050 g). The reaction mixture was stirred under 1 atmosphere of hydrogen for 48 hours. Then, the mixture was filtered through celite with ethanol washings, concentrated, and purified by silica gel chromatography, to afford the title compound (0.155 g, 70%). The product was further purified by reverse-phase HPLC, eluting with 10% to 90% CH$_3$CN in H$_2$O with 0.1% TFA, to afford the title compound as a white solid. $^1$H NMR (300 MHz, DMSO-d$_6$: δ 7.90 (s, 2H), 6.74 (d, J=2.3 Hz, 1H), 6.52 (s, J=2.3 Hz, 1H), 3.83-3.89 (m, 8H), 2.89 (t, J=5.6 Hz, 2H), 2.75-2.84 (m, 1H), 2.30 (s, 6H), 1.01 (d, J=6.2 Hz, 6H); APCI MS m/z 412 [M+H]$^+$.

Example 45. Preparation of N-(2-(4-(5,7-dimethoxy-4-oxo-3,4-dihydroquinazolin-2-yl)-2-methylphenoxy)ethyl)acetamide

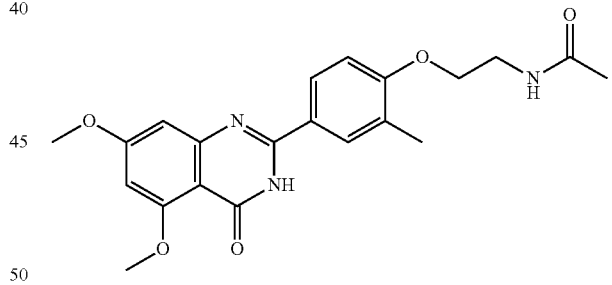

2-(4-(2-Aminoethoxy)-3-methylphenyl)-5,7-dimethoxyquinazolin-4(3H)-one was synthesized as described for 2-(4-(2-aminoethoxy)-3,5-dimethylphenyl)-5,7-dimethoxyquinazolin-4(3H)-one from 3-methyl-4-hydroxybenzaldehyde (See Example 43).

A suspension of 2-(4-(2-aminoethoxy)-3-methylphenyl)-5,7-dimethoxyquinazolin-4(3H)-one (0.12 g, 0.33 mmol) in CH$_2$Cl$_2$ (5 mL) was treated with Et$_3$N (0.05 mL, 0.41 mmol) and acetyl chloride (0.026 mL, 0.37 mmol) and the mixture stirred at room temperature for 3 hours. Then, the mixture was concentrated in vacuo and the residue purified by flash chromatography on silica gel, eluting with 97:3 to 90:10 CH$_2$Cl$_2$/MeOH to 92:7:1 CHCl$_3$/MeOH/concentrated NH$_4$OH, to afford crude product. Further purification on a reverse-phase C$_{18}$ column, eluting with 10% to 90% CH$_3$CN in H$_2$O with 0.05% TFA, afforded the title compound (0.080 g, 61%) as a white solid. $^1$H NMR (300 MHz, DMSO-d$_6$) δ 11.65 (s, 1H), 7.93-8.18 (m, 3H), 7.05 (d, J=8.4 Hz, 1H), 6.71 (d, J=2.3 Hz, 1H), 6.50 (d, J=2.3 Hz, 1H), 4.07 (t, J=5.6 Hz, 2H), 3.88 (s, 3H), 3.84 (s, 3H), 3.35-3.52 (m, 2H), 2.23 (s, 3H), 1.83 (s, 3H). APCI MS m/z 398 [M+H]$^+$.

Example 46. Preparation of 2-(4-(2-(dimethylamino)ethoxy)-3,5-dimethylphenyl)-5,7-dimethoxyquinazolin-4(3H)-one

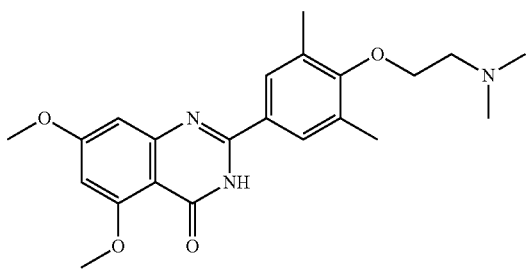

To a solution of 2-(4-(2-aminoethoxy)-3,5-dimethylphenyl)-5,7-dimethoxyquinazolin-4(3H)-one (0.150 g, 0.41 mmol) in MeOH (16 mL) and CH$_2$Cl$_2$ (5 mL) was added 37% aqueous formaldehyde (0.300 mL, 4.0 mmol) and the mixture stirred for 1 hour. Then, NaBH$_4$ (0.078 g, 2.05 mmol) was added and the reaction was stirred for 16 hours at room temperature. Additional 37% aqueous formaldehyde (1.0 mL) was added and stirred for 1 hour, at which time, additional NaBH$_4$ (0.100 g, 2.63 mmol) was added and stirred for 1 hour. The reaction mixture was concentrated, redissolved in CH$_2$Cl$_2$, washed with brine (100 mL), dried (Na$_2$SO$_4$), filtered, and concentrated. The residue was purified by silica gel chromatography, eluting with 9:1 CH$_2$Cl$_2$/MeOH to 92:7:1 CHCl$_3$/MeOH/concentrated aqueous NH$_4$OH. The residue was further purified by reverse-phase HPLC, eluting with 10% to 90% CH$_3$CN in H$_2$O with 0.1% TFA, to afford the title compound as a white solid (0.070 g, 43%). $^1$H NMR (300 MHz, DMSO-d$_6$) δ 11.70 (br s, 1H), 7.90 (s, 2H), 6.74 (d, J=2.3 Hz, 1H), 6.52 (d, J=2.3 Hz, 1H), 3.84-3.89 (m, 8H), 2.64 (t, J=5.8 Hz, 2H), 2.30 (s, 6H), 2.24 (s, 6H). APCI MS m/z 398 [M+H]$^+$.

Example 47. Preparation of N-(2-(4-(5,7-dimethoxy-4-oxo-3,4-dihydroquinazolin-2-yl)-2,6-dimethylphenoxy)ethyl)-N-methylacetamide

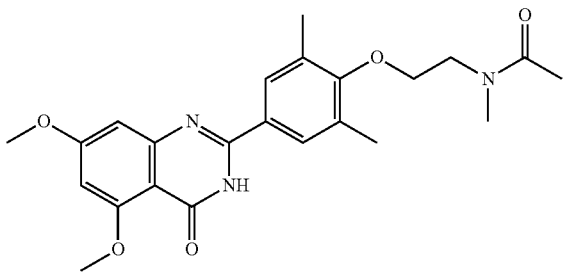 [SMILES: COc1cc(OC)c2c(=O)[nH]c(-c3cc(C)c(OCCN(C)C(C)=O)c(C)c3)nc2c1]

To a solution of 2-(3,5-dimethyl-4-(2-(methylamino)ethoxy)phenyl)-5,7-dimethoxyquinazolin-4(3H)-one (0.110 g, 0.287 mmol) in CH$_2$Cl$_2$ (10 mL) was added Et$_3$N (0.080 mL, 0.574 mmol), followed by acetyl chloride (0.022 mL, 0.315 mmol). The mixture was stirred at room temperature under nitrogen for 10 minutes, concentrated, and purified by silica gel chromatography, eluting with 9:1 CH$_2$Cl$_2$/MeOH, followed by reverse-phase HPLC, eluting with 10% to 90% CH$_3$CN in H$_2$O with 0.1% TFA, to afford the title compound as a white solid (0.078 g, 64%). $^1$H NMR (mixture of amide rotamers, 300 MHz, DMSO-d$_6$: δ 11.85 (s, 1H), 7.90 (d, J=2.7 Hz, 2H), 6.74 (d, J=2.2 Hz, 1H), 6.52 (d, J=2.2 Hz, 1H), 3.84-3.95 (m, 8H), 3.65-3.74 (m, 2H), 3.12 (s, 1.5H), 2.92 (s, 1.5H), 2.27 (d, J=1.1 Hz, 6H), 2.11 (s, 1.5H), 2.03 (s, 1.5H). APCI MS m/z 424 [M−H]$^-$.

Example 48. Preparation of N-(2-(4-(5,7-dimethoxy-4-oxo-3,4-dihydroquinazolin-2-yl)-2,6-dimethylphenoxy)ethyl)formamide

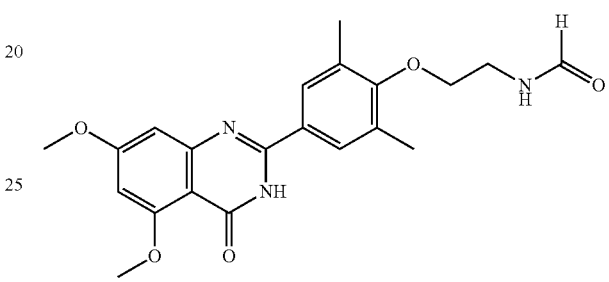

A solution of 2-(4-(2-aminoethoxy)-3,5-dimethylphenyl)-5,7-dimethoxyquinazolin-4(3H)-one (0.086 g, 0.23 mmol) in ethanol (10 mL) and methyl formate (0.028 mL, 0.46 mmol) was stirred at room temperature for 5 hours. At this time, an additional portion of methyl formate (5 mL, 80.6 mmol) was added and the mixture heated at reflux for 4 days. The mixture was concentrated and purified by silica gel chromatography, eluting with 92:7:1 CHCl$_3$/MeOH/concentrated NH$_4$OH. The product was freeze-dried from CH$_3$CN/H$_2$O to yield the title compound (0.065 g, 71%) as a white solid. $^1$H NMR (300 MHz, DMSO-d$_6$): δ 11.84 (s, 1H), 8.29-8.37 (m, 1H), 8.11 (d, J=1.3 Hz, 1H), 7.90 (s, 2H), 6.74 (d, J=2.3 Hz, 1H), 6.52 (d, J=2.3 Hz, 1H), 3.89 (s, 3H), 3.79-3.84 (m, 5H), 3.47-3.53 (m, 2H), 2.29 (s, 6H). APCI MS m/z 396 [M−H]$^-$.

Example 49. Preparation of N-(2-(4-(5,7-dimethoxy-4-oxo-3,4-dihydroquinazolin-2-yl)-2,6-dimethylphenoxy)ethyl)-N-methylformamide

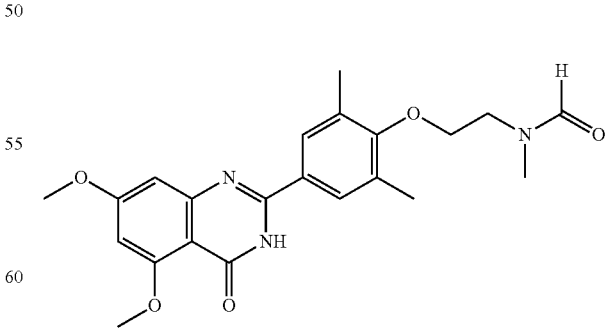

To a solution of 2-(3,5-dimethyl-4-(2-(methylamino)ethoxy)phenyl)-5,7-dimethoxyquinazolin-4(3H)-one (0.080 g, 0.21 mmol) in EtOH (15 mL) was added methyl formate (5 mL). The mixture was heated at reflux for 24 hours, concentrated, and purified by silica gel chromatography, eluting with 9:1 $CH_2Cl_2$/MeOH, to afford the title compound as a white solid (0.080 g, 93%): $^1$H NMR (mixture of amide rotamers, 300 MHz, DMSO-$d_6$): δ 11.85 (s, 1H), 8.12 (d, J=1.9 Hz, 1H), 7.90 (s, 2H), 6.74 (d, J=2.2 Hz, 1H), 6.52 (d, J=2.2 Hz, 1H), 3.88-3.93 (m, 5H), 3.84 (s, 3H), 3.62-3.68 (m, 2H), 3.08 (s, 0.5H), 2.88 (s, 0.5H), 2.25-2.35 (m, 6H); APCI MS m/z 410 [M−H]$^-$.

Example 50. Preparation of N-(2-(4-(5,7-dimethoxy-4-oxo-3,4-dihydroquinazolin-2-yl)-2,6-dimethylphenoxy)ethyl)dimethylamino-N-sulfonamide

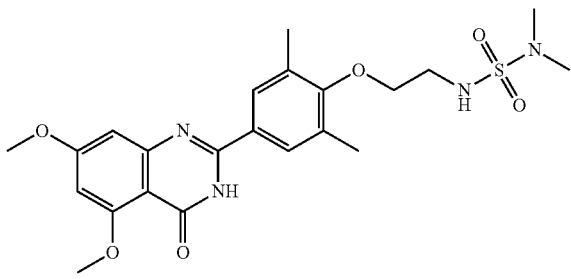

A solution of 2-(4-(2-aminoethoxy)-3,5-dimethylphenyl)-5,7-dimethoxyquinazolin-4(3H)-one (0.150 g, 0.41 mmol) in $CH_2Cl_2$ (10 mL) was treated with $Et_3N$ (0.083 g, 0.82 mmol), then dimethylsulfamoylchloride (0.065 g, 0.45 mmol), and the reaction mixture stirred under nitrogen at room temperature for 1 hour. Then, DBU (0.100 mL) was added and stirring continued for 1 hour at room temperature. Then, the reaction mixture was heated at reflux for 18 hours, additional dimethylsulfamoylchloride (0.150 mL) was added, and heating continued at reflux for a further 2 hours. The reaction mixture was cooled and purified by flash chromatography on silica gel, eluting with 100% $CH_2Cl_2$ to 100% (92:7:1 $CHCl_3$/MeOH/concentrated $NH_4OH$). The resulting solid was further purified by reverse-phase HPLC, eluting with 10% to 90% $CH_3CN$ in $H_2O$ with 0.1% TFA. The solids were then triturated with $CH_3CN$ to afford the title compound as a white solid. $^1$H NMR (300 MHz, $CDCl_3$) δ 9.20 (s, 1H), 7.69 (s, 2H), 6.82 (d, J=2.3 Hz, 1H), 6.5 (d, J=2.3 Hz, 1H), 4.72-4.80 (m, 1H), 3.93-3.98 (m, 8H), 3.46-3.56 (m, 2H), 2.87 (s, 6H), 2.38 (s, 6H); ESI MS m/z 477 [M+H]$^+$.

Example 51. Preparation of N-(2-(4-(5,7-dimethoxy-4-oxo-3,4-dihydroquinazolin-2-yl)-2,6-dimethylphenoxy)ethyl)cyanamide

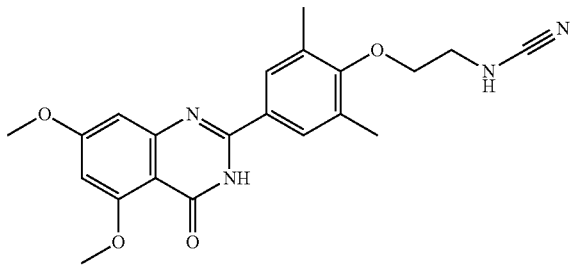 [SMILES: COc1cc(OC)c2c(=O)[nH]c(-c3cc(C)c(OCCNC#N)c(C)c3)nc2c1]

To a solution of 2-(4-(2-aminoethoxy)-3,5-dimethylphenyl)-5,7-dimethoxyquinazolin-4(3H)-one (0.150 g, 0.41 mmol) in MeOH (15 mL) was added BrCN (0.043 g, 0.41 mmol) and $NaHCO_3$ (0.044 g, 0.52 mmol). The reaction was stirred at room temperature for 1 hour and then concentrated in vacuo. Purification by flash chromatography on silica gel, eluting with 2% to 10% MeOH/$CH_2Cl_2$, afforded the title compound (0.120 g, 74%) as a white solid. $^1$H NMR (300 MHz, DMSO-$d_6$): δ 11.85 (s, 1H), 7.82-7.92 (m, 2H), 7.03-7.14 (m, 1H), 6.72 (d, J=1.4 Hz, 1H), 6.59 (d, J=1.4 Hz, 1H), 3.81-3.93 (m, 8H), 3.15-3.29 (m, 2H), 2.28 (s, 6H). APCI MS m/z 395 [M+H]$^+$.

Example 52. Preparation of 2-(3,5-dimethyl-4-(2-(5-methylisoxazol-3-ylamino)ethoxy)phenyl)-5,7-dimethoxyquinazolin-4(3H)-one

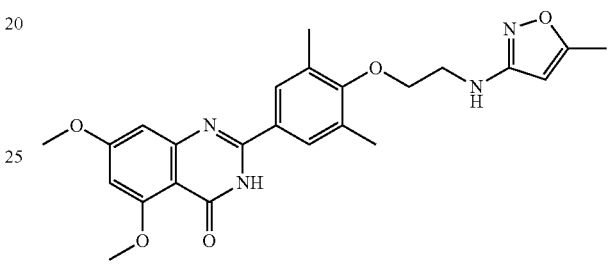

To a solution of 5-methylisoxazol-3-amine (1.0 g, 10.2 mmol) in $CH_2Cl_2$ was added $Et_3N$ (1.03 g, 10.2 mmol) and bromoacetyl chloride (1.60 g, 10.2 mmol). The mixture was stirred at room temperature for 1 hour, washed with water (100 mL), then brine (100 mL), dried ($Na_2SO_4$), filtered, and concentrated, to afford 2-bromo-N-(5-methylisoxazol-3-yl)acetamide as a white solid (1.2 g, 55%).

To a solution of 2-bromo-N-(5-methylisoxazol-3-yl)acetamide (0.223 g, 1.0 mmol) in THF (10 mL) under nitrogen was added 1.0 M $BH_3$.THF (3.0 mL, 3.0 mmol). The reaction mixture was stirred at room temperature for 18 hours, quenched with 1 M NaOH, extracted with ethyl acetate (2×100 mL), dried over anhydrous $Na_2SO_4$, filtered, and concentrated. The residue was purified by flash chromatography on silica gel, eluting with 1:1 ethyl acetate/hexane to 100% ethyl acetate, to afford N-(2-bromoethyl)-5-methylisoxazol-3-amine as a white solid (0.061 g, 30%).

To a solution of 4-hydroxy-3,5-dimethylbenzaldehyde (0.036 g, 0.24 mmol) in DMF (1.5 mL) was added $K_2CO_3$ (0.050 g, 0.36 mmol) and the mixture stirred at room temperature under nitrogen for 30 minutes. After this time, a solution of N-(2-bromoethyl)-5-methylisoxazol-3-amine (0.060 g, 0.29 mmol) in DMF (1.5 mL) was added and the reaction heated at reflux for 2 hours. The mixture was concentrated and purified by flash chromatography on silica gel, eluting with 1:1 ethyl acetate/heptane to 100% ethyl acetate, to afford 3,5-dimethyl-4-(2-(5-methylisoxazol-3-ylamino)ethoxy)benzaldehyde (0.028 g, 26%).

A mixture of 3,5-dimethyl-4-(2-(5-methylisoxazol-3-ylamino)ethoxy)benzaldehyde (0.121 g, 0.44 mmol), 2-amino-4,6-dimethoxybenzamide (0.087 g, 0.44 mmol), $NaHSO_3$ (0.050 g, 0.48 mmol), and p-TsOH (0.008 g, 0.044 mmol) in DMA (3 mL) was heated at 155° C. under nitrogen for 9 hours. Then, the reaction mixture was cooled, diluted with ethyl acetate (200 mL), and washed with water (100 mL), brine (100 mL), dried over anhydrous $Na_2SO_4$, filtered, and concentrated. The residue was purified by flash chromatography on silica gel, eluting with 100% CH$_2$Cl$_2$ to 100% 92:7:1 CHCl$_3$/MeOH/concentrated NH$_4$OH, to afford the title compound (0.129 g, 65%). $^1$H NMR (300 MHz, DMSO-d$_6$): δ 11.99 (s, 1H), 7.99 (s, 2H), 6.77 (d, J=2.3 Hz, 1H), 6.55 (d, J=2.3 Hz, 1H), 5.29 (s, 1H), 4.70-4.72 (m, 1H), 3.90 (s, 3H), 3.85 (s, 3H), 3.55-3.61 (m, 4H), 2.22 (s, 6H), 2.21 (s, 3H). APCI MS m/z 451 [M+H]$^+$.

Example 53. Preparation of 2-(3,5-dimethyl-4-(2-(pyrimidin-2-ylamino)ethoxy)phenyl)-5,7-dimethoxyquinazolin-4(3H)-one

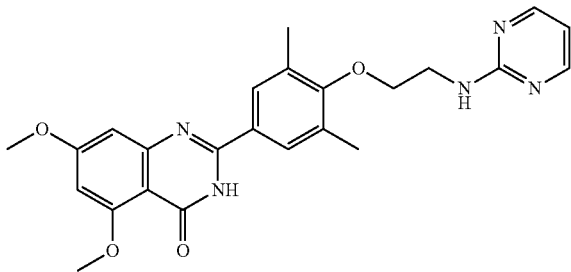 [SMILES: COc1cc(OC)c2c(=O)[nH]c(-c3cc(C)c(OCCNc4ncccn4)c(C)c3)nc2c1]

To a solution of 2-(4-(2-aminoethoxy)-3,5-dimethylphenyl)-5,7-dimethoxyquinazolin-4(3H)-one (0.145 g, 0.40 mmol) in t-butanol (10 mL) was added Et$_3$N (0.06 mL, 0.47 mmol) and 2-chloropyrimidine (0.045 g, 0.40 mmol). The reaction was stirred and heated at reflux temperature overnight, then concentrated in vacuo. Purification by flash chromatography on silica gel, eluting with 95:5 CH$_2$Cl$_2$/MeOH, afforded the title compound (0.038 g, 21%) as a white solid. $^1$H NMR (300 MHz, DMSO-d$_6$): δ 8.29 (d, J=4.7 Hz, 2H), 7.87 (s, 2H), 7.31 (t, J=6.1 Hz, 1H), 6.72 (d, J=2.3 Hz, 1H), 6.58 (t, J=4.7 Hz, 1H), 6.51 (s, 1H), 3.95 (t, J=5.9 Hz, 1H), 3.88 (s, 3H), 3.84 (s, 3H), 3.65-3.71 (m, 2H), 2.25 (s, 6H). ESI MS m/z 448 [M+H]$^+$.

Example 54. Preparation of 2-(4-(2-(isoxazol-3-ylamino)ethoxy)-3,5-dimethylphenyl)-5,7-dimethoxyquinazolin-4(3H)-one

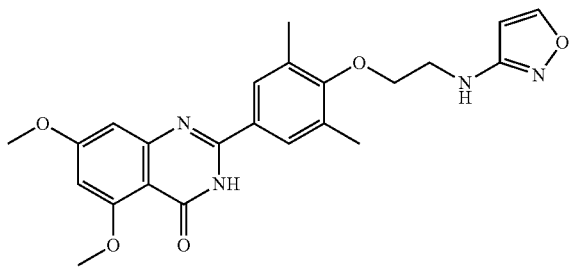 [SMILES: COc1cc(OC)c2c(=O)[nH]c(-c3cc(C)c(OCCNc4ccon4)c(C)c3)nc2c1]

To a solution of isoxazol-3-amine (2.28 g, 27.1 mmol) in CH$_2$Cl$_2$ at 0° C. under nitrogen was added Et$_3$N (2.74 g, 27.1 mmol), followed by bromoacetyl chloride (4.26 g, 27.1 mmol). The mixture was warmed to room temperature, stirred for 2 hours, washed sequentially with water (200 mL) and brine (200 mL), dried (Na$_2$SO$_4$), filtered, and concentrated, to afford 2-bromo-N-(isoxazol-3-yl)acetamide as a tan solid (4.5 g, 81%).

To a solution of 2-bromo-N-(isoxazol-3-yl)acetamide (1.0 g, 4.9 mmol) in THF (50 mL) under nitrogen was added 1.0 M BH$_3$.THF (14.6 mL, 14.6 mmol). The mixture was stirred at room temperature for 3.5 hours and then an additional portion of BH$_3$.THF (5.0 mL, 5.0 mmol) was added. After an additional 15 hours at room temperature, the reaction was quenched with 1 M NaOH, extracted with ethyl acetate (2×150 mL), dried (Na$_2$SO$_4$), filtered, and concentrated. The residue was purified by flash chromatography on silica gel, eluting with 1:1 ethyl acetate/heptane to 100% ethyl acetate, to afford N-(2-bromoethyl)isoxazol-3-amine (0.133 g, 14%).

To a solution of 4-hydroxy-3,5-dimethylbenzaldehyde (0.471 g, 3.14 mmol) in DMF (20 mL) was added K$_2$CO$_3$ (0.650 g, 4.71 mmol). The reaction mixture was stirred at room temperature under nitrogen for 30 minutes. Then, a solution of N-(2-bromoethyl)isoxazol-3-amine (0.600 g, 3.14 mmol) in DMF (10 mL) was added. The mixture was heated at reflux for 3 hours, concentrated, and purified by flash chromatography on silica gel, eluting with 30% ethyl acetate/heptane to 100% ethyl acetate, to afford 4-(2-(isoxazol-3-ylamino)ethoxy)-3,5-dimethylbenzaldehyde as a white solid (0.260 g, 32%).

A mixture of 4-(2-(isoxazol-3-ylamino)ethoxy)-3,5-dimethylbenzaldehyde (0.253 g, 0.97 mmol), 2-amino-4,6-dimethoxybenzamide (0.190 g, 0.97 mmol), NaHSO$_3$ (0.111 g, 1.07 mmol), and p-TsOH (0.018 g, 0.097 mmol) in DMA (10 mL) was heated at 150° C. under nitrogen for 44 hours. Then, the reaction mixture was concentrated, diluted with ethyl acetate (200 mL), and washed with water (150 mL), then brine (150 mL), dried over anhydrous Na$_2$SO$_4$, filtered, and concentrated. The residue was purified by flash chromatography on silica gel, eluting with 100% CH$_2$Cl$_2$ to 100% 92:7:1 CHCl$_3$/MeOH/concentrated NH$_4$OH, to afford the title compound (0.150 g, 35%). $^1$H NMR (300 MHz, DMSO-d$_6$): δ 11.82 (s, 1H), 8.39 (d, J=1.7 Hz, 1H), 7.89 (s, 2H), 6.73 (d, J=2.2 Hz, 1H), 6.51 (d, J=2.2 Hz, 1H), 6.44 (t, J=6.1 Hz, 1H), 6.02 (d, J=1.7 Hz, 1H), 3.94 (t, J=5.5 Hz, 2H), 3.89 (s, 3H), 3.84 (s, 3H), 3.46-3.51 (m, 2H), 2.27 (s, 6H). APCI MS m/z 437 [M+H]$^+$.

Example 55. Preparation of 2-(4-(2-(4,6-dimethoxypyrimidin-2-ylamino)ethoxy)-3,5-dimethylphenyl)-5,7-dimethoxyquinazolin-4(3H)-one

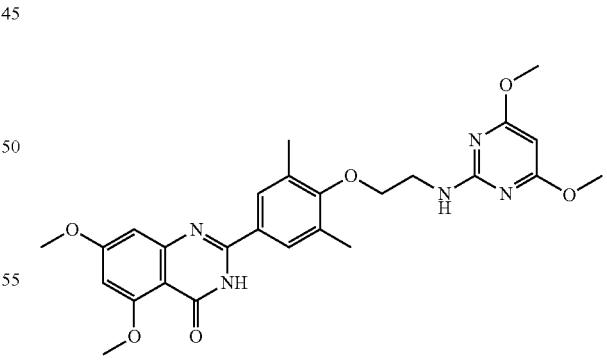

Following the method described for Example 51 above, the title compound was made from 2-chloro-4,6-dimethoxypyrimidine (0.071 g, 0.40 mmol) in 35% yield. $^1$H NMR (300 MHz, DMSO-d$_6$): δ 11.82 (s, 1H), 7.88 (s, 2H), 7.22 (t, J=6.1 Hz, 1H), 6.72 (d, J=2.3 Hz, 1H), 6.51 (s, 1H), 5.38 (s, 1H), 3.90-4.02 (m, 2H), 3.88 (s, 3H), 3.84 (s, 3H), 3.77 (s, 6H), 3.59-3.72 (m, 2H), 2.27 (s, 6H). APCI MS m/z 506 [M−H]$^−$.

Example 56. Preparation of 2-[4-(3-hydroxy-propyl)-3,5-dimethoxyphenyl]-5,7-dimethoxy-3H-quinazolin-4-one

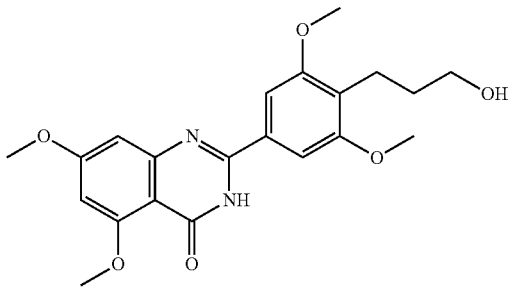 [SMILES: COc1cc(OC)c2c(=O)[nH]c(-c3cc(OC)c(CCCO)c(OC)c3)nc2c1]

To a stirred solution of 4-hydroxy-3,5-dimethoxylbenzaldehyde (5.87 g, 32.2 mmol) in CH$_2$Cl$_2$ (50 mL) and pyridine (8.6 mL) was added trifluoromethanesulfonic anhydride (10.0 g, 35.4 mmol) at 0° C. After the addition was complete, stirring was continued for 16 hours at room temperature. The reaction mixture was diluted with ethyl acetate (150 mL) and washed with water (3×100 mL). The separated organic phase was dried over anhydrous sodium sulfate, filtered, and concentrated. The crude product, trifluoromethanesulfonic acid 4-formyl-2,6-dimethoxyphenyl ester, was used in the next step without further purification. Yield: 10.0 g (98.9%).

To a stirred solution of trifluoromethanesulfonic acid 4-formyl-2,6-dimethoxyphenyl ester (8.00 g, 25.4 mmol) in anhydrous DMF (80 mL) under nitrogen at room temperature were sequentially added triethylamine (5.14 g, 50.8 mmol), methyl acrylate (21.9 g, 254.0 mmol), 1,3-bis-(diphenylphosphino)-propane (0.84 g, 2.03 mmol), and palladium acetate (0.40 g, 1.77 mmol). The reaction mixture was stirred at 115° C. for 16 hours. DMF was removed under reduced pressure and the residue was taken in ethyl acetate (200 mL) and washed with 1 N HCl solution (2×50 mL), and saturated sodium bicarbonate solution (100 mL). The organic phase was dried over anhydrous sodium sulfate, filtered, and concentrated. The residue was purified by column chromatography (silica gel 230-400 mesh; eluting with hexane/ethyl acetate=3:1) to give 3-(4-formyl-2,6-dimethoxyphenyl)-acrylic acid methyl ester. Yield: 4.0 g (62%).

To a solution of 3-(4-formyl-2,6-dimethoxyphenyl)-acrylic acid methyl ester (5.00 g, 20.0 mmol) in methanol (80 mL), 1.5 N sodium hydroxide (45 mL) was added. The suspension was stirred at room temperature for 16 hours. Methanol was evaporated and acetic acid (4.0 mL) was added. The aqueous layer was extracted with dichloromethane (200 mL) then acidified, to pH 3, with 2 N HCl. The solid was filtered and further washed with cold water (100 mL) to obtain 3-(4-formyl-2,6-dimethoxyphenyl)-acrylic acid as a yellow solid. Yield: 4.20 g (89%).

To a solution of 3-(4-formyl-2,6-dimethoxyphenyl)-acrylic acid (4.20 g, 17.7 mmol) and N,N-diisopropylethylamine (3.5 mL) in ethanol (80 mL) were added Pd/C (400 mg, 10 wt %). The suspension was vigorously stirred under 1 bar of hydrogen pressure for 16 hours. The mixture was filtered through a celite pad and the filtrate was evaporated. The residue was poured into chilled 1 N HCl (200 mL), the solid was filtered, and further washed with cold water (100 mL) to give a mixture of 3-(4-formyl-2,6-dimethoxyphenyl)-propionic acid and 3-(4-hydroxymethyl-2,6-dimethoxyphenyl)-propionic acid as a white solid. Yield: 3.30 g.

To a suspension of LiAlH$_4$ (1.00 g, 26.3 mmol) in anhydrous THF (40 mL) was added dropwise a solution of a mixture of 3-(4-formyl-2,6-dimethoxyphenyl)-propionic acid and 3-(4-hydroxymethyl-2,6-dimethoxyphenyl)-propionic acid (3.30 g, 13.8 mmol). After the addition was complete, the reaction mixture was stirred at reflux for 2 hours. The suspension was diluted with THF (20 mL) and another portion of LiAlH$_4$ (0.60 g, 15.8 mmol) was added. The mixture was refluxed for an additional 1 hour. The reaction was cooled to room temperature, carefully quenched with aqueous saturated NH$_4$Cl solution (8 mL), acidified to pH 1-2 with 2 N HCl, and extracted with ethyl acetate (200 mL). The organic phase was dried over sodium sulfate, filtered and concentrated to provide 3-(4-hydroxymethyl-2,6-dimethoxyphenyl)-propan-1-ol as a colorless crystalline solid. Yield: 3.08 g (98.7%).

To a solution of 3-(4-hydroxymethyl-2,6-dimethoxyphenyl)-propan-1-ol (3.08 g, 13.6 mmol) in ethanol (50 mL) was added activated MnO$_2$ (4.15 g, 47.6 mmol) and the resulting suspension was stirred at reflux for 16 hours. The reaction mixture was filtered through a celite pad and the filtrate was concentrated. The residue was purified by column chromatography (silica gel 230-400 mesh; eluting with 2:1 hexane and ethyl acetate) to give 4-(3-hydroxy-propyl)-3,5-dimethoxybenzaldehyde. Yield: 1.10 g (36%).

To a solution of 2-amino-4,6-dimethoxy-benzamide (0.35 g, 1.78 mmol) and 4-(3-hydroxy-propyl)-3,5-dimethylbenzaldehyde (0.40 g, 1.78 mmol) in N,N-dimethylacetamide (8 mL) were added NaHSO$_3$ (0.35 g, 1.96 mmol) and p-TSA (34 mg, 0.18 mmol) and the reaction mixture was heated at 115-120° C. for 5 hours, then cooled to room temperature. N,N-dimethylacetamide was removed under reduced pressure. The residue was diluted with water (50 mL) and the pH was adjusted to 7 by adding sodium bicarbonate solution. The solid was collected and washed with ether and further mixed with methanol (30 mL) and stirred for 1 hour, filtered, and dried under vacuum to give the title compound as a white solid. Yield: 0.25 g (35%). $^1$H NMR (400 MHz, CDCl$_3$): δ 11.13 (s, 1H), 7.30 (s, 2H), 6.86 (d, J=2.4 Hz, 1H), 6.47 (d, J=2.4 Hz, 1H), 3.98 (s, 6H), 3.95 (s, 3H), 3.94 (s, 3H), 3.52 (m, 2H), 2.86 (t, J=6.6 Hz 2H), 2.27 (t, J=6.6 Hz, 1H), 1.81 (m, 2H). MS (ES$^+$) m/z: 401.49 (M+1).

Example 57. Preparation of 2-[4-(3-hydroxy-propyl)-3-methoxy-phenyl]-5,7-dimethoxy-3H-quinazolin-4-one

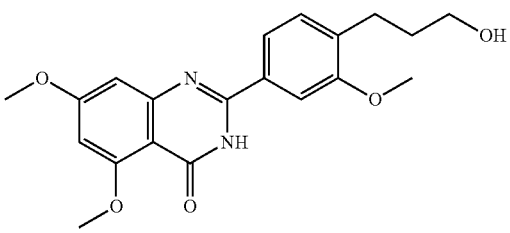 [SMILES: COc1cc(OC)c2c(=O)[nH]c(-c3ccc(CCCO)c(OC)c3)nc2c1]

To a stirred solution of 4-hydroxy-3-methoxy-benzaldehyde (5.00 g, 32.8 mmol) in CH$_2$Cl$_2$ (50 mL) and pyridine (8 mL) was added trifluoromethanesulfonic anhydride (10.19 g, 36.1 mmol) at 0° C. After addition was complete, stirring was continued for 16 hours at room temperature. The reaction mixture was diluted with ethyl acetate (200 mL)

and washed with water (3×100 mL) and brine (100 mL). The separated organic layer was dried over anhydrous sodium sulfate, filtered, and concentrated. The crude product was purified by column chromatography (silica gel 230-400 mesh; 20% ethyl acetate in hexanes as eluent) to give trifluoromethanesulfonic acid 4-formyl-2-methoxy-phenyl ester. Yield: 8.00 g, (85%).

To a stirred solution of trifluoromethanesulfonic acid 4-formyl-2-methoxy-phenyl ester (5.00 g, 17.5 mmol) in anhydrous DMF (75 mL) under nitrogen at room temperature were sequentially added triethylamine (3.50 g, 34.5 mmol), ethyl acrylate (17.50 g, 174.7 mmol), 1,3-bis-(diphenylphosphino)-propane (0.40 g, 0.96 mmol), and palladium (II) acetate (0.20 g, 0.87 mmol). The reaction mixture was stirred at 100° C. for 5 hours. DMF was removed under reduced pressure, and the residue was taken in ethyl acetate (200 mL) and washed with 1 N HCl solution (2×50 mL), and saturated sodium bicarbonate solution (100 mL) and brine (100 mL). The organic phase was dried over sodium sulfate, filtered, and concentrated. The residue was purified by column chromatography (silica gel 230-400 mesh; 20% ethyl acetate in hexanes as eluent) to give 3-(4-formyl-2-methoxy-phenyl)-acrylic acid ethyl ester as a beige solid. Yield: 3.00 g (73%).

To a solution of 3-(4-formyl-2-methoxy-phenyl)-acrylic acid ethyl ester (3.00 g, 13.6 mmol) and N,N-diisopropylethylamine (3.0 mL) in ethanol (100 mL) were added Pd/C (10 wt %, 400 mg). The suspension was hydrogenated under 25 psi pressure for 5 hours. The mixture was filtered through a celite pad and the filtrate was evaporated. The residue was poured into chilled 1 N HCl (200 mL), the solid was filtered, and further washed with cold water (100 mL) to give a 3-(4-hydroxymethyl-2-methoxy-phenyl)-propionic acid ethyl ester as a beige solid. Yield: 2.80 g (93%).

To a suspension of LiAlH$_4$ (0.51 g, 26.3 mmol) in anhydrous THF (100 mL) was added dropwise a solution of 3-(4-hydroxymethyl-2-methoxyphenyl)-propionic acid ethyl ester (2.5 g, 11.1 mmol) in THF (10 mL). After the addition was complete, the reaction mixture was stirred at reflux for 3 hours. Then, the reaction was cooled to room temperature, carefully quenched with aqueous saturated NH$_4$Cl solution (8 mL), acidified to pH approximately 1-2 with 2 N HCl, and extracted with ethyl acetate (200 mL). The organic phase was dried over sodium sulfate, filtered, and concentrated, to provide 3-(4-hydroxymethyl-2-methoxy-phenyl)-propan-1-ol as a colorless crystalline solid. Yield: 1.80 g (90%).

To a solution of 3-(4-hydroxymethyl-2-methoxy-phenyl)-propan-1-ol (1.8 g, 9.1 mmol) in ethanol (50 mL) was added activated MnO$_2$ (2.79 g, 32.0 mmol) and the resulting suspension was stirred at reflux for 16 hours. The reaction mixture was filtered through celite pad and the filtrate was concentrated. The residue was purified by column chromatography (silica gel 230-400 mesh; 2:1 hexane and ethyl acetate as eluent) to give 4-(3-hydroxy-propyl)-3-methoxy-benzaldehyde. Yield: 1.2 g (67%).

To a solution of 2-amino-4,6-dimethoxy-benzamide (0.48 g, 2.44 mmol) and 4-(3-hydroxy-propyl)-3-methoxy-benzaldehyde (0.40 g, 2.05 mmol) in N,N-dimethylacetamide (10 mL) were added NaHSO$_3$ (58.5 wt %, 0.40 g, 2.25 mmol) and p-toluenesulfonic acid monohydrate (78 mg, 0.41 mmol) and the reaction mixture was heated at 115° C. for 16 hours, then cooled to room temperature. The solvent was removed under reduced pressure. The residue was diluted with water (50 mL) and the pH was adjusted to approximately 7 by adding sodium bicarbonate solution. The solid was filtered and washed with water. The crude compound was purified by column chromatography (silica gel 230-400 mesh; 5% methanol in dichloromethane as eluent) to give the title compound as an off-white solid. Yield: 0.35 g (46%). $^1$H NMR (400 MHz, DMSO-d$_6$): δ 12.02 (s, 1H), 7.75-7.73 (m, 2H), 7.28 (d, J=7.8 Hz, 1H), 6.75 (d, J=2.3 Hz, 1H), 6.53 (d, J=1.9 Hz, 1H), 4.48 (t, J=5.0 Hz, 1H), 3.90 (d, J=4.2 Hz, 6H), 3.85 (s, 3H), 3.44 (q, J=6.6 Hz, 2H), 2.65 (t, J=7.4 Hz 2H), 1.71-1.67 (m, 2H). MS (ES$^+$) m/z: 371.51 (M+1).

Example 58. Preparation of 2-[2-(2-hydroxyethyl)-1H-indol-6-yl]-5,7-dimethoxy-3H-quinazolin-4-one

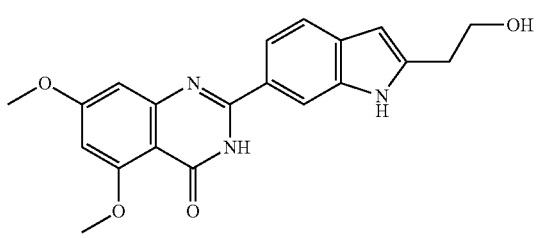 [SMILES: COc1cc(OC)c2c(=O)[nH]c(-c3ccc4cc(CCO)[nH]c4c3)nc2c1]

To a degassed solution of methyl-3-amino-4-iodobenzoate (2.00 g, 7.22 mmol) in a mixture of 5:1 DMF-triethylamine (30 mL) were added PdCl$_2$(PPh$_3$)$_2$ (0.25 g, 0.36 mmol) and copper (I) iodide (0.41 g, 2.16 mmol) and the mixture was degassed again. A degassed solution of 2-(3-butynyloxy)tetrahydro-2H-pyran (1.7 mL, 10.83 mmol) in a mixture of 5:1 DMF-triethylamine (12 mL) was added drop-wise at 75° C. over a period of 45 minutes under nitrogen. Soon after the addition, TLC showed completion of the reaction. The reaction mixture was cooled to room temperature, solvent was removed under reduced pressure, and the residue was diluted with water (75 mL) and extracted with ethyl acetate (3×50 mL). The organic phase was washed with water (50 mL), brine (50 mL), and dried over anhydrous MgSO$_4$. The solvent was evaporated and the crude product was purified by column chromatography (silica gel 230-400 mesh; 2:1 hexanes and ethyl acetate as eluent) to obtain 3-amino-4-[4-(tetrahydropyran-2-yloxy)-but-1-ynyl]benzoic acid methyl ester as a brown solid. Yield: 1.70 g (78%).

To a stirred solution of 3-amino-4-[4-(tetrahydropyran-2-yloxy)-but-1-ynyl]benzoic acid methyl ester (1.68 g, 5.55 mmol) in anhydrous pyridine (5 mL) was added acetyl chloride (0.43 mL, 6.11 mmol) at 0° C. under nitrogen. Stirring was continued at 0° C. After 30 minutes TLC showed completion of the reaction. Pyridine was removed under reduced pressure and the residue was diluted with ethyl acetate (100 mL). The resulting mixture was washed with aq 2 N HCl (20 mL), water (2×15 mL) and brine (20 mL). After drying over anhydrous MgSO$_4$, solvent was removed to obtain 3-acetylamino-4-[4-(tetrahydropyran-2-yloxy)-but-1-ynyl]benzoic acid methyl ester as a beige solid. Yield: 1.67 g (87%). Crude product was used in the next step without further purification.

A 1.0 M solution of tetrabutylammonium fluoride (9.67 mL, 9.67 mmol) in THF was added to a solution of 3-acetylamino-4-[4-(tetrahydropyran-2-yloxy)-but-1-ynyl]benzoic acid methyl ester (1.67 g, 4.83 mmol) in anhydrous THF (20 mL) at room temperature. The resulting reddish-brown solution was heated at reflux for 2 hours and then allowed to cool to room temperature. The solvent was removed under reduced pressure and the residue was taken in water (50 mL)

and extracted with ethyl acetate (3×50 mL). The organic phase was washed with water (25 mL), brine (50 mL), and dried over anhydrous MgSO$_4$. The solvent was evaporated and the crude product was purified by column chromatography on (silica gel 230-400 mesh; dichloromethane as eluent) to give 2-[2-(tetrahydropyran-2-yloxy)ethyl]-1H-indole-6-carboxylic acid methyl ester as a light brown solid. Yield: 1.27 g (87%).

To a suspension of lithium aluminum hydride (0.32 g, 8.37 mmol) in anhydrous THF (20 mL) was added a solution of 2-[2-(tetrahydropyran-2-yloxy)ethyl]-1H-indole-6-carboxylic acid methyl ester (1.27 g, 4.19 mmol) in anhydrous THF (10 mL) at −30° C. to −20° C. dropwise over a period of 15 minutes under nitrogen. The temperature was allowed to warm to room temperature and stirring continued for 15 hours. The reaction mixture was quenched with saturated aqueous ammonium chloride solution at 0° C., diluted with ethyl acetate (50 mL), and filtered. The solid was washed with ethyl acetate. The combined organic phase was dried over anhydrous MgSO$_4$. The solvent was evaporated and the crude product was purified by the Simpliflash system (3:2 ethyl acetate-hexanes as eluent) to give {2-[2-(tetrahydropyran-2-yloxy)ethyl]-1H-indol-6-yl}-methanol as a white solid. Yield: 0.61 g (53%).

IBX (0.62 g, 2.21 mmol) was added to a solution of {2-[2-(tetrahydropyran-2-yloxy)ethyl]-1H-indol-6-yl}-methanol (0.61 g, 2.21 mmol) in DMSO (10 mL). After 30 min, the reaction mixture became a clear solution. Stirring was continued at room temperature for 2 hours and during this time, some solid precipitated. Water (50 mL) was added, the solid was filtered, and washed with ethyl acetate (50 mL). The filtrate was collected and extracted with ethyl acetate (3×20 mL). The organic phase was washed with brine (30 mL) and dried over anhydrous MgSO$_4$. Removal of solvent gave 2-[2-(tetrahydropyran-2-yloxy)ethyl]-1H-indole-6-carbaldehyde as a light brown solid. Yield: 0.60 g (99%).

To a solution of 2-amino-4,6-dimethoxy-benzamide (0.48 g, 2.42 mmol) and 2-[2-(tetrahydropyran-2-yloxy)ethyl]-1H-indole-6-carbaldehyde (0.60 g, 2.20 mmol) in N,N-dimethylacetamide (20 mL) were added NaHSO$_3$ (58.5 wt %, 0.60 g, 3.30 mmol) and p-toluenesulfonic acid monohydrate (0.17 g, 0.88 mmol). The reaction mixture was heated at 110° C. for 20 hours and then cooled to room temperature. N,N-dimethylacetamide was removed under reduced pressure. The residue was diluted with saturated sodium carbonate solution (50 mL) and extracted with dichloromethane (4×25 mL). The combined organic phase was washed with brine and dried over anhydrous magnesium sulfate. The solvent was removed and the crude product was purified by column chromatography (silica gel 230-400 mesh; 7% methanol in dichloromethane as eluent). Yield: 0.45 g (56%). The compound was further purified by preparative HPLC to give the title compound as an off-white solid. Yield: 123 mg. $^1$H NMR (400 MHz, DMSO-d$_6$): δ 11.89 (s, 1H), 11.25 (s, 1H), 8.18 (s, 1H), 7.82 (d, J=8.40 Hz, 1H), 7.50 (d, J=8.40 Hz, 1H), 6.73 (d, J=2.4 Hz, 1H), 6.49 (d, J=2.0 Hz, 1H), 6.27 (s, 1H), 4.80 (t, J=5.2 Hz, 1H), 3.90 (s, 3H), 3.85 (s, 3H), 3.78-3.73 (m, 2H), 2.92 (t, J=7.2 Hz, 2H). MS (ES+) m/z 366.54 (100%, M+1).

Example 59. Quantification of hIL-6 mRNA

In this example, hIL-6 mRNA in tissue culture cells was quantitated to measure the transcriptional inhibition of hIL-6 when treated with a compound of the invention.

A human leukemic monocytic lymphoma cell line (U937) was plated (3.2×10$^5$ cells per well) in a 96-well plate in 100 μL RPMI 1640+10% FBS, and differentiated into macrophages with PMA (60 ng/mL) for 3 days prior to the addition of the compound of interest. The cells were pretreated for 1 h with the test compound in DMSO prior to stimulation with lipopolysaccharide from *Escherichia coli* at 1 μg/mL. The cells were incubated for 3 h before harvest. At the time of harvest, cells were rinsed in 200 μL PBS. Cell lysis solution (70 μL) was added the cells for 10 min, and mRNA was then prepared using the "mRNA Catcher PLUS plate" (Invitrogen), according to the protocol supplied.

The eluted mRNA isolated was then used in a one-step quantitative real-time PCR reaction, using components of the UltraSense kit together with Applied Biosystems primer-probe mixes. 10 μL of template was amplified with 1.75 μL of IL-6 primer-probe, and 1 μL of hCyclophilin primer probe, and the reaction was carried out in multiplex. Real-time PCR data was analyzed, normalizing the Ct values for hIL-6 to hCyclophilin, prior to determining the fold induction of each unknown sample, relative to the control.

In Table 2, an active compound is one that causes a ≥20% inhibition in IL-6 mRNA at a concentration less than or equal to 10 μM.

TABLE 2

| Example | Inhibition of IL-6 expression |
|---|---|
| 1 | Active |
| 2 | Active |
| 3 | Active |
| 4 | Active |
| 5 | Active |
| 6 | Active |
| 7 | Active |
| 8 | Active |
| 9 | Active |
| 10 | Active |
| 11 | Active |
| 12 | Active |
| 13 | Active |
| 14 | Active |
| 15 | Active |
| 16 | Active |
| 17 | Active |
| 18 | Active |
| 19 | Active |
| 20 | Active |
| 21 | Active |
| 22 | Active |
| 23 | Active |
| 24 | Active |
| 25 | Active |
| 26 | Active |
| 27 | Active |
| 28 | Active |
| 29 | Active |
| 30 | Active |
| 31 | Active |
| 32 | Active |
| 33 | Active |
| 34 | Active |
| 35 | Active |
| 36 | Active |
| 37 | Active |
| 38 | Active |
| 39 | Active |
| 40 | Active |
| 41 | Active |
| 42 | Active |
| 43 | Active |
| 44 | Active |
| 45 | Active |
| 46 | Active |
| 47 | Active |

TABLE 2-continued

| Example | Inhibition of IL-6 expression |
|---|---|
| 48 | Active |
| 49 | Active |
| 50 | Active |
| 51 | Active |
| 52 | Active |
| 53 | Active |
| 54 | Active |
| 55 | Active |
| 56 | Active |
| 57 | Active |
| 58 | Active |

Example 60. Quantification of hVCAM-1 mRNA

In this example, hVCAM-1 mRNA in tissue culture cells was quantitated to measure the transcriptional inhibition of hVCAM when treated with a compound of the invention. A human umbilical vein endothelial cell line (HUV-EC-C) was plated in a 96-well plate ($5.0 \times 10^3$ cells/well) in 100 µL EGM complete media and incubated for 24 h prior to the addition of the compound of interest. The cells were pretreated for 1 h with the test compound in DMSO prior to stimulation with tumor necrosis factor-α (10 ng/mL). The cells were incubated for an additional 24 h before harvest. At time of harvest, the cells were rinsed in 200 µL PBS, and cell lysis solution (70 µL) was then added the cells for 10 min. mRNA was then prepared using the "mRNA Catcher PLUS plate" (Invitrogen), according to the protocol supplied.

The eluted mRNA was then used in a one-step quantitative real-time PCR reaction, using components of the UltraSense kit together with Applied Biosystems primer-probe mixes. 10 µL of template was amplified with 1.75 µL of hVCAM-1 primer-probe, and 1 µL of hCyclophilin primer probe, and the reaction was carried out in multiplex. Real-time PCR data was analyzed, normalizing the Ct values for hVCAM-1 to hCyclophilin, prior to determining the fold induction of each unknown sample, relative to the control.

In Table 3, an active compound is one that causes a ≥20% inhibition in VCAM-1 mRNA at a concentration less than or equal to 10 µM.

TABLE 3

| Example | Inhibition of VCAM-1 expression |
|---|---|
| 3 | Active |
| 4 | Active |
| 5 | Active |
| 7 | Active |
| 9 | Active |
| 10 | Active |
| 15 | Inactive |
| 17 | Inactive |
| 18 | Active |
| 20 | Active |
| 21 | Inactive |
| 22 | Active |
| 23 | Active |
| 25 | Active |
| 26 | Active |
| 28 | Active |
| 29 | Active |
| 30 | Inactive |
| 31 | Active |
| 32 | Active |
| 33 | Active |
| 34 | Active |
| 35 | Active |
| 36 | Active |
| 37 | Inactive |
| 38 | Active |
| 39 | Active |
| 40 | Active |
| 42 | Active |
| 44 | Active |
| 47 | Active |
| 51 | Active |
| 58 | Active |

What is claimed is:

1. A method of treating or reducing the risk of acquiring asthma, chronic obstructive pulmonary disease (COPD), or a non-cardiovascular inflammatory disease mediated by IL-6 in a subject in need thereof, comprising administering a therapeutically effective amount of a composition consisting essentially of a compound of Formula II:

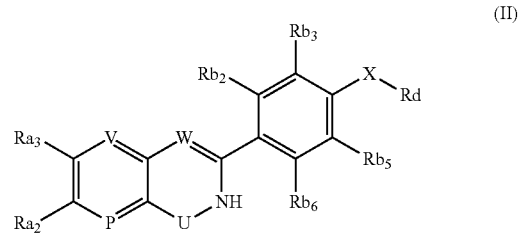

or a stereoisomer, tautomer, pharmaceutically acceptable salt, or hydrate thereof, wherein:

P is selected from N and $CRa_1$;
V is selected from N and $CRa_4$;
W is selected from N and CH;
U is selected from C=O, C=S, $SO_2$, S=O, and $SR_1$;
$Ra_1$ and $Ra_4$ are independently selected from hydrogen, $C_1$-$C_6$ alkyl, $C_1$-$C_6$ alkoxy, $C_3$-$C_6$ cycloalkyl, and halogen;
$Ra_3$ is selected from hydrogen, $C_1$-$C_6$ alkyl, $C_1$-$C_6$ alkoxy, $C_3$-$C_6$ cycloalkyl, and halogen, wherein the $C_1$-$C_6$ alkoxy is optionally

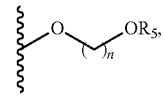

n is 1, 2, or 3; and
$R_5$ is $C_1$-$C_6$ alkyl substituted with phenyl or heteroaryl;
$Ra_2$ is selected from hydrogen, $C_1$-$C_6$ alkyl optionally substituted with heterocyclyl, $C_1$-$C_6$ alkoxy, heterocycle, amino, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl optionally substituted with heterocyclyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl or heterocycle; and
XRd is selected from 2-hydroxyethoxy, 2,3-dihydroxypropoxy, aminocarbonylethoxy, methylaminocarbonylethoxy, (4-methoxyphenyl)aminocarbonylethoxy, benzylaminocarbonylethoxy, 4-hydroxybutoxy, methylcarbonylaminoethoxy, methylcarbonylaminomethyl, (2,2,2-trifluoro-ethyl-amino)ethoxy, methanesulfonylaminoethoxy, isobutyrylaminoethoxy, methylaminoethoxy, isopropylsulfonylaminoethoxy, methylcarbonylaminoethoxy, dimethylaminoethoxy, N-(2-hydroxyethyl)-N-methylacetamide, formamide-N-2-ethoxy, methylformamide-N-2-ethoxy, dimethylsulfonylaminoethoxy, cyanoaminoethoxy, 3-hydroxypropyl, and 2-hydroxyethyl, provided that at least one of $Ra_1$, $Ra_2$, $Ra_1$, and $Ra_4$ is not hydrogen; and if —XRd is —OCH$_2$CH$_2$OH, then $Rb_3$ is not pyrrolidine.

2. The method according to claim 1, wherein:

U is C=O

P is CRa$_1$;

$Ra_1$ is selected from hydrogen, $C_1$-$C_6$ alkyl, $C_1$-$C_6$ alkoxy, and halogen;

$Ra_2$ is selected from hydrogen, $C_1$-$C_6$ alkyl optionally substituted with heterocyclyl, $C_1$-$C_6$ alkoxy, heterocycle, amide, and amino;

$Ra_4$ is selected from hydrogen, $C_1$-$C_6$ alkoxy, $C_1$-$C_6$ alkyl, and halogen;

$Ra_3$ is selected from hydrogen, $C_1$-$C_6$ alkyl, $C_1$-$C_6$ alkoxy, and halogen, wherein the $C_1$-$C_6$ alkoxy is optionally

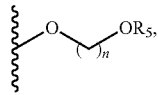

n is 1, 2, or 3; and $R_5$ is $C_1$-$C_6$ alkyl substituted with phenyl or heteroaryl; and $Rb_3$ and $Rb_5$ are independently selected from hydrogen, $C_1$-$C_6$ alkyl optionally substituted with heterocyclyl, $C_3$-$C_6$ cycloalkyl, $C_1$-$C_6$ alkoxy, halogen, and amino, wherein $Rb_2$ and $Rb_3$ and/or $Rb_5$ and $Rb_6$ may be connected to form a phenyl ring.

3. The method according to claim 2, wherein $Ra_1$ is selected from hydrogen, unsubstituted $C_1$-$C_6$ alkyl, unsubstituted $C_1$-$C_6$ alkoxy, and halogen.

4. The method according to claim 2, wherein $Ra_2$ is selected from hydrogen, $C_1$-$C_6$ alkyl substituted with heterocyclyl, unsubstituted $C_1$-$C_6$ alkoxy, amino, and heterocycle.

5. The method according to claim 2, wherein:

$Ra_3$ is selected from hydrogen, methoxy, unsubstituted $C_1$-$C_6$ alkyl, halogen, and

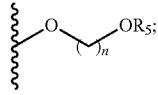

n is 1, 2, or 3; and $R_5$ is $C_1$-$C_6$ alkyl substituted with phenyl or heteroaryl.

6. The method according to claim 2, wherein $Ra_4$ is selected from hydrogen, unsubstituted $C_1$-$C_6$ alkoxy, and halogen.

7. The method according to claim 2, wherein $Rb_3$ and $Rb_5$ are independently selected from hydrogen, methyl, $C_1$-$C_6$ alkyl substituted with heterocyclyl, and unsubstituted $C_1$-$C_6$ alkoxy wherein $Rb_2$ and $Rb_3$ and/or $Rb_5$ and $Rb_6$ may be connected to form a phenyl ring.

8. The method according to claim 7, wherein $Rb_3$ and $Rb_5$ are independently selected from hydrogen, methyl, methoxy, and morpholinomethyl, and wherein $Rb_2$ and $Rb_3$ and/or $Rb_5$ and $Rb_6$ may be connected to form a phenyl ring.

9. A method of treating or reducing the risk of acquiring a non-cardiovascular inflammatory disease mediated by IL-6 in a subject in need thereof, comprising administering a therapeutically effective amount of a composition consisting essentially of a compound selected from:

2-(4-(2-hydroxyethoxy)-3,5-dimethylphenyl)-5,7-dimethoxyquinazolin-4(3H)-one;

2-(4-(2-hydroxyethoxy)-3,5-dimethylphenyl)-6,7-dimethoxyquinazolin-4(3H)-one;

2-(4-(2-hydroxyethoxy)-3,5-dimethylphenyl)-5,7-dimethoxypyrido[2,3-d]pyrimidin-4(3H)-one;

N-(2-(4-(2-hydroxyethoxy)-3,5-dimethylphenyl)-4-oxo-3,4-dihydroquinazolin-6-yl)acetamide;

2-(4-(2-hydroxyethoxy)-3,5-dimethylphenyl)-6-morpholinoquinazolin-4(3H)-one;

2-(4-(2-hydroxyethoxy)-3,5-dimethylphenyl)-5,7-dimethylpyrido[2,3-d]pyrimidin-4(3H)-one;

5,7-difluoro-2-(4-(2-hydroxyethoxy)-3,5-dimethylphenyl)quinazolin-4(3H)-one;

5,7-dichloro-2-(4-(2-hydroxyethoxy)-3,5-dimethylphenyl)quinazolin-4(3H)-one;

2-[4-(2-hydroxy-ethoxy)-3,5-dimethyl-phenyl]-5,7-diisopropoxy-3H-quinazolin-4-one;

2-[4-(2-hydroxyethoxy)-3,5-dimethyl-phenyl]-6-morpholin-4-ylmethyl-3H-quinazolin-4-one;

2-[4-(2,3-Dihydroxy-propoxy)-3,5-dimethyl-phenyl]-5,7-dimethoxy-3H-quinazolin-4-one;

2-[4-(2-hydroxy-ethoxy)-3,5-dimethylphenyl]-5,7-dimethoxy-6-morpholin-4-ylmethyl-3H-quinazolin-4-one;

2-[4-(2-hydroxy-ethoxy)-phenyl]-5,7-dimethoxy-3H-quinazolin-4-one;

2-[4-(2-hydroxy-ethoxy)-naphthalen-1-yl]-5,7-dimethoxy-3H-quinazolin-4-one;

7-(2-benzyloxy-ethoxy)-2-[4-(2-hydroxy-ethoxy)-3,5-dimethyl-phenyl]-5-methoxy-3H-quinazolin-4-one;

7-(2-benzyloxy-ethoxy)-2-(2-hydroxymethyl-benzofuran-5-yl)-5-methoxy-3H-quinazolin-4-one;

2-[4-(5,7-dimethoxy-4-oxo-3,4-dihydro-quinazolin-2-yl)-2,6-dimethyl-phenoxy]-acetamide;

2-[4-(5,7-dimethoxy-4-oxo-3,4-dihydro-quinazolin-2-yl)-2,6-dimethyl-phenoxy]-N-methyl-acetamide;

2-[4-(5,7-Dimethoxy-4-oxo-3,4-dihydro-quinazolin-2-yl)-2,6-dimethyl-phenoxy]-N-(4-methoxy-phenyl)-acetamide;

N-benzyl-2-[4-(5,7-dimethoxy-4-oxo-3,4-dihydroquinazolin-2-yl)-2,6-dimethylphenoxy]acetamide;

2-[4-(4-hydroxy-butoxy)-3,5-dimethyl-phenyl]-5,7-dimethoxy-3H-quinazolin-4-one;

2-(4-(2-hydroxyethoxy)-3,5-dimethylphenyl)-6-methoxyquinazolin-4(3H)-one;

2-(4-(2-hydroxyethoxy)-3,5-dimethylphenyl)-5-methoxyquinazolin-4(3H)-one;

7-chloro-2-(4-(2-hydroxyethoxy)-3,5-dimethylphenyl)quinazolin-4(3H)-one;

8-chloro-2-(4-(2-hydroxyethoxy)-3,5-dimethylphenyl)quinazolin-4(3H)-one;

2-(4-(2-hydroxyethoxy)-3,5-dimethylphenyl)-8-methoxyquinazolin-4(3H)-one;

5-chloro-2-(4-(2-hydroxyethoxy)-3,5-dimethylphenyl)quinazolin-4(3H)-one;

2-(4-(2-hydroxyethoxy)-3,5-dimethylphenyl)-7-methoxyquinazolin-4(3H)-one;
2-(4-(2-hydroxyethoxy)-3-methylphenyl)-5,7-dimethoxyquinazolin-4(3H)-one;
2-(4-(2-hydroxyethoxy)-3,5-dimethylphenyl)-6-((4-methylpiperazin-1-yl)methyl)quinazolin-4(3H)-one;
N-{2-[4-(5,7-dimethoxy-4-oxo-3,4-dihydro-pyrido[2,3-d]pyrimidin-2-yl)-2,6-dimethyl-phenoxy]-ethyl}-acetamide;
N-(4-(5,7-dimethoxy-4-oxo-3,4-dihydroquinazolin-2-yl)-2,6-dimethylbenzyl)acetamide;
N-[4-(5,7-dimethoxy-4-oxo-3,4-dihydro-pyrido[2,3-d]pyrimidin-2-yl)-2,6-dimethyl-benzyl]-acetamide;
2-{3,5-Dimethyl-4-[2-(2,2,2-trifluoro-ethylamino)-ethoxy]-phenyl}-5,7-dimethoxy-3H-quinazolin-4-one;
N-{2-[4-(6, 8-Dimethoxy-1-oxo-1,2-dihydro-isoquinolin-3-yl)-2,6-dimethyl-phenoxy]-ethyl}-formamide;
N-(2-(4-(5,7-dimethoxy-4-oxo-3,4-dihydroquinazolin-2-yl)-2,6-dimethylphenoxy)ethyl)methanesulfonamide;
N-(2-(4-(5,7-dimethoxy-4-oxo-3,4-dihydroquinazolin-2-yl)-2,6-dimethylphenoxy)ethyl)-4-methoxybenzamide;
N-(2-(4-(5,7-dimethoxy-4-oxo-3,4-dihydroquinazolin-2-yl)-2,6-dimethylphenoxy)ethyl)acetamide;
N-(2-(4-(5,7-dimethoxy-4-oxo-3,4-dihydroquinazolin-2-yl)-2,6-dimethylphenoxy)ethyl)isobutyramide;
2-(3,5-dimethyl-4-(2-(methylamino)ethoxy)phenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)propane-2-sulfonamide;
2-(4-(2-(isopropylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2-methylphenoxy)ethyl)acetamide;
N-(2-(4-(5,7-dimethoxy-4-oxo-3,4-dihydroquinazolin-2-yl)-2-methylphenoxy)ethyl)isobutyramide;
N-(2-(4-(5,7-dimethoxy-4-oxo-3,4-dihydroquinazolin-2-yl)-2-methylphenoxy)ethyl)methanesulfonamide;
2-(4-(2-(dimethylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2, 6-dimethylphenoxy)ethyl)-N-methylacetamide;
N-(2-(4-(5,7-dimethoxy-4-oxo-3,4-dihydroquinazolin-2-yl)-2, 6-dimethylphenoxy)ethyl)formamide;
N-(2-(4-(5,7-dimethoxy-4-oxo-3,4-dihydroquinazolin-2-yl)-2, 6-dimethylphenoxy)ethyl)-N-methylformamide;
N-(2-(4-(5,7-Dimethoxy-4-oxo-3,4-dihydroquinazolin-2-yl)-2,6-dimethylphenoxy)ethyl)dimethylamino-N-sulfonamide;
N-(2-(4-(5,7-dimethoxy-4-oxo-3,4-dihydroquinazolin-2-yl)-2, 6-dimethylphenoxy)ethyl)cyanamide;
2-[4-(3-hydroxy-propyl)-3,5-dimethoxyphenyl]-5,7-dimethoxy-3H-quinazolin-4-one;
2-[4-(3-hydroxy-propyl)-3-methoxy-phenyl]-5,7-dimethoxy-3H-quinazolin-4-one;
2-[2-(2-hydroxyethyl)-1H-indol-6-yl]-5,7-dimethoxy-3H-quinazolin-4-one, and
tautomers, stereoisomers, pharmaceutically acceptable salts and hydrates thereof.

10. The method according to claim 1, wherein the therapeutically effective amount of the compound is administered with at least one pharmaceutically acceptable carrier in a pharmaceutically acceptable composition.

11. The method according to claim 1, wherein the disease is selected from cystic fibrosis, post transplantation late and chronic solid organ rejection, systemic lupus erythematosus, ocular inflammation, uveitis, rhinitis, glomerulonephritis, Grave's disease, gastrointestinal allergies, and conjunctivitis.

12. A method for treating a cancer associated with elevated levels of IL-6, comprising administering to a subject in need thereof a therapeutically effective amount of at least one compound of Formula II:

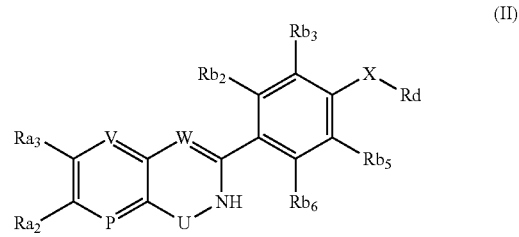

(II)

or a stereoisomer, tautomer, pharmaceutically acceptable salt, or hydrate thereof, wherein:

P is selected from N and $CRa_1$;
V is selected from N and $CRa_4$;
W is selected from N and CH;
U is selected from C=O, C=S, $SO_2$, S=O, and $SR_1$;
$Ra_1$ and $Ra_4$ are independently selected from hydrogen, $C_1$-$C_6$ alkyl, $C_1$-$C_6$ alkoxy, $C_3$-$C_6$ cycloalkyl, and halogen;
$Ra_3$ is selected from hydrogen, $C_1$-$C_6$ alkyl, $C_1$-$C_6$ alkoxy, $C_3$-$C_6$ cycloakyl, and halogen, wherein the $C_1$-$C_6$ alkoxy is optionally

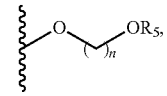

n is 1, 2, or 3; and
$R_5$ is $C_1$-$C_6$ alkyl substituted with phenyl or heteroaryl;
$Ra_2$ is selected from hydrogen, $C_1$-$C_6$ alkyl optionally substituted with heterocyclyl, $C_1$-$C_6$ alkoxy, heterocycle, amino, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl optionally substituted with heterocyclyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl or heterocycle; and
XRd is selected from 2-hydroxyethoxy, 2,3-dihydroxypropoxy, aminocarbonylethoxy, methylaminocarbonylethoxy, (4-methoxyphenyl)aminocarbonylethoxy, benzylaminocarbonylethoxy, 4-hydroxybutoxy, methylcarbonylaminoethoxy, methylcarbonylaminomethyl, (2,2,2-trifluoro-ethylamino)ethoxy, methanesulfonylaminoethoxy, isobutyrylaminoethoxy, methylaminoethoxy, isopropylsulfonylaminoethoxy, methylcarbonylaminoethoxy, dimethylaminoethoxy, N-(2-hydroxyethyl)-N-methylacetamide, formamide-N-2-ethoxy, methylformamide-N-2-ethoxy, dimethylsulfonylaminoethoxy, cyanoaminoethoxy, 3-hydroxypropyl, and 2-hydroxyethyl, provided that
at least one of $Ra_1$, $Ra_2$, $Ra_3$, and $Ra_4$ is not hydrogen; and
if —XRd is —OCH$_2$CH$_2$OH, then $Rb_3$ is not pyrrolidine.

13. The method according to claim 12, wherein:
U is C=O
P is $CRa_1$;
$Ra_1$ is selected from hydrogen, $C_1$-$C_6$ alkyl, $C_1$-$C_6$ alkoxy, and halogen;
$Ra_2$ is selected from hydrogen, $C_1$-$C_6$ alkyl optionally substituted with heterocyclyl, $C_1$-$C_6$ alkoxy, heterocycle, amide, and amino;
$Ra_4$ is selected from hydrogen, $C_1$-$C_6$ alkoxy, $C_1$-$C_6$ alkyl, and halogen;
$Ra_3$ is selected from hydrogen, $C_1$-$C_6$ alkyl, $C_1$-$C_6$ alkoxy, and halogen, wherein the $C_1$-$C_6$ alkoxy is optionally

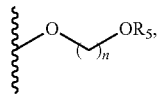

n is 1, 2, or 3; and
$R_5$ is $C_1$-$C_6$ alkyl substituted with phenyl or heteroaryl; and
$Rb_3$ and $Rb_5$ are independently selected from hydrogen, $C_1$-$C_6$ alkyl optionally substituted with heterocyclyl, $C_3$-$C_6$ cycloalkyl, $C_1$-$C_6$ alkoxy, halogen, and amino, wherein $Rb_2$ and $Rb_3$ and/or $Rb_5$ and $Rb_6$ may be connected to form a phenyl ring.

14. The method according to claim 13, wherein $Ra_1$ is selected from hydrogen, unsubstituted $C_1$-$C_6$ alkyl, unsubstituted $C_1$-$C_6$ alkoxy, and halogen.

15. The method according to claim 13, wherein $Ra_2$ is selected from hydrogen, $C_1$-$C_6$ alkyl substituted with heterocyclyl, unsubstituted $C_1$-$C_6$ alkoxy, amino, and heterocycle.

16. The method according to claim 13, wherein:
$Ra_3$ is selected from selected from hydrogen, methoxy, unsubstituted $C_1$-$C_6$ alkyl, halogen, and

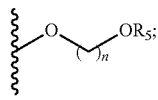

n is 1, 2, or 3; and
$R_5$ is $C_1$-$C_6$ alkyl substituted with phenyl or heteroaryl.

17. The method according to claim 13, wherein $Ra_4$ is selected from hydrogen, unsubstituted $C_1$-$C_6$ alkoxy, and halogen.

18. The method according to claim 13, wherein $Rb_3$ and $Rb_5$ are independently selected from hydrogen, methyl, $C_1$-$C_6$ alkyl substituted with heterocyclyl, and unsubstituted $C_1$-$C_6$ alkoxy wherein $Rb_2$ and $Rb_3$ and/or $Rb_5$ and $Rb_6$ may be connected to form a phenyl ring.

19. The method according to claim 18, wherein $Rb_3$ and $Rb_5$ are independently selected from hydrogen, methyl, methoxy, and morpholinomethyl, and wherein $Rb_2$ and $Rb_3$ and/or $Rb_5$ and $Rb_6$ may be connected to form a phenyl ring.

20. A method for treating a cancer associated with elevated levels of IL-6, comprising administering to a subject in need thereof a therapeutically effective amount of at least one compound selected from:

2-(4-(2-hydroxyethoxy)-3,5-dimethylphenyl)-5,7-dimethoxyquinazolin-4(3H)-one;
2-(4-(2-hydroxyethoxy)-3,5-dimethylphenyl)-6,7-dimethoxyquinazolin-4(3H)-one;
2-(4-(2-hydroxyethoxy)-3,5-dimethylphenyl)-5,7-dimethoxypyrido[2,3-d]pyrimidin-4(3H)-one;
N-(2-(4-(2-hydroxyethoxy)-3,5-dimethylphenyl)-4-oxo-3,4-dihydroquinazolin-6-yl)acetamide;
2-(4-(2-hydroxyethoxy)-3,5-dimethylphenyl)-6-morpholinoquinazolin-4(3H)-one;
2-(4-(2-hydroxyethoxy)-3,5-dimethylphenyl)-5,7-dimethylpyrido[2,3-d]pyrimidin-4(3H)-one;
5,7-difluoro-2-(4-(2-hydroxyethoxy)-3,5-dimethylphenyl)quinazolin-4(3H)-one;
5,7-dichloro-2-(4-(2-hydroxyethoxy)-3,5-dimethylphenyl)quinazolin-4(3H)-one;
2-[4-(2-hydroxy-ethoxy)-3,5-dimethyl-phenyl]-5,7-diisopropoxy-3H-quinazolin-4-one;
2-[4-(2-hydroxyethoxy)-3,5-dimethyl-phenyl]-6-morpholin-4-ylmethyl-3H-quinazolin-4-one;
2-[4-(2,3-Dihydroxy-propoxy)-3,5-dimethyl-phenyl]-5,7-dimethoxy-3H-quinazolin-4-one;
2-[4-(2-hydroxy-ethoxy)-3,5-dimethylphenyl]-5,7-dimethoxy-6-morpholin-4-ylmethyl-3H-quinazolin-4-one;
2-[4-(2-hydroxy-ethoxy)-phenyl]-5,7-dimethoxy-3H-quinazolin-4-one;
2-[4-(2-hydroxy-ethoxy)-naphthalen-1-yl]-5,7-dimethoxy-3H-quinazolin-4-one;
7-(2-benzyloxy-ethoxy)-2-[4-(2-hydroxy-ethoxy)-3,5-dimethyl-phenyl]-5-methoxy-3H-quinazolin-4-one;
7-(2-benzyloxy-ethoxy)-2-(2-hydroxymethyl-benzofuran-5-yl)-5-methoxy-3H-quinazolin-4-one;
2-[4-(5,7-dimethoxy-4-oxo-3,4-dihydro-quinazolin-2-yl)-2,6-dimethyl-phenoxy]-acetamide;
2-[4-(5,7-dimethoxy-4-oxo-3,4-dihydro-quinazolin-2-yl)-2,6-dimethyl-phenoxy]-N-methyl-acetamide;
2-[4-(5,7-Dimethoxy-4-oxo-3,4-dihydro-quinazolin-2-yl)-2,6-dimethyl-phenoxy]-N-(4-methoxy-phenyl)-acetamide;
N-benzyl-2-[4-(5,7-dimethoxy-4-oxo-3,4-dihydroquinazolin-2-yl)-2,6-dimethylphenoxy]acetamide;
2-[4-(4-hydroxy-butoxy)-3,5-dimethyl-phenyl]-5,7-dimethoxy-3H-quinazolin-4-one;
2-(4-(2-hydroxyethoxy)-3,5-dimethylphenyl)-6-methoxyquinazolin-4(3H)-one;
2-(4-(2-hydroxyethoxy)-3,5-dimethylphenyl)-5-methoxyquinazolin-4(3H)-one;
7-chloro-2-(4-(2-hydroxyethoxy)-3,5-dimethylphenyl)quinazolin-4(3H)-one;
8-chloro-2-(4-(2-hydroxyethoxy)-3,5-dimethylphenyl)quinazolin-4(3H)-one;
2-(4-(2-hydroxyethoxy)-3,5-dimethylphenyl)-8-methoxyquinazolin-4(3H)-one;
5-chloro-2-(4-(2-hydroxyethoxy)-3,5-dimethylphenyl)quinazolin-4(3H)-one;
2-(4-(2-hydroxyethoxy)-3,5-dimethylphenyl)-7-methoxyquinazolin-4(3H)-one;
2-(4-(2-hydroxyethoxy)-3-methylphenyl)-5,7-dimethoxyquinazolin-4(3H)-one;
2-(4-(2-hydroxyethoxy)-3,5-dimethylphenyl)-6-((4-methylpiperazin-1-yl)methyl)quinazolin-4(3H)-one;
N-{2-[4-(5,7-dimethoxy-4-oxo-3,4-dihydro-pyrido[2,3-d]pyrimidin-2-yl)-2,6-dimethyl-phenoxy]-ethyl}-acetamide;
N-(4-(5,7-dimethoxy-4-oxo-3,4-dihydroquinazolin-2-yl)-2,6-dimethylbenzyl)acetamide;

N-[4-(5,7-dimethoxy-4-oxo-3,4-dihydro-pyrido[2,3-d]pyrimidin-2-yl)-2,6-dimethyl-benzyl]-acetamide;
2-{3,5-Dimethyl-4-[2-(2,2,2-trifluoro-ethylamino)-ethoxy]-phenyl}-5,7-dimethoxy-3H-quinazolin-4-one;
N-{2-[4-(6, 8-Dimethoxy-1-oxo-1,2-dihydro-isoquinolin-3-yl)-2,6-dimethyl-phenoxy]-ethyl}-formamide;
N-(2-(4-(5,7-dimethoxy-4-oxo-3,4-dihydroquinazolin-2-yl)-2,6-dimethylphenoxy)ethyl)methanesulfonamide;
N-(2-(4-(5,7-dimethoxy-4-oxo-3,4-dihydroquinazolin-2-yl)-2,6-dimethylphenoxy)ethyl)-4-methoxybenzamide;
N-(2-(4-(5,7-dimethoxy-4-oxo-3,4-dihydroquinazolin-2-yl)-2,6-dimethylphenoxy)ethyl)acetamide;
N-(2-(4-(5,7-dimethoxy-4-oxo-3,4-dihydroquinazolin-2-yl)-2,6-dimethylphenoxy)ethyl)isobutyramide;
2-(3,5-dimethyl-4-(2-(methylamino)ethoxy)phenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)propane-2-sulfonamide;
2-(4-(2-(isopropylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2-methylphenoxy)ethyl)acetamide;
N-(2-(4-(5,7-dimethoxy-4-oxo-3,4-dihydroquinazolin-2-yl)-2-methylphenoxy)ethyl)isobutyramide;
N-(2-(4-(5,7-dimethoxy-4-oxo-3,4-dihydroquinazolin-2-yl)-2-methylphenoxy)ethyl)methanesulfonamide;
2-(4-(2-(dimethylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)-N-methylacetamide;
N-(2-(4-(5,7-dimethoxy-4-oxo-3,4-dihydroquinazolin-2-yl)-2, 6-dimethylphenoxy)ethyl)formamide;
N-(2-(4-(5,7-dimethoxy-4-oxo-3,4-dihydroquinazolin-2-yl)-2, 6-dimethylphenoxy)ethyl)-N-methylformamide;
N-(2-(4-(5,7-Dimethoxy-4-oxo-3,4-dihydroquinazolin-2-yl)-2,6-dimethylphenoxy)ethyl)dimethylamino-N-sulfonamide;
N-(2-(4-(5,7-dimethoxy-4-oxo-3,4-dihydroquinazolin-2-yl)-2, 6-dimethylphenoxy)ethyl)cyanamide;
2-[4-(3-hydroxy-propyl)-3,5-dimethoxyphenyl]-5,7-dimethoxy-3H-quinazolin-4-one;
2-[4-(3-hydroxy-propyl)-3-methoxy-phenyl]-5,7-dimethoxy-3H-quinazolin-4-one; and
2-[2-(2-hydroxyethyl)-1H-indol-6-yl]-5,7-dimethoxy-3H-quinazolin-4-one, and
tautomers, stereoisomers, pharmaceutically acceptable salts, and hydrates thereof.

21. The method according to claim 12, wherein the therapeutically effective amount of the compound is administered with at least one pharmaceutically acceptable carrier in a pharmaceutically acceptable composition.

22. The method according to claim 12, wherein the cancer is selected from multiple myeloma, lymphoma, leukemia, solid tumors, prostate and bladder cancers, cardiac myxoma, tumor-induced cachexia, cancer-associated depression, cerebral edema secondary to brain tumors, hormone-independent prostate cancer, B cell lymphoma, AIDS-associated lymphoma, and metastatic renal cell carcinoma.

23. A method of treating or reducing the risk of acquiring asthma chronic obstructive pulmonary disease (COPD), or a non-cardiovascular inflammatory disease mediated by IL-6 in a subject in need thereof, comprising administering a therapeutically effective amount of at least one compound of Formula II:

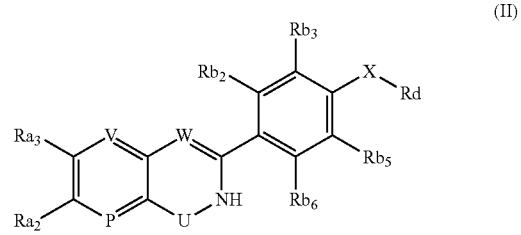

or a stereoisomer, tautomer, pharmaceutically acceptable salt, or hydrate thereof, wherein:
P is selected from N and $CRa_1$;
V is selected from N and $CRa_4$;
W is selected from N and CH;
U is selected from C=O, C=S, $SO_2$, S=O, and $SR_1$;
$Ra_1$ and $Ra_4$ are independently selected from hydrogen, $C_1$-$C_6$ alkyl, $C_1$-$C_6$ alkoxy, $C_3$-$C_6$ cycloalkyl, and halogen;
$Ra_3$ is selected from hydrogen, $C_1$-$C_6$ alkyl, $C_1$-$C_6$ alkoxy, $C_3$-$C_6$ cycloakyl, and halogen, wherein the $C_1$-$C_6$ alkoxy is optionally

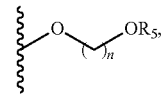

n is 1, 2, or 3; and
$R_5$ is $C_1$-$C_6$ alkyl substituted with phenyl or heteroaryl;
$Ra_2$ is selected from hydrogen, $C_1$-$C_6$ alkyl optionally substituted with heterocyclyl, $C_1$-$C_6$ alkoxy, heterocycle, amino, amide, fluoro, and bromo;
$Rb_2$ and $Rb_6$ are independently selected from hydrogen, methyl, and fluoride;
$Rb_3$ and $Rb_5$ are independently selected from hydrogen, $C_1$-$C_6$ alkyl optionally substituted with heterocyclyl, $C_3$-$C_6$ cycloalkyl, $C_1$-$C_6$ alkoxy, halogen, and amino;
$Rb_2$ and $Rb_3$ and/or $Rb_5$ and $Rb_6$ may be connected to form a cycloalkyl, phenyl or heterocycle; and
XRd is selected from 2-hydroxyethoxy, 2,3-dihydroxypropoxy, aminocarbonylethoxy, methylaminocarbonylethoxy, (4-methoxyphenyl)aminocarbonylethoxy, benzylaminocarbonylethoxy, 4-hydroxybutoxy, methylcarbonylaminoethoxy, methylcarbonylaminomethyl, (2,2,2-trifluoro-ethylamino)ethoxy, methanesulfonylaminoethoxy, isobutyrylaminoethoxy, methylaminoethoxy, isopropylsulfonylaminoethoxy, methylcarbonylaminoethoxy, dimethylaminoethoxy, N-(2-hydroxyethyl)-N-methylacetamide, formamide-N-2-ethoxy, methylformamide-N-2-ethoxy, dimethylsulfonylaminoethoxy, cyanoaminoethoxy, 3-hydroxypropyl, and 2-hydroxyethyl,
provided that
at least one of $Ra_1$, $Ra_2$, $Ra_3$, and $Ra_4$ is not hydrogen;
if —XRd is —$OCH_2CH_2OH$, then $Rb_3$ is not pyrrolidine;
and
wherein the compound is not 2-(4-(2-hydroxyethoxy)-3,5-dimethylphenyl)-5,7-dimethoxyquinazolin-4 (3H)-one.

24. The method according to claim 23, wherein:
U is C=O
P is $CRa_1$;
$Ra_1$ is selected from hydrogen, $C_1$-$C_6$ alkyl, $C_1$-$C_6$ alkoxy, and halogen;

Ra$_2$ is selected from hydrogen, C$_1$-C$_6$ alkyl optionally substituted with heterocyclyl, C$_1$-C$_6$ alkoxy, heterocycle, amide, and amino;

Ra$_4$ is selected from hydrogen, C$_1$-C$_6$ alkoxy, C$_1$-C$_6$ alkyl, and halogen;

Ra$_3$ is selected from hydrogen, C$_1$-C$_6$ alkyl, C$_1$-C$_6$ alkoxy, and halogen, wherein the C$_1$-C$_6$ alkoxy is optionally

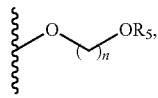

n is 1, 2, or 3; and

R$_5$ is C$_1$-C$_6$ alkyl substituted with phenyl or heteroaryl; and

Rb$_3$ and Rb$_5$ are independently selected from hydrogen, C$_1$-C$_6$ alkyl optionally substituted with heterocyclyl, C$_3$-C$_6$ cycloalkyl, C$_1$-C$_6$ alkoxy, halogen, and amino, wherein Rb$_2$ and Rb$_3$ and/or Rb$_5$ and Rb$_6$ may be connected to form a phenyl ring.

25. The method according to claim 24, wherein Ra$_1$ is selected from hydrogen, unsubstituted C$_1$-C$_6$ alkyl, unsubstituted C$_1$-C$_6$ alkoxy, and halogen.

26. The method according to claim 24, wherein Ra$_2$ is selected from hydrogen, C$_1$-C$_6$ alkyl substituted with heterocyclyl, unsubstituted C$_1$-C$_6$ alkoxy, amino, and heterocycle.

27. The method according to claim 24, wherein:

Ra$_3$ is selected from selected from hydrogen, methoxy, unsubstituted C$_1$-C$_6$ alkyl, halogen, and

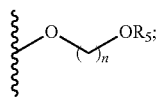

n is 1, 2, or 3; and

R$_5$ is C$_1$-C$_6$ alkyl substituted with phenyl or heteroaryl.

28. The method according to claim 24, wherein Ra$_4$ is selected from hydrogen, unsubstituted C$_1$-C$_6$ alkoxy, and halogen.

29. The method according to claim 24, wherein Rb$_3$ and Rb$_5$ are independently selected from hydrogen, methyl, C$_1$-C$_6$ alkyl substituted with heterocyclyl, and unsubstituted C$_1$-C$_6$ alkoxy wherein Rb$_2$ and Rb$_3$ and/or Rb$_5$ and Rb$_6$ may be connected to form a phenyl ring.

30. The method according to claim 29, wherein Rb$_3$ and Rb$_5$ are independently selected from hydrogen, methyl, methoxy, and morpholinomethyl, and wherein Rb$_2$ and Rb$_3$ and/or Rb$_5$ and Rb$_6$ may be connected to form a phenyl ring.

31. A method of treating or reducing the risk of acquiring a non-cardiovascular inflammatory disease mediated by IL-6 in a subject in need thereof, comprising administering a therapeutically effective amount of at least one compound selected from:

2-(4-(2-hydroxyethoxy)-3,5-dimethylphenyl)-6,7-dimethoxyquinazolin-4(3H)-one;

2-(4-(2-hydroxyethoxy)-3,5-dimethylphenyl)-5,7-dimethoxypyrido[2,3-d]pyrimidin-4(3H)-one;

N-(2-(4-(2-hydroxyethoxy)-3,5-dimethylphenyl)-4-oxo-3,4-dihydroquinazolin-6-yl)acetamide;

2-(4-(2-hydroxyethoxy)-3,5-dimethylphenyl)-6-morpholinoquinazolin-4(3H)-one;

2-(4-(2-hydroxyethoxy)-3,5-dimethylphenyl)-5,7-dimethylpyrido[2,3-d]pyrimidin-4(3H)-one;

5,7-difluoro-2-(4-(2-hydroxyethoxy)-3,5-dimethylphenyl)quinazolin-4(3H)-one;

5,7-dichloro-2-(4-(2-hydroxyethoxy)-3,5-dimethylphenyl)quinazolin-4(3H)-one;

2-[4-(2-hydroxy-ethoxy)-3,5-dimethyl-phenyl]-5,7-diisopropoxy-3H-quinazolin-4-one;

2-[4-(2-hydroxyethoxy)-3,5-dimethyl-phenyl]-6-morpholin-4-ylmethyl-3H-quinazolin-4-one;

2-[4-(2,3-Dihydroxy-propoxy)-3,5-dimethyl-phenyl]-5,7-dimethoxy-3H-quinazolin-4-one;

2-[4-(2-hydroxy-ethoxy)-3,5-dimethylphenyl]-5,7-dimethoxy-6-morpholin-4-ylmethyl-3H-quinazolin-4-one;

2-[4-(2-hydroxy-ethoxy)-phenyl]-5,7-dimethoxy-3H-quinazolin-4-one;

2-[4-(2-hydroxy-ethoxy)-naphthalen-1-yl]-5,7-dimethoxy-3H-quinazolin-4-one;

7-(2-benzyloxy-ethoxy)-2-[4-(2-hydroxy-ethoxy)-3,5-dimethyl-phenyl]-5-methoxy-3H-quinazolin-4-one;

7-(2-benzyloxy-ethoxy)-2-(2-hydroxymethyl-benzofuran-5-yl)-5-methoxy-3H-quinazolin-4-one;

2-[4-(5,7-dimethoxy-4-oxo-3,4-dihydro-quinazolin-2-yl)-2,6-dimethyl-phenoxy]-acetamide;

2-[4-(5,7-dimethoxy-4-oxo-3,4-dihydro-quinazolin-2-yl)-2,6-dimethyl-phenoxy]-N-methyl-acetamide;

2-[4-(5,7-Dimethoxy-4-oxo-3,4-dihydro-quinazolin-2-yl)-2,6-dimethyl-phenoxy]-N-(4-methoxy-phenyl)-acetamide;

N-benzyl-2-[4-(5,7-dimethoxy-4-oxo-3,4-dihydroquinazolin-2-yl)-2,6-dimethylphenoxy]acetamide;

2-[4-(4-hydroxy-butoxy)-3,5-dimethyl-phenyl]-5,7-dimethoxy-3H-quinazolin-4-one;

2-(4-(2-hydroxyethoxy)-3,5-dimethylphenyl)-6-methoxyquinazolin-4(3H)-one;

2-(4-(2-hydroxyethoxy)-3,5-dimethylphenyl)-5-methoxyquinazolin-4(3H)-one;

7-chloro-2-(4-(2-hydroxyethoxy)-3,5-dimethylphenyl)quinazolin-4(3H)-one;

8-chloro-2-(4-(2-hydroxyethoxy)-3,5-dimethylphenyl)quinazolin-4(3H)-one;

2-(4-(2-hydroxyethoxy)-3,5-dimethylphenyl)-8-methoxyquinazolin-4(3H)-one;

5-chloro-2-(4-(2-hydroxyethoxy)-3,5-dimethylphenyl)quinazolin-4(3H)-one;

2-(4-(2-hydroxyethoxy)-3,5-dimethylphenyl)-7-methoxyquinazolin-4(3H)-one;

2-(4-(2-hydroxyethoxy)-3-methylphenyl)-5,7-dimethoxyquinazolin-4(3H)-one;

2-(4-(2-hydroxyethoxy)-3,5-dimethylphenyl)-6-((4-methylpiperazin-1-yl)methyl)quinazolin-4(3H)-one;

N-{2-[4-(5,7-dimethoxy-4-oxo-3,4-dihydro-pyrido[2,3-d]pyrimidin-2-yl)-2,6-dimethyl-phenoxy]-ethyl}-acetamide;

N-(4-(5,7-dimethoxy-4-oxo-3,4-dihydroquinazolin-2-yl)-2,6-dimethylbenzyl)acetamide;

N-[4-(5,7-dimethoxy-4-oxo-3,4-dihydro-pyrido[2,3-d]pyrimidin-2-yl)-2,6-dimethyl-benzyl]-acetamide;

2-{3,5-Dimethyl-4-[2-(2,2,2-trifluoro-ethylamino)-ethoxy]-phenyl}-5,7-dimethoxy-3H-quinazolin-4-one;

N-{2-[4-(6, 8-Dimethoxy-1-oxo-1,2-dihydro-isoquinolin-3-yl)-2,6-dimethyl-phenoxy]-ethyl}-formamide;

N-(2-(4-(5,7-dimethoxy-4-oxo-3,4-dihydroquinazolin-2-yl)-2,6-dimethylphenoxy)ethyl)methanesulfonamide;

N-(2-(4-(5,7-dimethoxy-4-oxo-3,4-dihydroquinazolin-2-yl)-2,6-dimethylphenoxy)ethyl)-4-methoxybenzamide;

N-(2-(4-(5,7-dimethoxy-4-oxo-3,4-dihydroquinazolin-2-yl)-2,6-dimethylphenoxy)ethyl)acetamide;
N-(2-(4-(5,7-dimethoxy-4-oxo-3,4-dihydroquinazolin-2-yl)-2,6-dimethylphenoxy)ethyl)isobutyramide;
2-(3,5-dimethyl-4-(2-(methylamino)ethoxy)phenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)propane-2-sulfonamide;
2-(4-(2-(isopropylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2-methylphenoxy)ethyl)acetamide;
N-(2-(4-(5,7-dimethoxy-4-oxo-3,4-dihydroquinazolin-2-yl)-2-methylphenoxy)ethyl)isobutyramide;
N-(2-(4-(5,7-dimethoxy-4-oxo-3,4-dihydroquinazolin-2-yl)-2-methylphenoxy)ethyl)methanesulfonamide;
2-(4-(2-(dimethylamino)ethoxy)-3,5-dimethylphenyl)-5,7-dimethoxyquinazolin-4(3H)-one;
N-(2-(4-(5,7-dimethoxy-4-oxo-3,4-dihydroquinazolin-2-yl)-2,6-dimethylphenoxy)ethyl)-N-methylacetamide;
N-(2-(4-(5,7-dimethoxy-4-oxo-3,4-dihydroquinazolin-2-yl)-2,6-dimethylphenoxy)ethyl)formamide;
N-(2-(4-(5,7-dimethoxy-4-oxo-3,4-dihydroquinazolin-2-yl)-2,6-dimethylphenoxy)ethyl)-N-methylformamide;
N-(2-(4-(5,7-Dimethoxy-4-oxo-3,4-dihydroquinazolin-2-yl)-2,6-dimethylphenoxy)ethyl)dimethylamino-N-sulfonamide;
N-(2-(4-(5,7-dimethoxy-4-oxo-3,4-dihydroquinazolin-2-yl)-2,6-dimethylphenoxy)ethyl)cyanamide;
2-[4-(3-hydroxy-propyl)-3,5-dimethoxyphenyl]-5,7-dimethoxy-3H-quinazolin-4-one;
2-[4-(3-hydroxy-propyl)-3-methoxy-phenyl]-5,7-dimethoxy-3H-quinazolin-4-one; and
2-[2-(2-hydroxyethyl)-1H-indol-6-yl]-5,7-dimethoxy-3H-quinazolin-4-one, and
tautomers, stereoisomers, pharmaceutically acceptable salts and hydrates thereof.

32. The method according to claim 23, wherein the therapeutically effective amount of the compound is administered with at least one pharmaceutically acceptable carrier in a pharmaceutically acceptable composition.

33. The method according to claim 23, wherein the disease is selected from cystic fibrosis, post transplantation late and chronic solid organ rejection, systemic lupus erythematosus, ocular inflammation, uveitis, rhinitis, glomerulonephritis, Grave's disease, gastrointestinal allergies, and conjunctivitis.

34. The method according to claim 1 or 23, wherein the disease is asthma.

35. The method of claim 11 or claim 33, wherein the disease is selected from liver transplant rejection, heart transplant rejection, kidney transplant rejection, proliferative glomerulonephritis, and membranous glomerulonephritis.

36. The method according to claim 12, wherein the cancer is selected from uterine cancer, multiple myeloma, histiocytomas, plasmacytoma, hormone-independent prostate cancer, cancer induced cachexia, B cell lymphoma, and metastatic renal cell carcinoma.

* * * * *

UNITED STATES PATENT AND TRADEMARK OFFICE
CERTIFICATE OF CORRECTION

PATENT NO. : 9,757,368 B2
APPLICATION NO. : 13/265060
DATED : September 12, 2017
INVENTOR(S) : Henrik C. Hansen et al.

It is certified that error appears in the above-identified patent and that said Letters Patent is hereby corrected as shown below:

Claim 1, Column 97, Line 13, "at least one of $Ra_1$, $Ra_2$, $Ra_1$, and $Ra_4$ is not hydrogen;" should read --at least one of $Ra_1$, $Ra_2$, $Ra_3$, and $Ra_4$ is not hydrogen;--.

Signed and Sealed this
Twenty-third Day of January, 2018

Joseph Matal
*Performing the Functions and Duties of the
Under Secretary of Commerce for Intellectual Property and
Director of the United States Patent and Trademark Office*